US012392001B2

(12) United States Patent
Peters et al.

(10) Patent No.: US 12,392,001 B2
(45) Date of Patent: *Aug. 19, 2025

(54) COMPOSITIONS AND METHODS FOR DETECTING AN RNA VIRUS

(71) Applicant: ENVIROLOGIX INC., Portland, ME (US)

(72) Inventors: Lars Peters, Portland, ME (US); Stephen A. Judice, Portland, ME (US); Daniel Shaffer, Portland, ME (US); Breck Parker, Portland, ME (US)

(73) Assignee: Envirologix Inc., Portland, ME (US)

( * ) Notice: Subject to any disclaimer, the term of this patent is extended or adjusted under 35 U.S.C. 154(b) by 489 days.

This patent is subject to a terminal disclaimer.

(21) Appl. No.: 16/991,216

(22) Filed: Aug. 12, 2020

(65) Prior Publication Data

US 2021/0025016 A1 Jan. 28, 2021

Related U.S. Application Data

(63) Continuation of application No. 15/520,328, filed as application No. PCT/US2015/056491 on Oct. 20, 2015, now Pat. No. 10,793,922.

(60) Provisional application No. 62/104,008, filed on Jan. 15, 2015, provisional application No. 62/066,277, filed on Oct. 20, 2014.

(51) Int. Cl.
*C12Q 1/70* (2006.01)
*C12Q 1/68* (2018.01)
*C12Q 1/6865* (2018.01)

(52) U.S. Cl.
CPC ........... *C12Q 1/701* (2013.01); *C12Q 1/6865* (2013.01); *C12Q 2600/158* (2013.01); *Y02A 50/30* (2018.01)

(58) Field of Classification Search
None
See application file for complete search history.

(56) References Cited

U.S. PATENT DOCUMENTS 5,455,166 A 10/1995 Walker
5,629,179 A 5/1997 Mierendorf et al.
5,952,202 A 9/1999 Aoyagi et al.
6,063,604 A 5/2000 Wick et al.
6,130,038 A 10/2000 Becker et al.
6,355,421 B1 3/2002 Coull et al.
6,617,137 B2 9/2003 Dean et al.
6,794,142 B2 9/2004 Laird et al.
6,977,148 B2 12/2005 Dean et al.
7,056,671 B2 6/2006 Enoki et al.
7,074,600 B2 7/2006 Dean et al.
7,094,539 B2 8/2006 Gu et al.
7,112,423 B2 9/2006 Van Ness et al.
7,282,328 B2 10/2007 Kong et al.
7,662,594 B2 * 2/2010 Kong ..................... C12P 19/34 435/183
8,574,847 B2 11/2013 Becker et al.
9,096,897 B2 8/2015 Shaffer et al.
9,322,053 B2 4/2016 Shaffer et al.
9,631,231 B2 4/2017 Shaffer et al.
9,845,510 B2 12/2017 Peters et al.
10,077,467 B2 9/2018 Shaffer et al.
10,100,370 B2 10/2018 Parker et al.
10,584,376 B2 3/2020 Shaffer et al.
10,793,922 B2 10/2020 Peters et al.
11,208,687 B2 12/2021 Shaffer et al.
2003/0060431 A1 3/2003 Simmonds et al.
2003/0082590 A1 5/2003 Van Ness et al.
2003/0211483 A1 11/2003 Schroeder et al.
2005/0059003 A1 3/2005 Enoki et al.
2006/0115838 A1 6/2006 Bazar et al.
2006/0216796 A1 9/2006 Hashiguchi et al.
2007/0054296 A1 3/2007 Piepenburg et al.
2007/0082011 A1 4/2007 Lehrer et al.
2008/0254458 A1 10/2008 Chou
2008/0274458 A1 11/2008 Latham et al.
2009/0017452 A1 1/2009 Ratain et al.
2009/0017453 A1 1/2009 Maples et al.
2009/0048439 A1 2/2009 Weisburg et al.
2009/0081670 A1 * 3/2009 Maples ............... C12Q 1/6844 435/6.12
2009/0197254 A1 8/2009 Lee
2010/0092957 A1 4/2010 Zhao et al.
2010/0099149 A1 4/2010 Birnboim et al.
(Continued)

FOREIGN PATENT DOCUMENTS

CN 1633505 A 6/2005
CN 101952459 A 1/2011
(Continued)

OTHER PUBLICATIONS

Vallone, P.M. and Butler, J.M., 2004. AutoDimer: a screening tool for primer-dimer and hairpin structures. Biotechniques, 37(2), pp. 226-231. (Year: 2004).*
Thornton B. and Basu, C., 2011. Real-time PCR (qPCR) primer design using free online software. Biochemistry and molecular biology education, 39(2), pp. 145-154. (Year:2011).*
Rychlik, W., 1995. Selection of primers for polymerase chain reaction, Molecular biotechnology, 3, pp. 129-134. (Year: 1995).*
Borah, P., 2011. Primer designing for PCR. Science Vision, 11(3), pp. 134-136. (Year: 2011).*
Office Action issued in corresponding Mexican Patent Application No. MX/a/2017/005159, dated Dec. 2, 2020 (7 pages).
(Continued)

*Primary Examiner* — Stephanie E Mummert
*Assistant Examiner* — Olayinka A Oyeyemi
(74) *Attorney, Agent, or Firm* — Greenberg Traurig, LLP; Melissa Hunter-Ensor; Nicholas R. Ballor

(57) ABSTRACT

The present invention provides methods for rapidly identifying an RNA viral infection using an isothermal nucleic acid amplification reaction that can be carried out extracted RNA in the context of a crude biological sample.

15 Claims, 50 Drawing Sheets

Specification includes a Sequence Listing.

(56) References Cited

U.S. PATENT DOCUMENTS

| | | | | |
|---|---|---|---|---|
| 2010/0255546 | A1* | 10/2010 | Uematsu | C12Q 1/6844 435/91.2 |
| 2011/0081685 | A1 | 4/2011 | Makarov et al. | |
| 2011/0151467 | A1 | 6/2011 | Usui et al. | |
| 2012/0021461 | A1 | 1/2012 | Millar et al. | |
| 2013/0217071 | A1 | 8/2013 | Montesclaros et al. | |
| 2013/0280706 | A1 | 10/2013 | Judice | |
| 2014/0093883 | A1* | 4/2014 | Maples | C07H 21/04 435/6.12 |
| 2017/0044628 | A1 | 2/2017 | Peters et al. | |
| 2017/0166960 | A1 | 6/2017 | Shaffer et al. | |
| 2017/0327911 | A1 | 11/2017 | Peters et al. | |
| 2018/0363046 | A1 | 12/2018 | Shaffer et al. | |
| 2020/0239947 | A1 | 7/2020 | Shaffer et al. | |
| 2022/0243262 | A1 | 8/2022 | Shaffer et al. | |

FOREIGN PATENT DOCUMENTS

| | | | | |
|---|---|---|---|---|
| EP | 1201768 | A2 | 5/2002 | |
| EP | 1420069 | A1 | 5/2004 | |
| EP | 2836609 | A1 | 2/2015 | |
| JP | 2002291490 | A | 10/2002 | |
| JP | 2004532615 | A | 10/2004 | |
| JP | 2008526228 | A | 7/2008 | |
| JP | 2010505396 | A | 2/2010 | |
| JP | 2010533494 | A | 10/2010 | |
| JP | 2011521624 | A | 7/2011 | |
| JP | 2014082936 | A | 5/2014 | |
| KR | 20040028991 | A | 4/2004 | |
| WO | 2002057479 | A2 | 7/2002 | |
| WO | 2003008622 | A2 | 1/2003 | |
| WO | 2003016569 | A1 | 2/2003 | |
| WO | 2006074162 | A2 | 7/2006 | |
| WO | 2008002920 | A2 | 1/2008 | |
| WO | 2008040126 | A1 | 4/2008 | |
| WO | 2009012246 | A2 | 1/2009 | |
| WO | 2009135093 | A2 | 11/2009 | |
| WO | 2010107946 | A2 | 9/2010 | |
| WO | 2012021493 | A2 | 2/2012 | |
| WO | 2012022755 | A1 | 2/2012 | |
| WO | 2013040491 | A2 | 3/2013 | |
| WO | 2013155056 | A1 | 10/2013 | |
| WO | WO-2013155056 | A9 * | 10/2013 | C12Q 1/68 |
| WO | 2014004852 | A2 | 1/2014 | |
| WO | 2015168134 | A1 | 11/2015 | |
| WO | 2016064894 | A2 | 4/2016 | |
| WO | 2016069345 | A1 | 5/2016 | |
| WO | 2016122698 | A1 | 8/2016 | |

OTHER PUBLICATIONS

English explanation of the Office Action issued in corresponding Mexican Patent Application No. MX/a/2017/005159, dated Dec. 2, 2020 (6 pages).
Office Action dated Jan. 26, 2022 in corresponding Mexican Patent Application No. MX/a/2017/005159 (5 pages).
English translation of the Office Action dated Jan. 26, 2022 in corresponding Mexican Patent Application No. MX/a/2017/005159 (4 pages).
Ahern, Holly, "Biochemical, Reagent Kits Offer Scientists Good Return on Investment," The Scientist, Jul. 24, 1995, vol. 9, No. 15, pp. 1-5.
Armitage et al., "Hairpin-Forming Peptide Nucleic Acid Oligomers," Biochemistry, 1998, vol. 37, pp. 9417-9425.
Craw et al., "Isothermal nucleic acid amplification technologies for point-of-care diagnostics: a critical review," Lab Chip, 2012, vol. 12, No. 14, pp. 2469-2486.
Dames et al., "Characterization of Aberrant Melting Peaks in Unlabeled Probe Assays," Journal of Molecular Diagnostics, Jul. 2007, vol. 9, No. 3, pp. 290-296.
Dirks et al., "Triggered amplification by hybridization chain reaction," Proceedings of the National Academy of Sciences of the United States of America, Oct. 26, 2004, vol. 101, No. 43, pp. 15275-15278.
Holland et al., "Detection of specific polymerase chain reaction product by utilizing the 5'-3' exonuclease activity of Thermus aquaticus DNA polymerase," Proceedings of the National Academy of Sciences of the United States of America, Aug. 1991, vol. 88, pp. 7276-7280.
IDT "The Polymerase Chain Reaction," Integrated DNA Technologies, 2011, pp. 1-21.
ITO, et al., "Synthesis, thermal stability and resistance to enzymatic hydrolysis of the oligonucleotides containing 5-(N-aminohexyl)carbamoyl-2'-O-methyluridines," Nucleic Acids Research, 2003, vol. 31, No. 10, pp. 2514-2523.
Krishnan et al., "Nucleic Acid Based Molecular Devices," Angewandte Chemie International Edition, 2011, vol. 50, pp. 3124-3156.
Li et al., "Enzymatic signal amplification of molecular beacons for sensitive DNA detection," Nucleic Acids Research, 2008, vol. 36, No. 6, e36, pp. 1-17.
Mann et al., "A thermodynamic approach to PCR primer design," Nucleic Acids Research, 2009, vol. 37, No. 13, e95, pp. 1-9.
Markham et al., "UNAFold: Software for Nucleic Acid Folding and Hybridization," Bioinformatics, vol. II: Structure, Function and Applications, Sep. 2, 2008, vol. 453, pp. 1-33.
Notomi et al., "Loop-mediated isothermal amplification of DNA," Nucleic Acids Research, 2000, vol. 28, No. 12, e63, pp. i-vii.
Owczarzy et al., "IDT SciTools: a suite for analysis and design of nucleic acid oligomers," Nucleic Acids Research, 2008, vol. 36, pp. W163-W169.
Paulasova et al., "The peptide nucleic acids (PNAs): a new generation of probes for genetic and cytogenetic analyses," Annales de Génétique, 2004, vol. 47, pp. 349-358.
"PCR Primer Design Guidelines," Premier Biosoft, www.premierbiosoft.com/tech_notes/PCR_Primer_Design.html.
Prediger, Ellen, "Designing PCR Primers and Probes," Decoded, Oct. 2013, vol. 3, No. 4, pp. 2-3.
"Primer Dimer," Wikipedia, the free encyclopedia, retrieved from the Internet Feb. 14, 2020 https://en.wikipedia.org/wiki/Primer_dimer.
Santalucia, Jr et al., "The Thermodynamics of DNA Structural Motifs," Annual Review of Biophysics and Biomolecular Structure, 2004, vol. 33, pp. 415-440.
Santangelo et al., "Dual FRET molecular beacons for mRNA detection in living cells," Nucleic Acids Research, 2004, vol. 32, No. 6, e57, pp. 1-9.
Stofer et al., "Free Energy Calculations of Watson-Crick Base Pairing in Aqueous Solution," Journal of the American Chemical Society, 1999, vol. 121, No. 41, pp. 9503-9508.
Stratagene Catalog, "Gene Characterization Kits," Stratagene Catalog, 1988, p. 39.
Thornton et al., "Real-time PCR (qPCR) Primer Design Using Free Online Software," Biochemistry and Molecular Biology Education, 2011, vol. 39, No. 2, pp. 145-154.
Tyagi et al., "Molecular Beacons: Probes that Fluoresce upon Hybridization," Nature Biotechnology, Mar. 1996, vol. 14, pp. 303-308.
Untergasser et al., "Primer3—new capabilities and interfaces," Nucleic Acids Research, 2012, vol. 40, No. 15, e115, pp. 1-12.
Examination and Search Report dated Sep. 9, 2021 in corresponding ARIPO Patent Application No. AP/P/2017/009907 (4 pages).
Office Action dated Apr. 30, 2021 in corresponding Chinese Patent Application No. 201580069867.5 (12 pages).
English translation of the Office Action dated Apr. 30, 2021 in corresponding Chinese Patent Application No. 201580069867.5 (16 pages).
Office Action dated Jul. 27, 2021 in corresponding Mexican Patent Application No. MX/a/2017/005159 (9 pages).
English translation of the Office Action dated Jul. 27, 2021 in corresponding Mexican Patent Application No. MX/a/2017/005159 (9 pages).
Office Action dated Nov. 24, 2021 in corresponding Chinese Patent Application No. 201580069867.5 (14 pages).
English translation of the Office Action dated Nov. 24, 2021 in corresponding Chinese Patent Application No. 201580069867.5 (3 pages).

(56) References Cited

OTHER PUBLICATIONS

Office Action dated Nov. 24, 2021 in corresponding Canadian Patent Application No. 2965137 (5 pages).
Office Action dated Nov. 30, 2021 in corresponding Japanese Patent Application No. JP 2020-189107 (5 pages).
English translation of the Office Action dated Nov. 30, 2021 in corresponding Japanese Patent Application No. JP 2020-189107 (5 pages).
Examination Report issued in corresponding Australian Patent Application No. 2015336086, dated Nov. 12, 2020 (3 pages).
Ehses et al., "Optimization and design of oligonucleotide setup for strand displacement amplification," Journal of Biochemical and Biophysical Methods, Jun. 30, 2005, vol. 63, Iss. 3, pp. 170-186.
Yan et al., "Isothermal amplified detection of DNA and RNA," Molecular BioSystems, 2014, vol. 10, No. 5, pp. 970-1003; http://dx.doi.org/10.1039/c3mb70304e.
Examination Report in corresponding Australian Patent Application 2015336086, dated Nov. 20, 2019 (6 pages).
Extended Search Report in corresponding European Patent Application No. 15852795.2, dated Mar. 22, 2018 (9 pages).
International Search and Examination Report issued in corresponding ARIPO Patent Application No. AP/P/2017/009907, dated May 25, 2020 (5 pages).
International Search Report and Written Opinion, for corresponding PCT/US2015/056491, dated Apr. 11, 2016 (27 pages).
Office Action in corresponding Brazilian Patent Application No. BR 112017008082-6, dated Dec. 9, 2019 (4 pages).
English explanation of the Office Action in corresponding Brazilian Patent Application No. BR 112017008082-6, dated Dec. 9, 2019 (2 pages).
Office Action in corresponding Chinese Patent Application No. 201580069867.5, dated Jun. 3, 2020 (15 pages).
English translation of the Office Action in corresponding Chinese Patent Application No. 201580069867.5, dated Jun. 3, 2020 (21 pages).
Office Action in corresponding European Patent Application No. 15852795.2, dated Nov. 5, 2019 (6 pages).
Office Action in corresponding Japanese Patent Application No. 2017-521095, dated Nov. 5, 2019 (8 pages).
English translation of the Office Action in corresponding Japanese Patent Application No. 2017-521095, dated Nov. 5, 2019 (8 pages).
Examination Report dated Sep. 14, 2022 in corresponding Australian Patent Application No. 2021201378 (4 pages).
Examination and Search Report issued in corresponding ARIPO Patent Application No. AP/P/2017/009907, dated Mar. 2, 2021 (4 pages).
First Examination Report issued in corresponding Indian Patent Application No. 201747017620, dated Mar. 1, 2021 (9 pages).
Office Action issued in corresponding European Patent Application No. 15852795.2, dated Jul. 20, 2020 (4 pages).
Chu, Y.L., "Fundamental Concepts of Bioinformatics for Medical Use," Shaanxi Science and Technology Press, Oct. 31, 2005, p. 222.
Office Action dated Apr. 2, 2022 in corresponding Chinese Patent Application No. 201580069867.5 (8 pages).
English translation of the Office Action dated Apr. 2, 2022 in corresponding Chinese Patent Application No. 201580069867.5 (16 pages).
Office Action dated Jul. 25, 2022 in corresponding Mexican Patent Application No. MX/a/2017/005159 (5 pages).
English translation of the Office Action dated Jul. 25, 2022 in corresponding Mexican Patent Application No. MX/a/2017/005159 (5 pages).
Office Action dated Nov. 1, 2022 in corresponding Canadian Patent Application No. 2,965,137 (6 pages).
Notice of Opposition dated Jun. 14, 2023 in corresponding European Patent Application No. 15852795.2.
Comparison between granted Claim 1 of European Patent No. 3209802 and Claim 1 of European Patent Application No. 22187762.4 filed on Sep. 26, 2022.
Nie et al., "Evaluation of Alere i influenza A&B for Rapid Detection of Influenza Viruses A and B," Journal of Clinincal Microbiology, Sep. 2014, vol. 52, No. 9, pp. 3339-3344.
Niemz et al., "Point-of-care nucleic acid testing for infectious diseases," Trends in Biotechnology, May 2011, vol. 29, No. 5, pp. 240-250.
Sambrook et al., "Extraction, Purification, and Analysis of mRNA from Eukaryotic Cells," Chapter 7, Protocol 1, Molecular Cloning, 2001.
Screenshots of the User Manual on Viral RNA and DNA isolation, NucleoSpin 8 Virus manual from Sep. 1, 2013.
Affidavit of Professor John SantaLucia submitted Sep. 29, 2021 in the opposition proceedings of corresponding European Patent Application No. 15783300.5 (21 pages).
Curriculum vitae of Professor John SantaLucia submitted Sep. 29, 2021 in the opposition proceedings of corresponding European Patent Application No. 15783300.5 (23 pages).
European Search Report and Search Opinion issued on divisional application (EPA 22187762.4) and Claims 1-15 of EPA 22187762.4 filed on Sep. 26, 2022.
Lodish et al,. "Glossary," 4th edition, Molecular Cell Biology, NCBI Bookshelf, 2000. New York W. H. Freeman, pp. 1-46.
Van Ness et al,. "Isothermal reactions for the amplification of oligonucleotides," Proceedings of the National Academy of Sciences, 2003, vol. 100, No. 8, 4504-4509.
Walker et al,. "Isothermal in vitro amplification of DNA by a restriction enzyme/DNA polymerase system," Proceedings of the National Academy of Sciences, 1992, vol. 89, pp. 392-396.
Walker et al., "Strand displacement amplification—an isothermal, in vitro DNA amplification technique" Nucleic Acids Research, 1992, vol. 2, No. 7, pp. 1691-1696.
Summons to attend oral proceedings dated Oct. 12, 2020, in the opposition proceedings of corresponding European Patent Application No. 13775206.9 (1 page).
Notice of Opposition dated Mar. 3, 2021 in corresponding European Patent Application No. 15783300.5 (36 pages).
Written submission from patentee dated Jul. 9, 2021, in preparation to/during oral proceedings in the opposition proceedings of corresponding European Patent Application No. 13775206.9 (2 pages).
Written submission from opponent dated Jul. 22, 2021, in preparation to/during oral proceedings in the opposition proceedings of corresponding European Patent Application No. 13775206.9 (13 pages).
Written submission from patentee dated Aug. 20, 2021, in preparation to/during oral proceedings in the opposition proceedings of corresponding European Patent Application No. 13775206.9 (4 pages).
Minutes of the oral proceedings taking place on Sep. 22, 2021, in the opposition proceedings of corresponding European Patent Application No. 13775206.9. Document dated Nov. 5, 2021 (2 pages).
Interlocutor decision and grounds for decision dated Nov. 8, 2021 in the opposition proceedings of corresponding European Patent Application No. 13775206.9 (13 pages).
Notice of Appeal dated Jan. 17, 2022, against decision in the opposition proceedings of corresponding European Patent Application No. 13775206.9 (2 pages).
Summons to attend postponed oral proceedings dated Oct. 10, 2022 in the opposition proceedings of corresponding European Patent Application No. 157833005 (1 page).
Summons to attend postponed oral proceedings dated Oct. 21, 2022 in the opposition proceedings of corresponding European Patent Application No. 157833005 (1 page).
Written submission from patentee dated Mar. 13, 2023 in preparation to/during oral proceedings in the opposition proceedings of corresponding European Patent Application No. 15783300.5 (2 pages).
Written submission from opponent dated Mar. 16, 2023 in preparation to/during oral proceedings in the opposition proceedings of corresponding European Patent Application No. 15783300.5 (23 pages).
Notice of Opposition dated Jul. 6, 2023 in corresponding European Patent Application No. 15852795.2 (13 pages).

(56) References Cited

OTHER PUBLICATIONS

Interlocutor decision and grounds for decision dated Aug. 31, 2023, in the opposition proceedings of corresponding European Patent Application No. 15783300.5 (17 pages).
Notice to Appeal dated Nov. 9, 2023, against decision in the opposition proceedings of corresponding European Patent Application No. 15783300.5 (2 pages).
Statement of Grounds of Appeal Dated Jan. 10, 2024, against decision in the opposition proceedings of corresponding European Patent Application No. 15783300.5 (47 pages).
Reply to Appeal dated May 16, 2024 against decision in the opposition proceedings of corresponding European Patent Application No. 15783300.5 (29 pages).
Reply to Notice of Opposition dated Jul. 20, 2020 in corresponding European Patent Application No. 13775206.9 (33 pages).
Reply to Notice of Opposition dated Sep. 29, 2021 in corresponding European Patent Application No.15783300.5 (15 pages).
Provisional and Non-binding opinion of the Opposition Division dated Oct. 10, 2022 in corresponding European Application No. 15783300.5 (8 pages).
Provisional and Non-binding opinion of the Opposition Division dated Oct. 12, 2022 in corresponding European Application No. 13775206.9 (8 pages).
Office Action received Apr. 25, 2025 in corresponding Canadian Application No. 2,965,137 (5 pages).

* cited by examiner

Candidate Assays

FIG. 2

Screened Assays

| | | | | |
|---|---|---|---|---|
| Top Beacon | Zeb.Probe.T | **gctac**ACGACTTTYGCTGAAG**gtagc** | | |
| | Zeb.Probe.B | **gctac**CTTCAGCRAAAGTCG**gtagc** | | |
| Assay 1 | Zeb.P1F7 | GACTCGATATCGAGTCCTTCCACWGTTATCTWXXYW | W | mA |
| Assay 2 | Zeb.P1F8 | GACTCGATATCGAGTCGCTTCCAXAGTTATCZWXXY | X | mC |
| | Zeb.P1F2 | GACTCGATATCGAGTCACAGTTAZCTACCGAYYWWX | Y | mG |
| | Zeb.P1R1 | GACTCGATATCGAGTCAAATGCAWCGACWXXZZ | Z | mT |
| Assay 1/2 | Zeb.P1R2 | GACTCGATATCGAGTCGAAATGCWACGAXWXXZ | | |
| | Zeb.P1R3 | GACTCGATATCGAGTCAGAAATGXAACGWXWXX | | |
| | | | | |
| | Zeb.P2F2 | GACTCGCGCGCGAGTCACAGTTAZCTACCGAYYWWX | | |
| | Zeb.P2F3 | GACTCGCGCGCGAGTCCACAGTTWTCTACCGWYYWW | | |
| | Zeb.P2F4 | GACTCGCGCGCGAGTCCCACAGTZATCTACCYWYYW | | |
| | Zeb.P2R1 | GACTCGCGCGCGAGTCAAATGCAWCGACWXXZZ | | |
| | Zeb.P2R2 | GACTCGCGCGCGAGTCGAAATGCWACGAXWXXZ | | |
| | Zeb.P2R3 | GACTCGCGCGCGAGTCAAATGXAACGWXWXX | | |

| | |
|---|---|
| Zeb.gBlock | CCACAGTTATCTACCGAGGAACGACTTTCGCTGAAGGTGTCG |

2.5K Copies gBlock in 18 ng Human cDNA
Assay 1

Reaction Set-Up:
5ul 2X MM
5ul sample

Equivalent to:
500 cp/ul
500,000 cp/ml

312 Copies gBlock in 18 ng Human cDNA
Assay 1

Reaction Set-Up:
5ul 2X MM
5ul sample

Equivalent to:
62.5 cp/ul
62,500 cp/ml

156 Copies gBlock in 18 ng Human cDNA
Assay 1

78 Copies gBlock in 18 ng Human cDNA
Assay 1

0 Copies gBlock in 18 ng Human cDNA
Assay 1

Reaction Set-Up:
5ul 2X MM
5ul sample

Equivalent to:
0 cp/ul
0 cp/ml

156 Copies gBlock in 18 ng Human cDNA
Assay 2

78 Copies gBlock in 18 ng Human cDNA
Assay 2

39 Copies gBlock in 18 ng Human cDNA
Assay 2

19.5 Copies gBlock in 18 ng Human cDNA
Assay 2

9.8 Copies gBlock in 18 ng Human cDNA
Assay 2

Reaction Set-Up:
5ul 2X MM
5ul sample

Equivalent to:
1.95 cp/ul
1,950 cp/ml

0 Copies gBlock in 18 ng Human cDNA
Assay 2

ZEB titration starting at $1x10^6$ copies per reaction (——), $1x10^4$ per reaction (——); $1x10^2$ per reaction (-····); and $1x10^0$ per reaction (——), synthetic RNA in a background of a 1ug human RNA. Target specific first strand RT (Maxima) in a homogeneous reaction B. One-Step RNAble® RPPH1 Detection with Purified Human RNA 20 ng human RNA utilizing a specific reverse transcription primer Reaction Set-Up:
5 ul 2x MM
5ul Sample

FIG. 12

Zaire Ebola One-Step RNAble® Reaction in a Crude Blood Prep #4

Fluorescence History

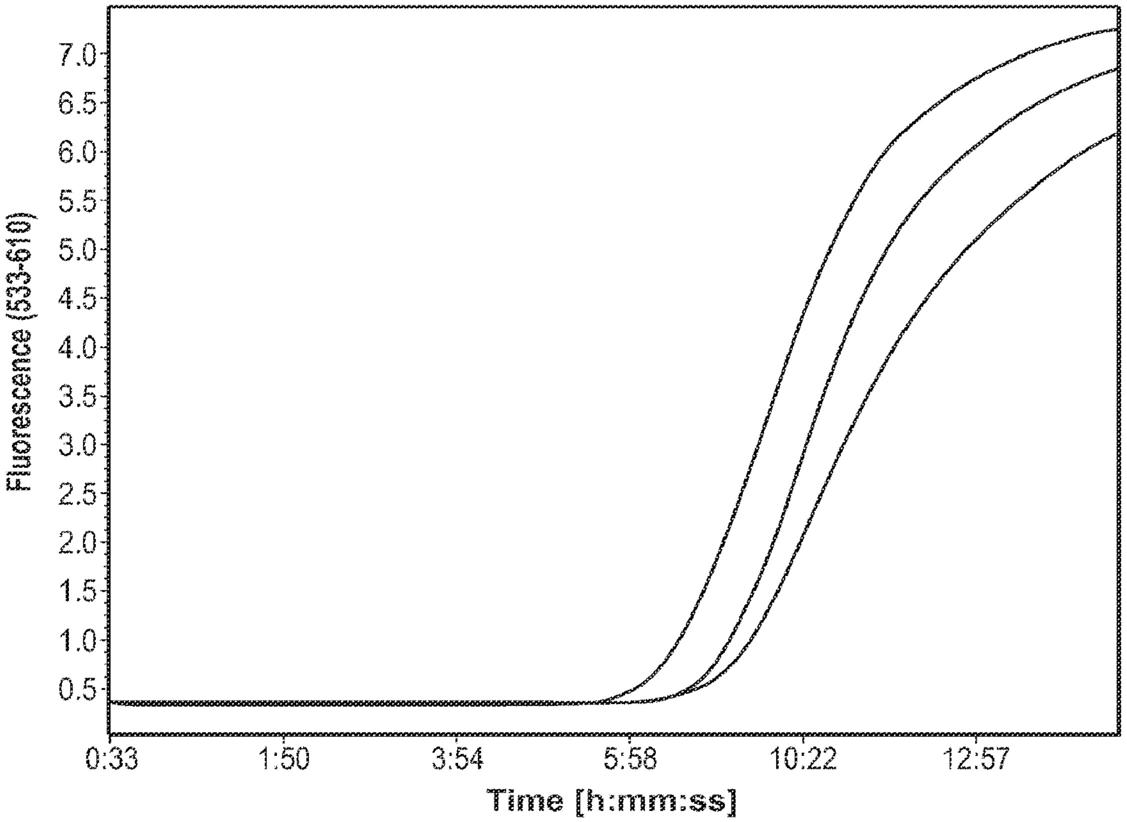

Crude Blood Prep Method #4

To 20μL whole blood, add:
20μL 0.5% SDS in $H_2O$.
Mix.
Incubate for 3 minutes at room temperature.
Add 20μL 2% BSA in $H_2O$.
Mix.
Incubate for 1 minute at room temperature.
Add 1uL of crude blood prep. to a 10uL reaction with 1000 copies synthetic RNA target. Rune reaction in triplicate at 56° C on LC480.

FIG. 13

One-Step RNAble®
Zaire Ebolavirus Mayinga vs. Sudan Ebolavirus Boniface Specificity Example

Fluorescence History

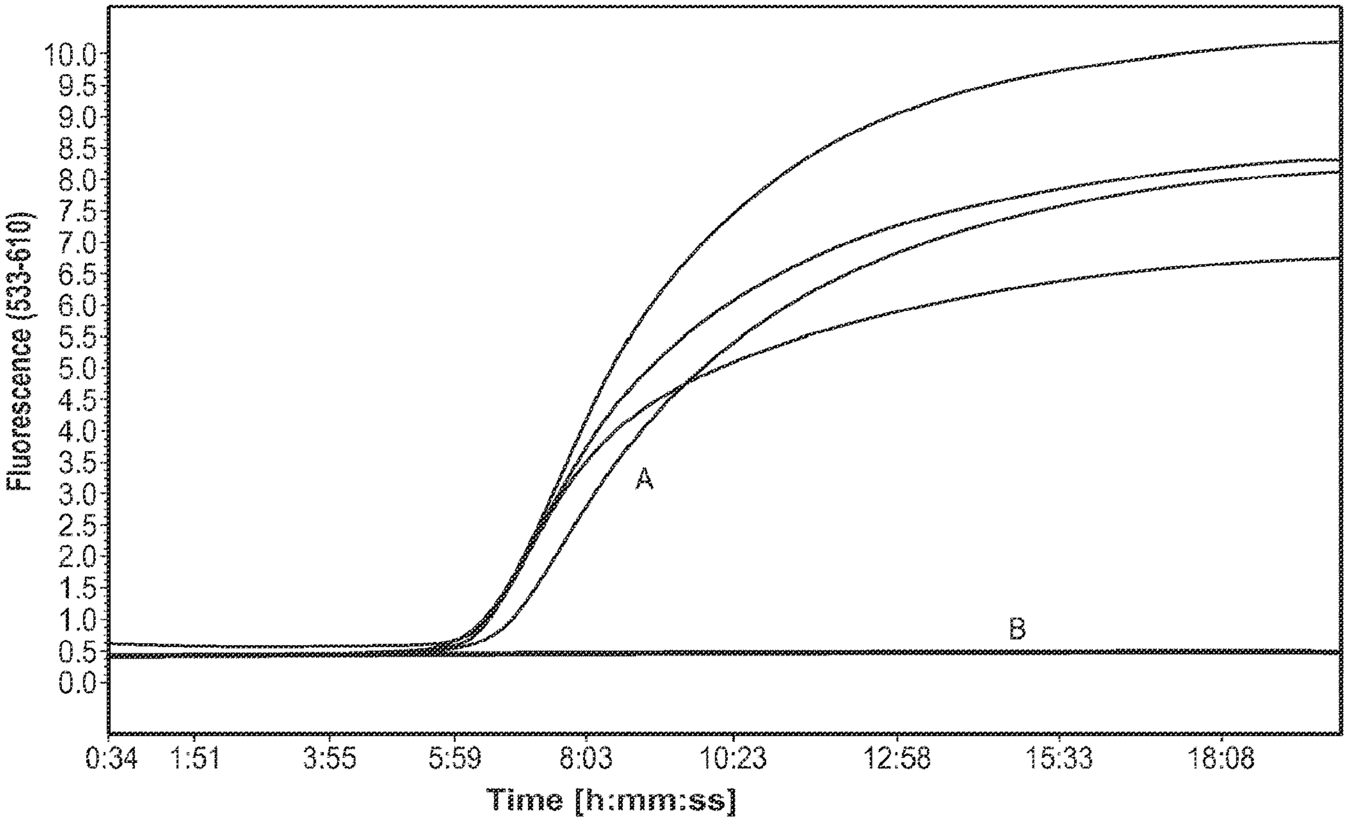

A = 693 copies Zaire Ebolavirus Mayinga

B = 650 copies Sudan Ebolavirus Boniface

Results - the Zaire Ebola assay does not detect Sudan Ebolavirus Boniface.

Reactions run with purified RNA from Vero E6 cells infected with one fo the two viruses shown. Quadruplicate 10uL reactions run on LC480.

Instrument Comparison Zaire Ebolavirus Mayinga
Roche LightCycler 480 II
Fluorescence History A) $1.0 \times 10^7$
B) $9 \times 10^5$
C) $8 \times 10^4$
D) 7513
E) 683
F) 62
G) 5.6
H) 0.5
I) NTC Quadruplicates Axxin Singles Amplifire Singles

FIG. 16A

HIV One-step RNAble
Candidate assay
gag protein target

F2/R1 Amplicon Map

Forward Probe T → Reverse External primer

5' TGACTAGCGGAGGCTAGAAGGAGAGAGATGGGTGCGAGAGCGTCAATATTAAGAGGCGAAAAATTAGATGC

5' TGACTAGCAGAGGCTAGAAGGAGAGAGATGGGTGCGAGAGCGTCAGTA

Spacer: ------------ 11bp

Amplicon: -------------------------------------------------- 40bp

*Note: bold bases indicate population sequence variations

Hgag(HIV gag target)

| Primer | Sequence |
| --- | --- |
| Hgag.F2a | GACTCGATATCGAGTCTGACTAGmCGGAGGmCmTmAmGmAmAmG |
| Hgag.F2b | GACTCGATATCGAGTCTGACTAGmCAGAGGmCmTmAmGmAmAmG |
| Hgag.R1a | GACTCGATATCGAGTCTATTGACmGCTCmTmCmGmCmAmC |
| Hgag.R1b | GACTCGATATCGAGTCTACTGACmGCTCmTmCmGmCmAmC |
| Hgag.rt3.subC* | GCATCTAATTTTTCGCC (ecternal) |
| Hgag.probe.T | cgcaagGGAGAGAGATGGGTGcttgcg |

Primers: mN indicates methoxy base
Probe sequence: lowercase = stems, uppercase = recognition

*External primer sequence is specific to HIV subtype C (for the purified RNA sample used)

HIV One-step RNAble
Candidate assay
gag protein target

| Copies | 1000 | 500 | 250 | 125 | NTC |
|---|---|---|---|---|---|
| | 30.23 | 33.94 | 36.48 | 48.45 | - |
| | 30.79 | 30.39 | 34.8 | 40.1 | - |
| | 30.85 | 30.22 | 37.88 | 53.18 | - |
| | 31.87 | 32.5 | 36.06 | 38.3 | - |
| | 30.37 | 32.91 | 34.75 | 38.23 | - |
| **Avg.** | **30.8** | **32.0** | **36.0** | **43.7** | **N/A** |
| **St. dev.** | **0.6** | **1.6** | **1.3** | **6.8** | **N/A** |

Cp values across 5 technical replicates (10uL reactions): Purified HIV RNA (subtype C) from SeraCare, quantified by COBAS TaqMan HIV-1 v2.0 test.

FIG. 17A

Dengue 4 One-step RNAble
Candidate assay
3' UTR target

Amplicon Map

Forward ←Probe B Reverse External primer

CAAAAACAGCATATTGACGCTGGGAAAGACCACAGATCCTGCTGTCTCTRCAAC*ATCAATCCAGGCACAGA*

CAAAAACAGCATATTGACGCTGGGAAAGACCACAGATCCTGCTGTCT

Spacer: ---------- 9bp

Amplicon: -------------------------------------------- 39bp

Den4 (Dengue type 4)

| Primer | Sequence |
|---|---|
| Den4.F2 | GACTCGATATCGAGTCCAAAAACmAGCATATTmGmAmCmGmC |
| Den4.R1a | GACTCGATATCGAGTCAGACAGCmAGGATCmTmCmTmGmG |
| Den4.R1b | GACTCGATATCGAGTCAGACAGCmAGGATCmTmGmTmGmG |
| Den4.extRT1 | TCTGTGCCTGGATTGAT (external primer) |
| Den4.probe.B | cgcatcTGGTCTTTCCCAGCgatgcg |

Primers: mN indicates methoxy base
Probe sequence: lowercase = stems, uppercase = recognition

Dengue 4 One-step RNAble
Candidate assay
3' UTR target
*Preliminary data

| | 20pg RNA | NTC |
|---|---|---|
| | 27.90 | - |
| | 32.19 | - |
| | 27.97 | - |
| | 34.00 | - |
| **Avg.** | **30.5** | **N/A** |
| **St. dev.** | **3.1** | **N/A** |

Cp values across 4 technical replicates (10uL reactions): Isolated total RNA from cell culture includes both viral and host cell RNA, total copy number is unknown.

FIG. 18A

Influenza B One-step RNAble
Candidate assay
Segment 7 target

Amplicon Map

Forward Probe T → Reverse External primer

AAATGCAGATGGTCTCAGCTATGAACACAGCAAAAACAATGAATGGAATGGGAAAA*GGAGAAGACGTCCAAAA*
AAATGCAAATGGTCTCAGCTATGAACACAGCAAACACAATGAATGGAATGGGAAAC*GGAGAAGACGTTCAAAA*
AAATGCAGATGGTTTCAGCTATGAACACAGCAAAACCAATGAATGGAATGGCAAAGGAG

Spacer: -------------- 13bp

Amplicon: ---------------------------------------------- 48bp

FluB (influenza B)

| Primer | Sequence |
|---|---|
| FluB.F2a | GACTCGATATCGAGTCAAATGCAmGATGGTCTCmAmGmCmTmA |
| FluB..F2b | GACTCGATATCGAGTCAAATGCAmAATGGTCTCmAmGmCmTmA |
| FluB..F2c | GACTCGATATCGAGTCAAATGCAmGATGGTTTCmAmGmCmTmA |
| FluB..R3a | GACTCGATATCGAGTCCTCCTTTmTCCCATTCCATmTmCmAmTmT |
| FluB..R3b | GACTCGATATCGAGTCCTCCCTTmTCCCATTCCATmTmCmAmTmT |
| FluB..R3c | GACTCGATATCGAGTCCTCCTTTmCCCCATTCCATmTmCmAmTmT |
| **FluB.extRT1a** | **TTTTGGACGTCTTCTCC** |
| **FluB.extRT1b** | **TTTTGAACGTCTTCTCC** |
| **FluB.probe.T** | gccaaGCTATGAACACAGCAAActtggc |

Influenza B One-step RNAble
Candidate assay
Segment 7 target
*Preliminary data

| | Sample 1 (----) | Sample 2 (——) |
|---|---|---|
| | 39.89 | 42.05 |
| | 40.83 | 41.72 |
| | 41.29 | 43.92 |
| | 42.75 | 42.77 |
| Avg. | 41.2 | 42.6 |
| St. dev. | 1.2 | 1.0 |

Cp values across 4 technical replicates (10ul reactions): Isolated total RNA from cell culture includes both viral and host cell RNA, total copy number is unknown. Samples 1 and 2 are different viral isolates.

FIG. 19A

BVDV1 One-step RNAble
Candidate assay
Polyprotein gene target

Amplicon Map

| | Forward | Probe T → | Reverse | External primer |
|---|---|---|---|---|
| F1a | **GGCCCACTGTATTGCTACTGAAA** | ATCTCTGCTGTACATG | **GCACATGGAGTTGATCA** | *CAAATGAACTTTTATACAAAACATA* |
| F1b | **GGCCCACTGCACTGCTACTAAAA** | ATCTCTGCTGTACATG | GCACATGGAGTTGATCACA | |

Spacer: --------------- 15bp

Amplicon: -------------------------------------------------- 50bp

BVDV1

| Primer | Sequence |
|---|---|
| BVDV1.F1a | GACTCGATATCGAGTCGGCCCACmTGTATTGCTmAmCmTmGmAmAmA |
| BVDV1.F1b | GACTCGATATCGAGTCGGCCCACmTGCACTGCTmAmCmTmAmAmAmA |
| BVDV1.R1 | GACTCGATATCGAGTCTGTGATCmAACTCCmAmTmGmCmC |
| BVDV1.RT1v | TATGTTTTGTATAAAAGTTCATTTG |
| BVDV1.ProbeT | cgctacATCTCTGCTGTACATGgtagcg |

BVDV1 One-step RNAble
Candidate assay
Polyprotein gene target

COMPOSITIONS AND METHODS FOR DETECTING AN RNA VIRUS

CROSS REFERENCE TO RELATED APPLICATIONS

This application is a continuation of U.S. patent application Ser. No. 15/520,328, filed on Apr. 19, 2017, now U.S. Pat. No. 10,793,922; which is the U.S. national phase application, pursuant to 35 U.S.C. § 371, of PCT International Application Serial No.: PCT/US2015/056491, filed Oct. 20, 2015, designating the United States and published in English, which claims priority to and the benefit of U.S. Provisional Patent Application Serial Nos. 62/066,277, filed Oct. 20, 2014, and 62/104,008, filed Jan. 15, 2015. The entire contents of each of these applications are hereby incorporated by reference herein.

SEQUENCE LISTING

This application contains a Sequence Listing which has been submitted electronically in ASCII format and is hereby incorporated by reference in its entirety. Said ASCII copy, created on Aug. 7, 2020, is named 167665_010403.txt and is 48,985 bytes in size.

BACKGROUND OF THE INVENTION

The Ebola virus causes hemorrhagic fever with mortality rates reaching 50% to 90% of infected humans. Ebola virus (EBOV) includes four species, Zaire EBOV, Sudan EBOV, Ivory Coast EBOV, and Reston EBOV. Human infection with Ebola typically results from contact with contaminated blood, tissues, and/or excretions of animals or patients with an Ebola infection. Patients typically exhibit symptoms 4 to 10 days after Ebola infection. This long incubation period provides an opportunity for the virus to be carried to new areas before the carrier displays any signs of illness. Symptoms of Ebola include fever, chills, malaise, and myalgia. Because such symptoms are displayed in a variety of illnesses, there is a significant risk that Ebola infection may be misdiagnosed in the early stages, thereby facilitating spread of the disease. In later stages, Ebola-infected subjects typically develop vomiting, diarrhea, coughing, vascular symptoms, headache, confusion, coma, mucosal hemorrhages, bloody diarrhea and ultimately multiorgan failure, resulting in death. The bodily fluids of Ebola patients are highly infectious as are the dead bodies of Ebola patients.

Public health concerns about Ebola infection are mounting as Ebola infections in West Africa in late 2014 are predicted to rise to 10,000 people per week. Because of their exposure to the bodily fluids of Ebola patients, health care workers are at risk for catching Ebola from infected patients. The risk of infection increases as the extent and the frequency of contact increased. In a 1976 Sudan Ebola outbreak 81% of healthcare workers nursing Ebola patients were infected with the virus. In order for medical staff and health care workers to avoid unnecessary infections, early detection of Ebola is critical so that appropriate infection control measures are instituted and the risk of transmission is minimized.

To stop the spread of Ebola within West Africa and internationally, rapid diagnosis is essential so that infected subjects may be immediately quarantined and proper protective equipment used by health care workers caring for these subjects. High titers of infectious filovirus are present in the blood and tissues during early stages of illness. Currently, Ebola is identified by virus isolation, reverse transcription-PCR (RT-PCR), including real-time quantitative RT-PCR, antigen-capture enzyme-linked immunosorbent assay (ELISA), antigen detection by immunostaining, and IgG- and IgM-ELISA using authentic virus antigens. Unfortunately, these tests are time-consuming because they can only be carried out on purified and isolated RNA and require access to laboratory equipment and trained technicians that are scarce in many areas where Ebola is endemic.

Accordingly, improved methods for rapidly identifying patients infected with Ebola virus are urgently required.

SUMMARY OF THE INVENTION

The present invention provides methods for rapidly identifying an Ebola infection using an isothermal nucleic acid amplification reaction that can be carried out on extracted RNA in the context of a crude biological sample.

In one aspect, the invention provides a method of detecting a specific target polynucleotide (e.g., RNA) in an isothermal amplification reaction coupled with reverse transcription, the method involving (a) contacting a target polynucleotide molecule in a sample with a primer in the presence of a reverse transcriptase and dNTPs under conditions permissive for cDNA synthesis, thereby generating a cDNA;

(b) contacting the cDNA with forward and reverse primers each carrying at least one nicking enzyme recognition sequence within their respective 5'-terminal regions which specifically bind the cDNA with their respective 3'-terminal regions in the presence of a nicking enzyme, dNTPs, a detectable oligonucleotide probe, and a strand-displacement polymerase under conditions permissive for the isothermal amplification of the cDNA; and (c) detecting a signal specific for detectable oligonucleotide probe hybridization to the amplicon, where detection of the signal indicates the presence or quantity of the target polynucleotide present in the sample and failure to detect the signal indicates the absence of target polyribonucleotide in the sample.

In another aspect, the invention provides a method of detecting an RNA virus in a sample, the method involving (a) contacting an RNA virus polynucleotide molecule in a biological sample with a primer in the presence of a reverse transcriptase and dNTPs under conditions permissive for cDNA synthesis, thereby generating a cDNA;

(b) contacting the cDNA with forward and reverse primers each carrying at least one nicking enzyme recognition sequence within their respective 5'-terminal regions which specifically bind the cDNA with their respective 3'-terminal regions in the presence of a nicking enzyme, dNTPs, a detectable oligonucleotide probe, and a strand-displacement polymerase under conditions permissive for the isothermal amplification of the cDNA; and (c) detecting a signal specific for detectable oligonucleotide probe hybridization to the amplicon, where detection of the signal indicates the presence or quantity of the RNA virus polynucleotide molecule present in the sample and failure to detect the amplicon indicates the absence of an RNA virus.

In a related aspect, the invention provides a method of detecting an Ebola virus in a sample, the method involving (a) contacting an Ebola polynucleotide molecule in a biological sample with a primer in the presence of a reverse transcriptase and dNTPs under conditions permissive for cDNA synthesis, thereby generating a cDNA;

(b) contacting the cDNA with forward and reverse primers each carrying at least one nicking enzyme recognition sequence within their respective 5'-terminal regions which specifically bind the cDNA with their respective 3'-terminal regions in the presence of a nicking enzyme, dNTPs, a detectable oligonucleotide probe, and a strand-displacement polymerase under conditions permissive for the isothermal amplification of the cDNA; and (c) detecting a signal specific for detectable oligonucleotide probe hybridization to the amplicon, where detection of the signal indicates the presence or quantity of the Ebola polynucleotide present in the sample and failure to detect the signal indicates the absence of Ebola polynucleotide present in the sample.

In various embodiments of the above aspects or any other aspect of the invention delineated herein, the Ebola polynucleotide is obtained by contacting a biological sample with an agent capable of extracting an RNA molecule present in the sample and an agent capable of stabilizing an RNA molecule against degradation.

In yet another aspect, the invention provides a method of detecting an Ebola virus in a sample, the method involving (a) contacting a biological sample with an agent capable of extracting a polynucleotide molecule present in the sample and an agent capable of stabilizing a polynucleotide molecule against degradation;

(b) contacting the extracted and stabilized Ebola RNA with a primer in the presence of a reverse transcriptase and dNTPs under conditions permissive for cDNA synthesis, thereby generating an Ebola cDNA;

(c) contacting the Ebola cDNA with forward and reverse primers each carrying at least one nicking enzyme recognition sequence within their respective 5'-terminal regions which specifically bind the Ebola cDNA with their respective 3'-terminal regions in the presence of a nicking enzyme, dNTPs, and a strand-displacement polymerase under conditions permissive for the isothermal amplification of the cDNA, thereby generating amplicons; and (d) detecting the amplicons, where the presence of an Ebola amplicon detects an Ebola polynucleotide in the sample and failure to detect the amplicon indicates the absence of an Ebola polynucleotide in the sample.

In yet another aspect, the invention provides a kit for detecting an RNA virus polynucleotide molecule involving primers that specifically bind an RNA viral sequence, a detectable probe that specifically binds a viral (e.g., Ebola) amplicon, a reverse transcriptase enzyme, a nicking enzyme, and a strand-displacement polymerase. In one embodiment, the primers contain the following sequences:

Forward primer:
(SEQ ID NO: 1)
GACTCGATATCGAGTCGCTTCCA[MeOC]AGTTATC[MeOU][MeOA][MeOC][MeOC][MeOG]

Reverse Primer:
(SEQ ID NO: 2)
GACTCGATATCGAGTCGAAATGC[MeOA]ACGA[MeOC][MeOA][MeOC][MeOC][MeOU];

and the probe contains the following sequence: gctacACGACTTTYGCTGAAGgtagc (SEQ ID NO: 3).

In another embodiment, the probe has a fluorescent dye at the 5' end, and a quencher at the 3' end or vice versa. In one embodiment, the probe is (SEQ ID NO: 4)
5'-CALRed$_{610\ nm}$-gctacACGACTTTYGCTGAAGgtagc BHQ2-3'
or (SEQ ID NO: 5)
5'-FAM or FITC-gctacACGACTTTYGCTGAAGgtagc-BHQ1-3'.

In one embodiment, the 3' quencher is replaced by DABsyl.

In another aspect, the invention provides a kit for amplifying an Ebola polynucleotide molecule in a reverse transcriptase nicking amplification reaction, the kit containing the following primers:

Forward primer:
(SEQ ID NO: 1)
GACTCGATATCGAGTCGCTTCCA[MeOC]AGTTATC[MeOU][MeOA][MeOC][MeOC][MeOG]

Reverse Primer:
(SEQ ID NO: 2)
GACTCGATATCGAGTCGAAATGC[MeOA]ACGA[MeOC][MeOA][MeOC][MeOC][MeOU];

the following probe:

(SEQ ID NO: 3)
gctacACGACTTTYGCTGAAGgtagc;

a reverse transcriptase enzyme, a nicking enzyme, a strand-displacement polymerase, and directions for use of the aforementioned primers, probes and enzymes for detecting an Ebola polynucleotide molecule.

In one embodiment, the kit further contains a capillary tube that may or may not contain lyophilized lysis or RNA stabilization reagents for viral polynucleotide extraction. In another embodiment, the kit further contains one or more vessels containing a buffer suitable for carrying out a reverse transcriptase and/or amplification reaction. In another embodiment, the kit further contains vessels containing the reverse transcriptase enzyme, nicking enzyme, and strand-displacement polymerase in lyophilized form.

In yet another aspect, the invention provides a method of diagnosing a human or animal subject with an RNA virus, the method involving (a) contacting a sample of the subject with an agent capable of extracting an RNA virus present in the sample and an agent capable of stabilizing the extracted polynucleotide molecule against degradation;

(b) contacting the polynucleotide molecule with a reverse transcriptase primer in the presence of a reverse transcriptase and dNTPs under conditions permissive for cDNA synthesis, thereby generating a cDNA copy of the polynucleotide molecule;

(c) contacting the cDNA with forward and reverse primers carrying at least one nicking enzyme recognition sequence within their respective 5'-terminal regions which specifically bind the cDNA with their respective 3'-terminal regions in the presence of a nicking enzyme, dNTPs, and a strand-displacement polymerase under conditions permissive for the isothermal amplification of the cDNA, thereby generating amplicons; and (d) detecting the amplicons, where the presence of an RNA viral amplicon diagnoses an RNA viral infection in the subject and failure to detect the amplicon diagnoses the absence of an RNA viral infection in the subject.

In various embodiments of any aspect delineated herein, no detectable signal is present in a control assay lacking a target polynucleotide at seven minutes, ten minutes, and/or fifteen minutes following initiation of the assay. In other embodiments of any aspect delineated herein, the primer used in step (a) has the same sequence or a different sequence than a primer used in step (b). In other embodiments of any of the above, steps (a)-(c) are carried out in a single reaction. In still other embodiments of the above aspects, the reverse transcriptase enzyme and the strand-displacement DNA polymerase are the same or different enzymes. In still other embodiments, the cDNA of step (a) is generated in a first reaction vessel, then transferred to a second reaction vessel where step (b) is carried out. In still other embodiments of any aspect delineated herein, the polynucleotide molecule is an Ebola polynucleotide. In still other embodiments of any aspect delineated herein, the sample is a bodily fluid (e.g., saliva, sweat, tears, fluids accumulating in a bodily cavity, urine, ejaculate, vaginal secretion, cerebrospinal fluid, lymph, feces, sputum, decomposition fluid, vomit, sweat, breast milk, blood, serum, and plasma). In still other embodiments of any aspect delineated herein, the bodily cavity is peritoneal cavity or pericardial cavity. In still other embodiments of any aspect delineated herein, the limit of detection is 10 or 20 copies per reaction. In still other embodiments of any aspect delineated herein, the method is carried out in about 5, 7, 10, 15, 20, 25 or thirty minutes. In still other embodiments of any aspect delineated herein, steps a-d are carried out in the context of the biological sample. In still other embodiments of any aspect delineated herein, Ebola or other viral RNA is not purified or isolated away from the biological sample (e.g, crude). In still other embodiments of any aspect delineated herein, the method is carried out at a point of care or diagnosis in a portable battery powered device. In still other embodiments of any aspect delineated herein, no separate reverse transcriptase primer is required, but the forward and/or reverse primers are used. In still other embodiments of any aspect delineated herein, the sample is a biological sample or an environmental sample. In still other embodiments of any aspect delineated herein, the biological sample is obtained from a subject, bat, bush meat, or a domestic animal. In still other embodiments of any aspect delineated herein, the biological sample is a swab of a mucosal membrane that is any one or more of buccal, nasal, eye, rectal, and vaginal or skin. In still other embodiments of any aspect delineated herein, the biological sample is a tissue sample obtained from a subject, necropsy, or culture media. In still other embodiments of any aspect delineated herein, the necropsy is of a human, primate, bat, or other mammal. In still other embodiments of any aspect delineated herein, the environmental sample is a material that may be contaminated with a biological fluid of a subject having or having a propensity to develop an Ebola viral infection. In still other embodiments of any aspect delineated herein, the environmental sample is bedding, a seat cushion, a rug, an air condition filter or other material. In still other embodiments of any aspect delineated herein, the polymerase are 5'-exo-derivatives of Bst DNA polymerase I, Gst DNA polymerase I, Gka DNA polymerase I, Gca DNA polymerase I, Gan DNA polymerase I, Gbo DNA polymerase I, Gsp70 DNA polymerase I, GspT3 DNA polymerase I, Gsp52 DNA polymerase I and/or fragments thereof. In still other embodiments of any aspect delineated herein, the nicking enzyme is one or more of Nt.BstNBI, Nt.BspD6I, Nt.BspQI, Nt.BsmAI, Nt.AlwI, N.Bst9I, or N.BstSEI. In still other embodiments of any aspect delineated herein, the reverse transcriptase is M-MLV RT, AMV RT, RSV RT, and/or mutants/derivates thereof. In still other embodiments of any aspect delineated herein, the detectable probe contains a molecular beacon. In various embodiments of any aspect delineated herein, an amplification primer (e.g., forward and/or reverse primer) comprises one or more 2' modified nucleotides (e.g., 2'-O-methyl ribonucleotides) in the 3' terminal region or recognition region. In particular embodiments, the amplification primer comprises one or more 2'-O-methyl modified nucleotides at the 3' end, including for example 2'-O-methyl, 2'-methoxyethoxy, 2'-fluoro, 2'-hydroxyl, 2'-alkyl, 2'-allyl, 2'-O-[2-(methylamino)-2-oxoethyl], 4'-thio, 4'-$CH_2$—O-2'-bridge, 4'-$(CH_2)_2$—O-2'-bridge, 2'-LNA, and 2'-O—(N-methylcarbamate).

In still other embodiments of any aspect delineated herein, the forward and reverse primers for detection of Ebola virus contain the following sequences, respectively:

```
Forward primer:
                                        (SEQ ID NO: 1)
GACTCGATATCGAGTCGCTTCCA[MeOC]AGTTATC[MeOU][MeOA]
[MeOC][MeOC][MeOG]

Reverse Primer:
                                        (SEQ ID NO: 2)
GACTCGATATCGAGTCGAAATGC[MeOA]ACGA[MeOC][MeOA][MeOC]
[MeOC[MeOU]
```

In still other embodiments of any aspect delineated herein, amplification is detected using a probe having the following sequence: gctacACGACTTTYGCTGAAGgtagc (SEQ ID NO: 3). In still other embodiments of any aspect delineated herein, the probe has a fluorescent dye at 5' end, and a quencher at 3' end or vice versa. In still other embodiments of any aspect delineated herein, the probe is (SEQ ID NO: 4)
5'-CALRed$_{610\ nm}$-gctacACGACTTTYGCTGAAGgtagc BHQ2-3'
or (SEQ ID NO: 5)
5'-FAM or FITC-gctacACGACTTTYGCTGAAGgtagc-BHQ1-3"

In still other embodiments of any aspect delineated herein, the 3' quencher is replaced by DABsyl.

In still other embodiments of any aspect delineated herein, the forward and reverse primers for detection of HIV virus contain one or more of the following sequences, respectively:

```
Forward primer:
                                        (SEQ ID NO: 6)
GACTCGATATCGAGTCTGACTAGmCGGAGGmCmTmAmGmAmAmG,

                                        (SEQ ID NO: 7)
GACTCGATATCGAGTCTGACTAGmCAGAGGmCmTmAmGmAmAmG;
and

Reverse Primer:
                                        (SEQ ID NO: 8)
GACTCGATATCGAGTCTATTGACmGCTCmTmCmGmCmAmC,

                                        (SEQ ID NO: 9)
GACTCGATATCGAGTCTACTGACmGCTCmTmCmGmCmAmC.
```

In still other embodiments of any aspect delineated herein, amplification is detected using a probe having the following sequence: cgcaagGGAGAGAGATGGGTGcttgcg (SEQ ID NO: 10).

In still other embodiments of any aspect delineated herein, the forward and reverse primers for detection of Dengue virus contain one or more of the following sequences, respectively:

Forward primer:

(SEQ ID NO: 11)
GACTCGATATCGAGTCCAAAAACmAGCATATTmGmAmCmGmC;
and

Reverse Primer:

(SEQ ID NO: 12)
GACTCGATATCGAGTCAGACAGCmAGGATCmTmCmTmGmG, (SEQ ID NO: 13)
GACTCGATATCGAGTCAGACAGCmAGGATCmTmGmTmGmG.

In still other embodiments of any aspect delineated herein, amplification is detected using a probe having the following sequence: cgcatcTGGTCTTTCCCAGCgatgcg (SEQ ID NO: 14).

In still other embodiments of any aspect delineated herein, the forward and reverse primers for detection of influenza B virus contain one or more of the following sequences, respectively:

Forward primer:

(SEQ ID NO: 15)
GACTCGATATCGAGTCAAATGCAmGATGGTCTCmAmGmCmTmA, (SEQ ID NO: 16)
GACTCGATATCGAGTCAAATGCAmAATGGTCTCmAmGmCmTmA, (SEQ ID NO: 17)
GACTCGATATCGAGTCAAATGCAmGATGGTTTCmAmGmCmTmA;
and Reverse Primer:

(SEQ ID NO: 18)
GACTCGATATCGAGTCCTCCTTTmTCCCATTCCATmTmCmAmTmT, (SEQ ID NO: 19)
GACTCGATATCGAGTCCTCCCTTmTCCCATTCCATmTmCmAmTmT, (SEQ ID NO: 20)
GACTCGATATCGAGTCCTCCTTTmCCCCATTCCATmTmCmAmTmT.

In still other embodiments of any aspect delineated herein, amplification is detected using a probe having the following sequence: gccaaGCTATGAACACAGCAAActtggc (SEQ ID NO: 21).

In still other embodiments of any aspect delineated herein, the forward and reverse primers for detection of BVDV1 virus contain one or more of the following sequences, respectively:

Forward primer:

(SEQ ID NO: 22)
GACTCGATATCGAGTCGGCCCACmTGTATTGCTmAmCmTmGmAmAmA, (SEQ ID NO: 23)
GACTCGATATCGAGTCGGCCCACmTGCACTGCTmAmCmTmAmAmAmA;
and Reverse Primer:

(SEQ ID NO: 24)
GACTCGATATCGAGTCTGTGATCmAACTCCmAmTmGmTmGmCmC.

In still other embodiments of any aspect delineated herein, amplification is detected using a probe having the following sequence: cgctacATCTCTGCTGTACATGgtagcg (SEQ ID NO: 25). In still other embodiments of any aspect delineated herein, the probe has a fluorescent dye at the 5' end and a quencher at the 3' end, or a fluorescent dye at the 3' end and a quencher at the 5' end. In particular embodiments, the fluorescent dye is $CALRed_{610nm}$, and the quencher is BHQ2 or DABsyl. In certain embodiments, the fluorescent dye is FAM or FITC and the quencher is BHQ1 or DABsyl.

In still other embodiments of any aspect delineated herein, the RNA virus is an Ebola virus, human immunodeficiency virus (HIV), Dengue virus, influenza virus (e.g., influenza B), Bovine Viral Diarrhea virus (e.g., BVDV Genotype 1), Yellow Fever virus, West Nile virus, Hepatitis C, Lassa virus, Flavivirus, Arenavirus, or single-stranded RNA virus. In still other embodiments of any aspect delineated herein, the agent capable of extracting the virus is one of or a combination of sodium dodecyl sulfate, sodium lauryl sulfate, Guanidinium thiocyanate, and/or guanidine hydrochloride. In various embodiments, the Guanidinium thiocyanate or other agent capable of extracting the virus is used at a concentration of about 0.1, 0.5, 1.0, 2.5, 5.0, 7.5, 10, 15, 20, 25, 50, 100, 250, 500 mM or more. In still other embodiments of any aspect delineated herein, the method is used for daily screening of health care workers. In still other embodiments of any aspect delineated herein, the samples are pooled and the screening is carried out on a human or animal population.

Definitions

By "Ebola virus (EBOV)" is meant a Filoviridae virus having at least about 85% amino acid sequence identity to an Ebola virus. Exemplary Ebola viruses include, but are not limited to, Ebola-Zaire virus, Ebola-Sudan virus, Ebola-Ivory Coast virus, and Ebola-Bundibugyo, which cause disease in humans, or Ebola-Reston virus, which affects non-human primates.

The sequence of an exemplary Ebola Zaire genome is provided at NCBI Accession No. KC242800.1 (SEQ ID NO: 26), which is reproduced below:

```
  1 cggacacaca aaaagaaaga agaattttta ggatcttttg tgtgcgaata actatgagga
 61 agattaataa ttttcctctc attgaaattt atatcggaat ttaaattgaa attgttactg
121 taatcacacc tggtttgttt cagagccaca tcacaaagat agagaacagc ctaggtctcc
181 gaagggaaca agggcaccag tgtgctcagt tgaaaatccc ttgtcaacat ctaggtctta
241 tcacatcaca agttccacct cagactctgc agggtgatcc aacaacccta atagaaaaat
301 tattgttaac ggacagcatt agttcacagt caaacaagca agattgagaa ttaaccttga
361 ttttgaactt caacacctag aggattggag attcaacaac cctaaaactt ggggtaaaac
421 attggaaata gttgaaagac aaattgctcg gaatcacaaa attccgagta tggattctcg
```

-continued 481 tcctcagaaa gtctggatga cgccgagtct tactgaatct gacatggatt accacaagat 541 cttgacagca ggtctgtccg ttcaacaggg gattgttcgg caaagagtca tcccagtgta 601 tcaagtaaac aatcttgagg aaatttgcca acttatcata caggcctttg aagcaggtgt 661 tgattttcaa gagagtgcgg acagtttcct tctcatgctt tgtcttcatc atgcgtacca 721 aggagatcac aaacttttct tggaaagtgg tgcagtcaag tatttggaag ggcacgggtt 781 ccgttttgaa gtcaagaaac gtgatggggt gaagcgcctt gaggaattgc tgccagcagt 841 atctagtgga aaaaacatta agagaacact tgctgccatg ccggaagagg agacgactga 901 agctaatgcc ggtcagtttc tctcttttgc aagtctattc cttccgaaat tggtagtagg 961 agaaaaggct tgccttgaga aagttcaaag gcaaattcaa gtacatgcag agcaaggact 1021 gatacaatat ccaacagctt ggcaatcagt aggacacatg atggtgattt tccgtttgat 1081 gcgaacaaat tttttgatca aatttctcct aatacaccaa gggatgcaca tggttgccgg 1141 gcatgatgcc aacgatgctg tgatttcaaa ttcagtggct caagctcgtt tttcaggttt 1201 attgattgtc aaaacagtcc ttgatcatat cctacaaaag acagaacgag gagttcgtct 1261 ccatcctctt gcaaggactg ccaaggtaaa aaatgaggtg aactccttta aggctgcact 1321 cagctccctg gccaagcatg gagagtatgc tcctttcgcc cgacttttga acctttctgg 1381 agtaaataat cttgagcatg gtcttttccc tcaactatcg gcaattgcac tcggagtcgc 1441 cacagcacac gggagcaccc tcgcaggagt aaatgttgga gaacagtatc aacagctcag 1501 agaggctgcc actgaagctg agaagcaact ccaacaatat gcagaatctc gcgaacttga 1561 ccatcttgga cttgatgatc aggaaaagaa aattcttatg aacttccatc agaaaaagaa 1621 cgaaatcagc ttccagcaaa caaacgctat ggtaactcta agaaaagagc gcctggccaa 1681 gctgacagaa gctatcactg ctgcatcact gcccaaaaca agtggacctt acgatgatga 1741 tgacgacatt ccctttccag gacccatcaa tgatgacgac aatcctggcc atcaagatga 1801 tgatccgact gactcacagg atacgaccat tcccgatgtg gtggttgatc ccgatgatgg 1861 aagctacggc gaataccaga gttactcgga aaacggcatg aatgcaccag atgacttggt 1921 cctattcgat ctagacgagg acgacgagga cactaagcca gtgcctaaca gattgaccaa 1981 gggtggacaa cagaaaaaca gtcaaaaggg ccagcataca gagggcagac agacacaatc 2041 caggccaact caaaatgtcc caggccctcg cagaacaatc caccacgcca gtgctccact 2101 cacggacaac gacagaggaa atgaaccctc cggctcaacc agccctcgca tgctgacacc 2161 aattaacgaa gaggcagacc cactggacga tgccgacgac gagacgtcta gtcttccgcc 2221 cttggagtca gacgatgaag aacaggacag ggacgaaact tccaaccgca cacccactgt 2281 cgccccaccg gctcccgtat acagagatca ctctgaaaag aaagaactcc cgcaagatga 2341 gcagcaagat caggaccaca ctcaagaggc caggaaccag gacagtgaca acacccagcc 2401 agaacactct tttgaggaga tgtatcgcca cattctaaga tcacagggac catttgatgc 2461 tgttttgtat tatcatatga tgaaggatga gcctgtagtt ttcagtacta gtgatggcaa 2521 agagtacacg tatccggact cccttgaaga ggaatatcca ccatggctca ctgaaaaaga 2581 ggccatgaat gaagagaata gatttgttac attggatggt caacaatttt attggccggt 2641 aatgaatcac aagaataaat tcatggcaat cctgcaacat catcagtgaa tgagaatgga 2701 ataatgggat gatttaaccg acaaatagct aacattaaat agtcaagaaa cgcaaacagg 2761 aagaattttt gatgtctaag gtgtgaatta ttatcacaat aaaagtgatt cttatttttg 2821 aatttaaagc tagcttatta ttactagccg tttttcaaag ttcaatttga gtcttaatgc -continued

```
2881 aaataggcgt taagccacag ttatagccat aattgtaact caatatctta gctagcgatt
2941 tatctaaatt aaattacatt atgcttttat aacttaccta ctagcctgcc caacatttac
3001 acgatcgttt tataattaag aaaaaactaa tgatgaagat taaaaccttc atcatcctta
3061 cgtcaattga attctctagc actcgaagct tattgtcttc aatgtaaaag aaaagctggt
3121 ccaacaagat gacaactaga acaaagggca ggggccatac tgtggccacg actcaaaacg
3181 acagaatgcc aggccctgag ctttcgggct ggatctccga gcagctaatg accggaagaa
3241 ttcctgtaag cgacatcttc tgtgatattg agaacaatcc aggattatgt tacgcatccc
3301 aaatgcaaca aacaaagcca aacccgaaga tgcgcaacag tcaaacccaa acggacccaa
3361 tttgcaatca tagttttgag gaggtagtac aaacattggc ttcattggct actgttgtgc
3421 aacaacaaac tatcgcatca gaatcattag aacaacgtat tacgagtctt gagaatggtc
3481 taaagccagt ttatgatatg gcaaaaacaa tctcctcatt gaacagggtt tgtgctgaga
3541 tggttgcaaa atatgatctt ctggtgatga caaccggtcg ggcaacagca accactgcgg
3601 caactgaggc ttattgggct gaacatggtc aaccaccacc tggaccatca ctttatgaag
3661 aaagtgcaat tcggggtaag attgaatcta gagatgagac cgtccctcaa agtgttaggg
3721 aggcattcaa caatctagac agtaccactt cactaactga ggaaaatttt gggaaacctg
3781 acatttcagc aaaggatttg agaaacatta tgtatgatca cttgcctggt tttggaactg
3841 ctttccacca attagtacaa gtgatttgta aattgggaaa agatagcaac tcattggata
3901 tcattcatgc tgagttccag gccagcctgg ctgaaggaga ctctcctcaa tgtgccctaa
3961 ttcaaattac aaaaagagtt ccaatcttcc aagatgctgc tccacctgtc atccacatcc
4021 gctctcgagg tgacattccc cgagcttgcc agaaaagctt gcgtccagtc ccgccatcac
4081 ccaagattga tcgaggttgg gtatgtgttt tccagcttca agatggtaaa acacttggac
4141 tcaaaatttg agccaatctc ccttccctcc gaaagaggcg accaatagca gaggcttcaa
4201 ctgctgaact acagggtacg ttacattaat gatacacttg tgagtatcag ccctagataa
4261 tataagtcaa ttaaacgacc aagccaaaat tgttcatatc ccgctagcag cttaaaatat
4321 aaatgaaata ggagctatat ctctgacagt attataatca attgttatta agtaacccaa
4381 accaaaaatg atgaagatta agaaaaacct acctcgactg agagagtgtt tttccattaa
4441 ccttcatctt gtaaacgttg agcaaaattg ttacgaatat gaggcgggtt atattgccta
4501 ctgctcctcc tgaatatatg gaggccatat accctgtcag gtcaaattca acaattgcta
4561 ggggtggcaa caacaataca ggcttcctga caccggagtc agtcaatgga gacactccat
4621 cgaatccact caggccaatt gctgatgaca ccatcgacca tgctagccac acaccaggca
4681 gtgtgtcatc agcattcatc cttgaagcta tggtgaatgt catatcgggc cccaaagtgc
4741 taatgaagca aattccaatt tggcttcctc taggtgtcgc tgatcaaaag acctacagct
4801 ttgactcaac tacggccgcc atcatgcttg cttcatatac tatcacccat ttcggcaagg
4861 caaccaatcc acttgtcaga gtcaatcggc tgggtcctgg aatcccggat caccccctca
4921 ggctcctgcg aattggaaac caggccttcc tccaggagtt cgttcttccg ccagtccaac
4981 taccccagta tttcaccttt gatttgacag cactcaaact gatcacccaa ccactgcctg
5041 ctgcaacatg gaccgatgac actccaacag gatcaaatgg agcgctgcgt ccaggaattt
5101 cgtttcatcc aaaacttcgc cccattcttt tacctaacaa aagtgggaag aaggggaaca
5161 gtgccgatct aacatctcca gagaaaatcc aagcaataat gacttcactc caggacttta
5221 agatcgttcc aattgatcca accaaaaata tcatgggtat cgaagtgcca gaaactctgg
5281 tccacaagct gaccggtaag aaggtgactt ctaaaaatgg acaaccaatc atccctgttc
```

-continued 5341 ttttgccaaa gtacattggg ttggacccgg tggctccagg agacctcacc atggtaatca
5401 cacaggattg tgacacgtgt cattctcctg caagtcttcc agctgtgatt gagaagtaat
5461 tgcaataatt gactcagatc cagttttaca gaatcttctc agggatagtg ataacatcta
5521 tttagtaatc cgtctattag aggagatact tttaattgat caatatacta aaggtgcttt
5581 acaccattgt ctttttctc tcctaaatgt agaacttaac aaaagactca caatatactt
5641 gtcttaaaga gattgattga tgaaagatca tgactaataa cattacaaat aatcctacta
5701 taatcaatac ggtgattcaa atattaatct ttctaattgc acatactctc tgcccctatc
5761 ctcaaattgc ctacatgcct acatctgagg atagccagtg tgacttggat tggagatgta
5821 gggaagaaat cggaacccat ctccaggttg ttcacaatcc aagcacagac atcgcccttc
5881 taattaagaa aaaatcggcg atgaagatta agccgacagt gagcgcaatc ttcatctctc
5941 ttagattatt tgttttccag agtaggggtc atcaggtcct ttccaatcat ataaccaaaa
6001 taaacttcac tagaaggata ttgtgaggca acaacacaat gggtattaca ggaatattgc
6061 agttacctcg tgatcgattc aagaggacat cattctttct ttgggtaatt atcctttttcc
6121 aaagaacatt ttccatccca cttggagtca tccacaatag cacattacaa gttagtgatg
6181 tcgacaaact agtttgtcgt gacaaactgt catccacaaa tcaattgaga tcagttggac
6241 tgaatctcga agggaatgga gtggcaactg acgtgccatc tgcaactaaa agatggggct
6301 tcaggtccgg tgtccctcca aaggtggtca attatgaagc tggtgaatgg gctgaaaact
6361 gctacaatct tgaaatcaaa aaacctgacg ggagtgagtg tctaccagca gcgccagacg
6421 ggattcgggg cttcccccgg tgccggtatg tgcacaaagt atcaggaacg ggaccgtgtg
6481 ccggagactt tgccttccac aaagagggtg ctttcttcct gtatgatcga cttgcttcca
6541 cagttatcta ccgaggaacg actttcgctg aaggtgtcgt tgcatttctg atactgcccc
6601 aagctaagaa ggacttcttc agctcacacc ccttgagaga gccggtcaat gcaacggagg
6661 acccgtccag tggctactat tctaccacaa ttagatatca ggctaccggt tttggaacca
6721 atgagacgga gtacttgttc gaggttgaca atttgaccta cgtccaactt gaatcaagat
6781 tcacgccaca gtttttgctc cagctgaatg agacaatata tgcaagtggg aaaaggagca
6841 acaccacggg aaaactaatt tggaaggtca accccgaaat tgatacaaca atcggggagt
6901 gggccttctg ggaaactaaa aaaacctcac tagaaaaatt cgcagtgaag agttgtcttt
6961 cacagctgta tcaaacggag ccaaagacat cagtggtcag agtccggcgc gaacttcttc
7021 cgacccagag acctacacaa caactgaaga ccacaaaatc atggcttcag aaaattcctc
7081 tgcaatggtt caagtgcaca atcaaggaag ggaagctgca gtgtcgcatc tgataaccct
7141 tgccacaatc tccacgagtc ctcaatcccc tacaaccaaa ccaggtcagg acaacagcac
7201 ccataataca cccgtgtata aacttgacat ctctgaggca actcaagttg aacaacatca
7261 tcgcagaaca gacaacgaca gcacagcctc cgacactccc cccgccacga ccgcagccgg
7321 acccccaaaa gcagagaaca tcaacacgag caagagcgct gactccctgg accccgccac
7381 cacgacaagt ccccaaaact acagcgagac cgctggcaac aacaacactc atcaccaaga
7441 taccggagaa gagagtgccg gcagcgggaa gctgggcttg attgccaata ctattgctgg
7501 agtcgcaggg ctgatcacag gcgggagaag aactcgaaga gaagcaattg tcaatgctca
7561 acccaaatgc aaccccaatc tacattactg gactactcag gatgaaggtg ctgcaatcgg
7621 attggcctgg ataccatatt tcgggccagc agccgaggga atttacacag aggggctaat
7681 gcacaatcaa gatggtttaa tctgtggatt gaggcagctg gccaatgaga cgactcaagc -continued

```
7741 tcttcaactg ttcctgagag ccacaactga gctacgcacc ttttcaatcc tcaaccgtaa
7801 ggcaattgat ttcttgctgc agcgatgggg cggcacatgc cacattttgg gaccggactg
7861 ctgtatcgaa ccacatgatt ggaccaagaa cataacagac aaaattgatc agattattca
7921 tgattttgtt gataaaaccc ttccggacca gggggacaat gacaattggt ggactggatg
7981 gagacaatgg ataccggcag gtattggagt tacaggcgtt ataattgcag ttattgcttt
8041 attctgtata tgcaaatttg tcttttagtt tttcttcaga ttgcttcatg gcaaagctca
8101 gcctcaaatc aatgagatta ggatttaatt atatggatca cttgaatcta agattacttg
8161 acaaatgata atataataca ctggagcttt aaatatagcc aatgtgattc taactccttt
8221 aaactcacaa ttaatcataa acaaggtttg acatcaatct agttatatct ttgagaatga
8281 taaacttgat gaagattaag aaaaaggtaa tctttcgatt atctttagtc ttcatccttg
8341 attctacaat catgacagtt gtctttagtg acaagggaaa gaagcctttt tagtaagttg
8401 taataatcag atctgcgaac cggtagagtt taattgcaac ctaacacaca taaagcattg
8461 gtcaaaaagt caatagaaat ttaaacagtg agtggagaca actttcaaat ggaagctcca
8521 tacgagagag gacgcccccg agctgccaga cagcattcaa gggatggaca cgaccatcat
8581 gttcgagcac gatcatcatc cagagagaat tatcgaggtg agtaccgtca atcaaggagc
8641 gcctcacaag tgcgcgttcc tactgtattt cataagagga gagttgaacc attaacagtt
8701 cctccagcac ctaaagacat atgtccgacc ttgaaaaaag gatttttgtg tgacagtagt
8761 ttttgcaaaa aagatcacca gttggaaagt ttaactgata gggaattact cctactaatc
8821 gcccgtaaga cttgtggatc agtagaacaa caattaaata taactgcacc caaggactcg
8881 cgcttagcaa atccaacggc tgatgatttc cagcaagagg aaggtccaaa aattaccttg
8941 ttgacactga tcaagacggc agaacactgg gcgagacaag acatcaggac cacagaggat
9001 tcaaaattaa gagcattgtt gactctatgt gctgtgatga cgaggaaatt ctcaaaatcc
9061 cagctgagtc ttttatgtga gacacacctg aggcgcgagg ggcttgggca agatcaggca
9121 gaacccgttc tcgaagtata tcaacgatta cacagtgata aaggaggcag tttcgaagct
9181 gcactatggc aacaatggga tcgacaatcc ctaattatgt ttatcactgc attcttgaat
9241 atcgctctcc agttaccgtg tgaaagttct gctgtcgttg tttcagggtt aagaacattg
9301 gttcctcaat cagataatga ggaagcttca accaacccgg ggacatgctc atggtctgat
9361 gatggtaccc cttaataagg ctgactaaaa cactatataa ccttctactt gatcacaata
9421 ctccgtatac ctatcatcat atattcaatc aagacggtat cctttaaaac ttattcagta
9481 ctataatcac tctcgtttca aattaataag atatgcataa ttgctttaat atatgaagag
9541 gtatgataca accctaacag tgatcaaaga aaatcataat ctcttatcgc tcgtaatata
9601 acctgccaag catacctctt gcacaaagtg attcttgtac acaaataatg ttttactcta
9661 caggaggtag caacgatcca tcccatcaaa aaataagtat tttatgactt actaatgatc
9721 tcttaaaata ttaagaaaaa ctgacggaac acaaattctt tctgcttcaa gttgtggagg
9781 aggtctttgg tattggctat tgttatatta caatcaataa caagcttgta aaaatattgt
9841 tcttgtttca agaggtagat tgtgaccgga aacgctaaac taatgatgaa gattaatgcg
9901 gaggtctgat aagaataaac cttattattc agattaggcc ccaagaggca ttcttcatct
9961 ccttttagca aagtactatt tcagggtagt ccaattagtg acacgtcttt tagctgtata
10021 tcagtcgccc ctgagatacg ccacaaaagt gtctctaagc taaattggtc tgtacacatc
10081 tcatacattg tattaggggc aataatatct aattgaactt agccgtttaa aatttagtgc
10141 ataaacctgg gctaactcca ccaggtcaac tccattggct gaaaagaagc ccacctacaa
```

-continued

```
10201 cgaacatcac tttgagcgcc cttacaatta aaaaatagga acgtcgttcc aacaattgag
10261 cgcaaggttt caaggttgaa ctgagagtgc ctaaacacca aaatatcgat aattcagaca
10321 ccaagcaaga cctgagaagg aaccatggct aaagctacgg gacgatacaa tctaatatcg
10381 cccaaaaagg acctggagaa aggggttgtc ttaagcgacc tctgtaactt cctagttagt
10441 caaactattc aagggtggaa ggtctattgg gctggtattg agtttgatgt gactcacaaa
10501 ggaatggccc tattgcatag actgaaaact aatgactttg cccctgcatg gtcaatgaca
10561 aggaatctat ttcctcattt atttcaaaat ccgaattcca caattgagtc accactgtgg
10621 gcattgagag tcatccttgc agcaggggta caggaccagc tgattgacca gtctttgatt
10681 gaacccttag caggagccct tggtctgatc tctgattggc tgctaacaac caacactaac
10741 catttcaaca tgcgaacaca acgtgttaag gaacaattga gcctaaaaat gctgtcgttg
10801 attcgatcca atattctcaa gtttattaac caattggatg ctctacatgt cgtgaactac
10861 aacgggttgt tgagcagtat tgaaattgga actcaaaatc atacaatcat tataactcga
10921 actaacatgg gttttctggt ggagctccaa gaacccgaca aatcggcaat gaaccgcaag
10981 aagcctgggc cggcgaaatt ttccctcctt catgagtcca cactgaaagc atttacacaa
11041 gggtcctcga cacgaatgca aagtttgatt cttgaattta atagctctct tgctatctaa
11101 ttaagatgga atacttcata ttgagctaac tcatatatgc tgactcaata gttatcttga
11161 catctctgct ttcataatca gatatataag cataataaat aaatactcat atttcttgat
11221 aatttgttta accacagata aatcctaact gtaagccagc ttccaagttg acacccttac
11281 aaaaaccagg actcagaatc cctcaaataa gagattccaa gacaacatca tagaattgct
11341 ttattatatg aataagcatg ttatcaccag aaatccaata tactaaatag ttaattgtaa
11401 ctgaacccgc aggtcacgtg tgttaggttt cacagattat atatattact aactccatac
11461 ccgtaattaa cattagataa gtagattaag aaaaacgctt gaggaagatt aagaaaaact
11521 gcttattggg tctttccgtg ttttagatga agcagttgac attcttcctc ttgatattaa
11581 atggctacac aacataccca atacccagac gccaggttat catcaccaat tgtattggac
11641 caatgtgacc tagtcactag agcttgcggg ttatattcat catactccct taatccgcaa
11701 ctacgcaact gtaaactccc gaaacatatc taccgtttaa aatatgatgt aactgttacc
11761 aagttcttaa gtgatgtacc agtggcgaca ttgccaatag atttcatagt cccaattctt
11821 ctcaaggcac tgtcaggcaa tgggttctgt cctgttgagc cgcggtgtca acagttctta
11881 gatgaaatca ttaagtacac aatgcaagat gctctcttcc tgaaatatta tctcaaaaat
11941 gtgggtgctc aagaggactg tgttgatgac cactttcaag agaaaatctt atcttcaatt
12001 cagggcaatg aatttttaca tcaaatgttc ttctggtatg acctggctat tttgactcga
12061 aggggtagat taaatcgagg aaactctaga tcaacatggt ttgttcatga tgatttaata
12121 gacatcttag gctatgggga ctatgttttt tggaagatcc caatttcaat gttacccctg
12181 aacacacaag gaatccccca tgctgctatg gattggtatc aggcatcagt attcaaagaa
12241 gcggttcaag ggcatacaca cattgtttct gtttctactg ccgacgtctt gataatgtgc
12301 aaagatttaa ttacatgtcg attcaacaca actctaatct caaagatagc agaggttgag
12361 gatccagttt gttctgatta tcccgatttt aagattgtgt ctatgcttta ccagagcgga
12421 gattacttac tctccatatt agggtctgat gggtataaaa ttattaagtt cctcgaacca
12481 ttgtgcttgg ccaaaattca attatgctca aagtacaccg agaggaaggg ccgattctta
12541 acacaaatgc atttagctgt aaatcacacc ctggaagaaa ttacagaaat gcgtgcacta
```

-continued 12601 aagccttcac aggatcaaaa gatccgtgaa ttccatagaa cattgataag gctggagatg 12661 acgccacaac aactttgtga gctattttcc attcaaaaac actgggggca tcctgtgcta 12721 catagtgaaa cagcaatcca aaaagttaaa aaacatgcca cggtgctaaa agcattacgc 12781 cctatagtga ttttcgagac atattgtgtt tttaaatata gtattgcaaa acattatttt 12841 gatagtcaag gatcttggta cagtgttact tcagatagga atttaacgcc aggtcttaat 12901 tcttatatca aaagaaatca attccccccg ttgccaatga ttaaagaact actatgggaa 12961 ttttaccacc ttgaccatcc tccacttttc tcaaccaaaa ttattagtga cttaagtatt 13021 tttataaaag acagagctac cgcagtggaa aggacatgct gggatgcagt attcgagcct 13081 aatgttctag gatataatcc acctcacaaa ttcagtacta aacgtgtacc agaacaattt 13141 ttagagcaag aaaacttttc tattgagaat gttctttcct acgcgcaaaa actcgagtat 13201 ctactaccac aataccggaa tttttctttc tcattgaaag agaaagagtt gaatgtaggt 13261 agaactttcg gaaaattgcc ttatccgact cgcaatgttc aaacactttg tgaagctctg 13321 ttagctgatg gtcttgctaa agcatttcct agcaatatga tggtagtcac agagcgtgag 13381 caaaaagaaa gcttattgca tcaagcatca tggcaccaca caagtgatga ttttggtgag 13441 catgccacag ttagagggag tagctttgta actgatttag agaaatacaa tcttgcattt 13501 agatatgagt ttacagcacc ttttatagaa tattgtaacc gttgctatgg tgttaagaat 13561 gtttttaatt ggatgcatta tacaatcccc cagtgttata tgcatgtcag tgattattat 13621 aatccaccgc ataacctcac tctggaaaat cgagacaacc cccccgaagg gcccagttca 13681 tacagaggtc atatgggagg gattgaagga ctgcaacaaa aactctggac aagtatttca 13741 tgtgctcaaa tttctttagt tgaaataaag actggtttta agttacgctc agctgtgatg 13801 ggtgacaatc agtgcattac cgttttatca gtcttcccct tagagactga cgcagacgag 13861 caggaacaga gcgccgaaga caatgcagcg agggtggccg ccagcctagc aaaagttaca 13921 agtgcctgtg gaatcttttt aaaacctgat gaaacatttg tacattcagg ttttatctat 13981 tttggaaaaa aacaatattt gaatggggtc caattgcctc agtcccttaa aacggctaca 14041 agaatggcac cattgtctga tgcaattttt gatgatcttc aagggaccct ggctagtata 14101 ggcactgctt ttgaacgatc catctctgag acacgacata tctttccttg caggataacc 14161 gcagctttcc atacgttttt ttcggtgaga atcttgcaac atcatcacct cgggttcaat 14221 aagggttttg accttggaca gttgacactt ggcaaacctc tggatttcgg aacaatatca 14281 ttggcactag cggtaccgca ggtgcttgga gggttatcct tcttgaatcc tgagaaatgt 14341 ttctaccgga atttaggaga tccagttacc tcaggcttat tccagttaaa aacttatctc 14401 cgaatgattg agatggatga tttattctta cctttaattg cgaagaaccc tgggaactgc 14461 actgccattg actttgtgct aaatcctagc ggattaaatg tccccgggtc gcaagactta 14521 acttcatttc tgcgccagat tgtgcgtagg actatcaccc taagtgcgaa aaacaaactt 14581 attaatactt tatttcatgc gtcagctgac ttcgaagacg aaatggtttg taaatggcta 14641 ttatcatcaa ctcctgttat gagtcgtttt gcggccgata tcttttcacg cacgcccagt 14701 gggaagcgat tgcaaattct aggatacctg gaaggaacac gcacattatt agcctctaag 14761 atcatcaaca ataatacaga aacaccggtt ttggacagac tgaggaaaat aacattgcaa 14821 aggtggagtc tatggtttag ttatcttgat cattgtgata atatcctggc agaggcttta 14881 acccaaataa cttgcacagt tgatttagca cagatcctga gggaatattc atgggcacat 14941 attttagagg ggagacctct tattggagcc acacttccat gtatgattga gcaattcaaa 15001 gtggtttggc tgaaacccta cgaacaatgt ccgcagtgtt caaatgcaaa gcaacctggt -continued 15061 gggaaaccat tcgtgtcagt ggcagtcaag aaacatattg ttagtgcatg gccgaacgca 15121 tcccgaataa gctggactat cggggatgga atcccataca ttggatcaag gacagaagat 15181 aagataggac aacctgctat taaaccaaaa tgtccttccg cagccttaag agaggccatt 15241 gaactggcgt cccgtttaac atgggtaact caaggcagtt cgaacagtga tttgctaata 15301 aaaccatttt tggaagcacg agtaaattta agtgttcaag aaatacttca aatgacccct 15361 tcacattact caggaaatat tgttcacagg tacaacgatc aatatagtcc tcattctttc 15421 atggccaatc gtatgagtaa ttcagcgacg cgattgattg tttctactaa cactttaggt 15481 gagttttcag gaggtggcca gtctgcacgc gacagcaata ttattttcca gaatgttata 15541 aattatgcag ttgcactgtt cgatattaaa tttagaaaca ctgaggctac agatatccaa 15601 tataatcgtg ctcaccttca tctaactaag tgttgcaccc gggaagtacc agctcagtat 15661 ttaacataca catctacatt ggatttagat ttaacaagat accgagaaaa cgaattgatt 15721 tatgacaata atcctctaaa aggaggactc aattgcaata tctcattcga taacccattt 15781 ttccaaggta aacggctaaa cattatagaa gatgatctta ttcgactgcc tcacttatct 15841 ggatgggagc tagccaagac catcatgcaa tcaattattt cagatagcaa caattcgtct 15901 acagacccaa ttagcagtgg agaaacaaga tcattcacta cccatttctt aacttatccc 15961 aagataggac ttctgtacag ttttggggcc tttataagtt attatcttgg caatacaatt 16021 cttcggacta agaaattaac acttgacaat tttttatatt acttaactac ccaaattcat 16081 aatctaccac atcgctcatt gcgaatactt aagccaacat tcaaacatgc aagcgttatg 16141 tcacggttaa tgagtattga tcctcatttt tctatttaca taggcggtgc ggcaggtgac 16201 agaggactct cagatgcggc caggttattt ttgagaacgt ccatttcatc ttttcttgca 16261 tttataaaag agtggataat taatcgcgga acaattgtcc ctttatggat agtatatccg 16321 ctagagggtc aaaacccaac acctgttaat aatttcctcc atcagatcgt agaactgctg 16381 gtgcatgatt catcaagaca acaggctttt aaaactacca taagtgatca tgtacatcct 16441 cacgacaatc ttgtttacac atgtaagagt acagccagca atttcttcca tgcgtcattg 16501 gcgtactgga gaagcaggca cagaaacagc aatcgaaaat acttggcaag agactcttca 16561 actggatcaa gcacaaacaa cagtgatggt catattgaga gaagtcaaga acaaaccacc 16621 agagatccac atgatggcac tgaacggaat ctagtcctac aaatgagcca tgaaataaaa 16681 agaacgacaa ttccacaaga aagcacgcac cagggtccgt cgttccagtc atttctaagt 16741 gactctgctt gtggtacagc aaatccaaaa ctaaatttcg atagatcgag acataatgtg 16801 aaatctcagg atcataactc ggcatccaag agggaaggtc atcaaataat ctcacaccgt 16861 ctagtcctac ctttctttac attgtctcaa gggacgcgcc aattaacgtc atccaatgag 16921 tcacaaaccc aagacgagat atcaaagtac ttacggcaat tgagatccgt cattgatacc 16981 acagtttatt gtaggtttac cggtatagtc tcgtccatgc attacaaact tgatgaggtc 17041 ctttgggaaa tagagagttt taagtcggct gtgacgctag cagagggaga aggtgctggt 17101 gccttactat tgattcagaa ataccaagtt aagaccttat ttttcaacac gctagctact 17161 gagtccagta tagagtcaga aatagtatca ggaacgacta ctcctaggat gcttctacct 17221 gttatgtcaa aattccataa tgaccaaatt gagattattc ttaacaattc ggcaagccaa 17281 ataacagaca taacaaatcc tacttggttc aaagaccaaa gagcaaggct acctaggcaa 17341 gtcgaggtta taaccatgga tgcagagacg acagaaaata taaacagatc gaaattgtac 17401 gaagctgtat ataaattgat cttacaccat attgatccca gcgtattgaa agcagtggtc -continued

```
17461 cttaaagtct ttctaagtga tactgagggt atgttatggc taaatgataa tttagccccg
17521 ttttttgcca ctggttattt aattaagcca ataacgtcaa gtgctagatc tagtgagtgg
17581 tatctttgtc tgacgaactt cttatcaact acacgtaaga tgccacacca aaaccatctc
17641 agttgtaaac aggtaatact tacggcattg caactgcaaa ttcaacggag cccatactgg
17701 ctaagtcatt taactcagta tgctgactgc gatttacatt taagttatat ccgccttggt
17761 tttccatcat tagagaaagt actataccac aggtataacc tcgtcgattc aaaaagaggt
17821 ccactagtct ctatcactca gcacttggca catcttagag cagagattcg agaattgact
17881 aatgattata atcaacagcg acaaagtcgg actcaaacat atcactttat tcgtactgca
17941 aaaggacgaa tcacaaaact agtcaatgat tatttaaaat tctttcttat tgtgcaagca
18001 ttaaaacata atgggacatg gcaagctgag tttaagaaat taccagagtt gattagtgtg
18061 tgcaataggt tctatcatat tagagattgc aattgtgaag aacgtttctt agttcaaacc
18121 ttatatctac atagaatgca ggattctgaa gttaagctta tcgaaaggct gacagggctt
18181 ctgagtttat tcccggatgg tctctacagg tttgattgaa ttaccgtgca tagtatcctg
18241 atacttgtga aggttgatta tcaacgtaca gattataaaa aactcacaaa ttgctctcat
18301 acatcatatt gatcgaattt caataaataa ctatttaaat aacgaaagaa gtccttatat
18361 tatacactat atttagcctc tctccctgcg tgataatcaa aaaattcaca atgcagcatg
18421 tgtgacatat tacttccgcg atgaatctaa cgcaacataa taaactctgc actctttata
18481 attaagcttt aacaaaaggt ctgggctcat attgttattg atataataat gttgtatcaa
18541 tatcctgtca gatggaatag tgttttggtt gataacacga cttcttaaaa caaaattgat
18601 cttcaagatt aagtttttta taattatcat tactttaatt tgtcgattta aaaatggtga
18661 tagccttaat ctttgtgtaa aataagagat taggtgtaat aactttaaca ttttgtctag
18721 taagctacta tttcatacag aatgataaaa ttaaaagaaa aggcatgact gtaaaatcag
18781 aaataccttc tttacaatat agcagactag ataataatct tcgtgttaat gataattaag
18841 acattgacca cgctcatcag gaggctcgcc aggataaacg ttgcaaaaag gattcctgga
18901 aaaatggtcg cacacaaaaa tttaaaaata aatctatttc ttcttttttg tgtgtcca
```

The invention further provides polynucleotides having at least about 85, 90, 95, 96, 97, 98, 99, or 100% identity to this sequence. Other Ebola Zaire genomes are known in the art and described, for example, by Baize et al., N Engl J Med 2014; 371:1418-25, which is incorporated herein by reference.

By "Ribonuclease P RNA component H1 (RPPH1) is meant the RNA component of the RNase P ribonucleoprotein, an endoribonuclease that cleaves tRNA precursor molecules to form the mature 5-prime termini of their tRNA sequences. An exemplary nucleic acid sequence is provided at NCBI Accession No. NR_002312 (SEQ ID NO: 27).

By "amplicon" is meant a polynucleotide generated during the amplification of a polynucleotide of interest. In one example, an amplicon is generated during a polymerase chain reaction.

By "amplification rate modifiers" is meant an agent capable of affecting the rate of polymerase extension.

By "base substitution" is meant a substituent of a nucleobase polymer that does not cause significant disruption of the hybridization between complementary nucleotide strands.

In this disclosure, "comprises," "comprising," "containing" and "having" and the like can have the meaning ascribed to them in U.S. Patent law and can mean

```
  1 atagggcgga gggaagctca tcagtggggc cacgagctga gtgcgtcctg tcactccact
 61 cccatgtccc ttgggaaggt ctgagactag ggccagaggc ggccctaaca gggctctccc
121 tgagcttcgg ggaggtgagt tcccagagaa cggggctccg cgcgaggtca gactgggcag
181 gagatgccgt ggaccccgcc cttcggggag gggcccggcg gatgcctcct ttgccggagc
241 ttggaacaga ctcacggcca gcgaagtgag ttcaatggct gaggtgaggt accccgcagg
301 ggacctcata acccaattca gactactctc ctccgcccat t
```

"includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "complementary" or "complementarity" is meant that a nucleic acid can form hydrogen bond(s) with another nucleic acid sequence by either traditional Watson-Crick or Hoogsteen base pairing. Complementary base pairing includes not only G-C and A-T base pairing, but also includes base pairing involving universal bases, such as inosine. A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). To determine that a percent complementarity is of at least a certain percentage, the percentage of contiguous residues in a nucleic acid molecule that can form hydrogen bonds (e.g., Watson-Crick base pairing) with a second nucleic acid sequence is calculated and rounded to the nearest whole number (e.g., 12, 13, 14, 15, 16, or 17 nucleotides out of a total of 23 nucleotides in the first oligonucleotide being based paired to a second nucleic acid sequence having 23 nucleotides represents 52%, 57%, 61%, 65%, 70%, and 74%, respectively; and has at least 50%, 50%, 60%, 60%, 70%, and 70% complementarity, respectively). As used herein, "substantially complementary" refers to complementarity between the strands such that they are capable of hybridizing under biological conditions. Substantially complementary sequences have 60%, 70%, 80%, 90%, 95%, or even 100% complementarity. Additionally, techniques to determine if two strands are capable of hybridizing under biological conditions by examining their nucleotide sequences are well known in the art.

As used herein, "duplex" refers to a double helical structure formed by the interaction of two single stranded nucleic acids. A duplex is typically formed by the pairwise hydrogen bonding of bases, i.e., "base pairing", between two single stranded nucleic acids which are oriented antiparallel with respect to each other. Base pairing in duplexes generally occurs by Watson-Crick base pairing, e.g., guanine (G) forms a base pair with cytosine (C) in DNA and RNA, adenine (A) forms a base pair with thymine (T) in DNA, and adenine (A) forms a base pair with uracil (U) in RNA. Conditions under which base pairs can form include physiological or biologically relevant conditions (e.g., intracellular: pH 7.2, 140 mM potassium ion; extracellular pH 7.4, 145 mM sodium ion). Furthermore, duplexes are stabilized by stacking interactions between adjacent nucleotides. As used herein, a duplex may be established or maintained by base pairing or by stacking interactions. A duplex is formed by two complementary nucleic acid strands, which may be substantially complementary or fully complementary. Single-stranded nucleic acids that base pair over a number of bases are said to "hybridize."

"Detect" refers to identifying the presence, absence or amount of the analyte to be detected. In one embodiment, the analyte is an Ebola polynucleotide or other RNA viral polynucleotide.

By "detectable moiety" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "fragment" is meant a portion of a nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 5, 10, 15, 20, 30, 40, 50, 60, 70, 80, 90, or 100 nucleotides. In one embodiment, the fragment comprises at least about 50, 75, 80, 85, 89, 90, or 100 nucleotides of an Ebola polynucleotide or other RNA viral polynucleotide.

By "free energy (ΔG)" is meant the net exchange of energy between the system and its environment at a constant temperature and pressure described by the formula: $\Delta G=\Delta H-T\Delta S$. Free energy represents how thermodynamically stable a structure is, with formation of structures having a negative ΔG (e.g., expressed in kcal/mole) being thermodynamically stable (i.e., a structure having a lower ΔG is more stable than one having a higher ΔG). The thermodynamic potential is minimized when a system reaches equilibrium at constant pressure and temperature.

By "hybridize" is meant to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507). Hybridization occurs by hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "isolated polynucleotide" is meant a nucleic acid (e.g., a DNA, RNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term “purified” can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By “melting temperature (Tm)” is meant the temperature of a system in equilibrium where 50% of the molecular population is in one state and 50% of the population is in another state. With regard to the nucleic acids of the invention, Tm is the temperature at which 50% of the population is single-stranded and 50% is double-stranded (e.g., intramolecularly or intermolecularly).

By “monitoring a reaction” is meant detecting the progress of a reaction. In one embodiment, monitoring reaction progression involves detecting polymerase extension and/or detecting the completion of an amplification reaction.

As used herein, “obtaining” as in “obtaining an agent” includes synthesizing, purchasing, or otherwise acquiring the agent.

As used herein, the term “nucleic acid” refers to deoxyribonucleotides, ribonucleotides, or modified nucleotides, and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, 2' modified nucleotides (e.g., 2'-O-methyl ribonucleotides, 2'-F nucleotides).

As used herein, “modified nucleotide” refers to a nucleotide that has one or more modifications to the nucleoside, the nucleobase, pentose ring, or phosphate group. For example, modified nucleotides exclude ribonucleotides containing adenosine monophosphate, guanosine monophosphate, uridine monophosphate, and cytidine monophosphate and deoxyribonucleotides containing deoxyadenosine monophosphate, deoxyguanosine monophosphate, deoxythymidine monophosphate, and deoxycytidine monophosphate. Modifications include those naturally occurring that result from modification by enzymes that modify nucleotides, such as methyltransferases. Modified nucleotides also include synthetic or non-naturally occurring nucleotides. Synthetic or non-naturally occurring modifications in nucleotides include those with 2' modifications, e.g., 2'-O-methyl, 2'-methoxyethoxy, 2'-fluoro, 2'-hydroxyl (RNA), 2'-allyl, 2'-O-[2-(methylamino)-2-oxoethyl], 4'-thio, 4'-$CH_2$—O-2'-bridge, 4'-$(CH_2)_2$—O-2'-bridge, and 2'-O—(N-methylcarbamate) or those comprising base analogs.

By “nucleotide adduct” is meant a moiety that is bound covalently or otherwise fixed to a standard nucleotide base.

By “nicking agent” is meant a chemical entity capable of recognizing and binding to a specific structure in double stranded nucleic acid molecules and breaking a phosphodiester bond between adjoining nucleotides on a single strand upon binding to its recognized specific structure, thereby creating a free 3'-hydroxyl group on the terminal nucleotide preceding the nick site. In preferred embodiments, the 3' end can be extended by an exonuclease deficient polymerase. Exemplary nicking agents include nicking enzymes, RNAzymes, DNAzymes, and transition metal chelators.

By “palindromic” is meant nucleic acid sequences that are identical or substantially identical when read from 5' to 3' on one strand or 5' to 3' on the complementary strand. A perfect palindrome refers to a sequence having two adjacent subsequences, such that when one subsequence is read from the 5' to 3' direction, it is identical to the other subsequence read from the 3' to 5' direction.

By “polymerase-arresting molecule” is meant a moiety associated with a polynucleotide template/primer that prevents or significantly reduces the progression of a polymerase on the polynucleotide template. Preferably, the moiety is incorporated into the polynucleotide. In one preferred embodiment, the moiety prevents the polymerase from progressing on the template.

By “polymerase extension” is meant the forward progression of a polymerase that matches incoming monomers to their binding partners on a template polynucleotide.

As used herein, “primer-dimer” is meant a dimer of two monomer oligonucleotide primers. In the oligonucleotide primers of the invention, the 5' tail regions of monomer primers dimerize.

By “semi-quantitative” is meant providing an estimate of relative quantity based on an internal control.

By “specific product” is meant a polynucleotide product resulting from the hybridization of primer oligonucleotides to a complementary target sequence and subsequent polymerase mediated extension of the target sequence.

By “substantially isothermal condition” is meant at a single temperature or within a narrow range of temperatures that does not vary significantly. In one embodiment, a reaction carried out under substantially isothermal conditions is carried out at a temperature that varies by only about 1-5° C. (e.g., varying by 1, 2, 3, 4, or 5 degrees). In another embodiment, the reaction is carried out at a single temperature within the operating parameters of the instrument utilized.

By “quantity threshold method” is meant providing an estimate of quantity based on either exceeding or not exceeding in quantity a comparative standard.

By “reference” is meant a standard or control condition. As is apparent to one skilled in the art, an appropriate reference is where an element is changed in order to determine the effect of the element.

By “reverse transcriptase” is meant an enzyme that replicates a primed single-stranded RNA template strand into a complementary DNA strand in the presence of deoxyribonucleotides and permissive reaction medium comprising, but not limited to, a buffer (pH 7.0-9.0), sodium and/or potassium ions and magnesium ions. As is apparent to one skilled in the art, concentration and pH ranges of a permissive reaction media may vary in regard to a particular reverse transcriptase enzyme. Examples of suitable “reverse transcriptases” well known in the art, but not limited to, are MmLV reverse transcriptase and its commercial derivatives “Superscript I, II and III” (Life Technologies), “MaxiScript” (Fermentas), RSV reverse transcriptase and its commercial derivative “OmniScript” (Qiagen), AMV reverse transcriptase and its commercial derivative “Thermoscript” (Sigma-Aldrich).

By “subject” is meant a mammal, including, but not limited to, a human or non-human mammal, such as a bovine, equine, canine, ovine, or feline.

By “target nucleic acid molecule” is meant a polynucleotide to be analyzed. Such polynucleotide may be a sense or antisense strand of the target sequence. The term “target nucleic acid molecule” also refers to amplicons of the original target sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 2 shows the various probes and primers tested (SEQ ID NOs: 52-65, respectively, in order of appearance), as well as the Ebola gBlock sequence used in assay development (SEQ ID NO: 66). A gBlock is a synthetic, double-stranded fragment of DNA ranging in size from 100 bp to 1000 bp that is entirely assembled in-vitro from synthetic single-stranded oligonucleotides and which represents a sequence-verified synthetic block of genomic DNA. Unless specifically stated or obvious from context, as used herein, the "gBlock®" is used as a synthetic target nucleic acid whenever a native target sequence or target genome is not available and/or not useful. Sequence-verified blocks of genomic DNA for any target sequence can be procured as a custom-order service from IDT Technologies Inc. (1710 Commercial Park, Coralville, Iowa 52241, USA) and the term "gBlock®" is a registered trademark of that company.

FIG. 6A indicates that a stabilization/lysis reagent (e.g., Guanidine isothiocyanate (GITC)) is lyophilized onto the inside of the capillary tube. FIG. 6B illustrates use of a paper impregnated with lyophilized GITC and buffer (e.g., Whatman™ FTA™ Elute Cards). FIG. 6C depicts a lyophilized assay procedure in multiplex (e.g., an 8-well strip) or single tube.

FIG. 7A depicts sample preparation from swab samples. FIG. 7B depicts sample preparation from a blood sample.

FIG. 11A is a graph showing detection of RPPH1 (RNase P RNA Component) in a 2-step reaction. FIG. 11B is a graph showing detection of RPPH1 in a 1-step reaction.

FIG. 12 is a graph showing the detection of Zaire Ebola in a crude blood preparation in a 1-step reaction.

FIG. 13 is a graph depicting that the Zaire Ebola assay specifically detects Zaire Ebola Mayinga but not Sudan Ebola Boniface.

FIG. 15A is a graph depicting detection in samples containing 100 copies of Ebola virus target RNA. FIG. 15B is a graph depicting detection in samples containing 50 copies of Ebola virus target RNA. FIG. 15C is a graph depicting detection in samples containing 25 copies of Ebola virus target RNA. FIG. 15D is a graph depicting detection in samples containing 12 copies of Ebola virus target RNA.

FIGS. 16A and 16B show detection of human immunodeficiency virus (HIV) in a one-step assay. FIG. 16A is an amplicon map showing sequences used in the design of assay primers and probes (SEQ ID NOs: 67-68, respectively, in order of appearance). Population sequence variations in forward and reverse primers are indicated (SEQ ID NOs: 6-9, 43 and 10, respectively, in order of appearance). External primer sequence is specific to HIV subtype C (for the purified RNA sample used). FIG. 16B shows real-time target specific amplification of HIV in a one-step assay. Cp values are shown across 5 technical replicates for each copy number (10 μL reactions). Copies of purified HIV RNA (subtype C) (SeraCare) are indicated, as quantified by COBAS TaqMan HIV-1 v2.0 test FIGS. 17A and 17B show detection of dengue virus type 4 (DENV-4) in a one-step assay. FIG. 17A is an amplicon map showing sequences used in the design of assay primers and probes (SEQ ID NOs: 69-70, respectively, in order of appearance). Population sequence variations in reverse primers are indicated (SEQ ID NOs: 11-13, 44 and 14, respectively, in order of appearance). FIG. 17B shows real-time target specific amplification of DENV-4 in a one-step assay. Cp values are shown across 4 technical replicates (10 μL reactions). Isolated total RNA (20 pg) from cell culture included both viral and host cell RNA and total copy number of viral RNA was unknown.

FIGS. 18A and 18B show detection of influenza B in a one-step assay. FIG. 18A is an amplicon map showing sequences used in the design of assay primers and probes (SEQ ID NOs: 71-73, respectively, in order of appearance). Population sequence variations in forward and reverse primers and external primers are indicated (SEQ ID NOs: 15-20, 45, 46 and 21, respectively, in order of appearance). FIG. 18B shows real-time target specific amplification of influenza B in a one-step assay. Cp values are shown across 4 technical replicates (10 μL reactions). Isolated total RNA (20 pg) from cell culture included both viral and host cell RNA and total copy number of viral RNA was unknown. Samples 1 and 2 are different viral isolates.

FIGS. 19A and 19B show detection of Bovine Viral Diarrhea Virus Genotype 1 (BVDV1) in a one-step assay. FIG. 19A is an amplicon map showing sequences used in the design of assay primers and probes (SEQ ID NOs: 74-75, respectively, in order of appearance). Population sequence variations in forward primers are indicated (SEQ ID NOs: 22-24, 47 and 25, respectively, in order of appearance). FIG. 19B shows real-time target specific amplification of Bovine Viral Diarrhea Virus Genotype 1 (BVDV1) in a one-step assay. Technical replicates (10 μL reactions) are shown. Isolated total RNA (20 pg) from cell culture included both viral and host cell RNA and total copy number of viral RNA was unknown. Cell culture crude lysate was used undiluted and at 1:100 dilution.

DETAILED DESCRIPTION OF THE INVENTION

Figure 1:
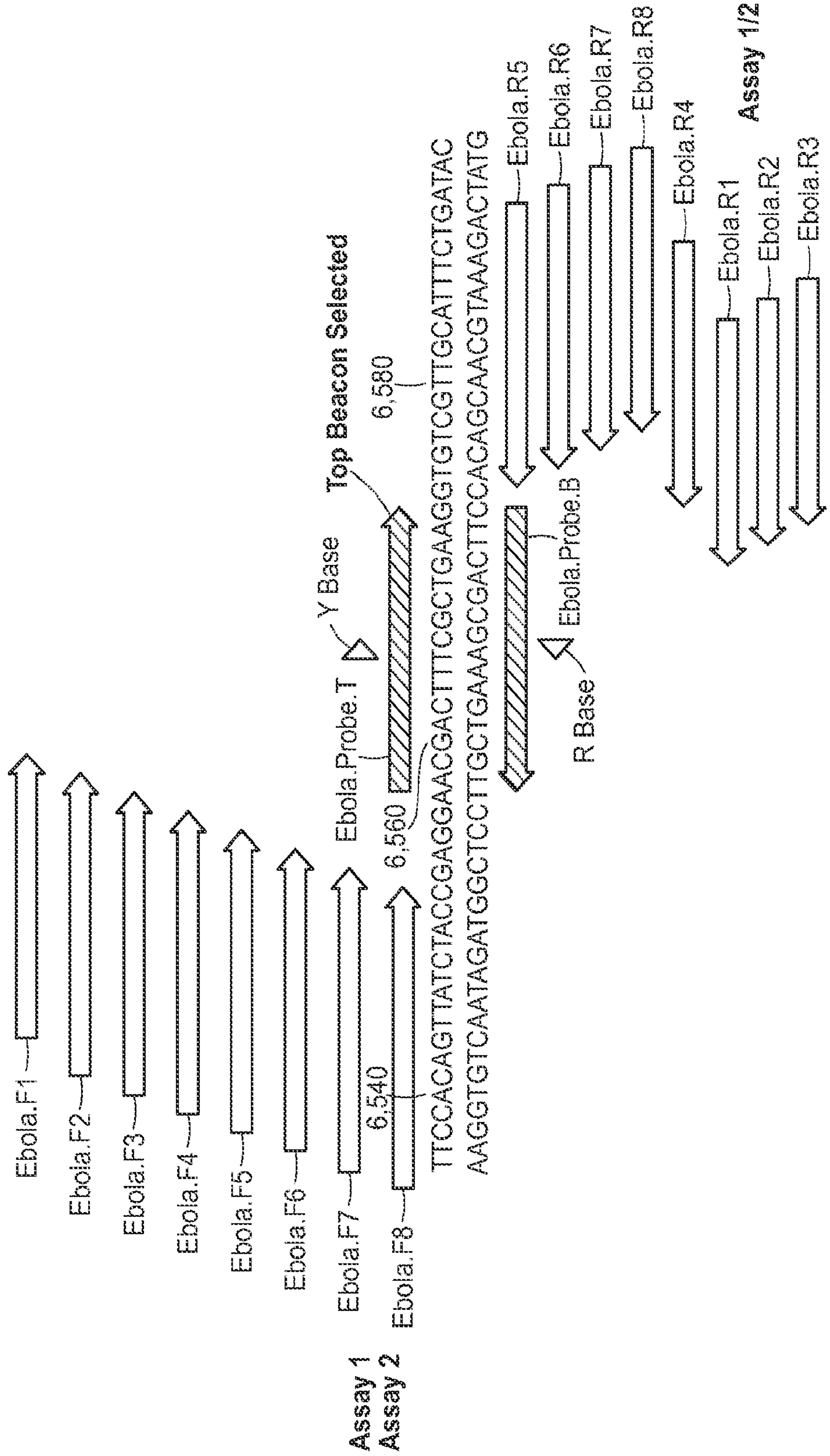
FIG. 1 is a schematic diagram illustrating the design of candidate assays for Ebola virus (EBOV). Assays 1 and 2 were tested for their ability to detect an EBOV polynucleotide (SEQ ID NO: 51).

The present invention provides methods for rapidly identifying an RNA viral infection (e.g., Ebola virus) using an isothermal nucleic acid amplification reaction that can be carried out on extracted RNA in the context of a crude biological sample.

Ebola is clinically difficult to diagnose and to distinguish. A rapid and reliable laboratory diagnosis is required in suspected cases of Ebola. The present invention provides such an assay. The invention is based, at least in part, on the discovery that an Ebola viral polynucleotide (e.g., RNA) can be detected in a one-step or two-step real-time reverse transcription-isothermal amplification assay for an Ebola viral polynucleotide.

Ebola Virus

The Ebola viruses are filamentous viruses with a negative-sense RNA genome. Virions are cylindrical/tubular containing a viral envelope, matrix, and nucleocapsid components, approximately 80 nm in diameter and 800-1000 nm in length. Ebola is classified as a biosafety level 4 agent. The period of incubation for the Ebola virus hemorrhagic fever is usually 5-18 days, but may extend from 2-21 days depending on the viral strain contracted and the condition of the infected individual. The Ebola virus acts quickly. Initial symptoms of Ebola resemble symptoms of malaria, influenza, or various bacterial infections. Therefore, days or weeks may pass before Ebola is diagnosed. Secondary symptoms include diarrhea, red eyes, vomiting blood, bleeding from the nose, mouth or rectum, and even bleeding in the brain. About 50%-90% of those infected with the virus go on to systemic multi-organ failure and death.

Patient Diagnosis and Monitoring

The condition of a patient as having or not having Ebola can be diagnosed by detecting an Ebola viral polynucleotide in a biological sample and correlating this detection with the existence of an Ebola infection. In one embodiment, a disease state of a patient having Ebola virus can be detected using the methods and compositions of the invention to detect Ebola virus in a biological sample of the patient. Exemplary biological samples include body fluids (e.g. saliva, sweat, tears, fluids accumulating in a bodily cavity, urine, ejaculate, vaginal secretion, cerebrospinal fluid, lymph, feces, sputum, decomposition fluid, vomit, sweat, breast milk, blood, serum, and plasma), tissue extracts, culture media (e.g., a liquid in which a cell, such as a pathogen cell, has been grown), or environmental samples obtained, for example, from a material that may be contaminated with a biological fluid of a subject.

In one embodiment, the invention provides a method of amplifying a target polynucleotide in a reverse transcriptase and nicking amplification reaction involving:

(a) contacting a target RNA molecule (e.g., Ebola virus genome) with a reverse transcriptase (RT) primer in the presence of a reverse transcriptase and dNTPs under conditions permissive for cDNA synthesis, thereby generating a cDNA; and (b) contacting the cDNA with forward and reverse primers carrying at least one nicking enzyme recognition sequence within their respective 5'-terminal regions which specifically bind the cDNA with their respective 3'-terminal regions in the presence of a nicking enzyme, dNTPs, and a strand-displacement polymerase under conditions permissive for the isothermal amplification of the cDNA, thereby generating amplicons.

In one particular embodiment, the invention provides a method of detecting an Ebola virus in a biological sample involving:

(a) contacting a sample with an agent capable of extracting an Ebola RNA present in the sample (e.g., SDS, sodium lauryl sulfate, guanidium isothio-cyanate, guanidium hydrochloride) and an agent capable of stabilizing Ebola RNA against degradation (e.g., SDS, RNAase inhibitors, antibodies against RNAse, competitive RNAse inhibitor, or an agent capable of reversibly chemically modifying RNA in situ (e.g., acetic anhydride);

(b) contacting the Ebola RNA with a RT primer in the presence of a reverse transcriptase and dNTPs under conditions permissive for cDNA synthesis, thereby generating a cDNA copy of the Ebola RNA;

(c) contacting the Ebola cDNA with forward and reverse primers carrying at least one nicking enzyme recognition sequence within their respective 5'-terminal regions which specifically binds the Ebola cDNA with their respective 3'-terminal regions in the presence of a nicking enzyme, dNTPs, and a strand-displacement polymerase under conditions permissive for the isothermal amplification of the cDNA, thereby generating amplicons; and (d) detecting the amplicons, wherein the presence of an Ebola virus amplicon detects an Ebola virus infection in the sample and failure to detect the amplicon indicates the absence of an Ebola virus infection.

In one embodiment, the methods of the invention described herein provide results in no longer than 5, 7, 10, 15, 20, 25 or 30 minutes. Advantageously, the methods of the invention can be applied to RNAs extracted—but not purified or isolated from—a crude biological sample (e.g., saliva, sweat, tears, fluids accumulating in a bodily cavity, urine, ejaculate, vaginal secretion, cerebrospinal fluid, lymph, feces, sputum, decomposition fluid, vomit, sweat, breast milk, blood, serum, and plasma). Because the test is carried out on-site (e.g., in a hospital, clinic, physician's office, urgent care center, home, community center, airport, ship (e.g., cruise ship or other vessel used for transporting humans or animals), train or train station, or point of entry into a nation (e.g., border crossing). Advantageously, in one embodiment, the testing is carried out in a portable battery powered device (e.g., Amplifire).

In one embodiment, the RNA is extracted from the biological sample using a chaotropic salt (e.g., GITC, GHCL) or a detergent (e.g., SDS, Tween and triton). If desired, an RNAse inhibitor is added before, during, or after the extraction step.

In another embodiment, the reverse transcriptase enzyme and the strand-displacement DNA polymerase are one and the same.

In another embodiment, no separate primer is required or the RT primer same as forward and/or reverse primers.

In another embodiment, the invention provides for detection of an EBOV or other viral amplicon using a Dual FRET molecular beacon for mRNA detection (e.g., as described by Santagelo, Nucleic Acids Res. 2004; 32(6): e57), turbidity release of pyrophosphate from DNTPs and precipitation with magnesium or calcium.

In another embodiment, the invention provides for detection of an Ebola viral amplicon using a lateral flow device where the Ebola virus amplicon comprises one member of a pair of binding partners (e.g., biotin and streptavidin) and the lateral flow device comprises the other member of the pair, and provides a means of detection (e.g., colorimetric) for the amplicon.

Reverse transcriptases used in the methods of the invention include, but are not limited to, a Maloney murine leukemia virus reverse transcriptase enzyme (MMLV RT) and derivatives or variants thereof comprising a mutation relative to wild-type MMLV RT; avian myeloblastosis virus (AMV RT) and derivatives or variants thereof comprising a mutation relative to that render them thermostable, Rous sarcoma virus (RSV) RT (e.g., Omniscript, Qiagen) and derivatives or variants thereof, and a pyroreverse transcriptase (e.g., Pyroscript luceigen) and derivatives or variants thereof, an RT described in U.S. Pat. No. 7,094,539, which is incorporated herein by reference in its entirety, or a commercially available High-fidelity Thermostable Reverse Transcriptase for RT PCR and Transcriptome analysis (e.g., Lucigen).

In one embodiment, at 56 degrees the primer and RNA or amplicon forms a stable complex. In one embodiment, more than 50% of primer sequence must be complementary to the target nucleic acid molecule. In one embodiment, the rT primer is about 18 bases in length. In one embodiment, the reverse transcriptase (RT) primer is a random primer (e.g., in each sequence position any one of four bases is possible, any of these primers hybridize with the target). In one embodiment, the rT primer is a hexamer, heptamer, octamer, or nonamer.

In one embodiment, the RT is derived from *Geobacillus stearothermophilus*, is M-MLV RT (i.e. Superscript/LifeTech, Maxima/Thermo-Fisher) and/or mutants/derivatives thereof, AMV RT (i.e. Thermoscript/LifeTech) and/or mutants/derivatives thereof, RSV RT (i.e. OmniScript/Qiagen) and/or mutants/derivatives thereof.

Methods of the invention provide a high degree of sensitivity. In one embodiment, EBOV is detected at $1\times10^3$, $1\times10^4$, $1\times10^5$, $1\times10^6$, $1\times10^7$, or $1\times10^9$ copies of EBOV RNA per ml in blood. In another embodiment, the invention provides for the detection of between about 1-10 (e.g, 1, 2, 3, 4, 5, 6, 7, 8, 9, 10) copies of RNA per reaction.

EBOV (or other virus) is detected by obtaining a sample (e.g., biological sample) from a subject having or suspected of having an EBOV infection or by obtaining an environmental sample from a home, hospital room, means of transportation that is or is suspected of being contaminated with an Ebola virus or EBOV-containing biological fluid.

In one embodiment, a biological sample is obtained by obtaining a blood sample, mucous sample, feces, or by swabbing an affected tissue. Swabs can be taken from the nose, throat, eyes, or other mucosal membrane. At necropsy, samples can be collected from blood or tissues of the deceased.

Advantageously, the diagnostic methods of the invention are suitable for use in virtually any setting. EBOV is endemic in much of west Africa including Liberia, Nigeria, Guinea, and Sierra Leone. Many areas within west Africa lack access to basic medical facilities and diagnostic laboratories. The present invention can be used in a battery powered hand held device that is well-suited to testing of biological samples in areas where access to electricity is non-existent. Moreover, the present methods are simple enough that they can easily be carried out by health workers who have limited training in the use of diagnostic technologies.

The present invention provides methods for rapidly identifying an EBOV or other viral infection using an isothermal nucleic acid amplification reaction that can be carried out on extracted RNA in the context of a crude biological sample.

Early in the disease process, only low levels of virus are present in a biological sample of the subject, such as a blood sample. If desired, the virions present in the sample are enriched using methods known in the art, for example, by precipitating the virions from the sample by adding PEG and NaCl then filtering virions out of the sample using a nanopore filter, thereby providing for early detection of a viral polynucleotide.

The disease state or treatment of a subject that may have been exposed to Ebola virus (or other virus) can be monitored using the methods and compositions of the invention. In one embodiment, the detection of an Ebola virus polynucleotide (or other virus polynucleotide) is present in a bodily fluid, such as saliva, sweat, tears, fluids accumulating in a bodily cavity, urine, ejaculate, vaginal secretion, cerebrospinal fluid, lymph, feces, sputum, decomposition fluid, vomit, sweat, breast milk, blood, serum, and plasma, is monitored. Such monitoring may be useful, for example, in diagnosing the subject as having Ebola (or other virus), or determining the efficacy of a particular drug in a subject or in assessing disease progression.

Nucleic Acid Amplification Methods

Nucleic acid amplification technologies have provided a means of understanding complex biological processes, detection, identification, and quantification of pathogenic organisms, such as EBOV or other RNA viruses. The present invention provides for the detection of an EBOV negative-sense RNA genome in a biological sample by using reverse transcriptase to synthesize an EBOV DNA molecule from the RNA genome and then amplifying the DNA in an isothermal nicking amplification reaction.

The polymerase chain reaction (PCR) is a common thermal cycling dependent nucleic acid amplification technology used to amplify DNA consisting of cycles of repeated heating and cooling of the reaction for DNA melting and enzymatic replication of the DNA using a DNA polymerase. Real-Time quantitative PCR (qPCR) is a technique used to quantify the number of copies of a given nucleic acid sequence in a biological sample. Currently, qPCR utilizes the detection of reaction products in real-time throughout the reaction and compares the amplification profile to the amplification of controls which contain a known quantity of nucleic acids at the beginning of each reaction (or a known relative ratio of nucleic acids to the unknown tested nucleic acid). The results of the controls are used to construct standard curves, typically based on the logarithmic portion of the standard reaction amplification curves. These values are used to interpolate the quantity of the unknowns based on where their amplification curves compared to the standard control quantities.

In addition to PCR, non-thermal cycling dependent amplification systems or isothermal nucleic acid amplification technologies exist including, without limitation: Nicking Amplification Reaction, Rolling Circle Amplification (RCA), Helicase-Dependent Amplification (HDA), Loop-Mediated Amplification (LAMP), Strand Displacement Amplification (SDA), Transcription-Mediated Amplification (TMA), Self-Sustained Sequence Replication (3SR), Nucleic Acid Sequence Based Amplification (NASBA), Single Primer Isothermal Amplification (SPIA), Q-β Replicase System, and Recombinase Polymerase Amplification (RPA).

Isothermal nicking amplification reactions have similarities to PCR thermocycling. Like PCR, nicking amplification reactions employ oligonucleotide sequences which are complementary to a target sequences referred to as primers. In addition, nicking amplification reactions of target sequences results in a logarithmic increase in the target sequence, just as it does in standard PCR. Unlike standard PCR, the nicking amplification reactions progress isothermally. In standard PCR, the temperature is increased to allow the two strands of DNA to separate. In nicking amplification reactions, the target nucleic acid sequence is nicked at specific nicking sites present in a test sample. The polymerase infiltrates the nick site and begins complementary strand synthesis of the nicked target nucleotide sequence (the added exogenous DNA) along with displacement of the existing complimentary DNA strand. The strand displacement replication process obviates the need for increased temperature. At this point, primer molecules anneal to the displaced complementary sequence from the added exogenous DNA. The polymerase now extends from the 3' end of the template, creating a complementary strand to the previously displaced strand. The second oligonucleotide primer then anneals to the newly synthesized complementary strand and extends making a duplex of DNA which includes the nicking enzyme recognition sequence. This strand is then liable to be nicked with subsequent strand displacement extension by the polymerase, which leads to the production of a duplex of DNA which has nick sites on either side of the original target DNA. Once this is synthesized, the molecule continues to be amplified exponentially through replication of the displaced strands with new template molecules. In addition, amplification also proceeds linearly from each product molecule through the repeated action of the nick translation synthesis at the template introduced nick sites. The result is a very rapid increase in target signal amplification; much more rapid than PCR thermocycling, with amplification results in less than ten minutes.

Nicking Amplification Assays

The invention provides for the detection of EBOV target nucleic acid molecules amplified in an isothermal nicking amplification assay.

Polymerases useful in the methods described herein are capable of catalyzing the incorporation of nucleotides to extend a 3' hydroxyl terminus of an oligonucleotide (e.g., a primer) bound to a target nucleic acid molecule and/or a 3' hydroxyl terminus at a nick site in a double-stranded DNA molecule in conjunction with strand displacement activity. Such polymerases also lack or have substantially reduced 5'-3' exonuclease activity and may include those that are thermophilic. DNA polymerases useful in methods involving primers having 2'-modified nucleotides in the primer region comprising the six 3'-terminal nucleotides include derivatives and variants of the DNA polymerase I isolated from *Bacillus stearothermophilus*, also classified as *Geobacillus stearothermophilus*, and from closely related bacterial strains, isolates and species comprising the genus *Geobacillus*, which lack or have substantially reduced 5'-3' exonuclease activity and have strand-displacement activity. Exemplary polymerases include, but are not limited to, the large fragments of Bst DNA polymerase I, Gst DNA polymerase I, and Gka DNA polymerase I.

A nicking agent useful in methods described herein is a chemical entity capable of recognizing and binding to a specific structure in double stranded nucleic acid molecules and breaking a phosphodiester bond between adjoining nucleotides on the top strand with a substantially higher rate than breaking the phosphodiester bond between adjoining nucleotides on the bottom strand upon binding to its recognized specific structure, thereby creating a free 3'-hydroxyl group on the terminal nucleotide preceding the nick site that can be extended by a 5'-3'-exonuclease deficient strand displacement polymerase. In a preferred embodiment of the methods disclosed herein, the top strand phosphodiester bond cleavage rate of the "nicking agent" approaches 100%, while the cleavage rate of the bottom strand phosphodiester bond approaches 0%. Nicking agents useful in methods described herein, can either be enzymes, i.e. self-regenerating catalysts turning over multiple substrate molecules, or non-regenerating catalysts turning over just a single substrate molecule at an equimolar ratio fashion.

A nicking enzyme binds double-stranded DNA and cleaves one strand of a double-stranded duplex. In the methods of the invention, the nicking enzyme cleaves the top stand (the strand comprising the 5'-3' sequence of the nicking agent recognition site). In a particular embodiment of the invention disclosed herein, the nicking enzyme cleaves the top strand only and 3' downstream of the recognition site. In exemplary embodiments, the reaction comprises the use of a nicking enzyme that cleaves or nicks downstream of the binding site such that the product sequence does not contain the nicking site. Using an enzyme that cleaves downstream of the binding site allows the polymerase to more easily extend without having to displace the nicking enzyme. Ideally, the nicking enzyme is functional under the same reaction conditions as the polymerase. Exemplary nicking enzymes include, but are not limited to, N.Bst9I, N.BstSEI, Nb.BbvCI(NEB), Nb.Bpu10I(Fermantas), Nb.BsmI(NEB), Nb.BsrDI(NEB), Nb.BtsI(NEB), Nt.AlwI(NEB), Nt.BbvCI(NEB), Nt.Bpu10I(Fermentas), Nt.BsmAI, Nt.BspD6I, Nt.BspQI(NEB), Nt.BstNBI(NEB), and Nt.CviPII(NEB). Sequences of nicking enzyme recognition sites are provided at Table 1.

TABLE 1

| Nicking enzyme recognition sequences | |
|---|---|
| N.Bst9I | 5'-GAGTCNNNNN↓NN-3' (SEQ ID NO: 28)<br>\|\|\|\|\|\|\|\|\|\| \|\|<br>3'-CTCAGNNNNN·NN-5' |
| N.BstSEI | 5'-GAGTCNNNNN↓NN-3' (SEQ ID NO: 28)<br>\|\|\|\|\|\|\|\|\|\| \|\|<br>3'-CTCAGNNNNN·NN-5' |

TABLE 1-continued

<table>
<tr><th colspan="2">Nicking enzyme recognition sequences</th></tr>
<tr><td>Nb.BbvCI(NEB)</td><td>5'-CCTCA·GC-3'<br>|||||  ||<br>3'-GGAGT↑CG-5'</td></tr>
<tr><td>Nb.Bpu10I(Fermantas)</td><td>5'-CCTNA·GC-3'<br>|||||  ||<br>3'-GGANT↑CG-5'</td></tr>
<tr><td>Nb.BsmI(NEB)</td><td>5'-GAATG·CN-3'<br>|||||  ||<br>3'-CTTAC↑GN-5'</td></tr>
<tr><td>Nb.BsrDI(NEB)</td><td>5'-GCAATG·NN-3'<br>|||||  ||<br>3'-CGTTAC↑NN-5'</td></tr>
<tr><td>Nb.BtsI(NEB)</td><td>5'-GCAGTG·NN-3'<br>|||||  ||<br>3'-CGTCAC↑NN-5'</td></tr>
<tr><td>Nt.AlwI(NEB)</td><td>5'-GGATCNNNN↓N-3' (SEQ ID NO: 29)<br>|||||||||  |<br>3'-CCTAGNNNN·N-5'</td></tr>
<tr><td>Nt.BbvCI(NEB)</td><td>5'-CC↓TCAGC-3'<br>||  |||||<br>3'-GG·AGTCG-5'</td></tr>
<tr><td>Nt.Bpu10I(Fermentas)</td><td>5'-CC↓TNAGC-3'<br>||  |||||<br>3'-GG·ANTCG-5'</td></tr>
<tr><td>Nt.BsmAI</td><td>5'-GTCTCN↓N-3'<br>||||||  |<br>3'-CAGAGN·N-5'</td></tr>
<tr><td>Nt.BspD6I</td><td>5'-GAGTCNNNN↓N-3' (SEQ ID NO: 30)<br>|||||||||  |<br>3'-CTCAGNNNN·N-5'</td></tr>
<tr><td>Nt.BspQI(NEB)</td><td>5'-GCTCTTCN↓-3'<br>||||||||<br>3'-CGAGAAGN-5'</td></tr>
<tr><td>Nt.BstNBI(NEB)</td><td>5'-GAGTCNNNN↓N-3' (SEQ ID NO: 30)<br>|||||||||  |<br>3'-CTCAGNNNN·N-5'</td></tr>
<tr><td>Nt.CviPII(NEB)</td><td>5'-↓CCD-3'<br>|||<br>3'- GGH-5'</td></tr>
</table>

Nicking enzymes also include engineered nicking enzymes created by modifying the cleavage activity of restriction endonucleases (NEB expressions July 2006, vol 1.2). when restriction endonucleases bind to their recognition sequences in DNA, two catalytic sites within each enzyme for hydrolyzing each strand drive two independent hydrolytic reactions which proceed in parallel. Altered restriction enzymes can be engineered that hydrolyze only one strand of the duplex, to produce DNA molecules that are "nicked" (3'-hydroxyl, 5'-phosphate), rather than cleaved. Nicking enzymes may also include modified CRISPR/Cas proteins, Transcription activator-like effector nucleases (TALENs), and Zinc-finger nucleases having nickase activity.

A nicking amplification reaction typically comprises nucleotides, such as, for example, dideoxyribonucleoside triphosphates (dNTPs). The reaction may also be carried out in the presence of dNTPs that comprise a detectable moiety including but not limited to a radiolabel (e.g., $^{32}P$, $^{33}P$, $^{125}I$, $^{35}S$) an enzyme (e.g., alkaline phosphatase), a fluorescent label (e.g., fluorescein isothiocyanate (FITC)), biotin, avidin, digoxigenin, antigens, haptens, or fluorochromes. The reaction further comprises certain salts and buffers that provide for the activity of the nicking enzyme and polymerase.

Advantageously, the nicking amplification reaction is carried out under substantially isothermal conditions where the temperature of the reaction is more or less constant during the course of the amplification reaction. Because the temperature does not need to be cycled between an upper temperature and a lower temperature, the nicking amplification reaction can be carried out under conditions where it would be difficult to carry out conventional PCR. Typically, the reaction is carried out at about between 35 C and 90 C (e.g., about 35, 37, 42, 55, 60, 65, 70, 75, 80, or 85° C.). Advantageously, it is not essential that the temperature be maintained with a great degree of precision. Some variability in temperature is acceptable.

Sets of primers for amplification reactions are selected as having ΔΔG's≤−15, −16, 17, −18, −19, −20, −25, −30 kcal/mole or more. The performance characteristics of amplification reactions may be altered by increasing the concentration of one or more oligonucleotides (e.g., one or more primers and/or probes) and/or their ratios. High concentrations of primers also favor primer-dimer formation. In various embodiments, concentration of a primers is 100, 200, 300, 400, 500, 600, 700, 800, 900, 1000 nM or more. Melt temperature (Tm) and reaction rate modifiers may also be used to lower the melting temperature of the oligonucleotides, such as (but not limited to) ethylene glycol and glycerol. In addition, DNA polymerase reaction rate modifiers (such as dNTP and magnesium concentration) may be used to alter the reaction rate to lead to a greater quantification precision. In particular embodiments, the 5' tail sequences of the forward and reverse primers have the same nucleic acid sequence.

This invention provides methods of monitoring a nicking amplification reaction in real time, including for example utilizing the amplification strategy as described herein. In one embodiment, quantitative nucleic acid amplification utilizes target nucleic acids amplification alongside a control amplification of known quantity. The amount of target nucleic acid can be calculated as an absolute quantification or a relative quantification (semi-quantitative) based on the source of the control (exogenous or endogenous control).

Quantification of the unknown nucleotide sequence can be achieved either through comparison of logarithmic threshold amplification of the unknown to a series of known target sequences in either a separate set of reactions or in the same reaction; or as an internal endogenous or exogenous co-amplification product, which produces a threshold value, indicative of either a positive result (if the unknown exceeds the threshold) or negative result (if the unknown does not exceed the threshold).

The invention also provides a method of designing a nicking agent-dependent isothermal strand-displacement amplification assay without experimental screening of a multitude of combinations of candidate forward primers and/or candidate reverse primers. A 35 to 70 bp long region within the target sequence is identified having a 12 to 20 bp sequence in the central portion with a Tm≥the assay temperature (e.g., ~55° C.). Adjacent sequences 12 bp to 20 bp long immediately downstream and upstream of the 15 to 20 bp long central region are identified, according to the above criteria. The Tm of the chosen double stranded downstream and upstream adjacent sequences deviate from each other by less than ±3° C. A target-specific pair of forward and reverse primers are created by attaching a 5'-tail region for a stable dimer-forming primer to the 5'-terminus of the 12-20 base upstream adjacent sequence and to the 5'-terminus of the complementary strand of the 12-20 base downstream adjacent sequence. When combining the forward primer, reverse primer, and a probe, the primer driving the synthesis of the strand complementary to the probe is in excess over the other primer at a molar ratio of about 1.1:1 to 10:1. The combined concentration of a primer in the assay is no higher than 1000 nM. The assay design method can also be used to convert a pre-validated PCR assay for an amplicon ≤70 bp to a nicking agent-dependent isothermal strand-displacement amplification assay.

Primer Design

Conventional methods for primer design have focused on primer melting temperature, primer annealing temperature, GC (guaninine and cytosine) content, primer length, and minimizing interactions of the primer with all but the target nucleic acid (see e.g., premierbiosoft.com). Contrary to these methods, it has been found that primers that form stable primer/dimers, expressed in terms of free energy of formation (ΔG), function predictably in nucleic acid amplification reactions. While Free Energy (ΔG) and Melting Temperature (Tm) share primary components Enthalpy (ΔH) and Entropy (ΔS), ΔG and Tm values are derived differently and have no correlative relationship, and the only way to relate a given ΔG with a given Tm value is to explicitly know the value of ΔH and ΔS from which they are derived (Manthey, "mFold, Delta G, and Melting Temperature" ©2005 and 2011 Integrated DNA Technologies). FIGS. 1-11 relate to the design of optimal primers.

The free energy of formation (ΔG) for intermolecular primer structures may be calculated using formulas known in the art. A number of programs are available for determining the formation of various intramolecular and intermolecular primer structures and calculating their ΔG's, including for example mfold and UNAfold prediction algorithms (see e.g., Markham and Zuker. UNAFold: Software for Nucleic Acid Folding and Hybridization. Bioinformatics: Volume 2, Chapter 1, pp 3-31, Humana Press Inc., 2008; Zuker et al. Algorithms and Thermodynamics for RNA Secondary Structure Prediction: A Practical Guide In RNA Biochemistry and Biotechnology, 11-43, NATO ASI Series, Kluwer Academic Publishers, 1999; M. Zuker. Prediction of RNA Secondary Structure by Energy Minimization. Methods in Molecular Biology, 267-294, 1994; Jaeger et al. Predicting Optimal and Suboptimal Secondary Structure for RNA. In Molecular Evolution: Computer Analysis of Protein and Nucleic Acid Sequences, Methods in Enzymology 183, 281-306, 1990; Zuker. On Finding All Suboptimal Foldings of an RNA Molecule. Science 244, 48-52, 1989). OligoAnalyzer 3.1 is one such implementation of mfold for primer design (idtdna.com). For example, with reference to OligoAnalyzer 3.1, ΔG calculations may be performed using the following parameters: Target Type: DNA; Oligo Concentration 0.25 μM; $Na^+$ Concentration: 60 mM; $Mg^{++}$ Concentration: 15 mM; and dNTPs Concentration: 0.3 mM.

3' Recognition Region

The invention provides a primer having a 3' recognition sequence whose primer-target formation is stable (ΔG≤about −20 kcal/mol or more) and has the potential to enhance nucleic acid amplification reaction performance. The 3' recognition region specifically binds to the nucleic acid molecule, for example a complementary sequence of the nucleic acid molecule. In certain embodiments, the 3' recognition region has a sequence that is complementary to 12, 13, 14, 15, 16, 17, 18, 19, or 20 bases or more of a nucleic acid sequence. In particular embodiments, the 3' recognition region comprises one or more inosine bases. In specific embodiments, the 3' recognition region comprises no more than 2/12 inosines. In various embodiments, the primer-target melting temperature is equal to or greater than 8° or 6° C. below the reaction or extension temperature of the assay (Tm≥assay temperature−8°). In particular embodiments, the 3' recognition sequence comprises 12-20, 12-17, or 12-14 bases. In particular embodiments, the primer-target formation is more stable than self dimer formation (e.g., ΔΔG≤about −15, −16, −17, −18, −19, −20 kcal/mol or more). Preferably, the 3' recognition sequence does not contain self-complementary sequences, short inverted repeats (e.g., >4 bases/repeat), or sequences that otherwise promote intramolecular interactions, which have the potential to interfere with primer-target annealing.

In one embodiment, a primer is designed having a Tm of 56° C. with 4 sequence specific bases at the end of the primer that may not contribute to annealing. In one embodiment, the primer is a 16, 17, 18, 19, 20 or 21-mer.

In particular, a primer of the invention having a 3' recognition sequence is useful in nicking amplification assays. Additionally, the EBOV or other viral target specific 3' recognition region comprises one or more 2' modified nucleotides (e.g., 2'-O-methyl, 2'-methoxyethoxy, 2'-fluoro, 2'-alkyl, 2'-allyl, 2'-O-[2-(methylamino)-2-oxoethyl], 2'-hydroxyl (RNA), 4'-thio, 4'-$CH_2$—O-2'-bridge, 4'-$(CH_2)_2$—O-2'-bridge, and 2'-O—(N-methylcarbamate)). Without being bound to theory, it is hypothesized that incorporating one or more 2' modified nucleotides in the recognition regions reduces or eliminates intermolecular and/or intramolecular interactions of primers/templates (e.g., primer-dimer formation), and, thereby, reduces or eliminates the background signal in isothermal amplification. The 2' modified nucleotide preferably has a base that base pairs with the target sequence. In particular embodiments, two or more 2' modified nucleotides (e.g., 2, 3, 4, 5 or more 2' modified nucleotides) in the EBOV or other viral target specific recognition region are contiguous (e.g., a block of modified nucleotides). In some embodiments, the block of 2' modified nucleotides is positioned at the 3' end of the target specific recognition region. In other embodiments, the block of 2' modified nucleotides is positioned at the 5' end of the EBOV or other viral target specific recognition region. When the block of 2' modified nucleotides is positioned at the 5' end of the target specific recognition region, the 2' modified nucleotides may be separated from the nick site by one or more non-modified nucleotides (e.g., 2, 3, 4, 5 or more 2' unmodified nucleotides). Applicants have found that positioning of one or more 2' modified nucleotides or of a block of 2' modified nucleotides alters the kinetics of amplification. When the one or more 2' modified nucleotides or block of 2' modified nucleotides are positioned at or near the 5' end of the recognition region or proximal to the nick site, real-time amplification reactions showed decreased time to detection. Additionally, the signal curve is contracted and the slope of the curve shifted.

In a related embodiment, ratios of a primer having one or more 2' modified nucleotides can be used to alter the time-to-detection and/or the efficiency of the reaction for the 'tuning' of reactions, resulting in a predictable control over reaction kinetics. Increasing the ratio of primer having one or more 2' modified nucleotides at the 3' end of the recognition sequence to primer having one or more 2' modified nucleotides at the 5' end of the recognition sequence contracted the signal curve and shifted the slope of the curve. It is advantageous to be able to "tune" a reaction providing a means to manipulate both the time-to-detection as well as the efficiency of the reaction. Relative quantification using an internal control requires that two important conditions be met. First, it is beneficial to be able to modify a reaction's time-to-detection creating a non-competitive reaction condition. Thus, by affecting the control reaction to be detectable at a later time-point (relative to the target of interest) the control reaction does not out-compete the specific target of interest even when the target of interest is in low initial abundance. Second, to ensure a true relative abundance calculation, it is required that the control and specific target reactions have matched efficiencies. By controlling the efficiency of each reaction using a "tuning" condition enables reactions to be matched allowing for satisfactory relative quantification calculations. Tuning the reactions can be used to match efficiencies of target nucleic acid amplification and reference nucleic amplification (e.g., internal standard) in quantitative PCR (qPCR). Additionally, amplification curves of the target nucleic acid and the internal standard may be altered so time of detection of their amplification products are separated, while providing the same efficiency for target nucleic acid amplification and internal standard amplification. Through the use of specific combinations and ratios of oligonucleotide structures within a reaction it is possible to create conditions which enable tuned reaction performance.

5' Tail Dimerization Region

The invention provides a primer having a 5' tail region capable of self-dimerization that enhances EBOV or other viral nucleic acid amplification reaction performance. Without being bound to theory, in a nucleic acid amplification reaction the primer anneals to the target nucleic acid as a primer-dimer. For example, nicking amplification primers have a nicking agent recognition site present at the 5' end that is unrelated to the binding specificity of the primer for the target recognition sequence. Non-specific background products from non-specific primer interactions have the potential to sequester reaction components that would otherwise have been utilized for the amplification of the specific product. In various embodiments, homodimer formation is stable (e.g., $\Delta G \leq$ about −30, −35, −40, −45, −50, −55, −60 kcal/mol or more). In various embodiments, the homodimer has a melting temperature higher than the extension reaction temperature. In particular embodiments, the 5' tail region has a sequence that is a palindrome. In further embodiments, the 5' tail region is at least 12 bases (e.g., 12, 13, 14, 15, 16, 17, 18, 19, 20, 21, 22, 23, 24 bases) in length. In additional embodiments, the 5' tail region has a GC content of 80-90%. In certain embodiments, homodimer formation is more stable than formation of other less stable primer dimer conformations formation (e.g., $\Delta\Delta G \leq$ about −12, −13, −14, −15, −16, −17, −18, −19, −20, −25, −30, −35, −40 kcal/mol or more).

In particular, a primer of the invention having a 5' tail sequence is useful in nicking amplification reactions. For use in nicking amplification reactions, the 5' tail region comprises one or more nicking agent recognition sites and the 5' tail region has a symmetrically inverted sequence. In particular embodiments, the 5' tail region contains an even number of nucleotides (e.g., 22, 24 nucleotides). The nick site is designed to be positioned between the nucleotide at the 3' end of the 5' tail region and the nucleotide at the 5' end of the 3' recognition region. Without being bound to theory, the nicking enzyme does not cleave at the nick site when the 3' recognition is single-stranded. However, cleavage at the nick site occurs when the 3' recognition region is double stranded (e.g., when the primer is incorporated into a double-stranded target nucleic acid molecule during the course of the nucleic acid amplification reaction).

In various embodiments, the 5' tail sequence comprises from 5' to 3' an inverted nicking enzyme recognition sequence that is operatively linked to a palindromic sequence (or self-complementary sequence) that is operatively linked to a nicking enzyme recognition sequence. In certain embodiments, the spacer region is an even number of nucleotides (e.g., 2, 4, 6, etc.). Exemplary 5' tails based on the Nt.BstNBI nicking enzyme recognition sequence (5'-GAGTC-3') having a 2, 4, and 6 nucleotide spacers comprise a nucleic acid sequences according to the formula below:

(SEQ ID NO: 31)

5'-$\underline{GACTC}N_1N_{1'}\underline{GAGTC}$-3'

(SEQ ID NO: 32)

5'-$\underline{GACTC}N_2N_1N_{1'}N_{2'}\underline{GAGTC}$-3'

(SEQ ID NO: 33)

5'-$\underline{GACTC}N_3N_2N_1N_{1'}N_{2'}N_{3'}\underline{GAGTC}$-3' where "N" is any nucleotide (e.g., having an adenine (A), thymine (T), cytosine (C), or guanine (G) nucleobase), and $N_1$ is complementary to $N_{1'}$, $N_2$ is complementary to $N_{2'}$, and $N_3$ is complementary to $N_{3'}$, etc.

Exemplary 5' tail region sequences 24 nucleotides in length having a Nt.BstNBI recognition sequence can be generated based on the following template 5'-NNNNGACTCNNNNNNGAGTCNNNN-3' (SEQ ID NO: 34). Based on this template, there are 537,824 5' tail sequences having the following properties: ΔG=−48 Kcal/mole to −62 kcal/mole; ΔΔG<−40 kcal/mole; and GC content 68% to 84%. Of these, 1050 selected sequences are provided, representing 0.2% of the entire sequence space (248,832). Exemplary 5' tail region sequences 22 nucleotides in length having a Nt.BstNBI recognition sequence and based on the following template 5'-NNNNGACTCNNNNGAGTCNNNN-3' (SEQ ID NO: 35). Based on this template, there are 248,832 5' tail sequences having the following properties: ΔG=−47 Kcal/mole to −55 kcal/mole; ΔΔG<−40 kcal/mole; and GC content 72% to 82%. Of these, 200 selected sequences are provided, representing 0.08% of the entire sequence space (248,832).

Target Nucleic Acid Molecules

Methods and compositions of the invention are useful for the amplification and/or identification of an EBOV or other viral nucleic acid molecule in a test sample. The target sequences are amplified from virtually any samples that comprises a viral nucleic acid molecule, including a EBOV nucleic acid molecule. In particular, the methods and compositions of the invention are useful for the amplification and/or identification of RNA viruses. In addition to EBOV, exemplary RNA viruses that can be detected using the methods and compositions of the invention include, without limitation, Human Immunodeficiency Virus (HIV), Dengue virus, influenza virus (e.g., influenza B), Bovine Viral Diarrhea virus (e.g., BVDV Genotype 1), Yellow Fever virus, West Nile Virus, Hepatitis C, Lassa virus, Flaviviridae, Arenaviridae, and single-stranded RNA viruses.

Exemplary test samples include body fluids (e.g. bsaliva, sweat, tears, fluids accumulating in a bodily cavity, urine, ejaculate, vaginal secretion, cerebrospinal fluid, lymph, feces, sputum, decomposition fluid, vomit, sweat, breast milk, blood, serum, and plasma), tissue extracts, culture media (e.g., a liquid in which a cell, such as a pathogen cell, has been grown), environmental samples, agricultural products or other foodstuffs, and their extracts, and DNA identification tags. If desired, the sample is purified prior to inclusion in a nicking amplification reaction using any standard method typically used for isolating a nucleic acid molecule from a biological sample.

In one embodiment, primers amplify a target nucleic acid of a pathogen to detect the presence of EBOV or other virus in a sample. For environmental applications, test samples may include water, liquid extracts of building materials (e.g., drywall, ceiling tiles, wall board, fabrics, wall paper, and floor coverings) that may have been exposed to a subject infected with EBOV, environmental swabs, or any other sample.

Methods of the invention provide for the detection of $1\times10^3$, $1\times10^4$, $1\times10^5$, $1\times10^6$, $1\times10^7$, or $1\times10^9$ copies of EBOV RNA per ml in blood.

Applications

Target nucleic acid amplification using primers of the invention have characteristics useful for rapid detection of viral (e.g., EBOV) nucleic acid molecules. Compositions and methods of the invention are useful in human diagnostics, where a rapid diagnostic answer is desired (e.g., detectable amplification in under 20, 15, 10, 9, 8, 7, 6, 5 minutes or less). In particular embodiments, the invention provides for the use of an EBOV nicking amplification reaction assay in human or veterinary diagnostics in clinical settings or in the field. In other embodiments, the invention provides for the use of nicking amplification reaction assays in diagnostic field work, where access to thermocycling equipment is unavailable or would be prohibitively expensive. In still other embodiments, the invention provides for the use of nicking amplification reaction assays in a clinical setting where rapid quantitative answers are desired.

Detectable Oligonucleotide Probes

The present invention provides for the detection of target nucleic acid molecules or amplicons thereof in a nicking amplification reaction using non-amplifiable detectable polynucleotide probes comprising at least one polymerase-arresting molecule (e.g., nucleotide modification or other moiety that renders the oligonucleotide capable of binding a target nucleic acid molecule, but incapable of supporting polymerase extension utilizing the detectable oligonucleotide probe as a target). Without wishing to be bound by theory, the presence of one or more moieties which does not allow polymerase progression likely causes polymerase arrest in non-nucleic acid backbone additions to the oligonucleotide or through stalling of a replicative polymerase (i.e. C3-spacer, damaged DNA bases, other spacer moiety, O-2-Me bases). These constructs thus prevent or reduce illegitimate amplification of the probe during the course of a nicking amplification reaction. This distinguishes them from conventional detection probes, which must be added at the end of the nicking amplification reaction to prevent their amplification.

Conventional detection probes have proven impractical for detecting a nicking amplification reaction in real time. If conventional detection probes are incorporated into the nicking amplification reaction, these conventional detection probes are amplified concurrently with the target. The amplification of these detection molecules masks the detection of legitimate target amplicons due to the number of starting molecules of the detection probe at the start of the reaction.

The invention provides non-amplifiable detectable polynucleotide probe that comprise least one polymerase-arresting molecule. A polymerase-arresting molecule of the invention includes, but is not limited to, a nucleotide modification or other moiety that blocks extension by replicative DNA polymerases, thereby preventing the amplification of detection molecules; but can allow proper hybridization or nucleotide spacing to the target molecule or amplified copies of the target molecule. In one embodiment, a detectable oligonucleotide probe of the invention comprises a 3 carbon spacer (C3-spacer) that prevents or reduces the illegitimate amplification of a detection molecule.

In one embodiment, a detectable oligonucleotide probe comprises one or more modified nucleotide bases having enhanced binding affinity to a complementary nucleotide. Examples of modified bases include, but are not limited to 2' Fluoro amidites, and 2'OMe RNA amidites (also functioning as a polymerase arresting molecule). Detectable oligonucleotide probes of the invention can be synthesized with different colored fluorophores and may be designed to hybridize with virtually any target sequence. In view of their remarkable specificity, a non-amplifiable detectable polynucleotide probe of the invention is used to detect a single target nucleic acid molecule in a sample, or is used in combination with detectable oligonucleotide probes each of which binds a different target nucleic acid molecule. Accordingly, the non-amplifiable detectable polynucleotide probes of the invention may be used to detect one or more target nucleic acid molecules in the same reaction, allowing these targets to be detected simultaneously. The present invention encompasses the use of such fluorophores in conjunction with the detectable oligonucleotide probes described herein.

Implementation in Hardware and/or Software

The methods described herein can be implemented on general-purpose or specially programmed hardware or software. For example, the methods can be implemented by a computer readable medium. Accordingly, the present invention also provides a software and/or a computer program product configured to perform the algorithms and/or methods according to any embodiment of the present invention. It is well-known to a skilled person in the art how to configure software which can perform the algorithms and/or methods provided in the present invention. The computer-readable medium can be non-transitory and/or tangible. For example, the computer readable medium can be volatile memory (e.g., random access memory and the like) or non-volatile memory (e.g., read-only memory, hard disks, floppy discs, magnetic tape, optical discs, paper table, punch cards, and the like). The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., $2^{nd}$ ed., 2001).

The present invention may also make use of various computer program products and software for a variety of purposes, such as probe design, management of data, analysis, and instrument operation. (See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.) Additionally, the present invention may have preferred embodiments that include methods for providing genetic information over networks such as the Internet as shown in U.S. Ser. Nos. 10/197,621, 10/063,559 (US Pub No 20020183936), Ser. Nos. 10/065,856, 10/065,868, 10/328,818, 10/328,872, 10/423,403, and 60/482,389.

Kits

The invention also provides kits for the amplification of an EBOV or other RNA virus nucleic acid molecule. Such kits are useful for the detection or quantitation of an EBOV or other RNA nucleic acid in a biological sample obtained from a subject. Kits of the present invention may comprise, for example, one or more of reverse transcriptase, DNA polymerases, forward and reverse primers, and one or more nicking enzymes, as described herein, and a detectable probe. Where EBOV or other RNA is to be amplified, one or two nicking enzymes may be included in the kit. Where multiple pathogen sequences are to be amplified, and the templates designed for those target sequences comprise the nicking enzyme sites for the same nicking enzyme, then one or two nicking enzymes may be included. Where the templates are recognized by different nicking enzymes, more nicking enzymes may be included in the kit, such as, for example, 3 or more.

In one aspect, the invention provides a kit for nucleic acid amplification comprising a reverse transcriptase, DNA polymerase; a primary primer, a secondary primer, a nicking enzyme with specificity to a nicking enzyme binding site within the primers, and deoxynucleotide triphosphates (dNTP's) (e.g., in a buffered solution containing components sufficient for amplification. In various embodiments, the primary primer and secondary primer, each have a 3'-end specific recognition region sequence complementary or substantially complementary to the target sequence, where the end specific recognition region comprises one or more 2' modified nucleotides; a 5'-end tail region containing a nicking enzyme binding site upstream of the 3'-end specific recognition region sequences that is able to dimerize with itself (e.g., self-complementary). In particular embodiments, one or more primers are in a primer-dimer configuration (e.g., produced by heating about Tm and slow cooling).

The kits of the present invention may also comprise one or more of the components in any number of separate containers, packets, tubes (e.g., <0.2 ml, 0.2 ml, 0.6 ml, 1.5 ml, 5.0 ml, >5.0 ml), vials, microtiter plates (e.g., <96-well, 96-well, 384-well, 1536-well, >1536-well), ArrayTape, and the like, or the components may be combined in various combinations in such containers. In various embodiments, the kit further comprises a pair of primers capable of binding to and amplifying a reference sequence. In particular embodiments, the kit comprises one or more primers in a primer-dimer configuration (e.g., produced by heating about Tm and slow cooling). In yet other embodiments, the kit comprises a sterile container which contains the primers; such containers can be boxes, ampules, bottles, vials, tubes, bags, pouches, blister-packs, or other suitable container form known in the art. Such containers can be made of plastic, glass, laminated paper, metal foil, or other materials suitable for holding nucleic acids.

The components of the kit may, for example, be present in one or more containers, for example, all of the components may be in one container, or, for example, the enzymes may be in a separate container from the primers. The components may, for example, be dried (e.g., powder) or in a stable buffer (e.g., chemically stabilized, thermally stabilized). Dry components may, for example, be prepared by lyophilization, vacuum and centrifugal assisted drying and/or ambient drying. In various embodiments, the polymerase and nicking enzymes are in lyophilized form in a single container, and the primers are either lyophilized, freeze dried, or in buffer, in a different container. In some embodiments, the polymerase, nicking enzymes, and the primers are, in lyophilized form, in a single container. In other embodiments, the polymerase and the nicking enzyme may be separated into different containers.

Kits may further comprise, for example, dNTPs used in the reaction, or modified nucleotides, cuvettes or other containers used for the reaction, or a vial of water or buffer for re-hydrating lyophilized components. The buffer used may, for example, be appropriate for both polymerase and nicking enzyme activity.

The kits of the present invention may also comprise instructions for performing one or more methods described herein and/or a description of one or more compositions or reagents described herein. Instructions and/or descriptions may be in printed form and may be included in a kit insert. A kit also may include a written description of an Internet location that provides such instructions or descriptions.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1. One-Step and Two-Step Real-Time Reverse Transcription-Isothermal Amplification Assays for EBOV A one-step reaction refers to a reverse transcriptase (RT) reaction in which reverse transcription and amplification occur in a single reaction protocol. A two-step reaction refers to a reverse transcriptase reaction in which the reverse transcription is carried out first; followed by a transfer to a second amplification reaction.

Assays 1 and 2 were tested for their ability to detect an EBOV polynucleotide EBOV (FIG. 1). Primers for these assays are shown at FIG. 2.

Figure 3A:
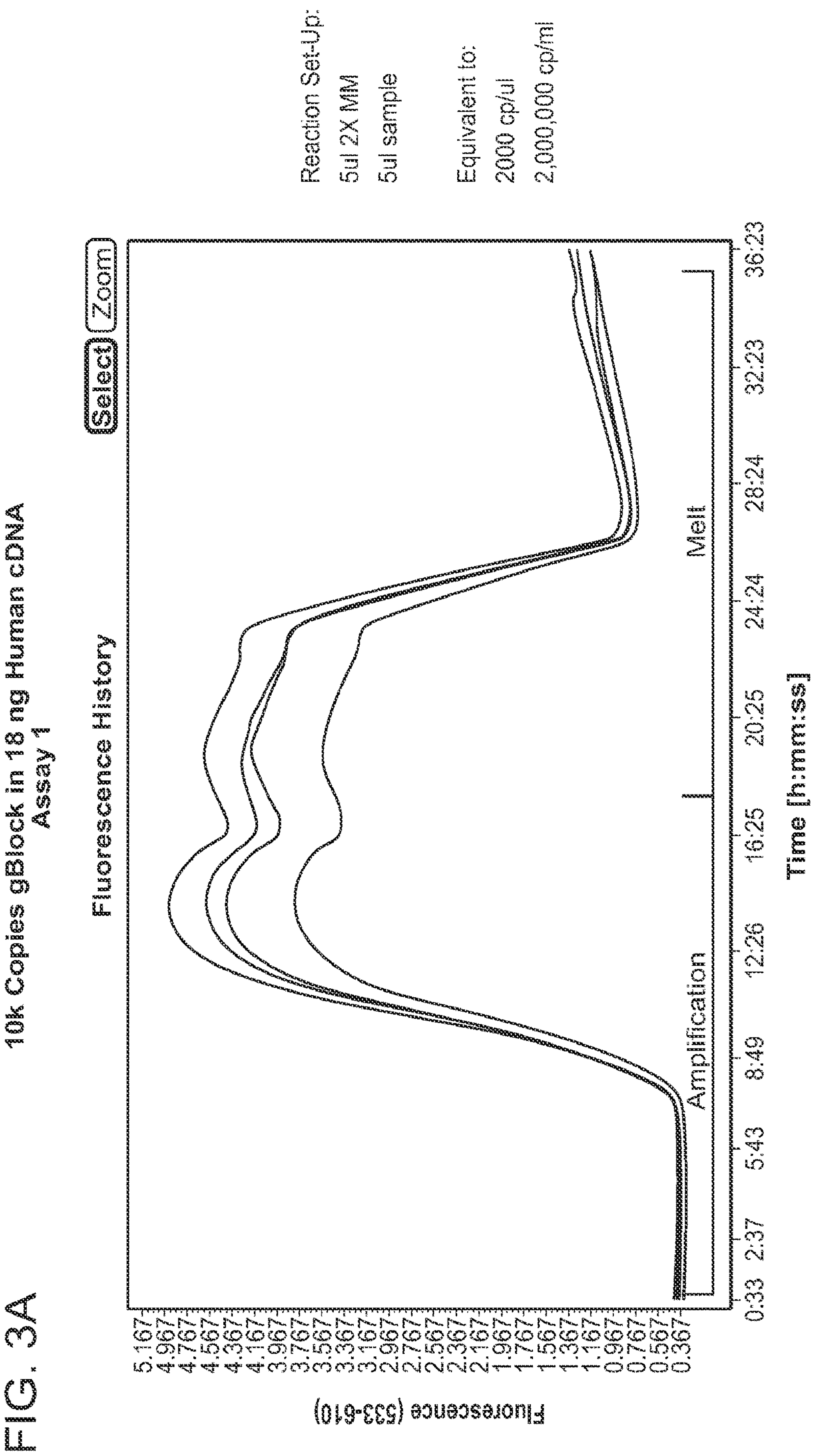
FIG. 3A-3X show amplification results obtained with Assay 1 and Assay 2.
Figure 3B:
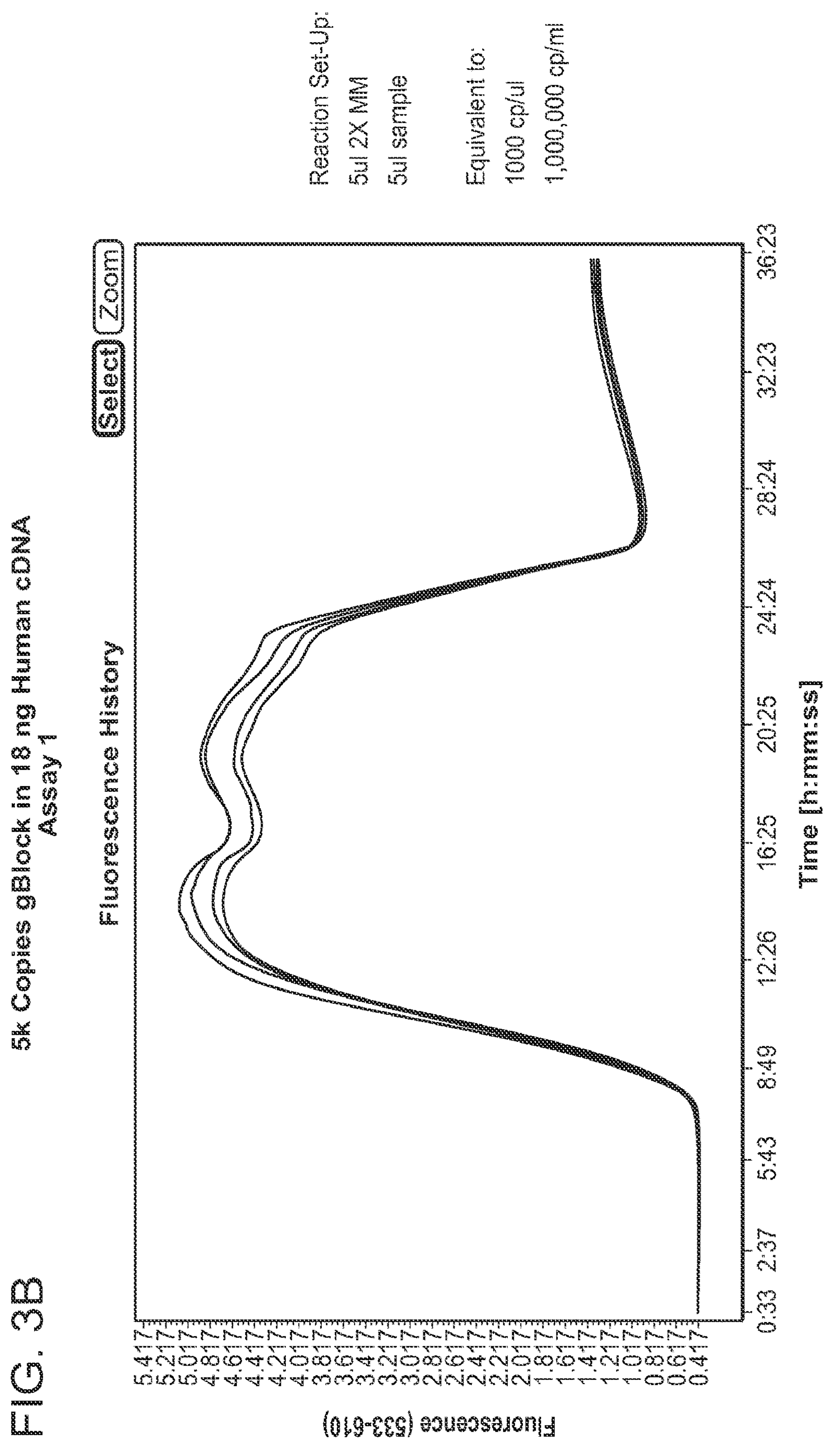
Figure 3C:
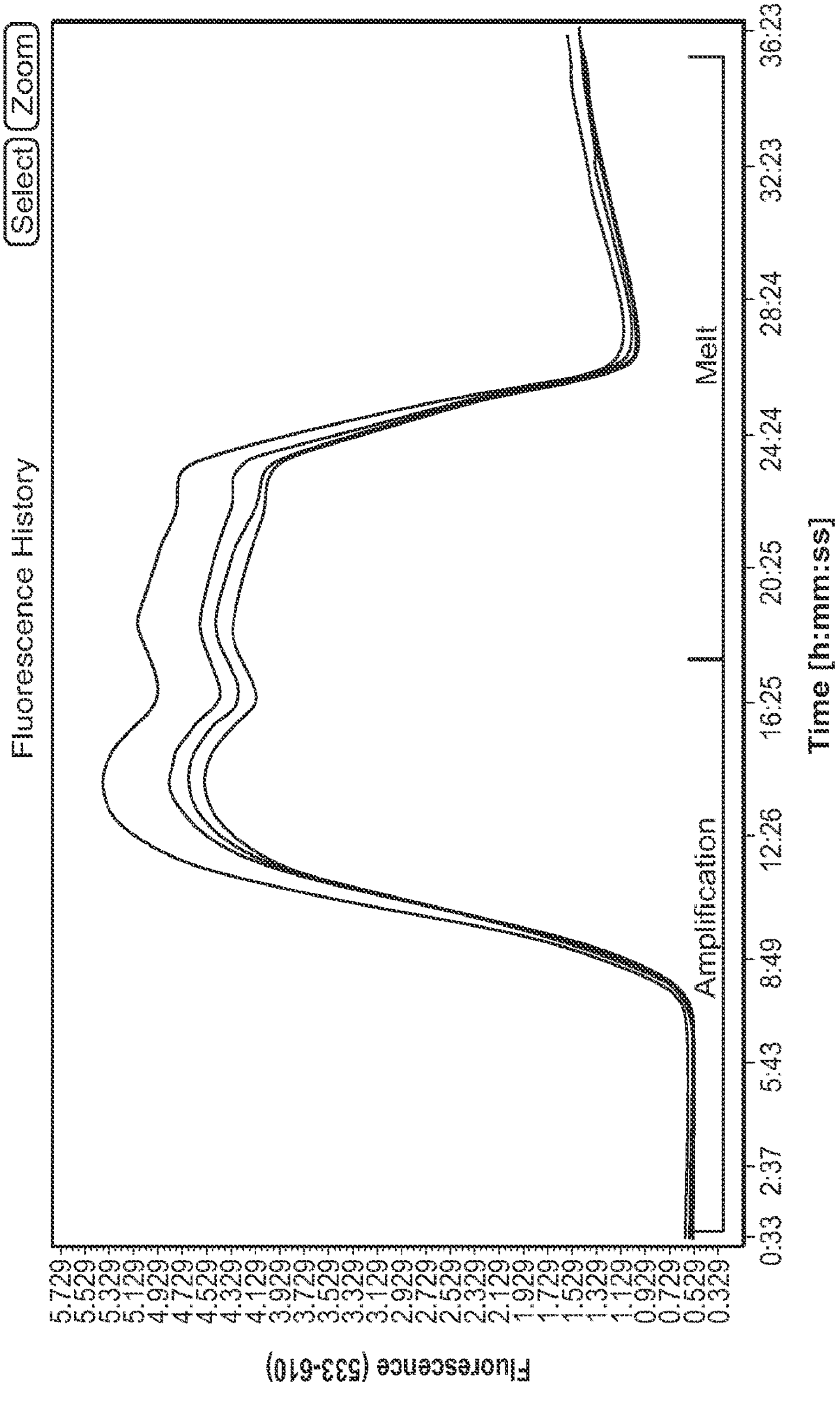
Figure 3D:
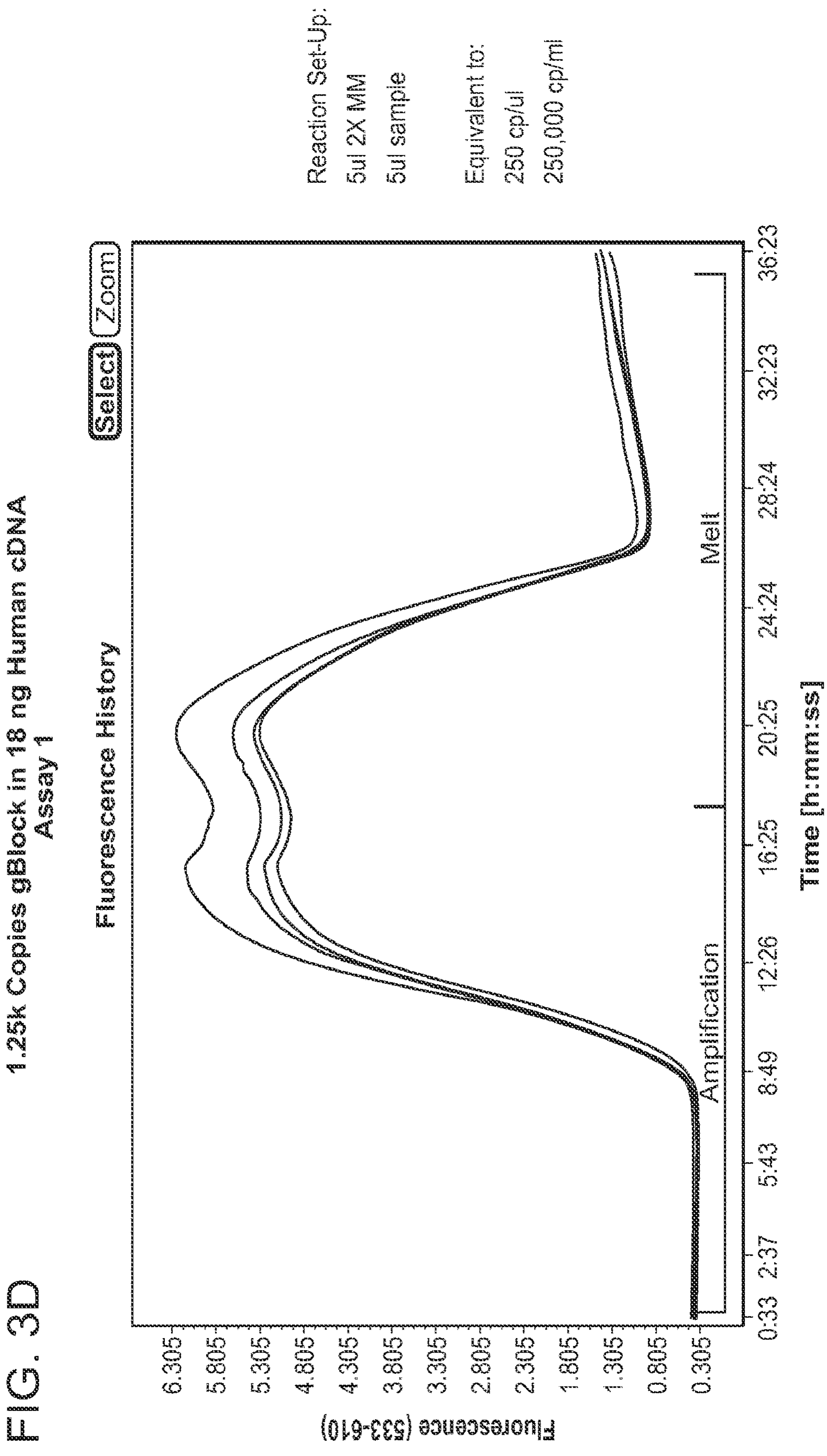
Figure 3E:
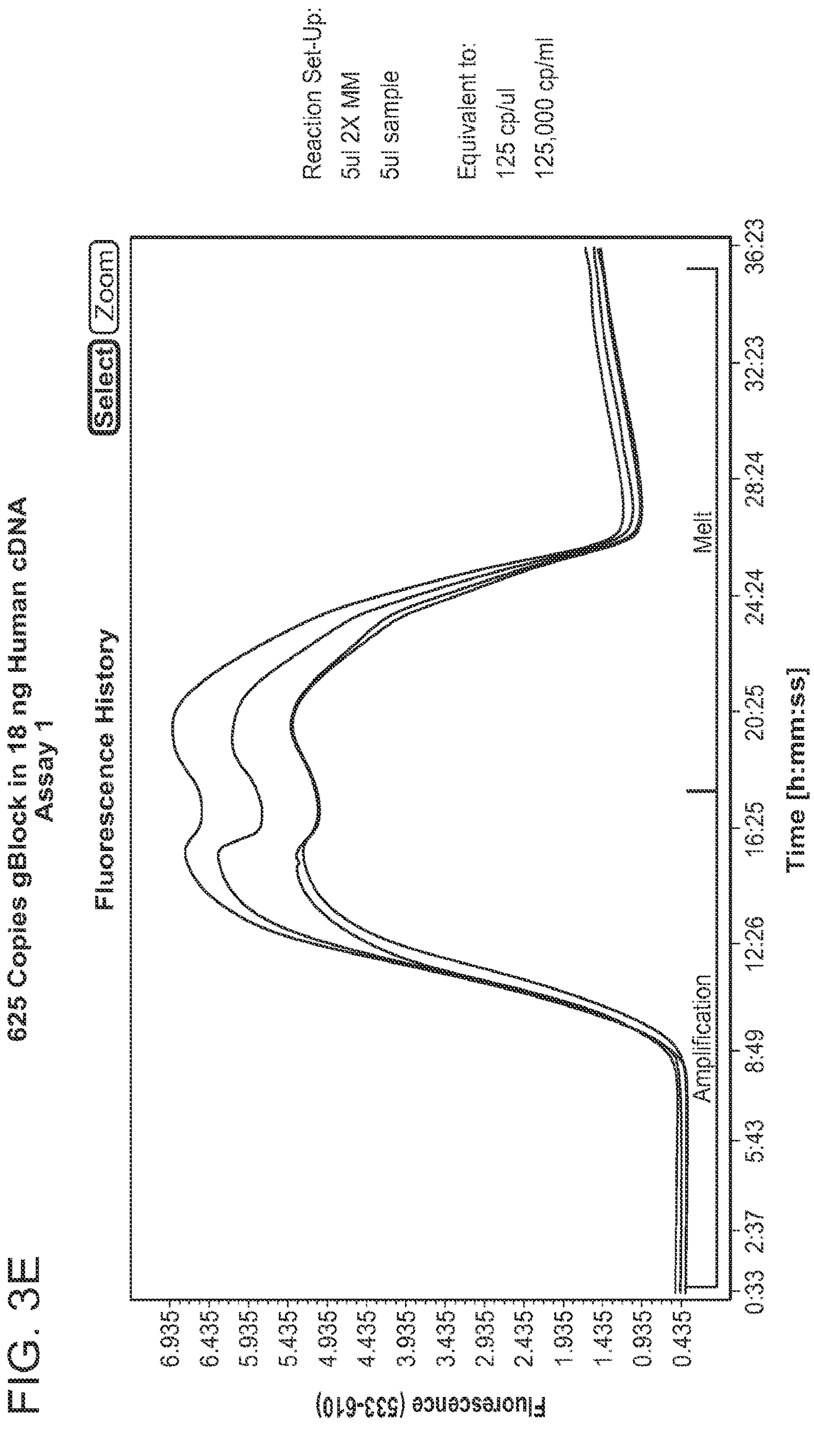
Figure 3F:
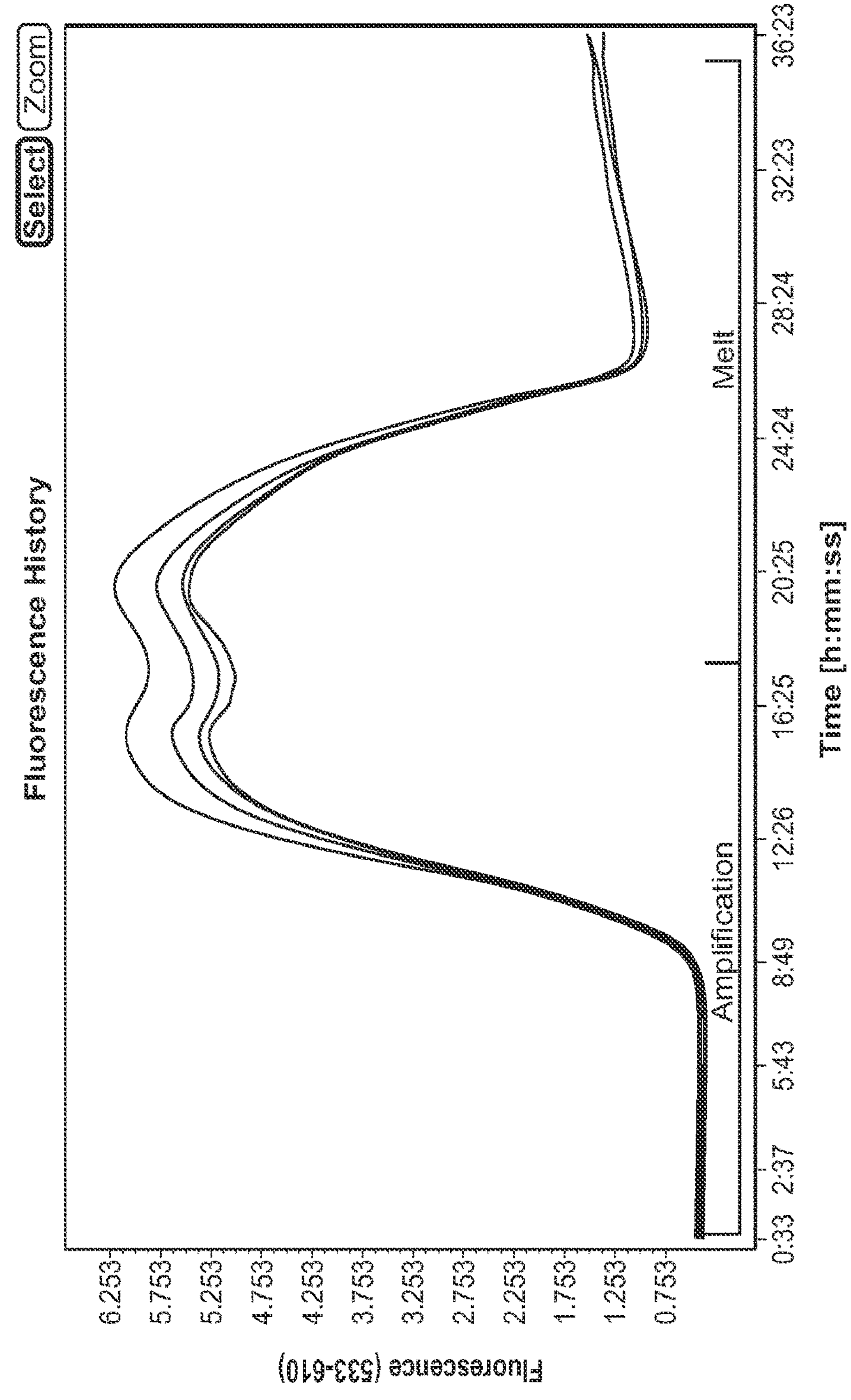
Figure 3G:
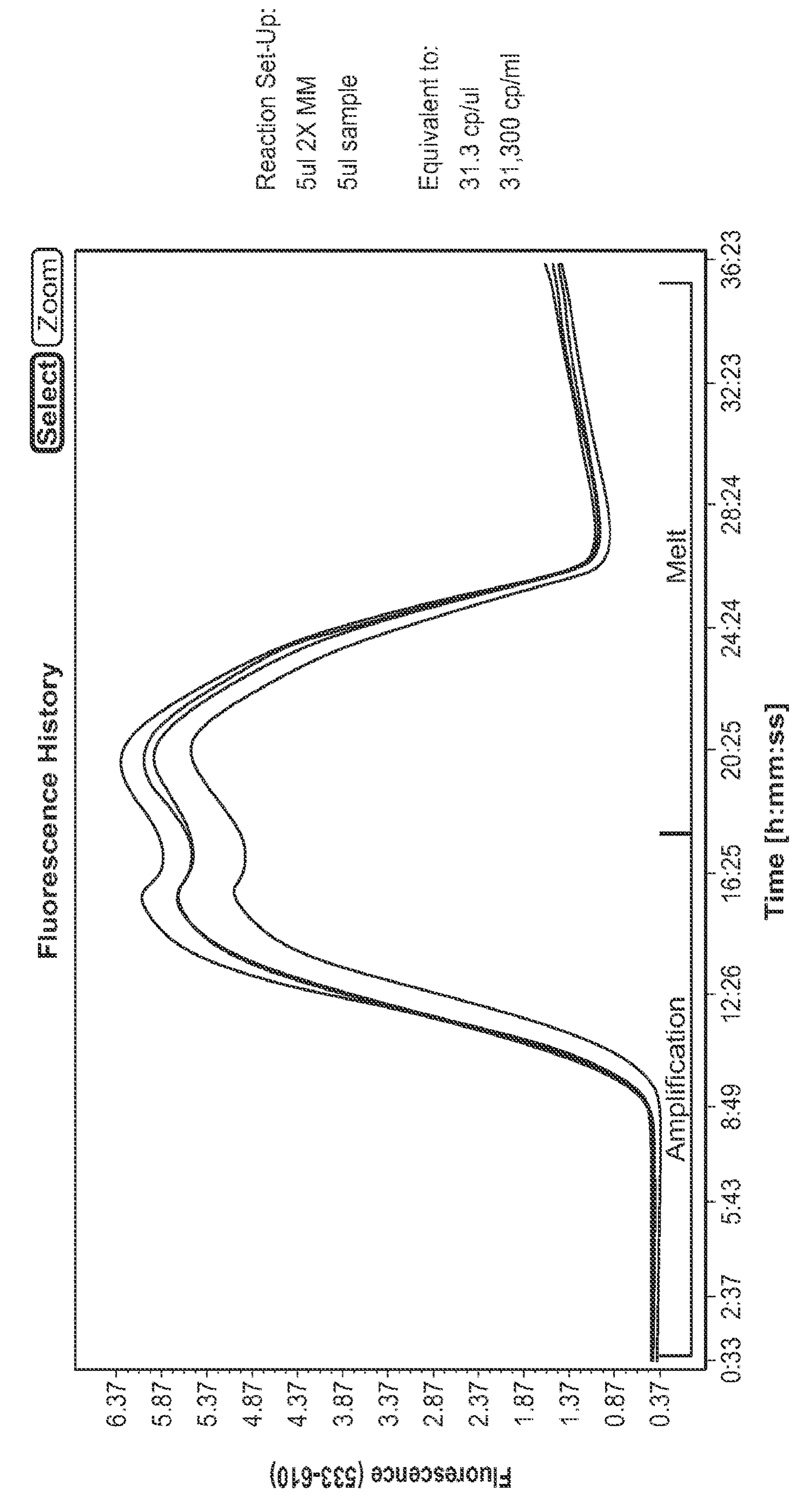
Figure 3H:
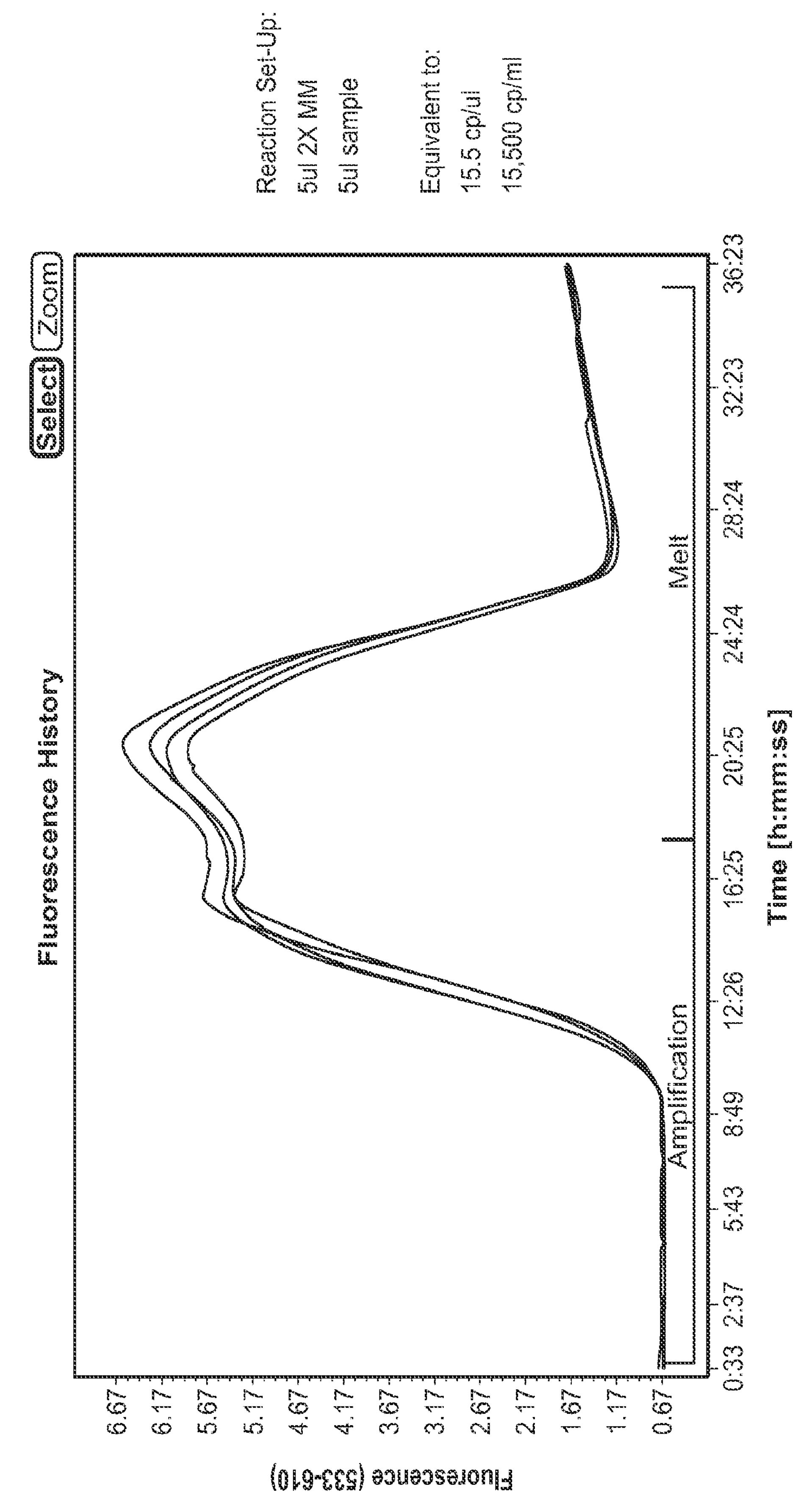
Figure 3I:
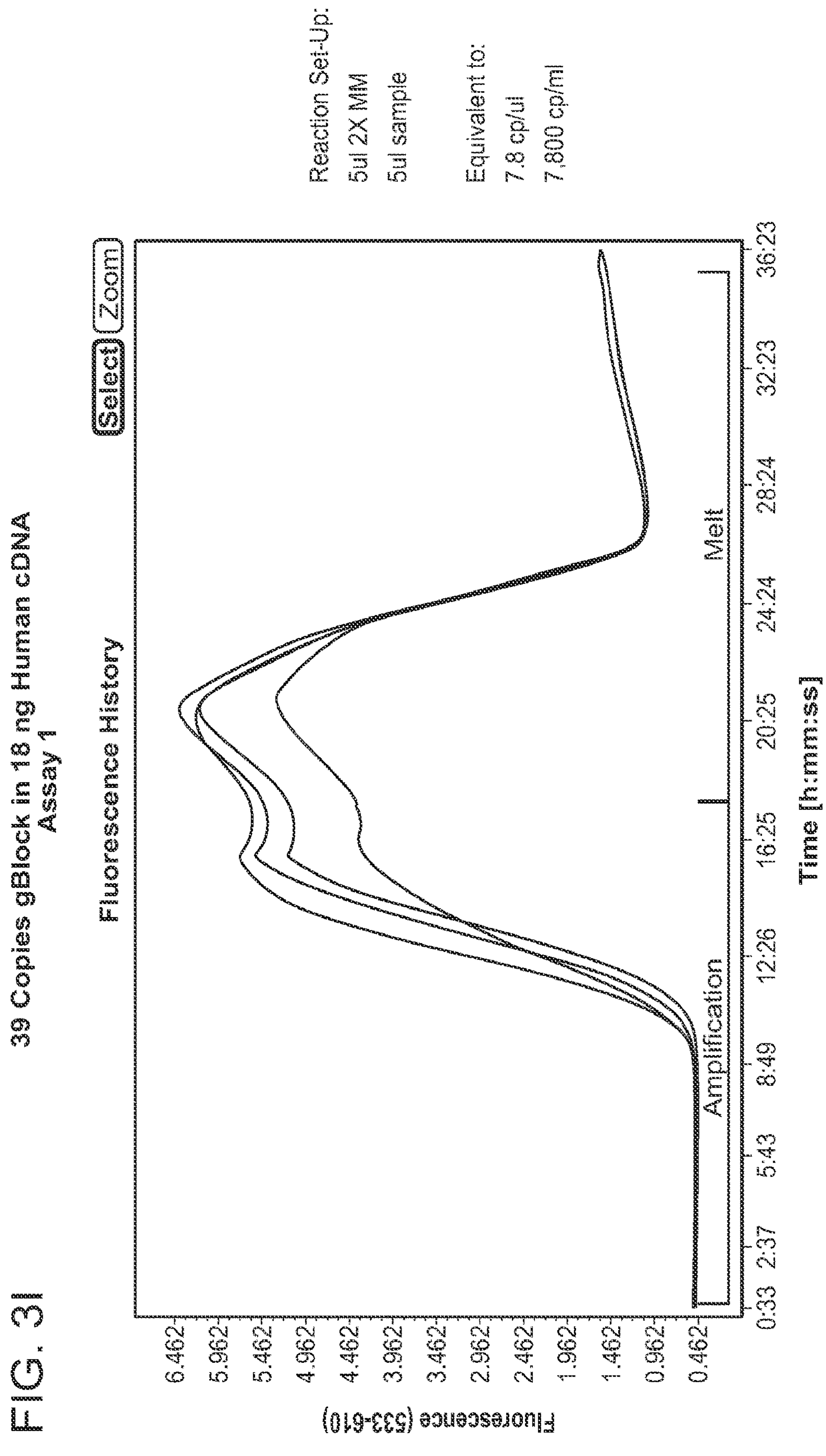
Figure 3J:
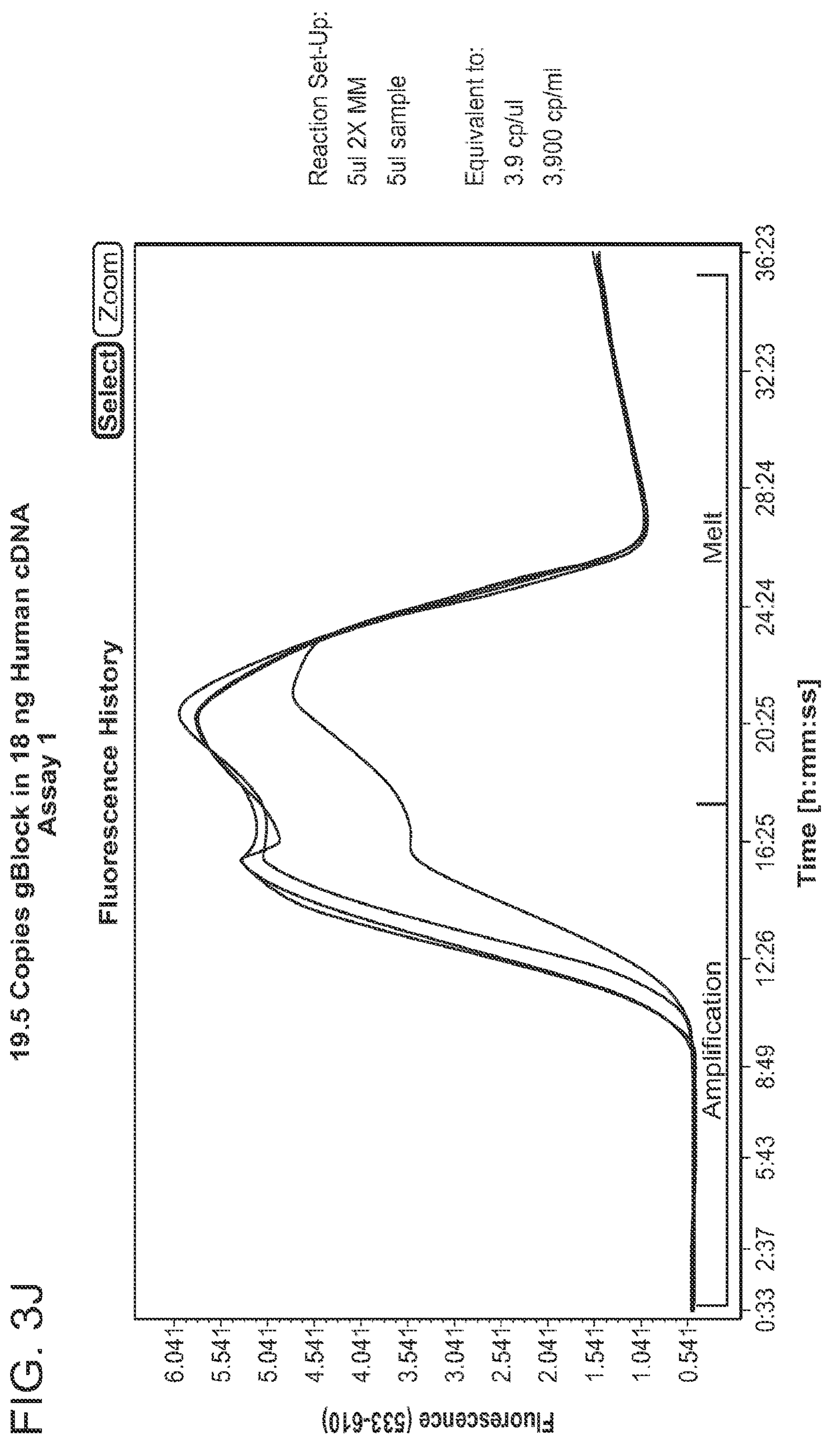
Figure 3K:
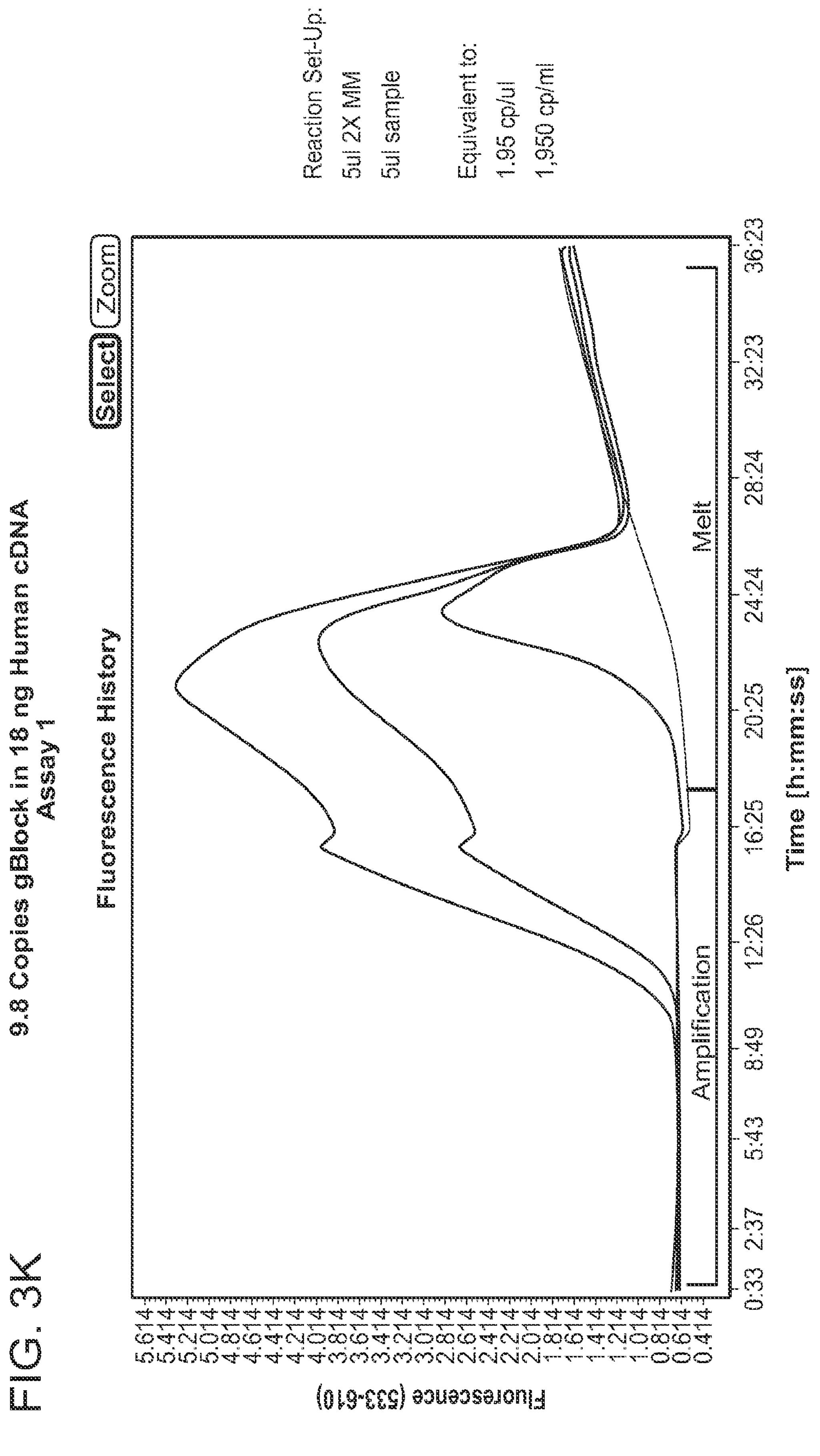
Figure 3L:
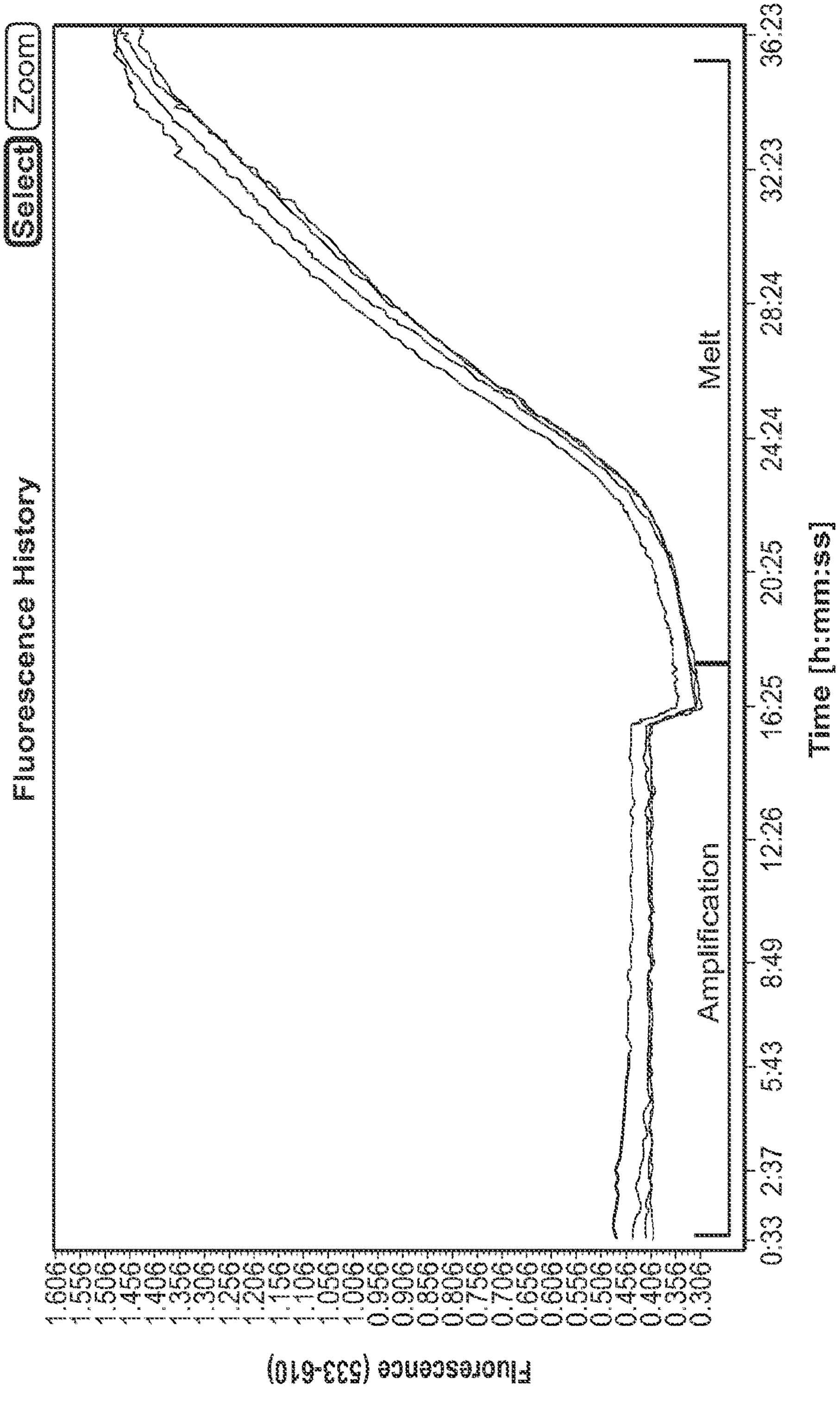
Figure 3M:
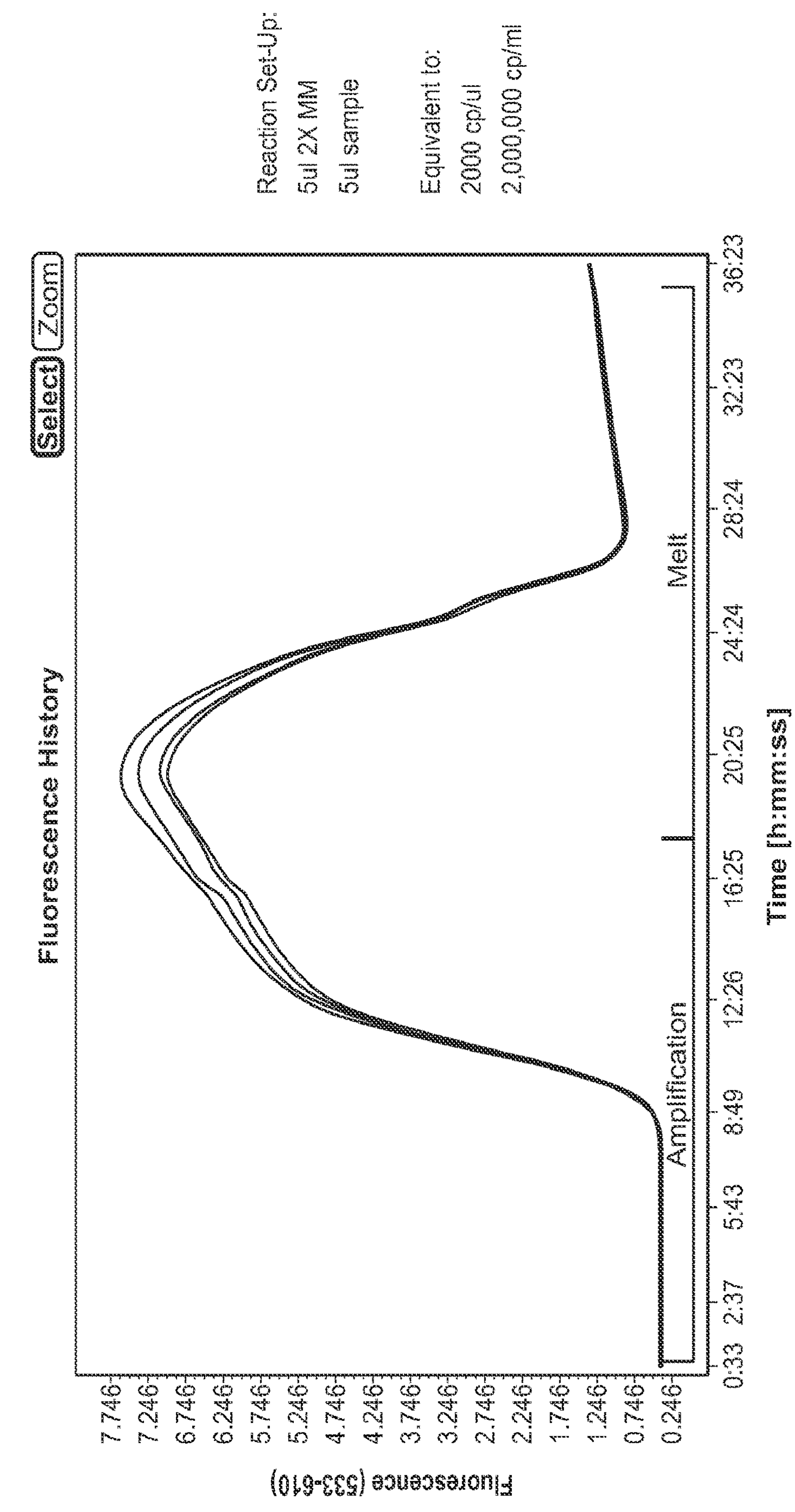
Figure 3N:
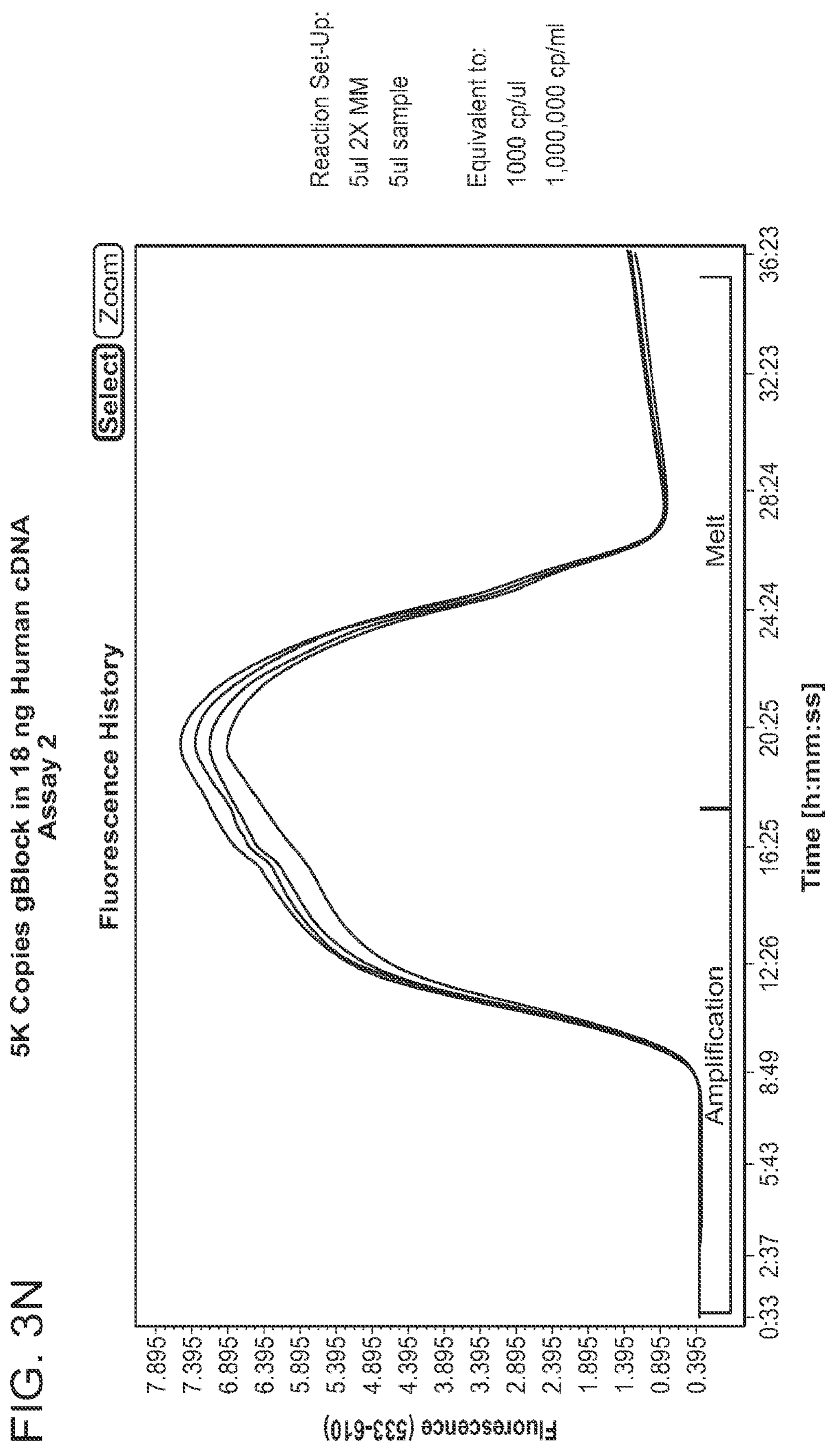
Figure 3O:
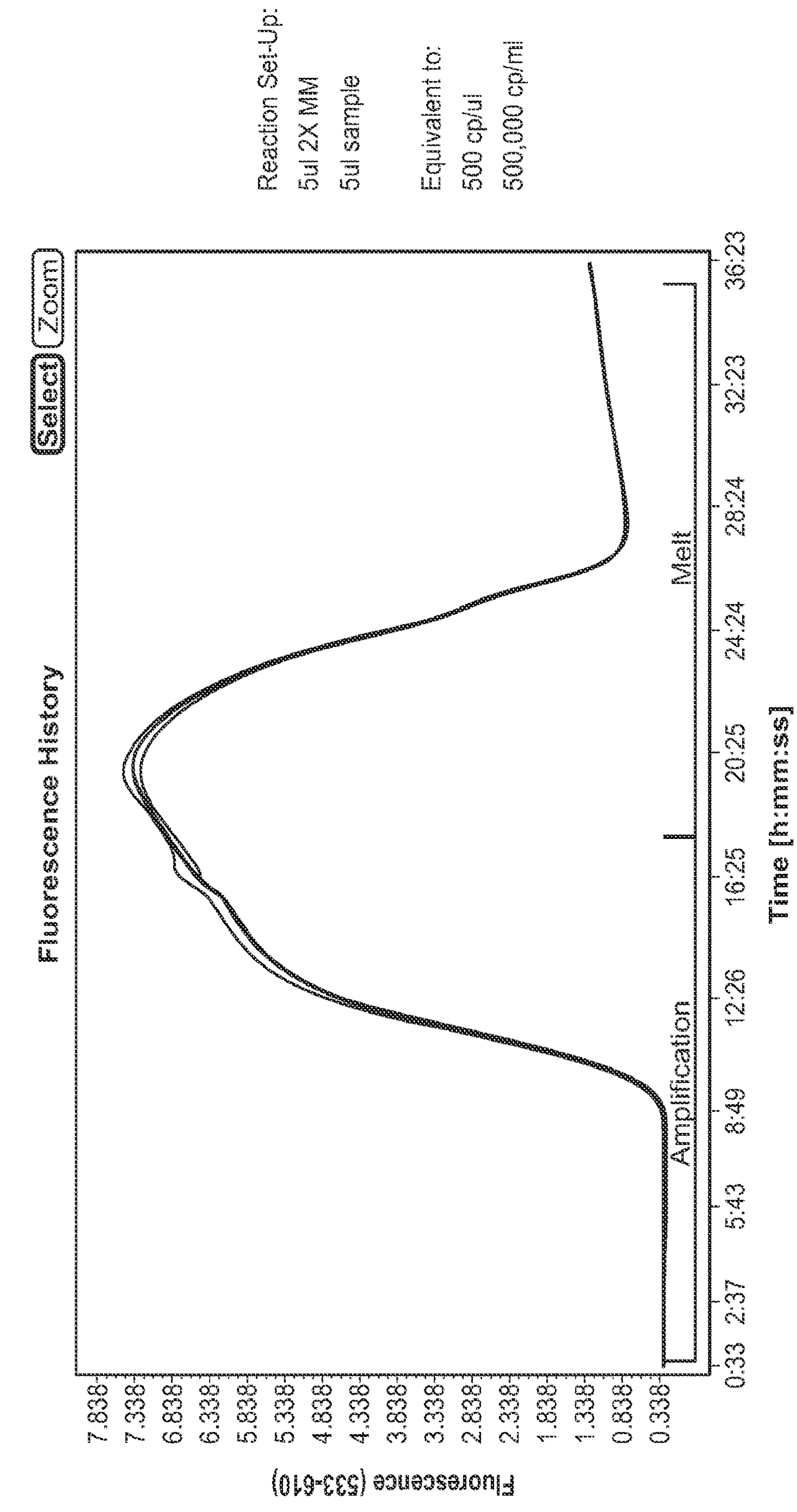
Figure 3P:
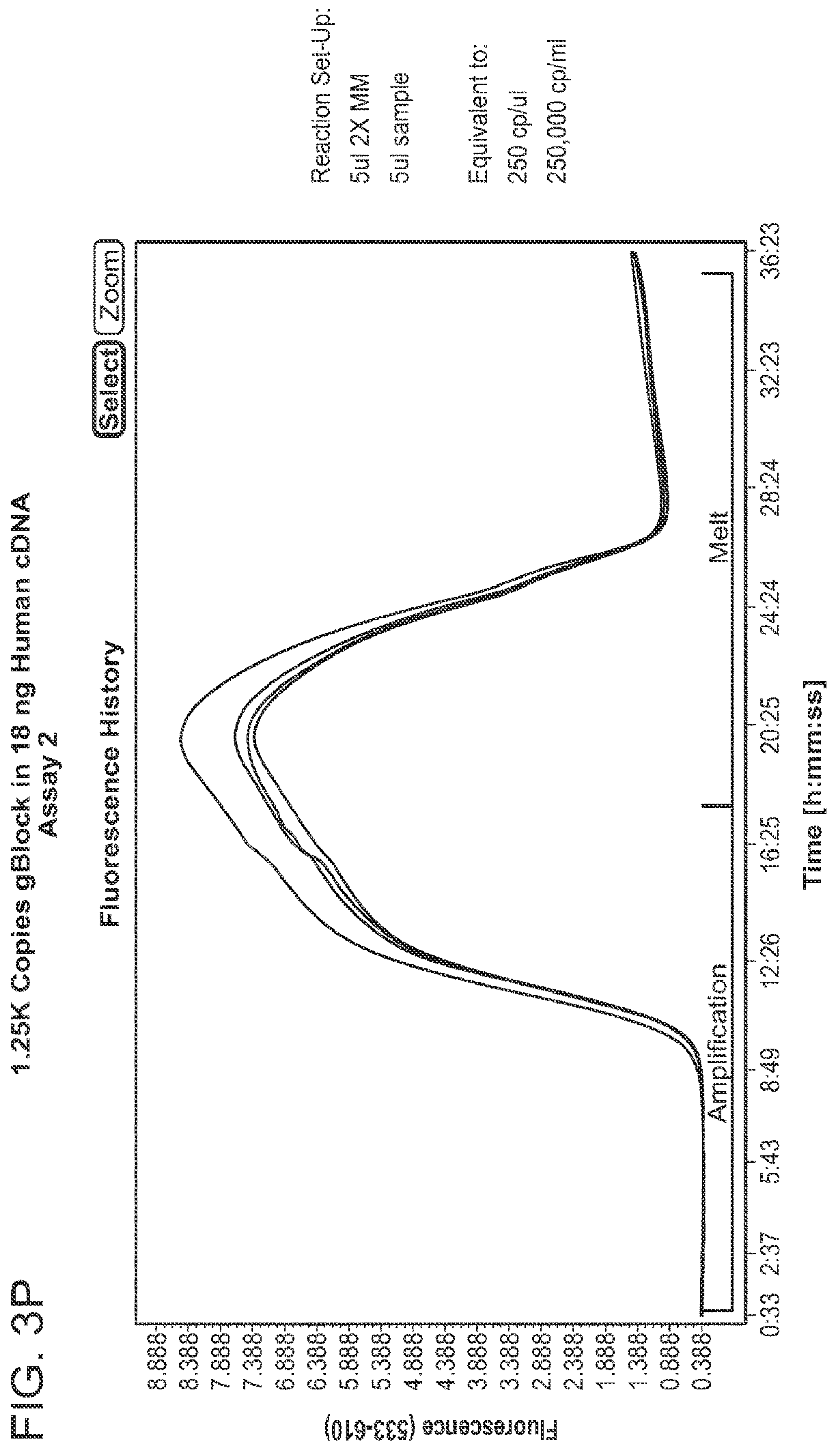
Figure 3Q:
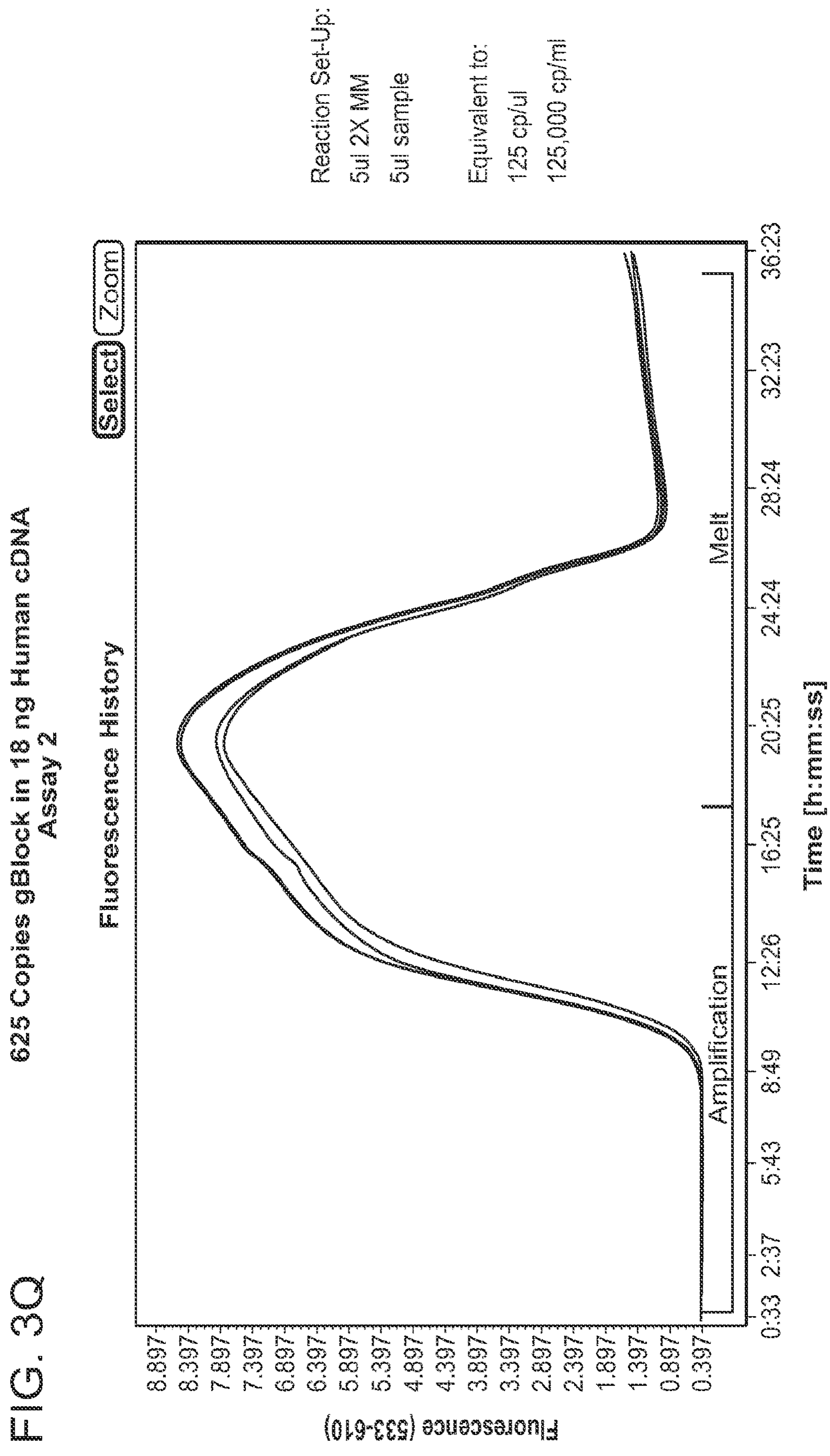
Figure 3R:
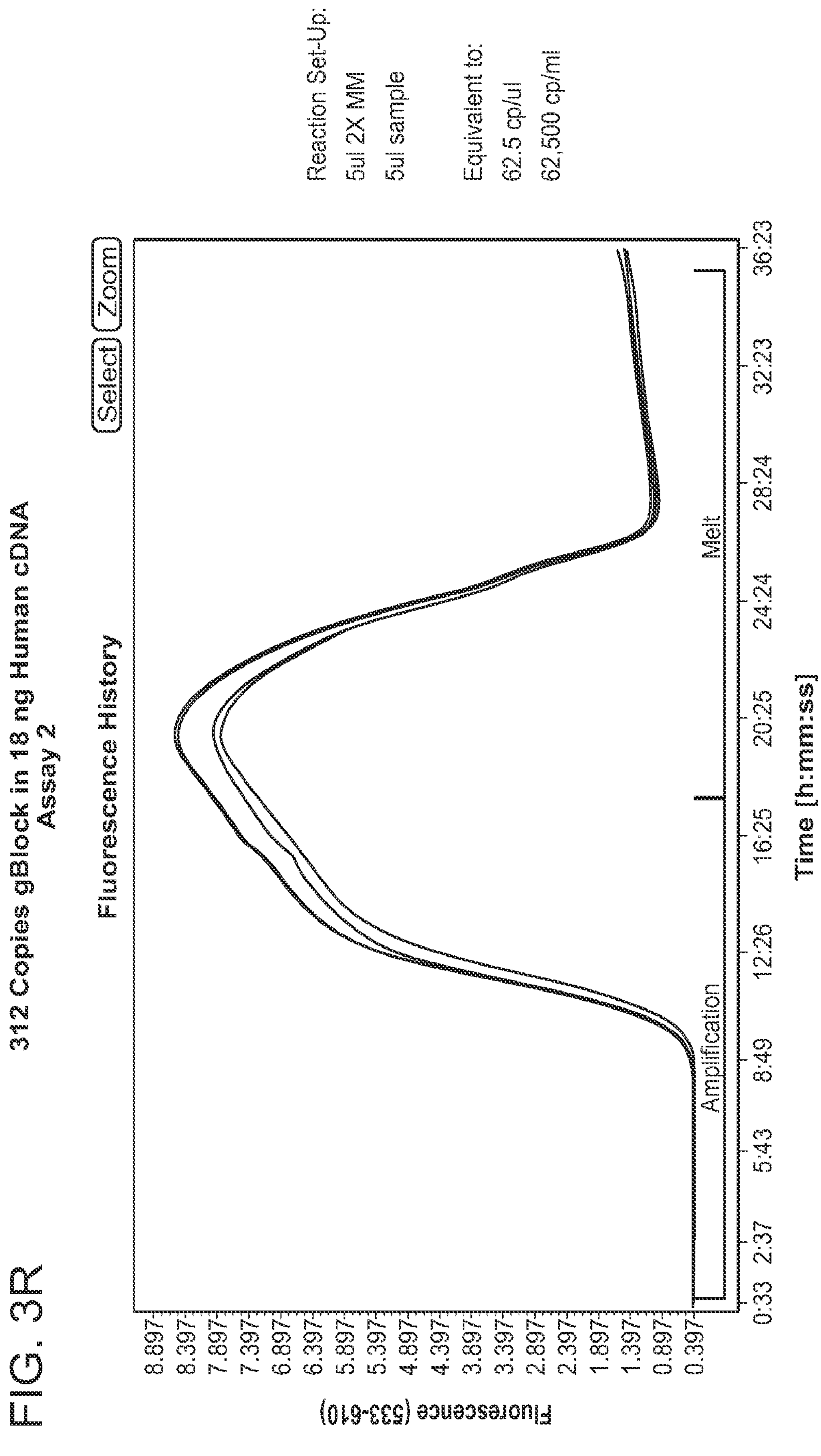
Figure 3S:
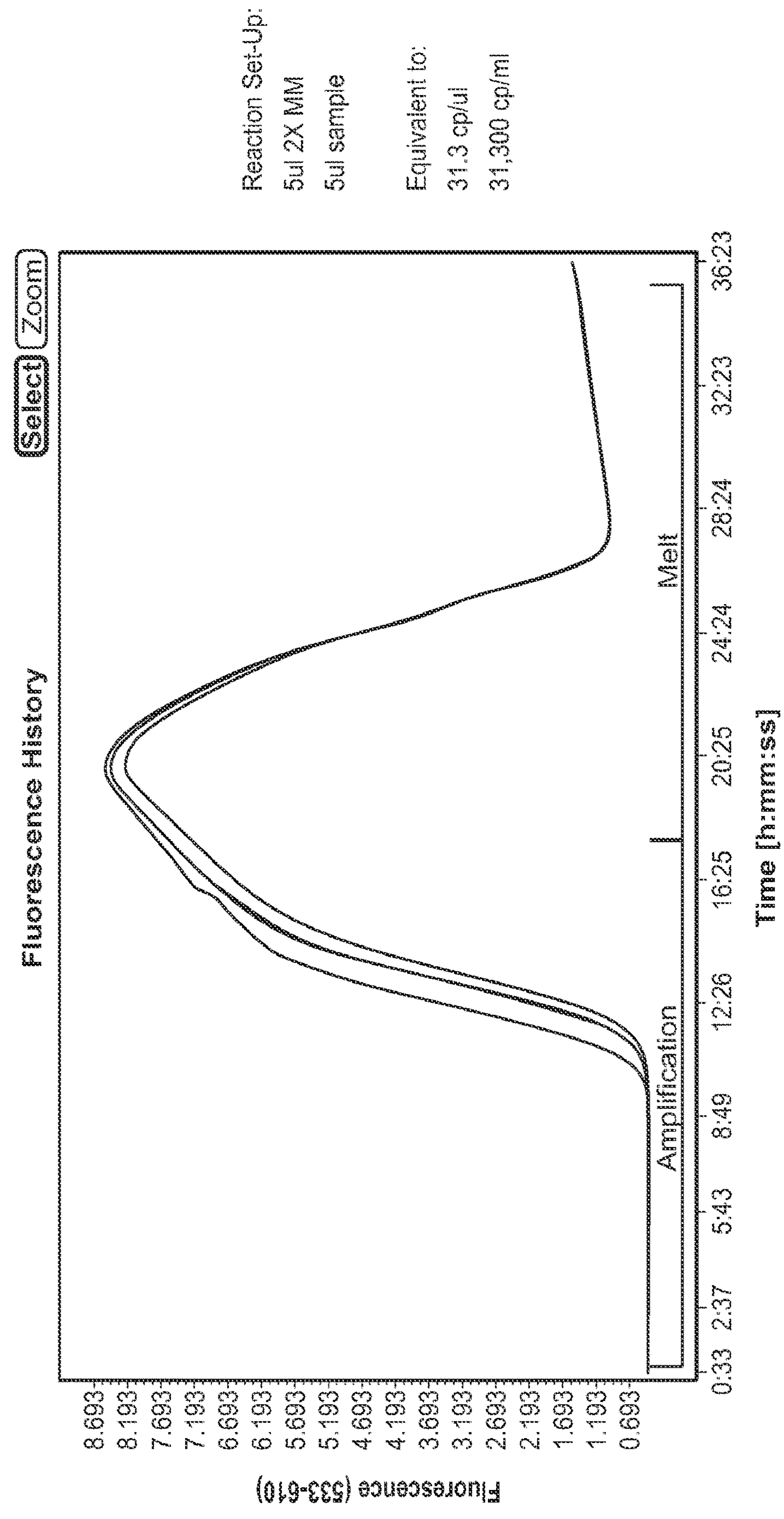
Figure 3T:
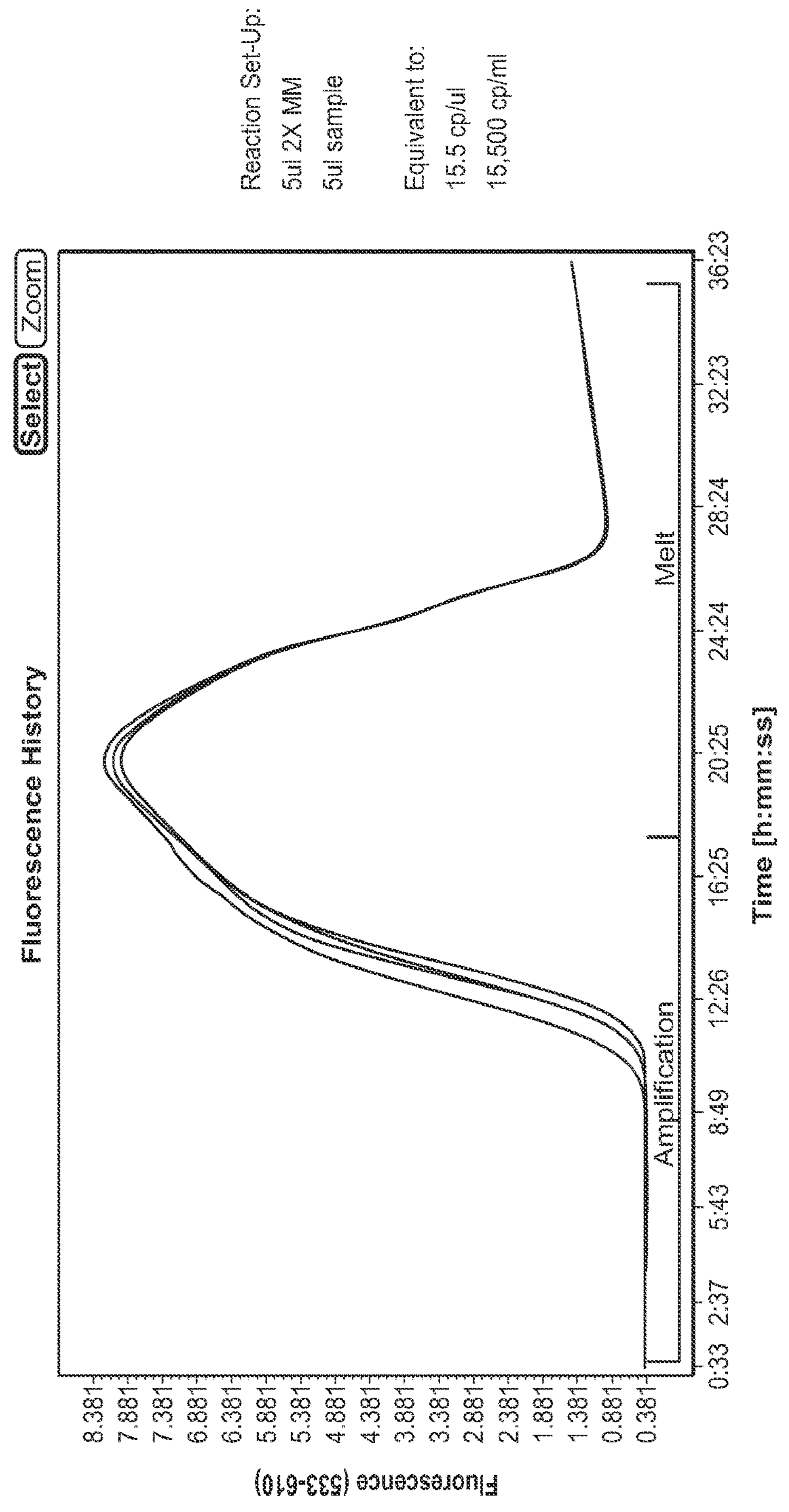
Figure 3U:
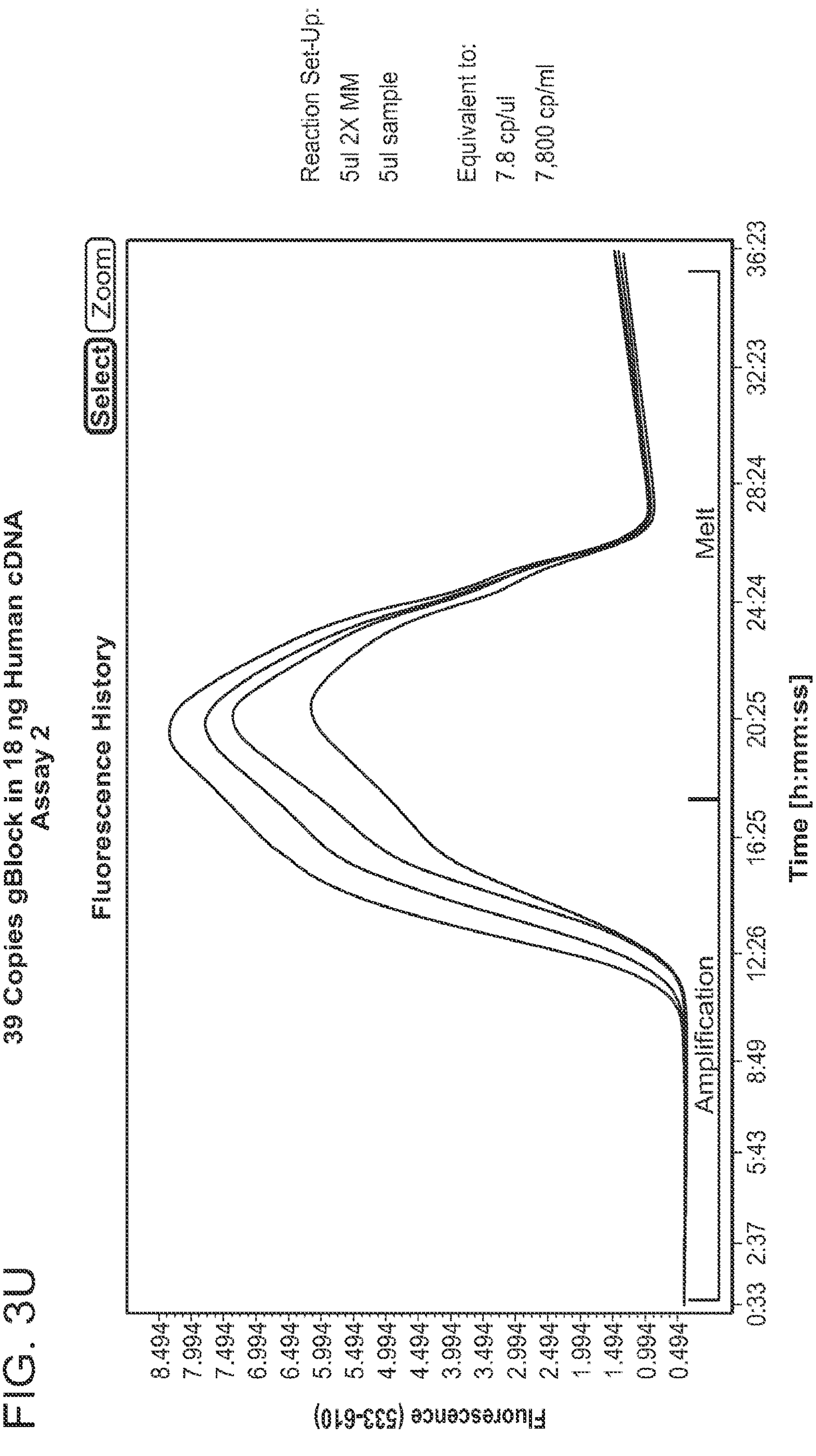
Figure 3V:
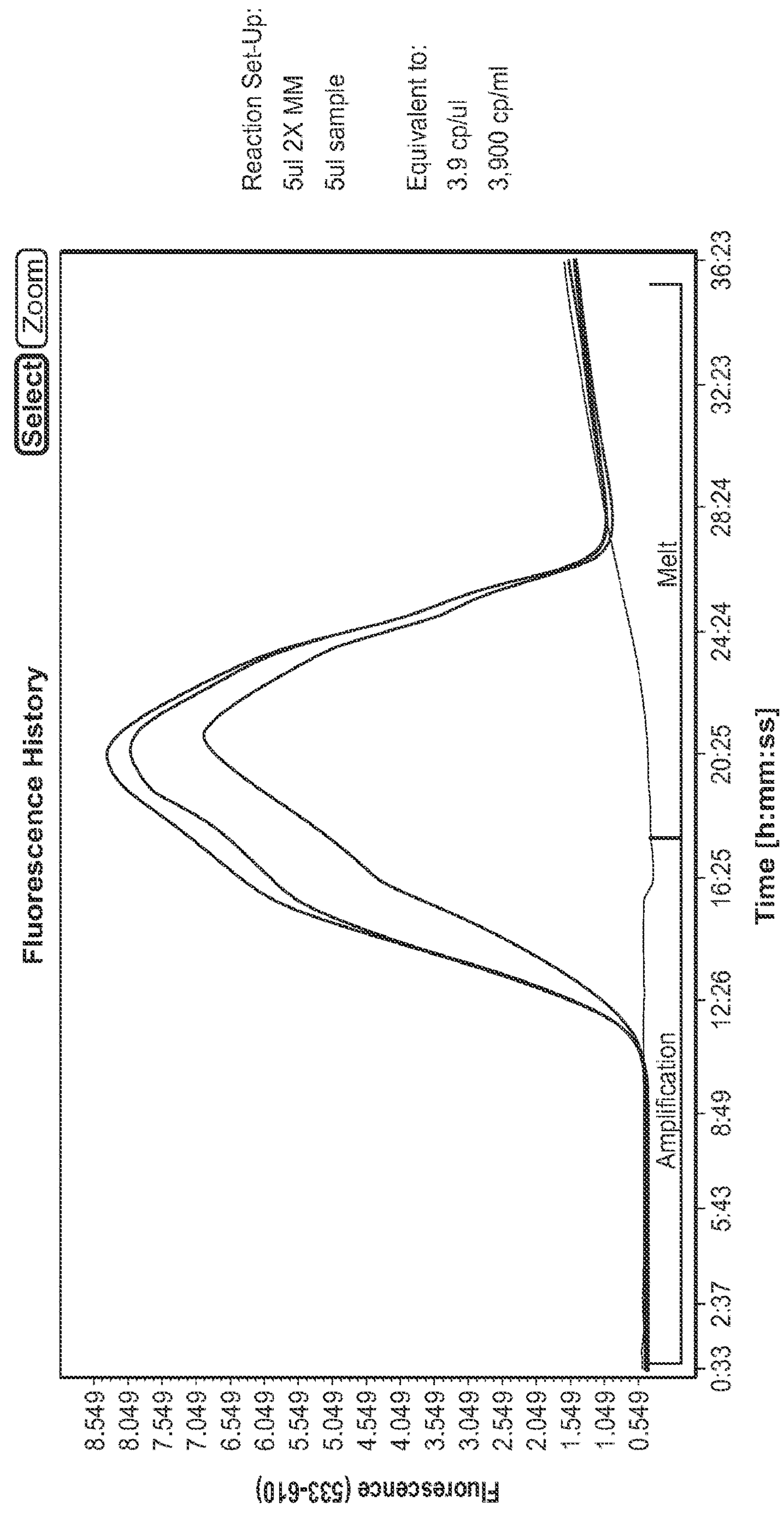
Figure 3W:
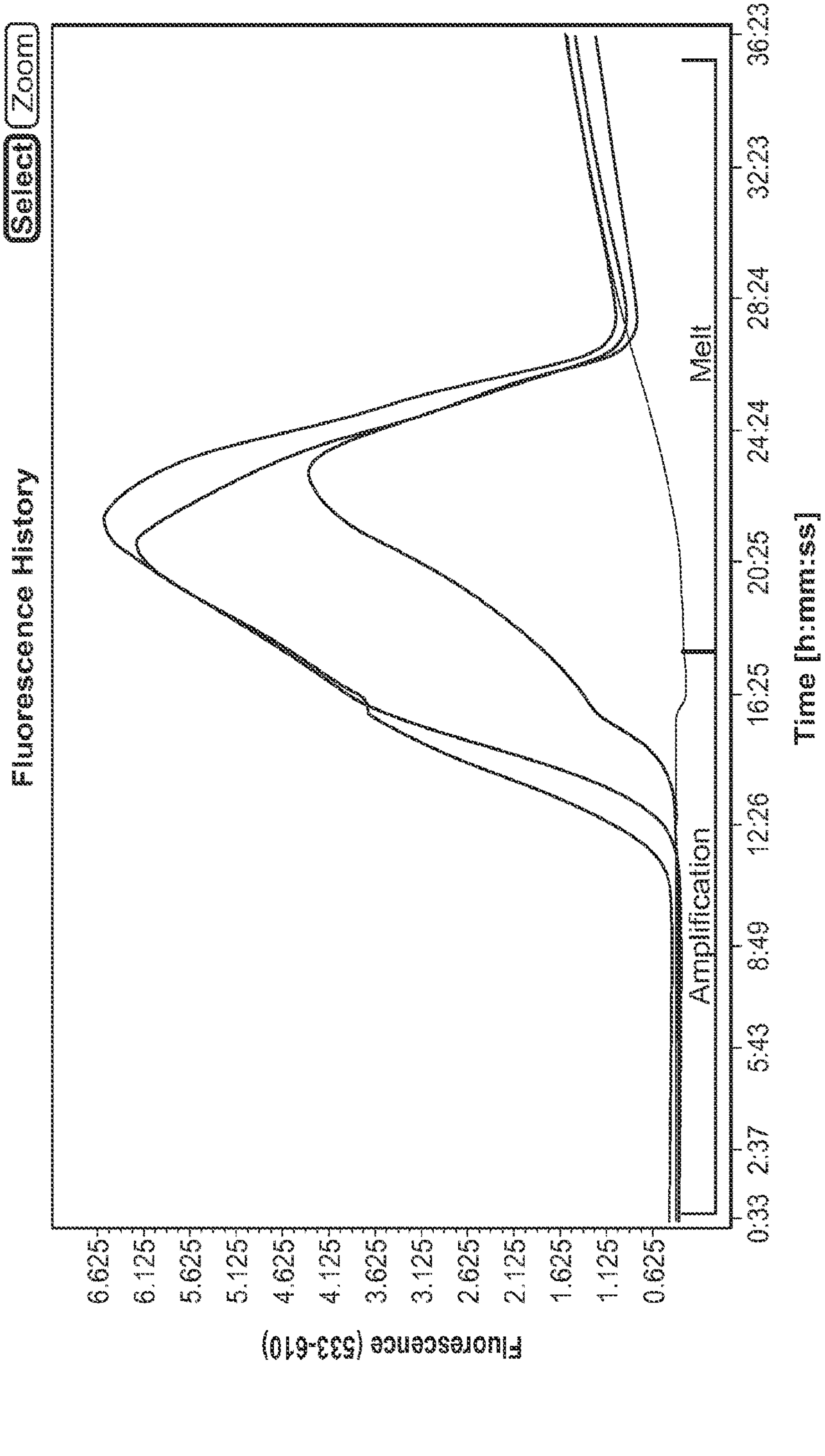
Figure 3X:
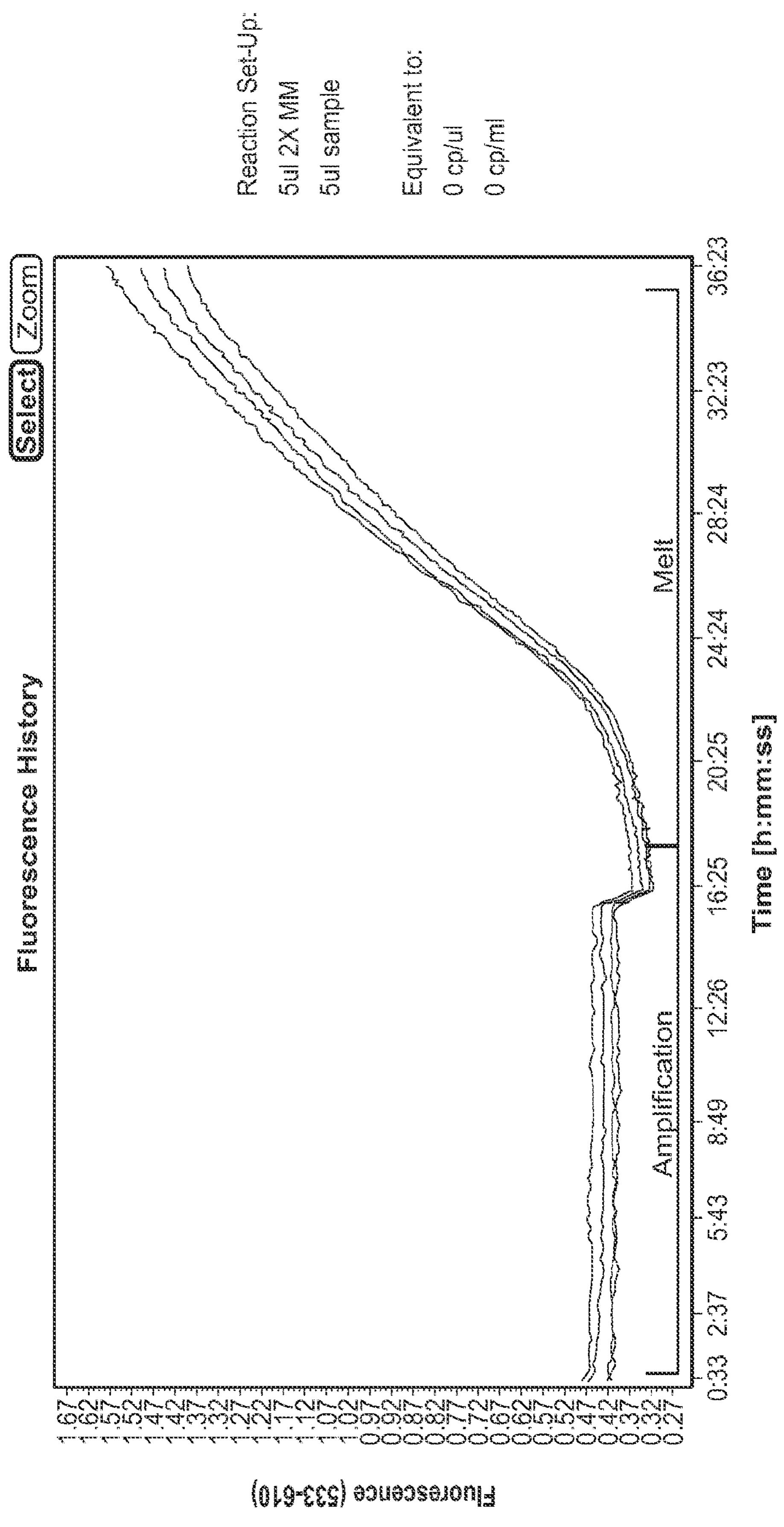

FIGS. 3A-3X show amplification results obtained with Assay 1 and Assay 2. The assays were used to detect copies of EBOV gBlock in a background of human cDNA.

Reaction conditions are specified.

Figure 4:
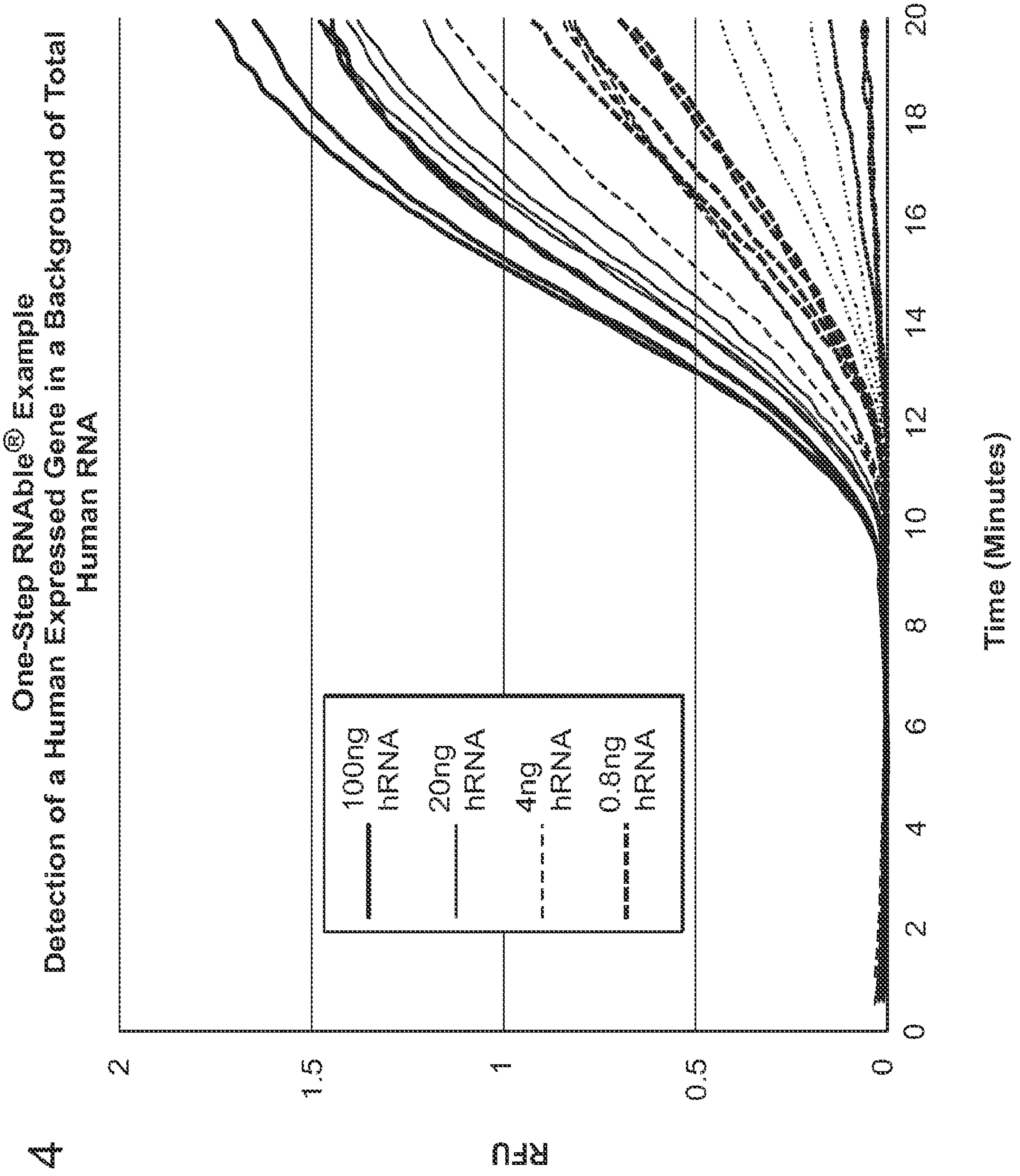
FIG. 4 shows detection of Ebola virus in a background of total human RNA in a one-step assay.

FIG. 4 shows detection of EBOV in a background of total human RNA in a one-step assay.

Figure 5:
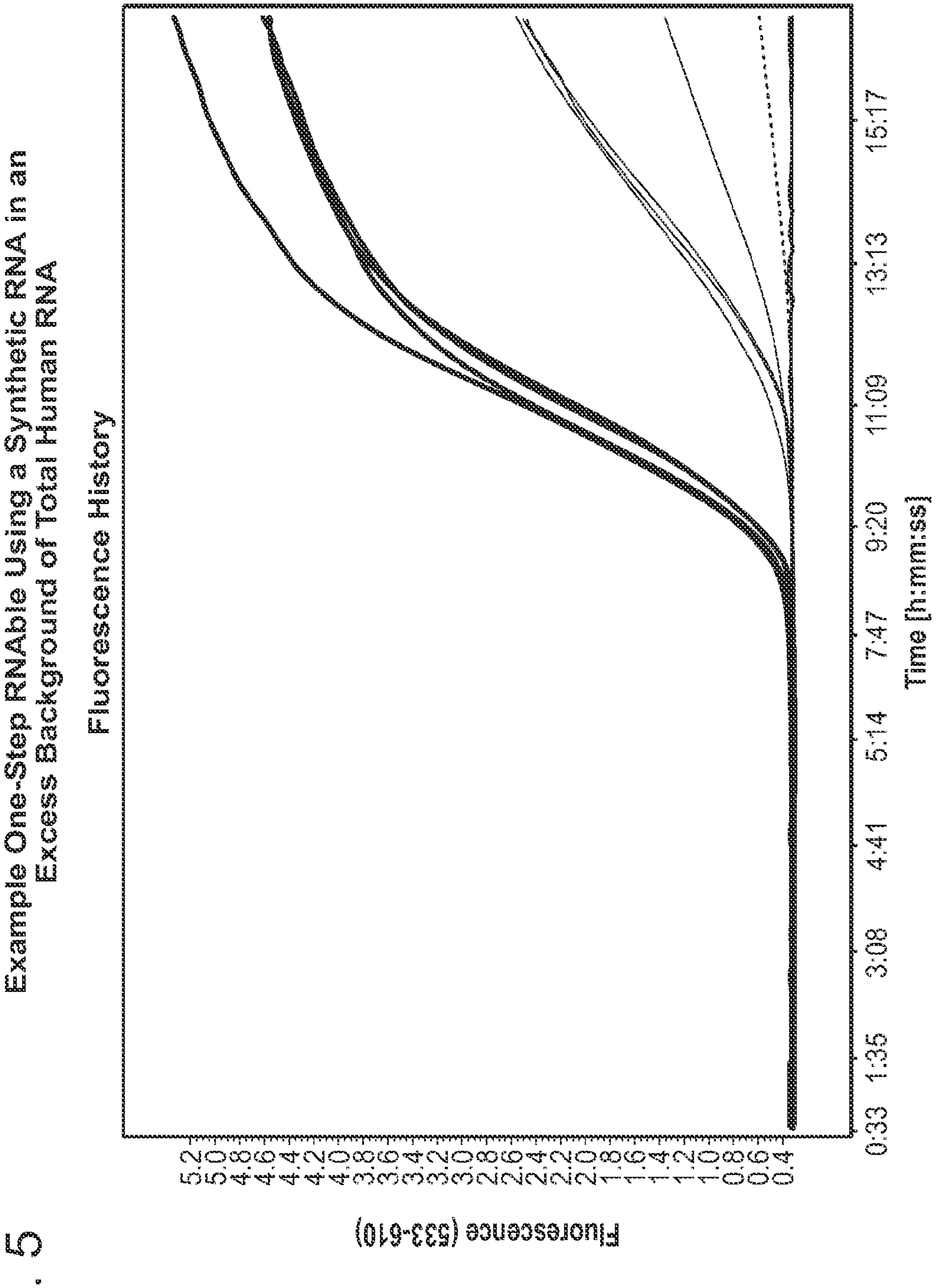
FIG. 5 shows detection of synthetic Ebola virus RNA in a background of total human RNA in a one-step assay.

FIG. 5 shows detection of synthetic EBOV RNA in a background of total human RNA in a one-step assay.

Figure 6A:
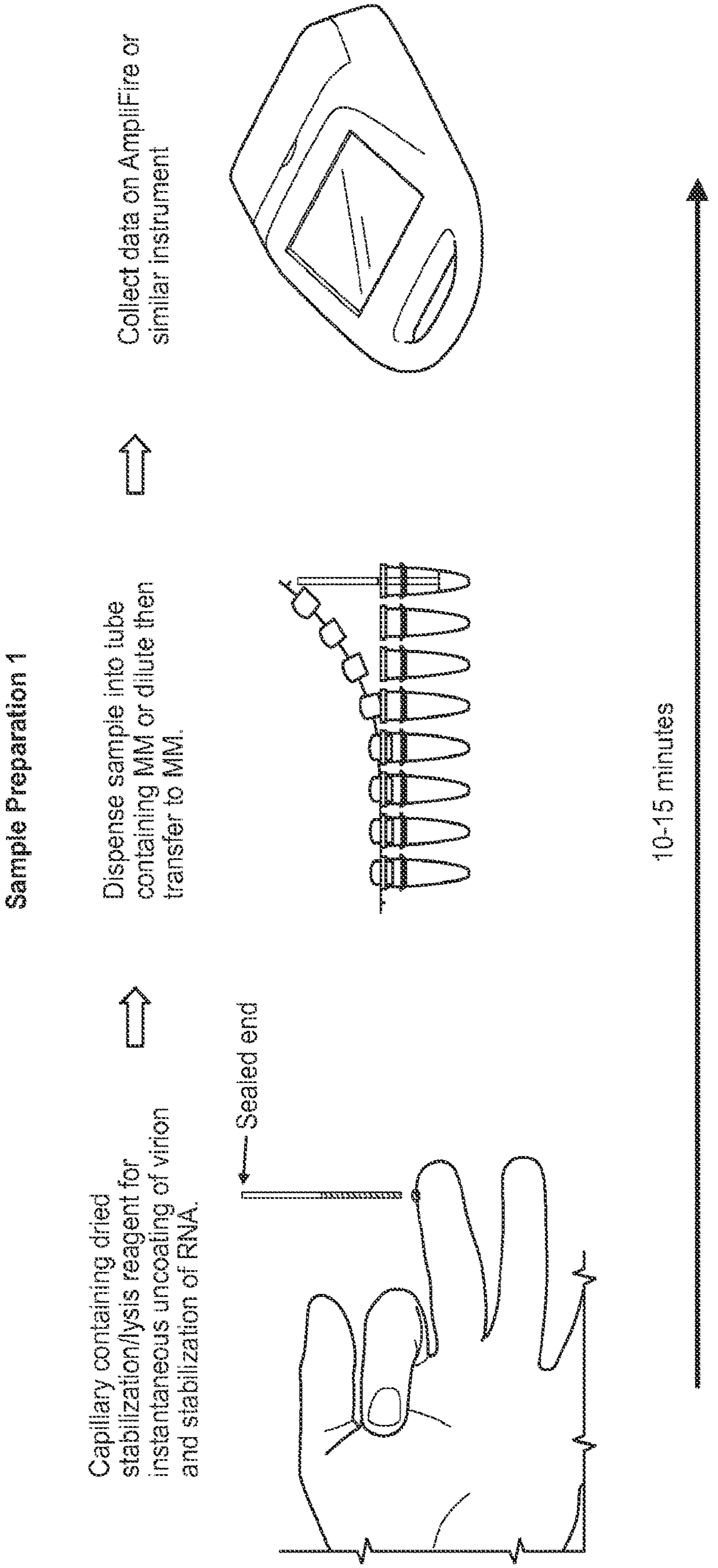
FIGS. 6A-6C provide flow charts illustrating sample processing for use in an amplification and detection instrument, including, for example, a hand-held device.
Figure 6B:
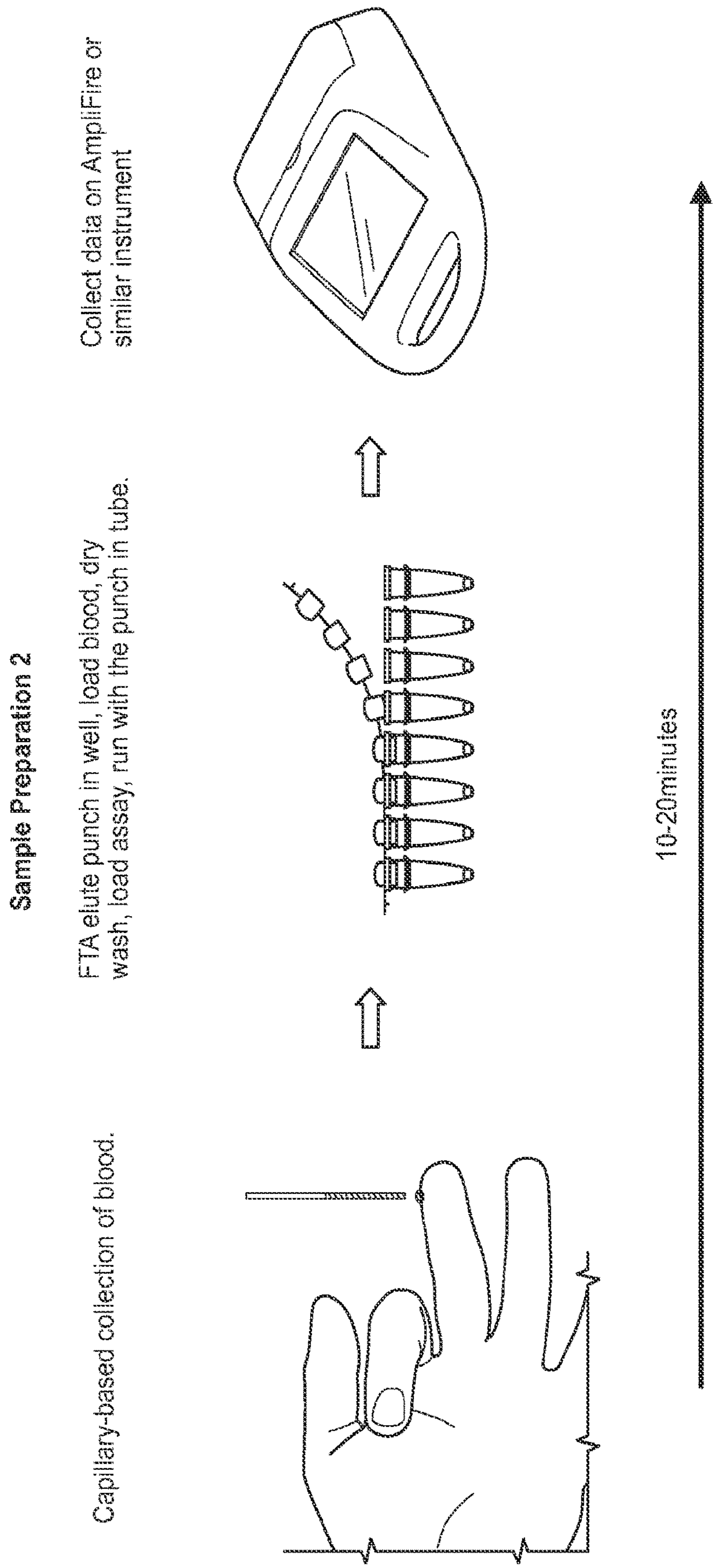
Figure 6C:
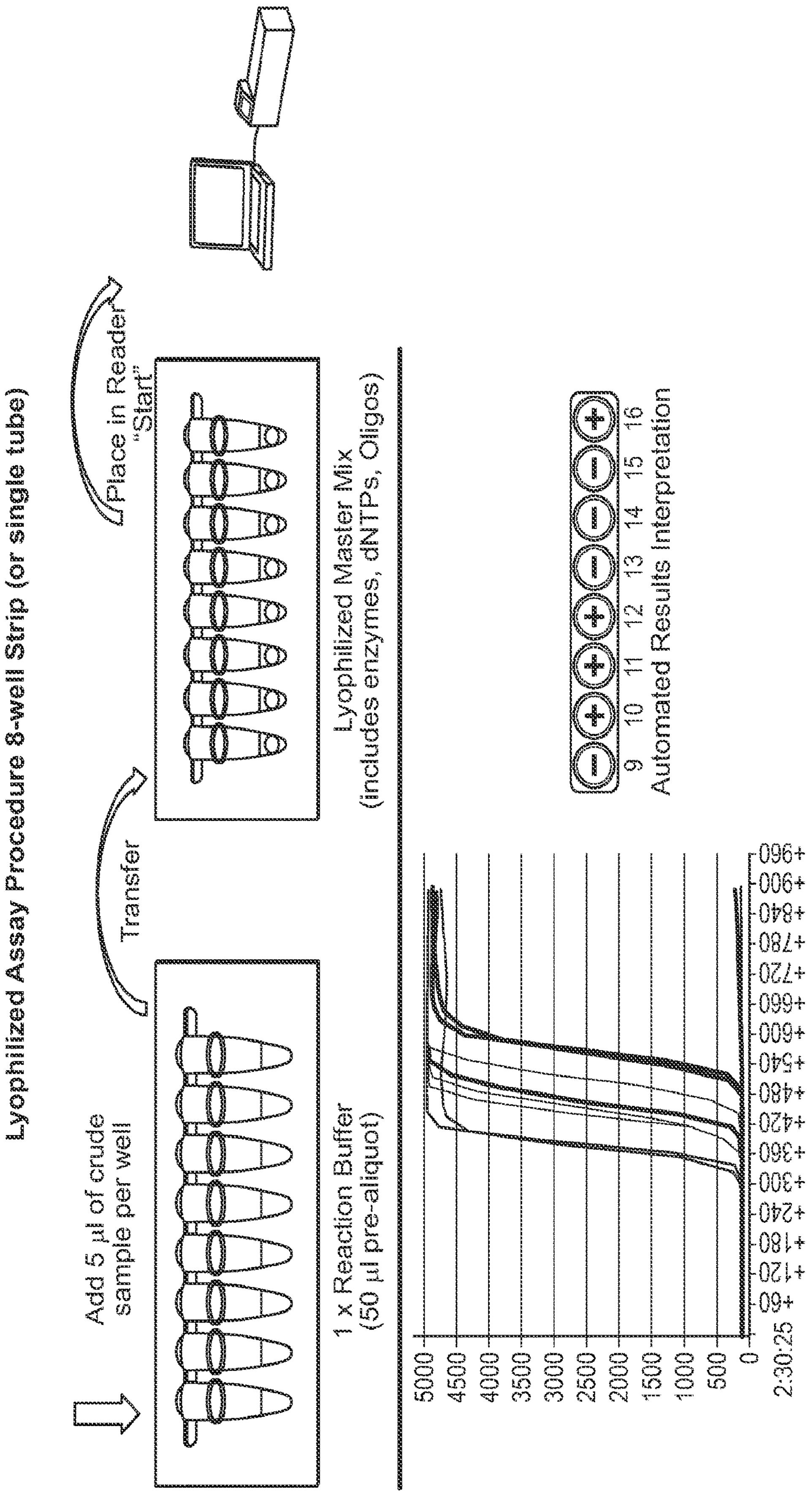

FIGS. 6A-6C provide flow charts illustrating sample processing for use in an amplification and detection instrument.

Figure 7A:
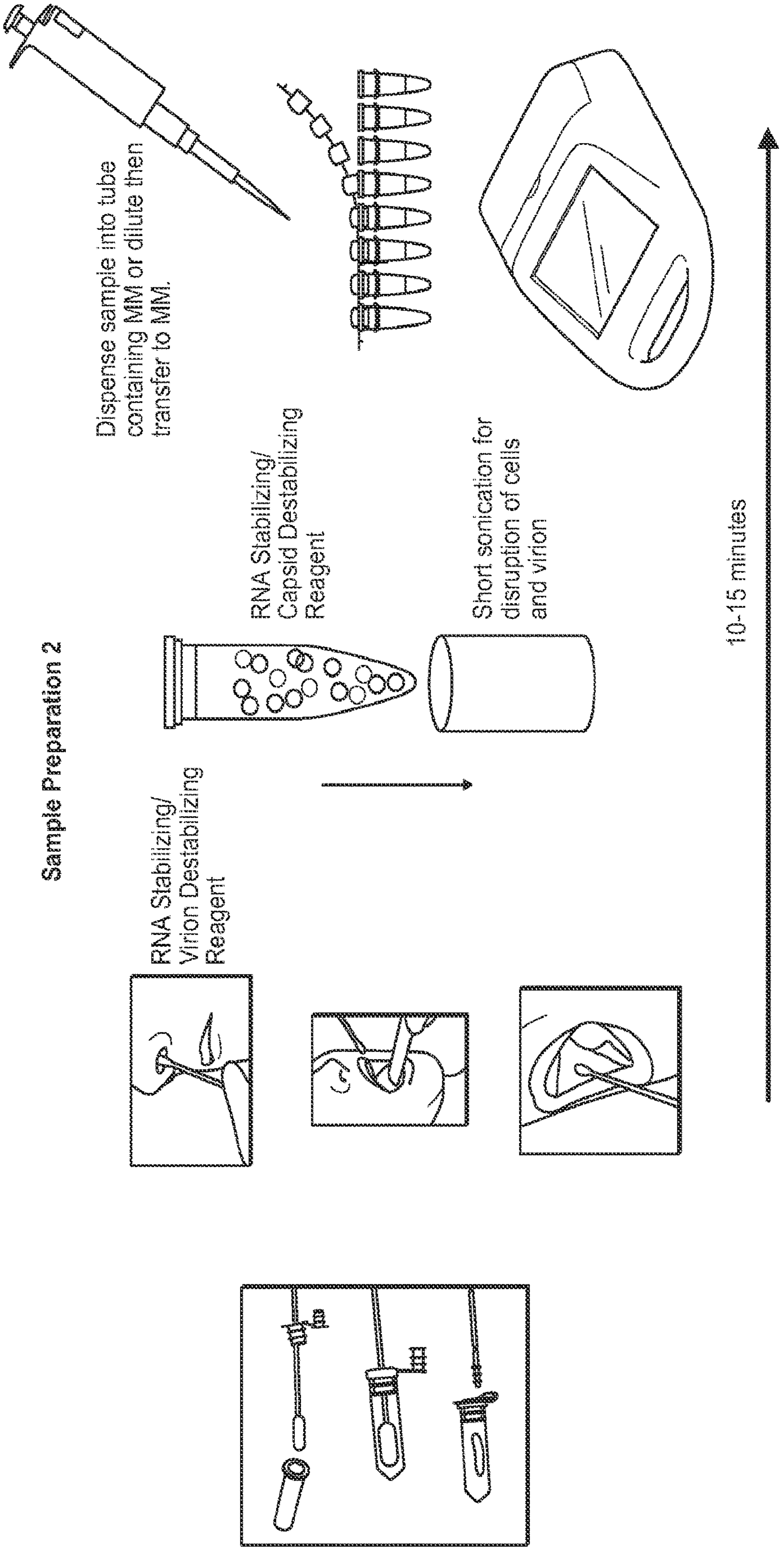
FIGS. 7A and 7B show sample preparation methods.
Figure 7B:
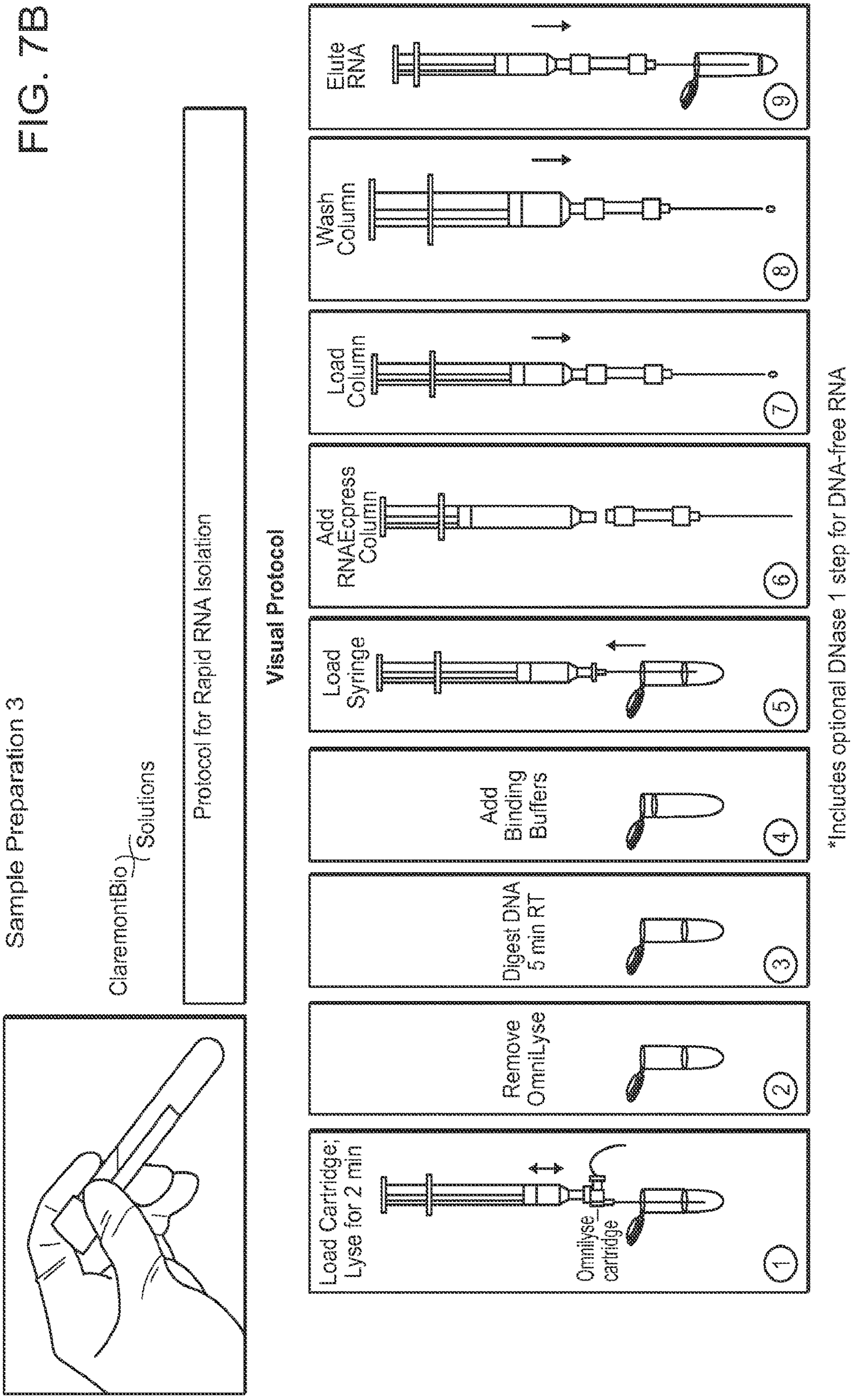

FIGS. 7A and 7B show sample preparation methods from swabs and blood, respectively.

In one working example, Ebola virus was detected using the following primers and probe sequences:

| | | |
|---|---|---|
| Forward Primer | GACTCGATATCGAGTCGCTTCCA[MeOC]AGTTATC [MeOU][MeOA][MeOC][MeOC][MeOG] | SEQ ID NO: 1 |
| Reverse Primer | GACTCGATATCGAGTCGAAATGC[MeOA]ACGA[MeOC] [MeOA][MeOC][MeOC][MeOU] | SEQ ID NO: 2 |
| Probe | gctacACGACTTT**Y**GCTGAAGgtagc | SEQ ID NO: 3 |
| External Primer | CTTCTTAGCTTGGGGCAGTATCA | SEQ ID NO: 36 |

Primers: [MeON] indicates methoxy base
Probe sequence: lowercase = stems, uppercase = recognition
1:5 1000 nM 0.3 U/ul nicking enzyme In the sequences above, GAGTC is the nicking enzyme recognition site. Pyrimidine provides for degeneracy detection of Ebola strains including Zaire.

```
                                              (SEQ ID NO: 37)
Synthetic DNA target:
AAGATGACTGCAGGAGTCAATGCGCAGTTGGTCCCGGCAGACCAGGCGAAC

ATTACCGAATTTTACAACAAGTCCCTTTCATCCTACAAGGAGAATGAGGAG

AACATCCAGTGTGGGGAGAACTTCATGGACATGGAGTGCTTCATGATTCTG

AACCCCAGTCAGCAGCTGGCAATTGCCGTCTTGTCTCTCACACTGGGCACC

TTCACAGTTCTGGAGAACTTGCTGGTGCTGTGTGTCACCACAGTTATCTAC

CGAGGAACGACTTTCGCTGAAGGTGTCGTTGCATTTCTGATTCCTTCACTC

CCGCAGCCTCCGCTGCCGGCCCTCTTACCACTTCATCATTAGCCTGGCCGT

GGCCGACCTTCTGGGGAGTGTCATTTTTGTCTACAGCTTTGTTGACTTTCA

TGTGTTCCACCGCAAGGACAGCCCCAACGTCTTTCTCTTCAAATTGGGTGG

GGTCACCGCCTCCTTCACGGCCTCTGTAGGCAGCCTCTTCC

                                              (SEQ ID NO: 38)
Synthetic RNA target:
rGrArCrUrGrCrArGrGrArGrUrCrUrGrCrUrGrCrUrUrCrCrArCr

ArGrUrUrArUrCrUrArCrCrGrArGrGrArArCrGrArCrUrUrUrCrG

rCrUrGrArArGrGrUrGrUrCrGrUrUrGrCrArUrUrUrCrUrGrArUr

UrCrCrUrUrCrArCrUrCrCrCrG
```

Both 1-step and 2-step reactions contained a final concentration of 166.7 nM forward primer and a final concentration of 833.3 nM reverse primer with 200 nM concentration of Probe and 0.1×SYBR green (final concentration). In addition both 1 and 2 step reactions contained a final concentration of 1×Extract Buffer 2, comprising Tris pH 8.0, $NH_4^+$, $Na^+$, and $Mg^{2+}$; dNTPs; 0.4 U/μl BST polymerase; and 0.3 U/μl Nt.BSTnbi nicking enzyme. In addition to these components; the 1 step reactions contained 10 U/μl of Maxima Reverse Transcriptase enzyme; 1.0 U/μl of an RNAse inhibitor (SUBERase IN by life technologies). Synthetic RNA had 1.0 U/μl of RNAse inhibitor added as well to prevent degradation. All water used was purchased nuclease free.

Figure 8:
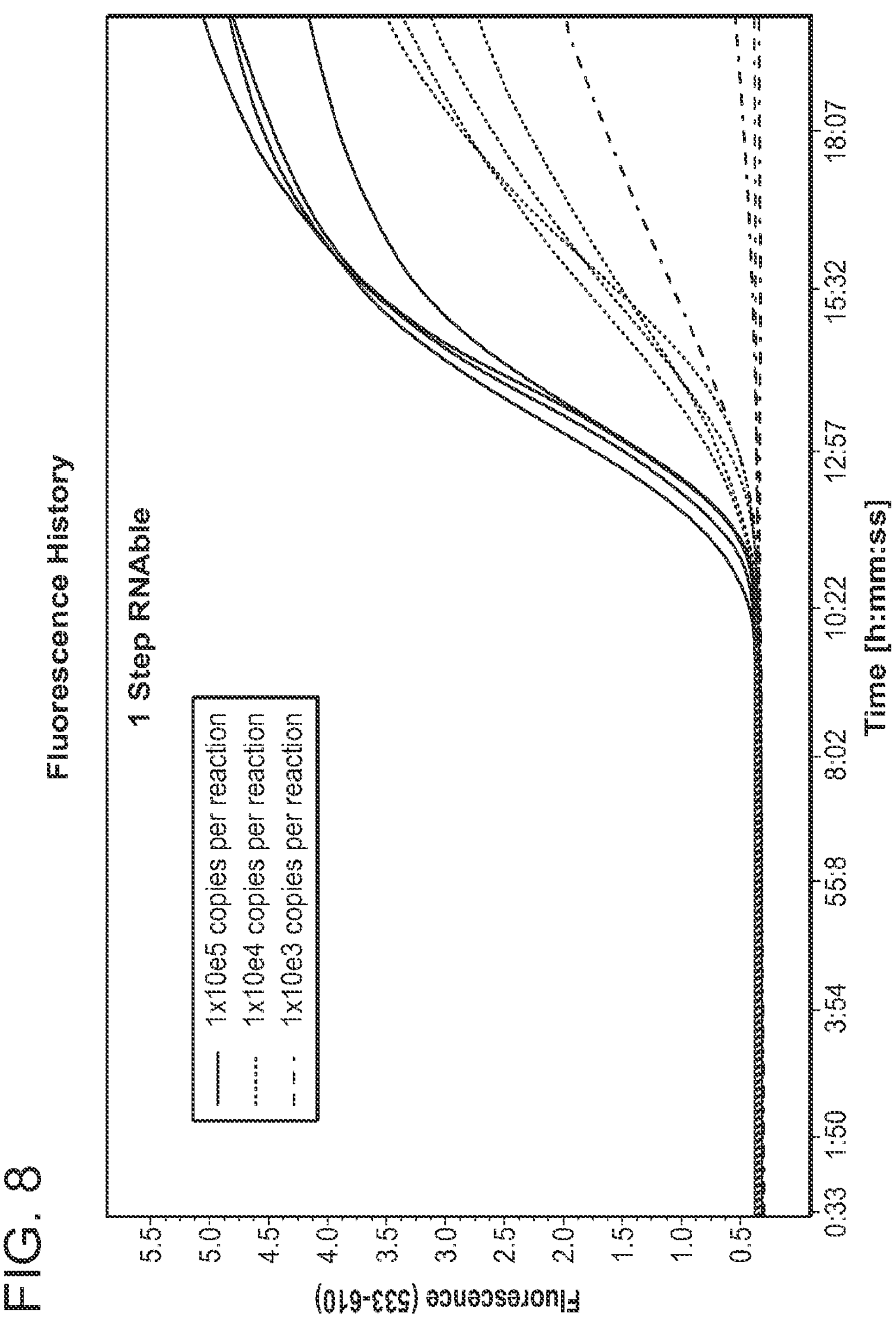
FIG. 8 is a graph showing results obtained in a one-step reaction process where the reverse transcriptase and polymerase are included in a single reaction.

Reactions were mixed on ice and kept cold until run on the Roche LC480. The Roche LC480 was run under a two color detection to detect the calfluor red 610 beacon signal (Abs 590 nm/Em 610 nm) and the SYBR green signal (Abs 495 nm/Em 520 nm). 1-Step reactions were carried out at 56° C. for 20 minutes. Results are shown at FIG. 8.

Figure 9:
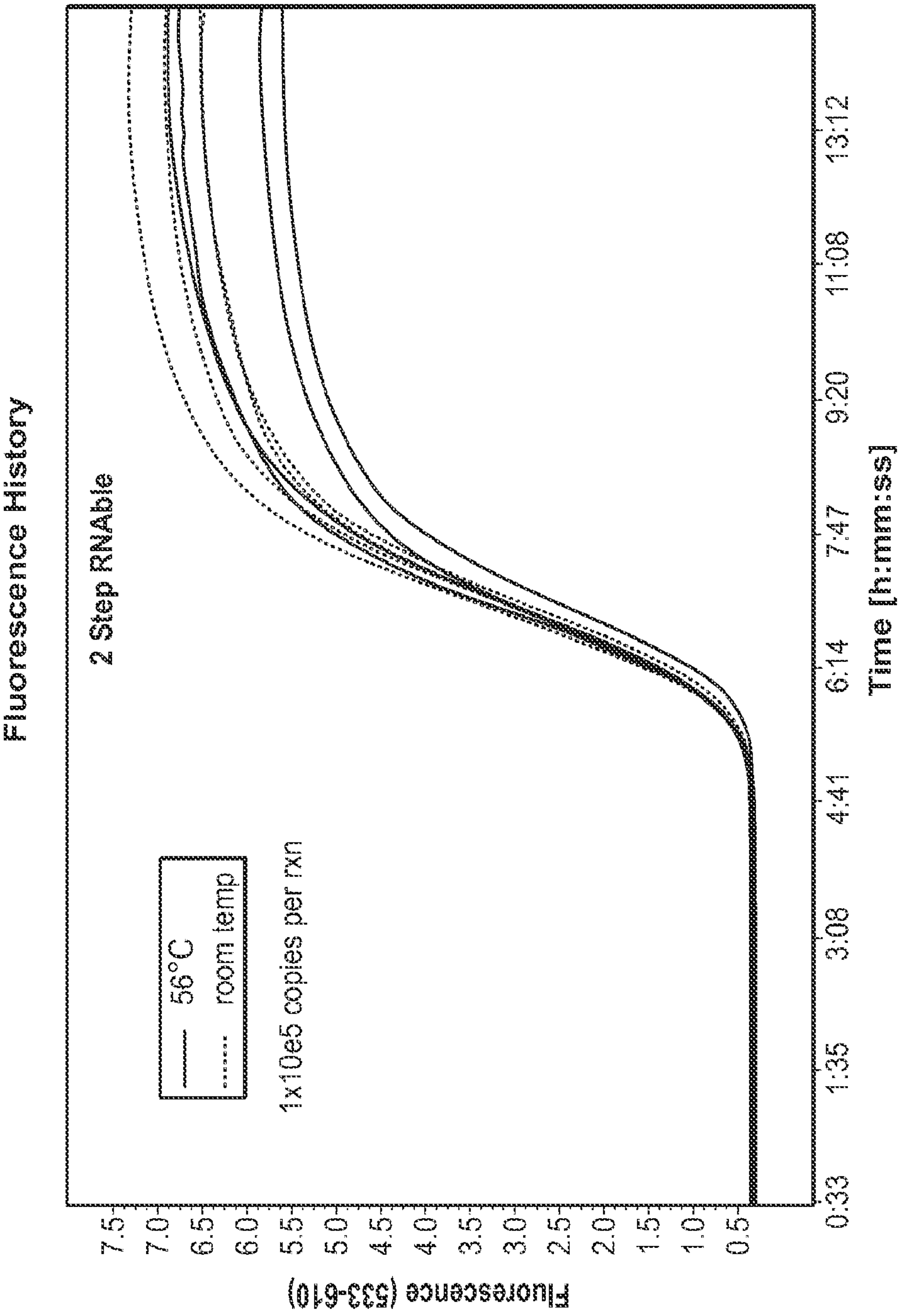
FIG. 9 is a graph showing results obtained in a two-step reaction process where the reverse transcriptase reaction is carried out at room temp or 56° C. and the cDNA is transferred to a second tube where the amplification reaction is carried out at 56° C.
Figure 10:
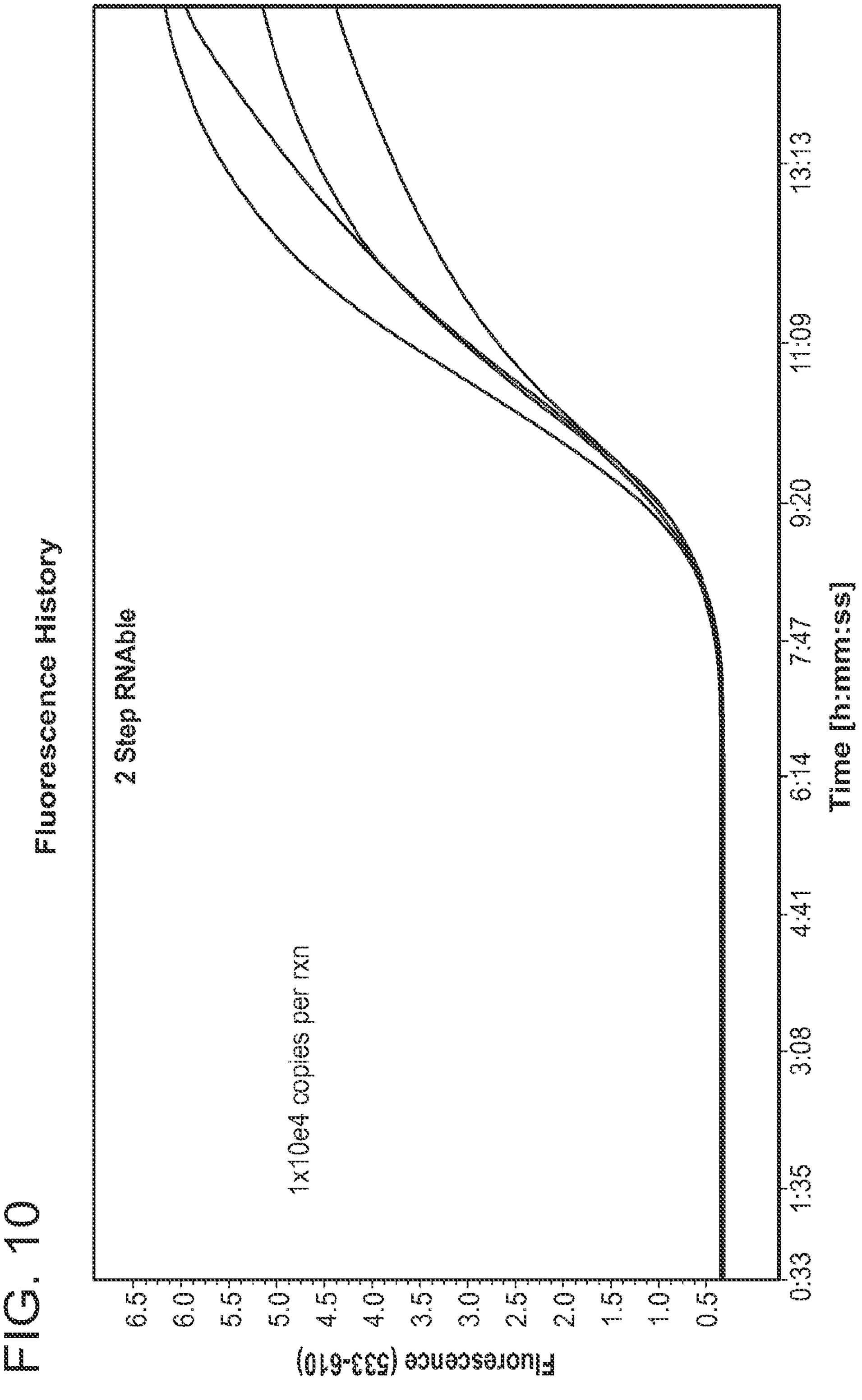
FIG. 10 is a graph showing RT at 56° C., DNAble at 56° C. on $1\times10e^4$ copies.

2-step reactions were carried out with the reverse transcriptase step at 56° C. for 5 minutes (in a heat block) or at room temperature for 5 minutes following the setup condition outlined by New England Biolabs (www.neb.com) (FIG. 9). Both these RT temperatures produced signal for $1\times10^5$ copies of target per reaction. The reverse transcriptase step was followed by an amplification step at 56° C. for 15 minutes on the LC480. Results of this assay are shown at FIG. 10. The copy number indicated per reaction was determined using the suppliers' calculations.

Example 2. Detection of a Target RNA in a Complex RNA Mixture

To determine whether the 1-step and 2-step reactions could detect a target RNA in complex mixtures of RNA molecules, assays were designed for the detection of RPPH1 (RNase P RNA Component) in total human RNA. In one working example, RPPH1 was detected using the following primers and probe sequences:

| | | | |
|---|---|---|---|
| Forward Primer | RPPH1.Fc | GACTCGATATCGAGTCCACGAGCmUG AGTGCmGmUmCmCmUmG | SEQ ID NO: 39 |
| Reverse Primer | RPPH1.Rc | GACTCGATATCGAGTCAGACCTTmCC CAAGGmGmAmCmAmU | SEQ ID NO: 40 |
| Probe | RPPH1.Probe.T | CCACGCCTGTCACTC-CACTCCGCGTGG | SEQ ID NO: 41 |
| External Primer | rpph1extprimR | CCTCTGGCCCTAGTCTCAG | SEQ ID NO: 42 |

Primers: mN indicates methoxy base

Figure 11A:
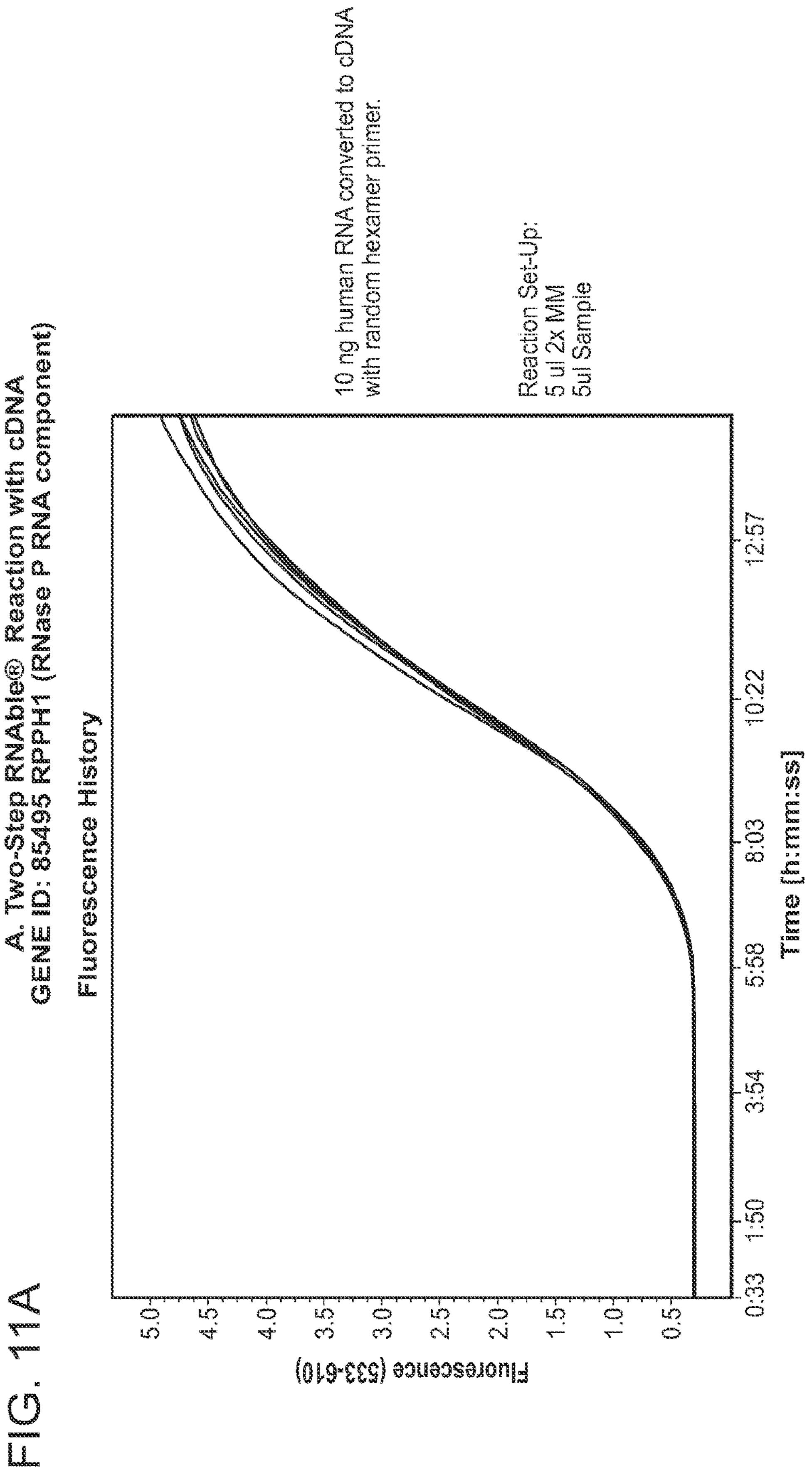
FIGS. 11A and 11B show the detection of a target RNA in a sample containing total cellular RNA.
Figure 11B:
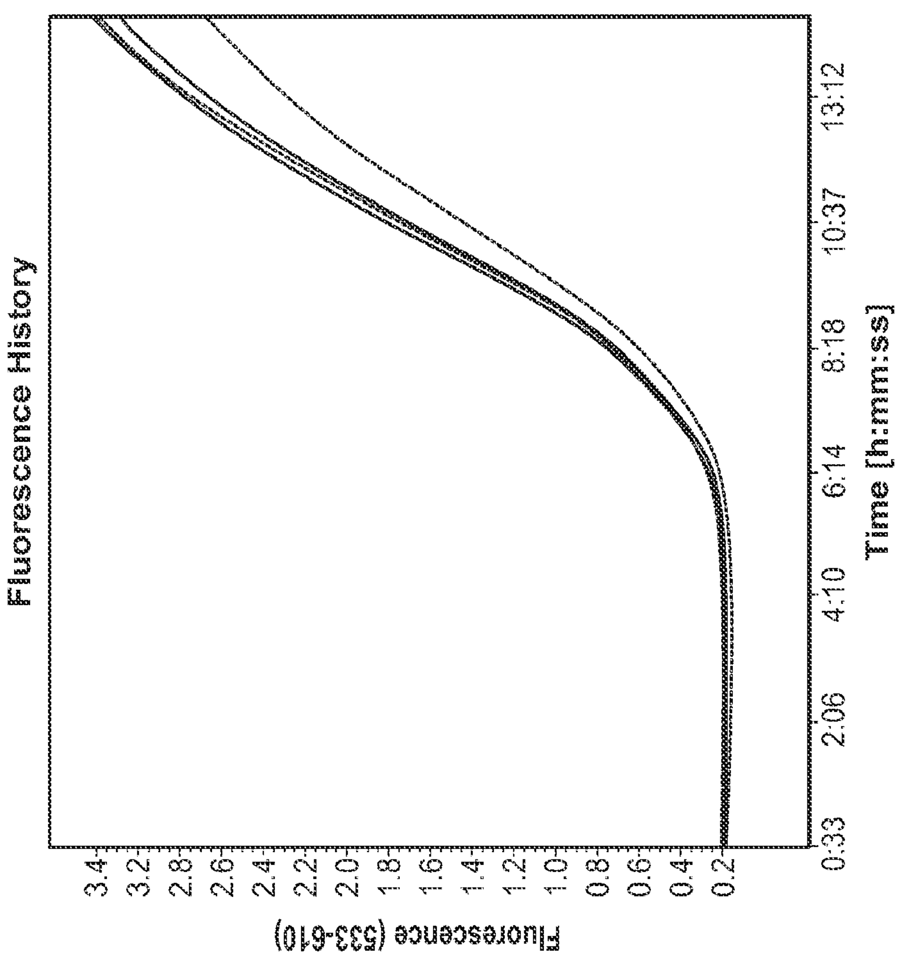

In a 2-step reaction, human RNA (10 ng) was converted to cDNA with random hexamer primer and RPPH1 was detected by amplification of a target specific sequence (FIG. 11A). In a 1-step reaction, human RNA (20 ng) was detected by amplification of a target specific sequence using specific reverse transcription primers (FIG. 11B).

Example 3: Detection of Ebola Virus in a Biological Sample

In another working example, a synthetic Ebola virus RNA target was detected when mixed with a crude blood preparation using the 1-step assay. The crude blood preparation was prepared by mixing whole blood (20 μl) and sodium dodecyl sulfate (0.5% SDS; 20 μl) and incubating the mixture at room temperature (3 min.). After incubation, bovine serum albumin was added (2% BSA; 20 μl) and the resulting mixture was incubated at room temperature (1 min.). The crude blood preparation (1 μl) was spiked with a synthetic Ebola virus RNA target (1000 copies). Reactions were run in triplicate at 56° C. on a Roche LC480. Results are shown at FIG. 12.

In an additional experiment, the 1-step assay was able to distinguish between Zaire Ebolavirus Mayinga and Sudan Ebolavirus Boniface RNA molecules. Vero E6 cells were infected with Zaire Ebolavirus Mayinga or Sudan Ebolavirus Boniface virus and viral RNAs were purified. Sets of reactions were run using purified RNA Zaire Ebolavirus Mayinga (683 copies) or Sudan Ebolavirus Boniface virus (650 copies). For each set, quadruplicate reactions (10 μl) were run on a Roche LC480. The assay detected Zaire Ebolavirus Mayinga RNA (FIG. 13; set of curves denoted A) and did not detect Sudan Ebolavirus Boniface RNA (FIG. 13; set of curves denoted B). Thus, the Zaire Ebola assay was specific for the detection of Zaire Ebola Mayinga.

Figure 14:
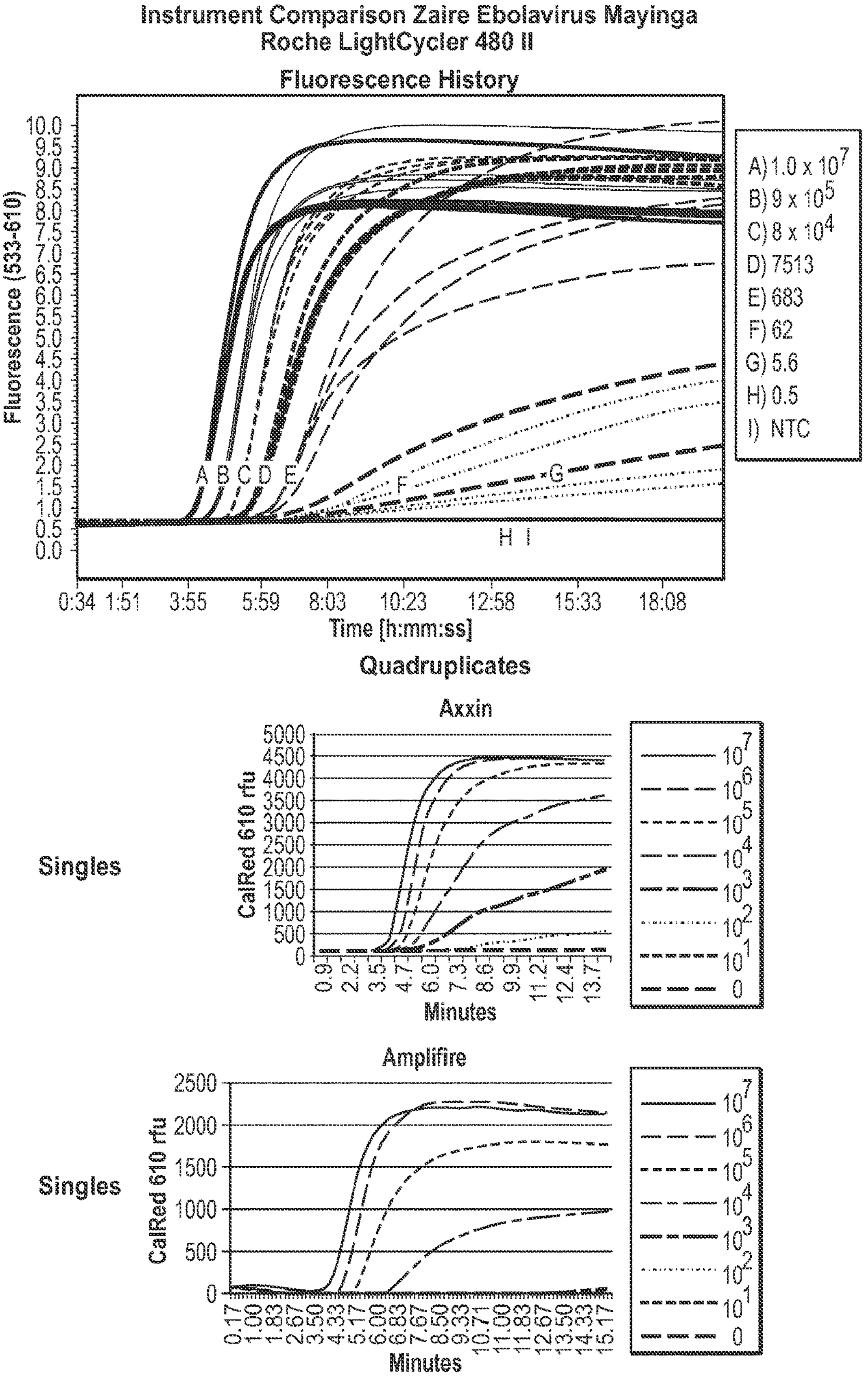
FIG. 14 are graphs depicting instrument comparison for the detection of various dilutions of Zaire Ebolavirus Mayinga.

An instrument comparison was run using various dilutions of Zaire Ebolavirus Mayinga RNA from about $10^1$-$10^7$ copies of target RNA, including a no target control (NTC) sample. Instruments tested included the Roche Lightcycler 480 II, Axxin Detector, and Douglas Scientific Amplifire amplification and detection instruments. While some instrument variability was observed, all instruments could detect copies of EBOV RNA over a wide range (FIG. 14).

Figure 15:
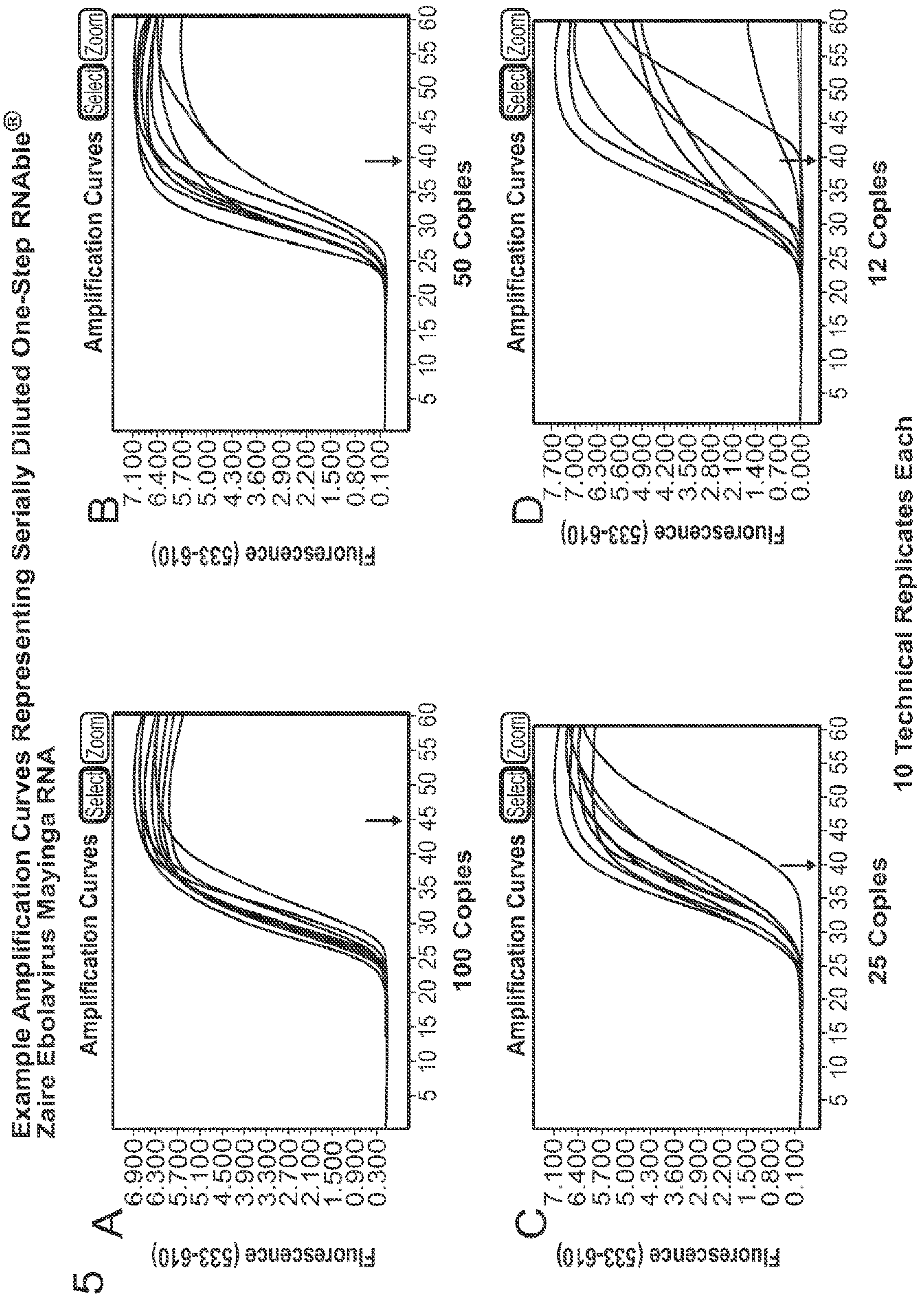
FIGS. 15A-15D depict the limit of detection of the Ebola virus assay.

To determine a lower limit of detection for the 1-step EBOV assay, serially diluted samples containing 100, 50, 25, and 12 copies of Zaire Ebolavirus Mayinga RNA were tested. The 1-step reactions (10 μl) were run on the Roche LightCycler 480 using at least 10 technical replicates for each dilution. Twenty (20) technical replicates were run for the 100 and 50 copy reactions. Forty (40) technical replicates were run for the 25 copy reactions. A 100% (20/20) detection rate was observed for the detection of 100 and 50 copies per reaction (FIGS. 15A and 15B). A 95% (38/40) detection rate was observed for the detection of 25 copies per reaction (FIG. 15C). Thus, these results show the sensitivity and specificity of the EBOV assay, even when performed as a 1-step assay.

Example 4: Detection of Human Immunodeficiency Virus (HIV) in a Biological Sample In one working example, human immunodeficiency virus (HIV) was detected in a 1-step RNAble® assay targeting a gag protein sequence. Purified HIV RNA (subtype C) was obtained (SeraCare), and known quantities of the HIV RNA, as quantified by COBAS TaqMan HIV-1 v2.0 test, were tested in the 1-step HIV RNAble® assay. The following primers and probe sequences were used:

Hgag (HIV gag target)

| Primer | Sequence | SEQ ID NO |
|---|---|---|
| Hgag.F2a | GACTCGATATCGAGTCTGACTAGmCGGAGGmCmTmAmGmAmAmG | SEQ ID NO: 6 |
| Hgag.F2b | GACTCGATATCGAGTCTGACTAGmCAGAGGmCmTmAmGmAmAmG | SEQ ID NO: 7 |

-continued

| Hgag (HIV gag target) | | |
|---|---|---|
| Primer | Sequence | SEQ ID NO |
| Hgag.R1a | GACTCGATATCGAGTCTATTGACmGCTCmTmCmGmCmAmC | SEQ ID NO: 8 |
| Hgag.R1b | GACTCGATATCGAGTCTACTGACmGCTCmTmCmGmCmAmC | SEQ ID NO: 9 |
| Hgag.rt3.subC* | GCATCTAATTTTTCGCC (external primer) | SEQ ID NO: 43 |
| Hgag.probe.T | cgcaagGGAGAGAGATGGGTGcttgcg | SEQ ID NO: 10 |

Primers: mN indicates methoxy base
Probe sequence: lowercase = stems, uppercase = recognition
*External primer sequence is specific to HIV subtype C (for the purified RNA sample used)

FIG. 16A is a map of the amplicon showing the locations of the sequences used. The sequence of the external primer was specific to HIV subtype C (for the purified RNA sample used). The 1-step HIV RNAble® assay was designed with two sets of forward and reverse primers to account for sequence variations in the population. In the sequences above, GAGTC is the nicking enzyme recognition site.

The 1-step reactions contained a final concentration of 9 nM forward primer (1:1 mix of Hgag.F2a+Hgag.F2b) and a final concentration of 91 nM reverse primer (1:1 mix of Hgag.R1a+Hgag.R1b) in a primer ratio of about 1:10 forward to reverse primers. Final concentrations of 200 nM probe and 100 nM external primer were used. In addition, the 1 step reactions contained a final concentration of 1×Run Buffer, comprising Tris, $K^+$, and $Mg^{2+}$; Guanidinium thiocyanate (GITC); dNTPs; 0.4 U/μl BST polymerase; and 0.3 U/μl Nt.BSTnbi nicking enzyme. In addition to these components; the 1 step reactions contained 0.2 U/μl of AMV Reverse Transcriptase High Spec Activity XL (Life Sciences Advanced Technologies) and 0.5 U/μl of an RNAse inhibitor (Superasin; Thermo Fisher). All water used was nuclease free.

Figure 16B:
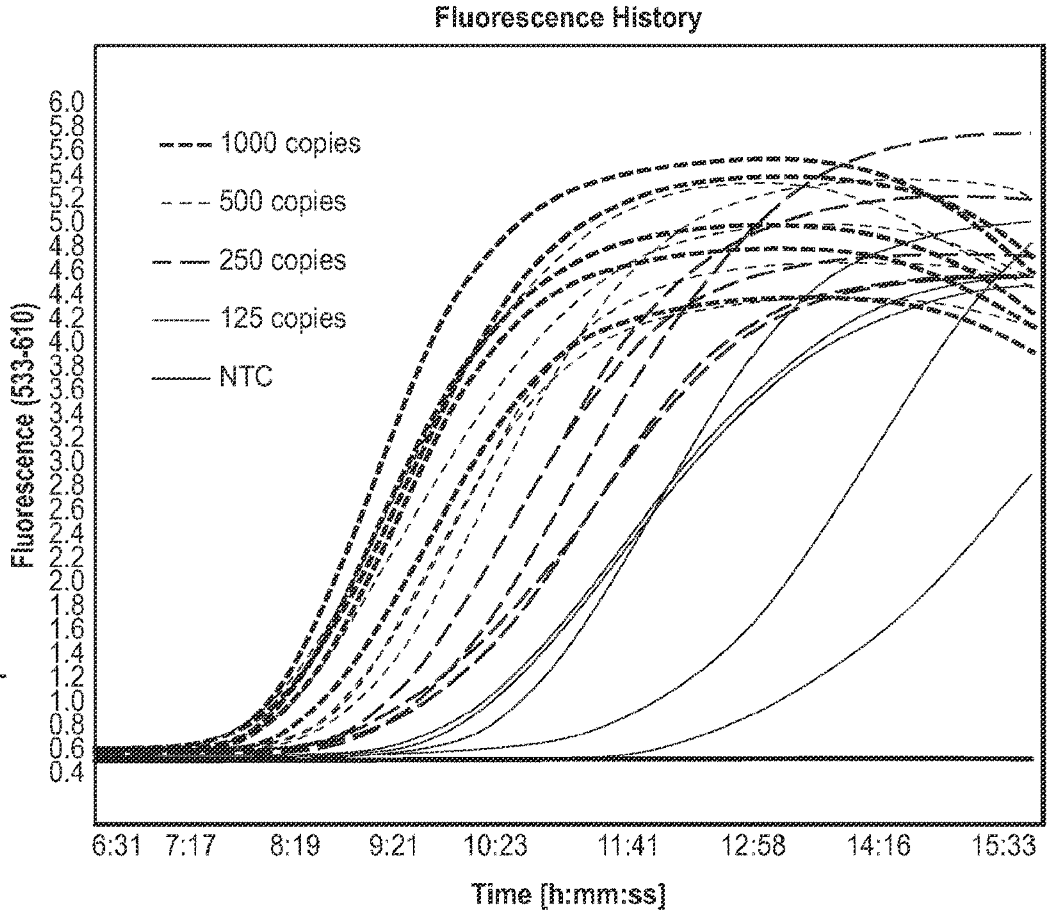

Reactions were run using real-time detection of calfluor red 610 beacon signal (Abs 590 nm/Em 610 nm). 1-Step reactions were carried out at 56° C. for 20 minutes using 125, 250, 500, and 1000 copies of HIV RNA. Specific detection of HIV RNA at all copy numbers was demonstrated in the 1-step HIV RNAble® assay (FIG. 16B).

Example 5: Detection of Dengue Virus Type 4 (DENV-4) in a Biological Sample

In one working example, dengue virus type 4 (DENV-4) was detected in a 1-step RNAble® assay targeting a 3' UTR sequence. Total RNA was isolated from cell culture, which included both viral and host cell RNA, and used in the 1-step DENV-4 RNAble® assay. Thus, total copy number was unknown. The following primers and probe sequences were used:

| Den4 (Dengue type 4) | | |
|---|---|---|
| Primer | Sequence | SEQ ID NO |
| Den4.F2 | GACTCGATATCGAGTCCAAAAACmAGCATATTmGmAmCmGmC | SEQ ID NO: 11 |
| Den4.R1a | GACTCGATATCGAGTCAGACAGCmAGGATCmTmCmTmGmG | SEQ ID NO: 12 |
| Den4.R1b | GACTCGATATCGAGTCAGACAGCmAGGATCmTmGmTmGmG | SEQ ID NO: 13 |
| Den4.extRT1 | TCTGTGCCTGGATTGAT (external primer) | SEQ ID NO: 44 |
| Den4.probe.B | cgcatcTGGTCTTTCCCAGCgatgcg | SEQ ID NO: 14 |

Primers: mN indicates methoxy base
Probe sequence: lowercase = stems, uppercase = recognition Primers: mN indicates methoxy base
Probe sequence: lowercase=stems, uppercase=recognition
FIG. 17A is a map of the amplicon showing the locations of the sequences used. The 1-step DENV-4 RNAble® assay was designed with two sets of reverse primers to account for sequence variations in the population. In the sequences above, GAGTC is the nicking enzyme recognition site.

The 1-step reactions contained a final concentration of 83 nM forward primer and a final concentration of 17 nM reverse primer (1:1 mix of Den4.R1a+Den4.R1b) in a primer ratio of about 5:1 forward to reverse primers. Final concentrations of 200 nM probe and 100 nM external primer were used. In addition, the 1 step reactions contained a final concentration of 1× Run Buffer, comprising Tris, $K^+$, and $Mg^{2+}$; dNTPs; 0.4 U/μl BST polymerase; and 0.3 U/μl Nt.BSTnbi nicking enzyme. In addition to these components; the 1 step reactions contained 0.2 U/μl of AMV Reverse Transcriptase High Spec Activity XL (Life Sciences Advanced Technologies) and 0.5 U/μl of an RNAse inhibitor (Superasin; Thermo Fisher). All water used was nuclease free.

Figure 17B:
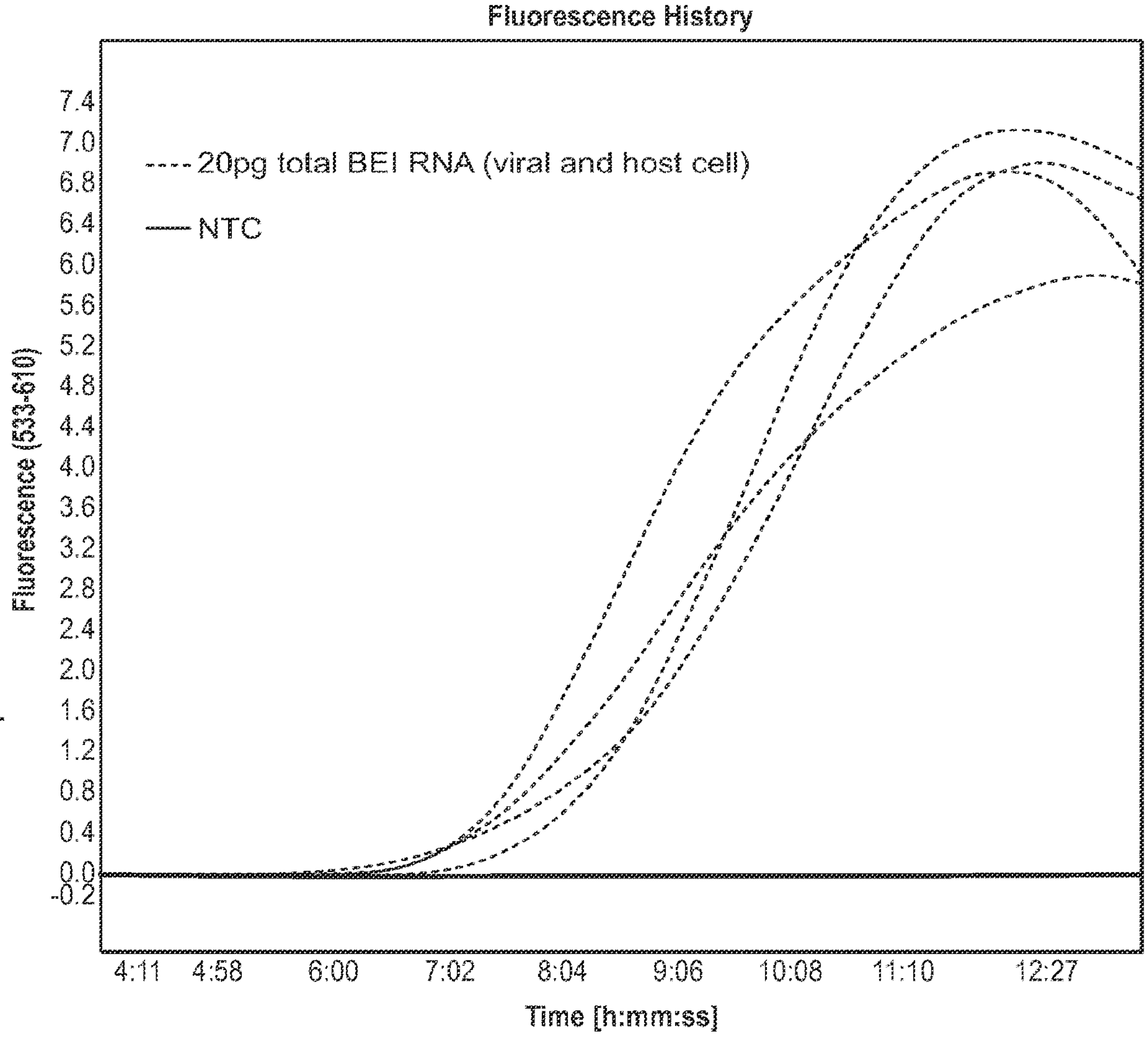

Reactions were run using real-time detection of calfluor red 610 beacon signal (Abs 590 nm/Em 610 nm). 1-Step reactions were carried out at 56° C. for 20 minutes using 20 pg total RNA. Specific detection of Dengue 4 RNA was demonstrated in the 1-step DENV-4 RNAble® assay (FIG. 17B).

Example 6: Detection of Influenza B in a Biological Sample

In one working example, influenza B was detected in a 1-step RNAble® assay targeting an influenza Segment 7 sequence. Total RNA was isolated from cell culture, which included both viral and host cell RNA, and used in the 1-step influenza B RNAble® assay. Thus, total copy number was unknown. The following primers and probe sequences were used:

FluB (influenza B)

| Primer | Sequence | SEQ ID NO |
|---|---|---|
| FluB.F2a | GACTCGATATCGAGTCAAATGCAmGATGGTCTCmA mGmCmTmA | SEQ ID NO: 15 |
| FluB.F2b | GACTCGATATCGAGTCAAATGCAmAATGGTCTCmA mGmCmTmA | SEQ ID NO: 16 |
| FluB.F2c | GACTCGATATCGAGTCAAATGCAmGATGGTTTCmA mGmCmTmA | SEQ ID NO: 17 |
| FluB.R3a | GACTCGATATCGAGTCCTCCTTTmTCCCATTCCAT mTmCmAmTmT | SEQ ID NO: 18 |
| FluB.R3b | GACTCGATATCGAGTCCTCCCTTmTCCCATTCCAT mTmCmAmTmT | SEQ ID NO: 19 |
| FluB.R3c | GACTCGATATCGAGTCCTCCTTTmCCCCATTCCAT mTmCmAmTmT | SEQ ID NO: 20 |
| FluB.extRT1a | TTTTGGACGTCTTCTCC (external primer) | SEQ ID NO: 45 |
| FluB.extRT1b | TTTTGAACGTCTTCTCC (external primer) | SEQ ID NO: 46 |
| FluB.probe.T | gccaaGCTATGAACACAGCAAActtggc | SEQ ID NO: 21 |

Primers: mN indicates methoxy base
Probe sequence: lowercase = stems, uppercase = recognition FIG. 18A is a map of the amplicon showing the locations of the sequences used. The 1-step Influenza B RNAble® assay was designed with three sets of forward and reverse primers and two external primers to account for sequence variations in the population. In the sequences above, GAGTC is the nicking enzyme recognition site.

The 1-step reactions contained a final concentration of 9 nM forward primer (1:1:1 mix of FluB.F2a+FluB.F2b+FluB.F2c) and a final concentration of 91 nM reverse primer (1:1:1 mix of FluB.R3a+FluB.R3b+FluB.R3c) in a primer ratio of about 1:10 forward to reverse primers. Final concentrations of 200 nM probe and 100 nM external primer were used. In addition, the 1 step reactions contained a final concentration of 1×Run Buffer, comprising Tris, $K^+$, and $Mg^{2+}$; dNTPs; 0.4 U/μl BST polymerase; and 0.3 U/μl Nt.BSTnbi nicking enzyme. In addition to these components; the 1 step reactions contained 0.2 U/μl of AMV Reverse Transcriptase High Spec Activity XL (Life Sciences Advanced Technologies) and 0.5 U/μl of an RNAse inhibitor (Superasin; Thermo Fisher). All water used was nuclease free.

Figure 18B:
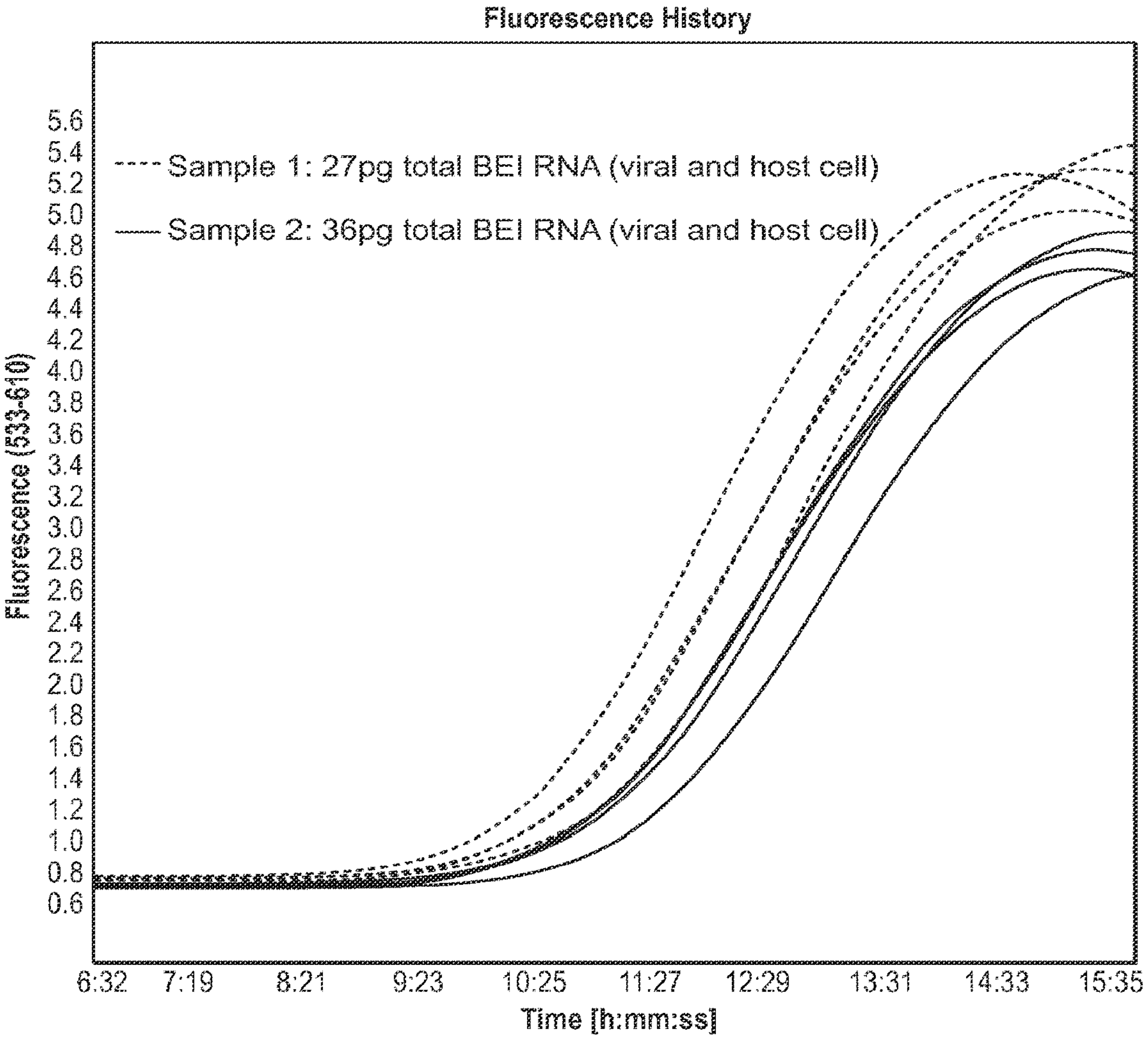

Reactions were run using real-time detection of calfluor red 610 beacon signal (Abs 590 nm/Em 610 nm). 1-Step reactions were carried out at 56° C. for 20 minutes using total RNA from different isolates. Specific detection of influenza B in all isolates was demonstrated in the 1-step influenza B RNAble® assay (FIG. 18B).

Example 7: Detection of Bovine Viral Diarrhea Virus Genotype 1 (BVDV1) in a Biological Sample In one working example, Bovine Viral Diarrhea Virus Genotype 1 (BVDV1) was detected in a 1-step RNAble® assay targeting an influenza Segment 7 sequence. Total RNA was isolated from cell culture, which included both viral and host cell RNA, and used in the 1-step BVDV1 RNAble® assay. Thus, total copy number was unknown. The following primers and probe sequences were used:

Bovine Viral Diarrhea Virus Type 1 (BVDV1)

| Primer | Sequence | SEQ ID NO |
|---|---|---|
| BVDV1.F1a | GACTCGATATCGAGTCGGCCCACmTGTATTGCT mAmCmTmGmAmAmA | SEQ ID NO: 22 |
| BVDV1.F1b | GACTCGATATCGAGTCGGCCCACmTGCACTGCT mAmCmTmAmAmAmA | SEQ ID NO: 23 |
| BVDV1.R1 | GACTCGATATCGAGTCTGTGATCmAACTCCmAm TmGmTmGmCmC | SEQ ID NO: 24 |
| BVDV1.RT1v | TATGTTTTGTATAAAAGTTCATTTG (external primer) | SEQ ID NO: 47 |
| BVDV1.ProbeT | **cgctacATCTCTGCTGTACATGgtagcg** | SEQ ID NO: 25 |

Primers: mN indicates methoxy base
Probe sequence: lowercase = stems, uppercase = recognition FIG. 19A is a map of the amplicon showing the locations of the sequences used. The 1-step BVDV1 RNAble® assay was designed with two sets of forward primers to account for sequence variations in the population. In the sequences above, GAGTC is the nicking enzyme recognition site.

The 1-step reactions contained a final concentration of 9 nM forward primer (1:1 mix of BVDV1.F1a+BVDV1.F1b) and a final concentration of 91 nM reverse primer in a primer ratio of about 1:10 forward to reverse primers. Final concentrations of 200 nM probe and 100 nM external primer were used. In addition, the 1 step reactions contained a final concentration of 1×Run Buffer, comprising Tris, $K^+$, and $Mg^{2+}$; dNTPs; 0.4 U/μl BST polymerase; and 0.3 U/μl Nt.BSTnbi nicking enzyme. In addition to these components; the 1 step reactions contained 0.2 U/μl of AMV Reverse Transcriptase High Spec Activity XL (Life Sciences Advanced Technologies) and 0.5 U/μl of an RNAse inhibitor (Superasin; Thermo Fisher). All water used was nuclease free.

Figure 19B:
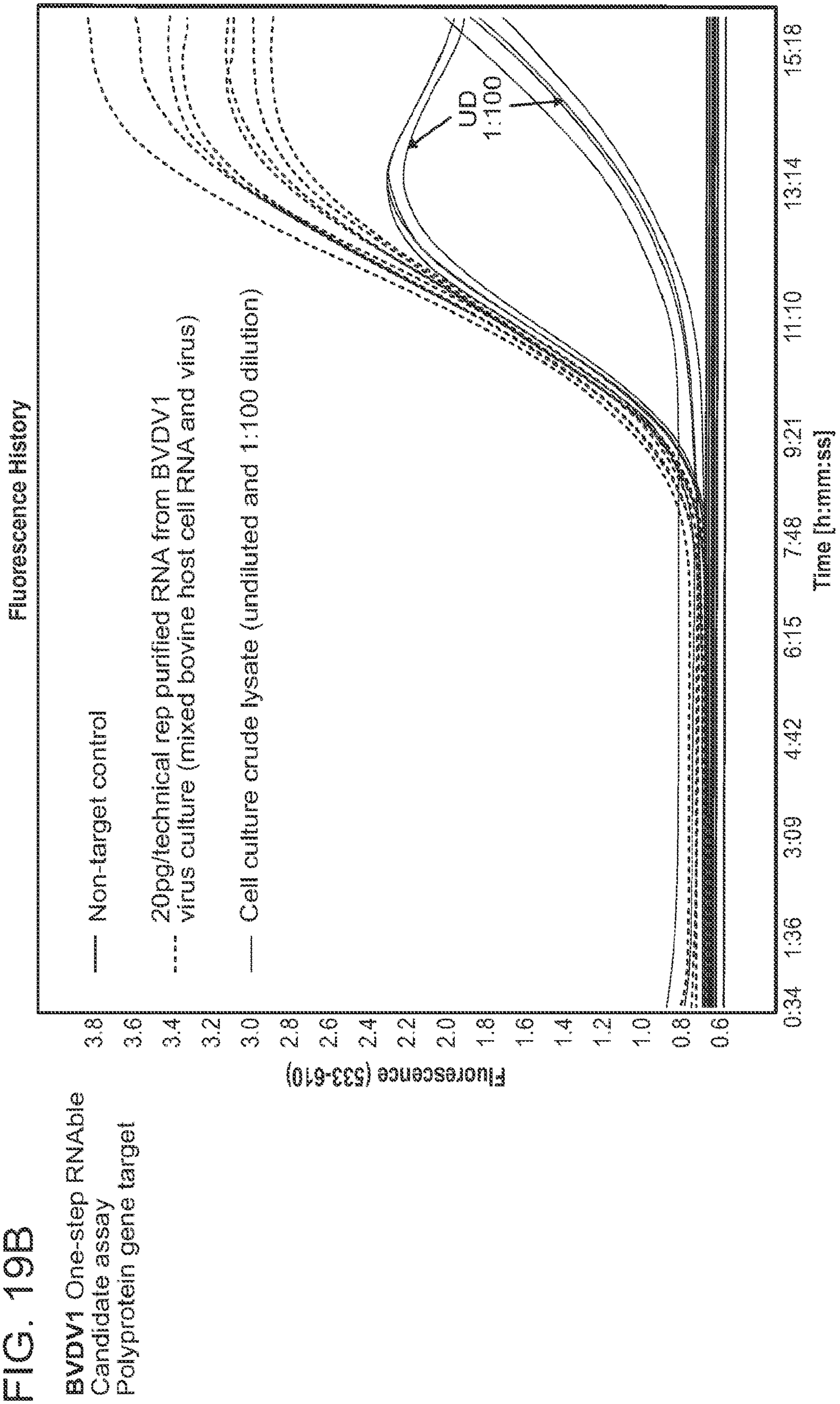

Reactions were run using real-time detection of calfluor red 610 beacon signal (Abs 590 nm/Em 610 nm). 1-Step reactions were carried out at 56° C. for 20 minutes using purified RNA (20 pg/technical replicate) from BVDV1 virus culture (mixed bovine host cell RNA and virus) and cell culture crude lysate (undiluted and 1:100 dilution). Specific detection of BVDV1 virus in all samples was demonstrated in the 1-step BVDV1 RNAble® assay (FIG. 19B).

Example 8: Molecular Beacon Recognition of Ebola Strains

Exemplary Beacon BLAST Alignment Output and Strains List:

```
Zaire ebolavirus isolate H.sapiens-
tc/COD/1976/Yambuku-Ecran, complete genome
Sequence ID: gb|KM655246.1| Length: 18797
Number of Matches: 5
Range 1: 6513 to 6528 GenBank Graphics
▼ Next Match ▲ Previous Match

Score
29.4      Expect   Identities   Gaps      Strand
bits(14)  0.017    15/16(94%)   0/16(0%)  Plus/Plus

Query        1    ACGACTTTYGCTGAAG        16
                  |||||||| |||||||
Sbjct     6513    ACGACTTTCGCTGAAG      6528
```

Query 1 (SEQ ID NO: 48)
Subject (SEQ ID NO: 49)

| | | | | | |
|---|---|---|---|---|---|
| Zaire ebolavirus isolate *H. sapiens*-tc/COD/1976/Yambuku-Ecran, complete genome | | | | | |
| 29.4 | 89.2 | 100% | 0.017 | 94% | KM655246.1 |
| Zaire ebolavirus isolate *H. sapiens*-wt/GIN/2014/Gueckedou-C05, complete genome | | | | | |
| 29.4 | 104 | 100% | 0.017 | 94% | KJ660348.2 |
| Zaire ebolavirus isolate *H. sapiens*-wt/GIN/2014/Gueckedou-C07, complete genome | | | | | |
| 29.4 | 104 | 100% | 0.017 | 94% | KJ660347.2 |
| Zaire ebolavirus isolate *H. sapiens*-wt/GIN/2014/Kissidougou-C15, complete genome | | | | | |
| 29.4 | 104 | 100% | 0.017 | 94% | KJ660346.2 |
| Zaire ebolavirus isolate Ebola virus *H. sapiens*-wt/SLE/2014/ManoRiver-NM042.3, partial genome | | | | | |
| 29.4 | 104 | 100% | 0.017 | 94% | KM233118.1 |
| Zaire ebolavirus isolate Ebola virus *H. sapiens*-wt/SLE/2014/ManoRiver-NM042.2, partial genome | | | | | |
| 29.4 | 104 | 100% | 0.017 | 94% | KM233117.1 |
| Zaire ebolavirus isolate Ebola virus *H. sapiens*-wt/SLE/2014/ManoRiver-NM042.1, partial genome | | | | | |
| 29.4 | 104 | 100% | 0.017 | 94% | KM233116.1 |
| Zaire ebolavirus isolate Ebola virus *H. sapiens*-wt/SLE/2014/ManoRiver-G3857, partial genome | | | | | |
| 29.4 | 104 | 100% | 0.017 | 94% | KM233115.1 |
| Zaire ebolavirus isolate Ebola virus *H. sapiens*-wt/SLE/2014/ManoRiver-G3856.3, partial genome | | | | | |
| 29.4 | 104 | 100% | 0.017 | 94% | KM233114.1 |
| Zaire ebolavirus isolate Ebola virus *H. sapiens*-wt/SLE/2014/ManoRiver-G3856.1, partial genome | | | | | |
| 29.4 | 104 | 100% | 0.017 | 94% | KM233113.1 |
| Zaire ebolavirus isolate Ebola virus *H. sapiens*-wt/SLE/2014/ManoRiver-G3851, partial genome | | | | | |
| 29.4 | 104 | 100% | 0.017 | 94% | KM233112.1 |
| Zaire ebolavirus isolate Ebola virus *H. sapiens*-wt/SLE/2014/ManoRiver-G3850, partial genome | | | | | |
| 29.4 | 104 | 100% | 0.017 | 94% | KM233111.1 |
| Zaire ebolavirus isolate Ebola virus *H. sapiens*-wt/SLE/2014/ManoRiver-G3848, partial genome | | | | | |
| 29.4 | 104 | 100% | 0.017 | 94% | KM233110.1 |
| Zaire ebolavirus isolate Ebola virus *H. sapiens*-wt/SLE/2014/ManoRiver-G3846, partial genome | | | | | |
| 29.4 | 104 | 100% | 0.017 | 94% | KM233109.1 |
| Zaire ebolavirus isolate Ebola virus *H. sapiens*-wt/SLE/2014/ManoRiver-G3841, partial genome | | | | | |
| 29.4 | 104 | 100% | 0.017 | 94% | KM233107.1 |
| Zaire ebolavirus isolate Ebola virus *H. sapiens*-wt/SLE/2014/ManoRiver-G3840, partial genome | | | | | |
| 29.4 | 104 | 100% | 0.017 | 94% | KM233106.1 |
| Zaire ebolavirus isolate Ebola virus *H. sapiens*-wt/SLE/2014/ManoRiver-G3838, partial genome | | | | | |
| 29.4 | 104 | 100% | 0.017 | 94% | KM233105.1 |
| Zaire ebolavirus isolate Ebola virus *H. sapiens*-wt/SLE/2014/ManoRiver-G3834, partial genome | | | | | |
| 29.4 | 104 | 100% | 0.017 | 94% | KM233104.1 |
| Zaire ebolavirus isolate Ebola virus *H. sapiens*-wt/SLE/2014/ManoRiver-G3831, partial genome | | | | | |
| 29.4 | 104 | 100% | 0.017 | 94% | KM233103.1 |
| Zaire ebolavirus isolate Ebola virus *H. sapiens*-wt/SLE/2014/ManoRiver-G3829, partial genome | | | | | |
| 29.4 | 104 | 100% | 0.017 | 94% | KM233102.1 |
| Zaire ebolavirus isolate Ebola virus *H. sapiens*-wt/SLE/2014/ManoRiver-G3827, partial genome | | | | | |
| 29.4 | 104 | 100% | 0.017 | 94% | KM233101.1 |
| Zaire ebolavirus isolate Ebola virus *H. sapiens*-wt/SLE/2014/ManoRiver-G3826, partial genome | | | | | |
| 29.4 | 104 | 100% | 0.017 | 94% | KM233100.1 |
| Zaire ebolavirus isolate Ebola virus *H. sapiens*-wt/SLE/2014/ManoRiver-G3825.2, partial genome | | | | | |
| 29.4 | 104 | 100% | 0.017 | 94% | KM233099.1 |
| Zaire ebolavirus isolate Ebola virus *H. sapiens*-wt/SLE/2014/ManoRiver-G3825.1, partial genome | | | | | |
| 29.4 | 104 | 100% | 0.017 | 94% | KM233098.1 |

-continued

| | | | | | |
|---|---|---|---|---|---|
| Zaire ebolavirus isolate Ebola virus *H. sapiens*-wt/SLE/2014/ManoRiver-G3823, partial genome | | | | | |
| 29.4 | 104 | 100% | 0.017 | 94% | KM233097.1 |
| Zaire ebolavirus isolate Ebola virus *H. sapiens*-wt/SLE/2014/ManoRiver-G3822, partial genome | | | | | |
| 29.4 | 104 | 100% | 0.017 | 94% | KM233096.1 |
| Zaire ebolavirus isolate Ebola virus *H. sapiens*-wt/SLE/2014/ManoRiver-G3821, partial genome | | | | | |
| 29.4 | 104 | 100% | 0.017 | 94% | KM233095.1 |
| Zaire ebolavirus isolate Ebola virus *H. sapiens*-wt/SLE/2014/ManoRiver-G3819, partial genome | | | | | |
| 29.4 | 104 | 100% | 0.017 | 94% | KM233093.1 |
| Zaire ebolavirus isolate Ebola virus *H. sapiens*-wt/SLE/2014/ManoRiver-G3818, partial genome | | | | | |
| 29.4 | 104 | 100% | 0.017 | 94% | KM233092.1 |
| Zaire ebolavirus isolate Ebola virus *H. sapiens*-wt/SLE/2014/ManoRiver-G3817, partial genome | | | | | |
| 29.4 | 104 | 100% | 0.017 | 94% | KM233091.1 |
| Zaire ebolavirus isolate Ebola virus *H. sapiens*-wt/SLE/2014/ManoRiver-G3816, partial genome | | | | | |
| 29.4 | 104 | 100% | 0.017 | 94% | KM233090.1 |
| Zaire ebolavirus isolate Ebola virus *H. sapiens*-wt/SLE/2014/ManoRiver-G3814, partial genome | | | | | |
| 29.4 | 104 | 100% | 0.017 | 94% | KM233089.1 |
| Zaire ebolavirus isolate Ebola virus *H. sapiens*-wt/SLE/2014/ManoRiver-G3810.2, partial genome | | | | | |
| 29.4 | 104 | 100% | 0.017 | 94% | KM233088.1 |
| Zaire ebolavirus isolate Ebola virus *H. sapiens*-wt/SLE/2014/ManoRiver-G3810.1, partial genome | | | | | |
| 29.4 | 104 | 100% | 0.017 | 94% | KM233087.1 |
| Zaire ebolavirus isolate Ebola virus *H. sapiens*-wt/SLE/2014/ManoRiver-G3809, partial genome | | | | | |
| 29.4 | 104 | 100% | 0.017 | 94% | KM233086.1 |
| Zaire ebolavirus isolate Ebola virus *H. sapiens*-wt/SLE/2014/ManoRiver-G3808, partial genome | | | | | |
| 29.4 | 104 | 100% | 0.017 | 94% | KM233085.1 |
| Zaire ebolavirus isolate Ebola virus *H. sapiens*-wt/SLE/2014/ManoRiver-G3807, partial genome | | | | | |
| 29.4 | 104 | 100% | 0.017 | 94% | KM233084.1 |
| Zaire ebolavirus isolate Ebola virus *H. sapiens*-wt/SLE/2014/ManoRiver-G3805.2, partial genome | | | | | |
| 29.4 | 104 | 100% | 0.017 | 94% | KM233083.1 |
| Zaire ebolavirus isolate Ebola virus *H. sapiens*-wt/SLE/2014/ManoRiver-G3805.1, partial genome | | | | | |
| 29.4 | 104 | 100% | 0.017 | 94% | KM233082.1 |
| Zaire ebolavirus isolate Ebola virus *H.* sapiens-wt/SLE/2014/ManoRiver-G3800, partial genome | | | | | |
| 29.4 | 104 | 100% | 0.017 | 94% | KM233081.1 |
| Zaire ebolavirus isolate Ebola virus *H. sapiens*-wt/SLE/2014/ManoRiver-G3799, partial genome | | | | | |
| 29.4 | 104 | 100% | 0.017 | 94% | KM233080.1 |
| Zaire ebolavirus isolate Ebola virus *H. sapiens*-wt/SLE/2014/ManoRiver-G3798, partial genome | | | | | |
| 29.4 | 104 | 100% | 0.017 | 94% | KM233079.1 |
| Zaire ebolavirus isolate Ebola virus *H. sapiens*-wt/SLE/2014/ManoRiver-G3795, partial genome | | | | | |
| 29.4 | 104 | 100% | 0.017 | 94% | KM233077.1 |
| Zaire ebolavirus isolate Ebola virus *H. sapiens*-wt/SLE/2014/ManoRiver-G3789.1, partial genome | | | | | |
| 29.4 | 104 | 100% | 0.017 | 94% | KM233076.1 |
| Zaire ebolavirus isolate Ebola virus *H. sapiens*-wt/SLE/2014/ManoRiver-G3788, partial genome | | | | | |
| 29.4 | 104 | 100% | 0.017 | 94% | KM233075.1 |
| Zaire ebolavirus isolate Ebola virus *H. sapiens*-wt/SLE/2014/ManoRiver-G3787, partial genome | | | | | |
| 29.4 | 104 | 100% | 0.017 | 94% | KM233074.1 |
| Zaire ebolavirus isolate Ebola virus *H. sapiens*-wt/SLE/2014/ManoRiver-G3786, partial genome | | | | | |
| 29.4 | 104 | 100% | 0.017 | 94% | KM233073.1 |
| Zaire ebolavirus isolate Ebola virus *H. sapiens*-wt/SLE/2014/ManoRiver-G3782, partial genome | | | | | |
| 29.4 | 104 | 100% | 0.017 | 94% | KM233072.1 |
| Zaire ebolavirus isolate Ebola virus *H. sapiens*-wt/SLE/2014/ManoRiver-G3771, partial genome | | | | | |
| 29.4 | 104 | 100% | 0.017 | 94% | KM233071.1 |
| Zaire ebolavirus isolate Ebola virus *H. sapiens*-wt/SLE/2014/ManoRiver-G3770.2, partial genome | | | | | |
| 29.4 | 104 | 100% | 0.017 | 94% | KM233070.1 |
| Zaire ebolavirus isolate Ebola virus *H. sapiens*-wt/SLE/2014/ManoRiver-G3770.1, partial genome | | | | | |
| 29.4 | 104 | 100% | 0.017 | 94% | KM233069.1 |
| Zaire ebolavirus isolate Ebola virus *H. sapiens*-wt/SLE/2014/ManoRiver-G3769.3, partial genome | | | | | |
| 29.4 | 104 | 100% | 0.017 | 94% | KM233067.1 |
| Zaire ebolavirus isolate Ebola virus *H. sapiens*-wt/SLE/2014/ManoRiver-G3769.2, partial genome | | | | | |
| 29.4 | 104 | 100% | 0.017 | 94% | KM233066.1 |
| Zaire ebolavirus isolate Ebola virus *H. sapiens*-wt/SLE/2014/ManoRiver-G3769.1, partial genome | | | | | |
| 29.4 | 104 | 100% | 0.017 | 94% | KM233065.1 |
| Zaire ebolavirus isolate Ebola virus *H. sapiens*-wt/SLE/2014/ManoRiver-G3765.2, partial genome | | | | | |
| 29.4 | 104 | 100% | 0.017 | 94% | KM233064.1 |
| Zaire ebolavirus isolate Ebola virus *H. sapiens*-wt/SLE/2014/ManoRiver-G3764, partial genome | | | | | |
| 29.4 | 104 | 100% | 0.017 | 94% | KM233063.1 |
| Zaire ebolavirus isolate Ebola virus *H. sapiens*-wt/SLE/2014/ManoRiver-G3758, partial genome | | | | | |
| 29.4 | 104 | 100% | 0.017 | 94% | KM233062.1 |
| Zaire ebolavirus isolate Ebola virus *H. sapiens*-wt/SLE/2014/ManoRiver-G3752, partial genome | | | | | |
| 29.4 | 104 | 100% | 0.017 | 94% | KM233061.1 |
| Zaire ebolavirus isolate Ebola virus *H. sapiens*-wt/SLE/2014/ManoRiver-G3750.3, partial genome | | | | | |
| 29.4 | 104 | 100% | 0.017 | 94% | KM233060.1 |
| Zaire ebolavirus isolate Ebola virus *H. sapiens*-wt/SLE/2014/ManoRiver-G3750.2, partial genome | | | | | |
| 29.4 | 104 | 100% | 0.017 | 94% | KM233059.1 |
| Zaire ebolavirus isolate Ebola virus *H. sapiens*-wt/SLE/2014/ManoRiver-G3750.1, partial genome | | | | | |
| 29.4 | 104 | 100% | 0.017 | 94% | KM233058.1 |
| Zaire ebolavirus isolate Ebola virus *H. sapiens*-wt/SLE/2014/ManoRiver-G3735.2, partial genome | | | | | |
| 29.4 | 104 | 100% | 0.017 | 94% | KM233057.1 |

-continued

| | | | | | |
|---|---|---|---|---|---|
| Zaire ebolavirus isolate Ebola virus *H. sapiens*-wt/SLE/2014/ManoRiver-G3735.1, partial genome | | | | | |
| 29.4 | 104 | 100% | 0.017 | 94% | KM233056.1 |
| Zaire ebolavirus isolate Ebola virus *H. sapiens*-wt/SLE/2014/ManoRiver-G3734.1, partial genome | | | | | |
| 29.4 | 104 | 100% | 0.017 | 94% | KM233055.1 |
| Zaire ebolavirus isolate Ebola virus *H. sapiens*-wt/SLE/2014/ManoRiver-G3729, partial genome | | | | | |
| 29.4 | 104 | 100% | 0.017 | 94% | KM233054.1 |
| Zaire ebolavirus isolate Ebola virus *H. sapiens*-wt/SLE/2014/ManoRiver-G3724, partial genome | | | | | |
| 29.4 | 104 | 100% | 0.017 | 94% | KM233053.1 |
| Zaire ebolavirus isolate Ebola virus *H. sapiens*-wt/SLE/2014/ManoRiver-G3713.4, partial genome | | | | | |
| 29.4 | 104 | 100% | 0.017 | 94% | KM233052.1 |
| Zaire ebolavirus isolate Ebola virus *H. sapiens*-wt/SLE/2014/ManoRiver-G3713.3, partial genome | | | | | |
| 29.4 | 104 | 100% | 0.017 | 94% | KM233051.1 |
| Zaire ebolavirus isolate Ebola virus *H. sapiens*-wt/SLE/2014/ManoRiver-G3713.2, partial genome | | | | | |
| 29.4 | 104 | 100% | 0.017 | 94% | KM233050.1 |
| Zaire ebolavirus isolate Ebola virus *H. sapiens*-wt/SLE/2014/ManoRiver-G3707, partial genome | | | | | |
| 29.4 | 104 | 100% | 0.017 | 94% | KM233049.1 |
| Zaire ebolavirus isolate Ebola virus *H. sapiens*-wt/SLE/2014/ManoRiver-EM124.4, partial genome | | | | | |
| 29.4 | 104 | 100% | 0.017 | 94% | KM233048.1 |
| Zaire ebolavirus isolate Ebola virus *H. sapiens*-wt/SLE/2014/ManoRiver-EM124.3, partial genome | | | | | |
| 29.4 | 104 | 100% | 0.017 | 94% | KM233047.1 |
| Zaire ebolavirus isolate Ebola virus *H. sapiens*-wt/SLE/2014/ManoRiver-EM124.2, partial genome | | | | | |
| 29.4 | 104 | 100% | 0.017 | 94% | KM233046.1 |
| Zaire ebolavirus isolate Ebola virus *H. sapiens*-wt/SLE/2014/ManoRiver-EM124.1, partial genome | | | | | |
| 29.4 | 104 | 100% | 0.017 | 94% | KM233045.1 |
| Zaire ebolavirus isolate Ebola virus *H. sapiens*-wt/SLE/2014/ManoRiver-EM121, partial genome | | | | | |
| 29.4 | 104 | 100% | 0.017 | 94% | KM233044.1 |
| Zaire ebolavirus isolate Ebola virus *H. sapiens*-wt/SLE/2014/ManoRiver-EM120, partial genome | | | | | |
| 29.4 | 104 | 100% | 0.017 | 94% | KM233043.1 |
| Zaire ebolavirus isolate Ebola virus *H. sapiens*-wt/SLE/2014/ManoRiver-EM119, partial genome | | | | | |
| 29.4 | 104 | 100% | 0.017 | 94% | KM233042.1 |
| Zaire ebolavirus isolate Ebola virus *H. sapiens*-wt/SLE/2014/ManoRiver-EM115, partial genome | | | | | |
| 29.4 | 104 | 100% | 0.017 | 94% | KM233041.1 |
| Zaire ebolavirus isolate Ebola virus *H. sapiens*-wt/SLE/2014/ManoRiver-EM113, partial genome | | | | | |
| 29.4 | 104 | 100% | 0.017 | 94% | KM233040.1 |
| Zaire ebolavirus isolate Ebola virus *H. sapiens*-wt/SLE/2014/ManoRiver-EM112, partial genome | | | | | |
| 29.4 | 104 | 100% | 0.017 | 94% | KM233039.1 |
| Zaire ebolavirus isolate Ebola virus *H. sapiens*-wt/SLE/2014/ManoRiver-EM111, partial genome | | | | | |
| 29.4 | 104 | 100% | 0.017 | 94% | KM233038.1 |
| Zaire ebolavirus isolate Ebola virus *H. sapiens*-wt/SLE/2014/ManoRiver-EM110, partial genome | | | | | |
| 29.4 | 104 | 100% | 0.017 | 94% | KM233037.1 |
| Zaire ebolavirus isolate Ebola virus *H. sapiens*-wt/SLE/2014/ManoRiver-EM106, partial genome | | | | | |
| 29.4 | 104 | 100% | 0.017 | 94% | KM233036.1 |
| Zaire ebolavirus isolate Ebola virus *H. sapiens*-wt/SLE/2014/ManoRiver-EM104, partial genome | | | | | |
| 29.4 | 104 | 100% | 0.017 | 94% | KM233035.1 |
| Zaire ebolavirus isolate Ebola virus *H. sapiens*-wt/SLE/2014/ManoRiver-G3687.1, partial genome | | | | | |
| 29.4 | 104 | 100% | 0.017 | 94% | KM034563.1 |
| Zaire ebolavirus isolate Ebola virus *H. sapiens*-wt/SLE/2014/ManoRiver-G3686.1, partial genome | | | | | |
| 29.4 | 104 | 100% | 0.017 | 94% | KM034562.1 |
| Zaire ebolavirus isolate Ebola virus *H. sapiens*-wt/SLE/2014/ManoRiver-G3683.1, partial genome | | | | | |
| 29.4 | 104 | 100% | 0.017 | 94% | KM034561.1 |
| Zaire ebolavirus isolate Ebola virus *H. sapiens*-wt/SLE/2014/ManoRiver-G3682.1, partial genome | | | | | |
| 29.4 | 104 | 100% | 0.017 | 94% | KM034560.1 |
| Zaire ebolavirus isolate Ebola virus *H. sapiens*-wt/SLE/2014/ManoRiver-G3680.1, partial genome | | | | | |
| 29.4 | 104 | 100% | 0.017 | 94% | KM034559.1 |
| Zaire ebolavirus isolate Ebola virus *H. sapiens*-wt/SLE/2014/ManoRiver-G3679.1, partial genome | | | | | |
| 29.4 | 104 | 100% | 0.017 | 94% | KM034558.1 |
| Zaire ebolavirus isolate Ebola virus *H. sapiens*-wt/SLE/2014/ManoRiver-G3677.2, partial genome | | | | | |
| 29.4 | 104 | 100% | 0.017 | 94% | KM034557.1 |
| Zaire ebolavirus isolate Ebola virus *H. sapiens*-wt/SLE/2014/ManoRiver-G3677.1, partial genome | | | | | |
| 29.4 | 104 | 100% | 0.017 | 94% | KM034556.1 |
| Zaire ebolavirus isolate Ebola virus *H. sapiens*-wt/SLE/2014/ManoRiver-G3676.2, partial genome | | | | | |
| 29.4 | 104 | 100% | 0.017 | 94% | KM034555.1 |
| Zaire ebolavirus isolate Ebola virus *H. sapiens*-wt/SLE/2014/ManoRiver-G3676.1, partial genome | | | | | |
| 29.4 | 104 | 100% | 0.017 | 94% | KM034554.1 |
| Zaire ebolavirus isolate Ebola virus *H. sapiens*-wt/SLE/2014/ManoRiver-G3670.1, partial genome | | | | | |
| 29.4 | 104 | 100% | 0.017 | 94% | KM034553.1 |
| Zaire ebolavirus isolate Ebola virus *H. sapiens*-wt/SLE/2014/ManoRiver-EM098, partial genome | | | | | |
| 29.4 | 104 | 100% | 0.017 | 94% | KM034552.1 |
| Zaire ebolavirus isolate Ebola virus *H. sapiens*-wt/SLE/2014/ManoRiver-EM096, partial genome | | | | | |
| 29.4 | 104 | 100% | 0.017 | 94% | KM034551.1 |
| Zaire ebolavirus isolate Ebola virus *H. sapiens*-wt/SLE/2014/ManoRiver-EM095, partial genome | | | | | |
| 29.4 | 104 | 100% | 0.017 | 94% | KM034550.1 |
| Zaire ebolavirus isolate *H. sapiens*-wt/SLE/2014/ManoRiver-EM095B, partial genome | | | | | |
| 29.4 | 104 | 100% | 0.017 | 94% | KM034549.1 |
| Mutant Zaire ebolavirus, complete sequence | | | | | |
| 29.4 | 89.2 | 100% | 0.017 | 94% | KF827427.1 |

Amplicon Similarity Analysis Across Ebola Strains
Exemplary BLAST Alignment Output and Strains List:

```
Zaire ebolavirus H.sapiens-tc/COD/1976/Yambuku-Ecran, complete genome
Sequence ID: gb|KM655246.1| Length: 18797 Number of Matches: 1
Range 1: 6492 to 6547 GenBank Graphics ▼ Next Match ▲ Previous Match

Score                                                           Strand
102 bits Expect Identities          Gaps                        Plus/
(112)    1e-23  56/56(100%)         0/56(0%)                    Plus

Query       1   TCCACAGTTATCTACCGAGGAACGACTTTCGCTGAAGGTGTCGTTGCATTTCTGAT   56
                ||||||||||||||||||||||||||||||||||||||||||||||||||||||||
Sbjct    6492   TCCACAGTTATCTACCGAGGAACGACTTTCGCTGAAGGTGTCGTTGCATTTCTGAT 6547
```

(SEQ ID NO: 50)
Strains List:

Zaire ebolavirus isolate *H. sapiens*-tc/COD/1976/Yambuku-Ecran, complete genome
102 102 100% 1e-23 100% KM655246.1
Zaire ebolavirus isolate *H. sapiens*-wt/GIN/2014/Gueckedou-C05, complete genome
102 102 100% 1e-23 100% KJ660348.2
Zaire ebolavirus isolate *H. sapiens*-wt/GIN/2014/Gueckedou-C07, complete genome
102 102 100% 1e-23 100% KJ660347.2
Zaire ebolavirus isolate *H. sapiens*-wt/GIN/2014/Kissidougou-C15, complete genome
102 102 100% 1e-23 100% KJ660346.2
Zaire ebolavirus isolate Ebola virus *H. sapiens*-wt/SLE/2014/ManoRiver-NM042.3, partial genome
102 102 100% 1e-23 100% KM233118.1
Zaire ebolavirus isolate Ebola virus *H. sapiens*-wt/SLE/2014/ManoRiver-NM042.2, partial genome
102 102 100% 1e-23 100% KM233117.1
Zaire ebolavirus isolate Ebola virus *H. sapiens*-wt/SLE/2014/ManoRiver-NM042.1, partial genome
102 102 100% 1e-23 100% KM233116.1
Zaire ebolavirus isolate Ebola virus *H. sapiens*-wt/SLE/2014/ManoRiver-G3857, partial genome
102 102 100% 1e-23 100% KM233115.1
Zaire ebolavirus isolate Ebola virus *H. sapiens*-wt/SLE/2014/ManoRiver-G3856.3, partial genome
102 102 100% 1e-23 100% KM233114.1
Zaire ebolavirus isolate Ebola virus *H. sapiens*-wt/SLE/2014/ManoRiver-G3856.1, partial genome
102 102 100% 1e-23 100% KM233113.1
Zaire ebolavirus isolate Ebola virus *H. sapiens*-wt/SLE/2014/ManoRiver-G3851, partial genome
102 102 100% 1e-23 100% KM233112.1
Zaire ebolavirus isolate Ebola virus *H. sapiens*-wt/SLE/2014/ManoRiver-G3850, partial genome
102 102 100% 1e-23 100% KM233111.1
Zaire ebolavirus isolate Ebola virus *H. sapiens*-wt/SLE/2014/ManoRiver-G3848, partial genome
102 102 100% 1e-23 100% KM233110.1
Zaire ebolavirus isolate Ebola virus *H. sapiens*-wt/SLE/2014/ManoRiver-G3846, partial genome
102 102 100% 1e-23 100% KM233109.1
Zaire ebolavirus isolate Ebola virus *H. sapiens*-wt/SLE/2014/ManoRiver-G3841, partial genome
102 102 100% 1e-23 100% KM233107.1
Zaire ebolavirus isolate Ebola virus *H. sapiens*-wt/SLE/2014/ManoRiver-G3840, partial genome
102 102 100% 1e-23 100% KM233106.1
Zaire ebolavirus isolate Ebola virus *H. sapiens*-wt/SLE/2014/ManoRiver-G3838, partial genome
102 102 100% 1e-23 100% KM233105.1
Zaire ebolavirus isolate Ebola virus *H. sapiens*-wt/SLE/2014/ManoRiver-G3834, partial genome
102 102 100% 1e-23 100% KM233104.1
Zaire ebolavirus isolate Ebola virus *H. sapiens*-wt/SLE/2014/ManoRiver-G3831, partial genome
102 102 100% 1e-23 100% KM233103.1
Zaire ebolavirus isolate Ebola virus *H. sapiens*-wt/SLE/2014/ManoRiver-G3829, partial genome
102 102 100% 1e-23 100% KM233102.1
Zaire ebolavirus isolate Ebola virus *H. sapiens*-wt/SLE/2014/ManoRiver-G3827, partial genome
102 102 100% 1e-23 100% KM233101.1
Zaire ebolavirus isolate Ebola virus *H. sapiens*-wt/SLE/2014/ManoRiver-G3826, partial genome
102 102 100% 1e-23 100% KM233100.1
Zaire ebolavirus isolate Ebola virus *H. sapiens*-wt/SLE/2014/ManoRiver-G3825.2, partial genome
102 102 100% 1e-23 100% KM233099.1
Zaire ebolavirus isolate Ebola virus *H. sapiens*-wt/SLE/2014/ManoRiver-G3825.1, partial genome
102 102 100% 1e-23 100% KM233098.1
Zaire ebolavirus isolate Ebola virus *H. sapiens*-wt/SLE/2014/ManoRiver-G3823, partial genome
102 102 100% 1e-23 100% KM233097.1
Zaire ebolavirus isolate Ebola virus *H. sapiens*-wt/SLE/2014/ManoRiver-G3822, partial genome
102 102 100% 1e-23 100% KM233096.1
Zaire ebolavirus isolate Ebola virus *H. sapiens*-wt/SLE/2014/ManoRiver-G3821, partial genome
102 102 100% 1e-23 100% KM233095.1
Zaire ebolavirus isolate Ebola virus *H. sapiens*-wt/SLE/2014/ManoRiver-G3819, partial genome
102 102 100% 1e-23 100% KM233093.1
Zaire ebolavirus isolate Ebola virus *H. sapiens*-wt/SLE/2014/ManoRiver-G3818, partial genome
102 102 100% 1e-23 100% KM233092.1

-continued

| | | | | | |
|---|---|---|---|---|---|
| Zaire ebolavirus isolate Ebola virus *H. sapiens*-wt/SLE/2014/ManoRiver-G3817, partial genome | | | | | |
| 102 | 102 | 100% | 1e-23 | 100% | KM233091.1 |
| Zaire ebolavirus isolate Ebola virus *H. sapiens*-wt/SLE/2014/ManoRiver-G3816, partial genome | | | | | |
| 102 | 102 | 100% | 1e-23 | 100% | KM233090.1 |
| Zaire ebolavirus isolate Ebola virus *H. sapiens*-wt/SLE/2014/ManoRiver-G3814, partial genome | | | | | |
| 102 | 102 | 100% | 1e-23 | 100% | KM233089.1 |
| Zaire ebolavirus isolate Ebola virus *H. sapiens*-wt/SLE/2014/ManoRiver-G3810.2, partial genome | | | | | |
| 102 | 102 | 100% | 1e-23 | 100% | KM233088.1 |
| Zaire ebolavirus isolate Ebola virus *H. sapiens*-wt/SLE/2014/ManoRiver-G3810.1, partial genome | | | | | |
| 102 | 102 | 100% | 1e-23 | 100% | KM233087.1 |
| Zaire ebolavirus isolate Ebola virus *H. sapiens*-wt/SLE/2014/ManoRiver-G3809, partial genome | | | | | |
| 102 | 102 | 100% | 1e-23 | 100% | KM233086.1 |
| Zaire ebolavirus isolate Ebola virus *H. sapiens*-wt/SLE/2014/ManoRiver-G3808, partial genome | | | | | |
| 102 | 102 | 100% | 1e-23 | 100% | KM233085.1 |
| Zaire ebolavirus isolate Ebola virus *H. sapiens*-wt/SLE/2014/ManoRiver-G3807, partial genome | | | | | |
| 102 | 102 | 100% | 1e-23 | 100% | KM233084.1 |
| Zaire ebolavirus isolate Ebola virus *H. sapiens*-wt/SLE/2014/ManoRiver-G3805.2, partial genome | | | | | |
| 102 | 102 | 100% | 1e-23 | 100% | KM233083.1 |
| Zaire ebolavirus isolate Ebola virus *H. sapiens*-wt/SLE/2014/ManoRiver-G3805.1, partial genome | | | | | |
| 102 | 102 | 100% | 1e-23 | 100% | KM233082.1 |
| Zaire ebolavirus isolate Ebola virus *H. sapiens*-wt/SLE/2014/ManoRiver-G3800, partial genome | | | | | |
| 102 | 102 | 100% | 1e-23 | 100% | KM233081.1 |
| Zaire ebolavirus isolate Ebola virus *H. sapiens*-wt/SLE/2014/ManoRiver-G3799, partial genome | | | | | |
| 102 | 102 | 100% | 1e-23 | 100% | KM233080.1 |
| Zaire ebolavirus isolate Ebola virus *H. sapiens*-wt/SLE/2014/ManoRiver-G3798, partial genome | | | | | |
| 102 | 102 | 100% | 1e-23 | 100% | KM233079.1 |
| Zaire ebolavirus isolate Ebola virus *H. sapiens*-wt/SLE/2014/ManoRiver-G3795, partial genome | | | | | |
| 102 | 102 | 100% | 1e-23 | 100% | KM233077.1 |
| Zaire ebolavirus isolate Ebola virus *H. sapiens*-wt/SLE/2014/ManoRiver-G3789.1, partial genome | | | | | |
| 102 | 102 | 100% | 1e-23 | 100% | KM233076.1 |
| Zaire ebolavirus isolate Ebola virus *H. sapiens*-wt/SLE/2014/ManoRiver-G3788, partial genome | | | | | |
| 102 | 102 | 100% | 1e-23 | 100% | KM233075.1 |
| Zaire ebolavirus isolate Ebola virus *H. sapiens*-wt/SLE/2014/ManoRiver-G3787, partial genome | | | | | |
| 102 | 102 | 100% | 1e-23 | 100% | KM233074.1 |
| Zaire ebolavirus isolate Ebola virus *H. sapiens*-wt/SLE/2014/ManoRiver-G3786, partial genome | | | | | |
| 102 | 102 | 100% | 1e-23 | 100% | KM233073.1 |
| Zaire ebolavirus isolate Ebola virus *H. sapiens*-wt/SLE/2014/ManoRiver-G3782, partial genome | | | | | |
| 102 | 102 | 100% | 1e-23 | 100% | KM233072.1 |
| Zaire ebolavirus isolate Ebola virus *H. sapiens*-wt/SLE/2014/ManoRiver-G3771, partial genome | | | | | |
| 102 | 102 | 100% | 1e-23 | 100% | KM233071.1 |
| Zaire ebolavirus isolate Ebola virus *H. sapiens*-wt/SLE/2014/ManoRiver-G3770.2, partial genome | | | | | |
| 102 | 102 | 100% | 1e-23 | 100% | KM233070.1 |
| Zaire ebolavirus isolate Ebola virus *H. sapiens*-wt/SLE/2014/ManoRiver-G3770.1, partial genome | | | | | |
| 102 | 102 | 100% | 1e-23 | 100% | KM233069.1 |
| Zaire ebolavirus isolate Ebola virus *H. sapiens*-wt/SLE/2014/ManoRiver-G3769.3, partial genome | | | | | |
| 102 | 102 | 100% | 1e-23 | 100% | KM233067.1 |
| Zaire ebolavirus isolate Ebola virus *H. sapiens*-wt/SLE/2014/ManoRiver-G3769.2, partial genome | | | | | |
| 102 | 102 | 100% | 1e-23 | 100% | KM233066.1 |
| Zaire ebolavirus isolate Ebola virus *H. sapiens*-wt/SLE/2014/ManoRiver-G3769.1, partial genome | | | | | |
| 102 | 102 | 100% | 1e-23 | 100% | KM233065.1 |
| Zaire ebolavirus isolate Ebola virus *H. sapiens*-wt/SLE/2014/ManoRiver-G3765.2, partial genome | | | | | |
| 102 | 102 | 100% | 1e-23 | 100% | KM233064.1 |
| Zaire ebolavirus isolate Ebola virus *H. sapiens*-wt/SLE/2014/ManoRiver-G3764, partial genome | | | | | |
| 102 | 102 | 100% | 1e-23 | 100% | KM233063.1 |
| Zaire ebolavirus isolate Ebola virus *H. sapiens*-wt/SLE/2014/ManoRiver-G3758, partial genome | | | | | |
| 102 | 102 | 100% | 1e-23 | 100% | KM233062.1 |
| Zaire ebolavirus isolate Ebola virus *H. sapiens*-wt/SLE/2014/ManoRiver-G3752, partial genome | | | | | |
| 102 | 102 | 100% | 1e-23 | 100% | KM233061.1 |
| Zaire ebolavirus isolate Ebola virus *H. sapiens*-wt/SLE/2014/ManoRiver-G3750.3, partial genome | | | | | |
| 102 | 102 | 100% | 1e-23 | 100% | KM233060.1 |
| Zaire ebolavirus isolate Ebola virus *H. sapiens*-wt/SLE/2014/ManoRiver-G3750.2, partial genome | | | | | |
| 102 | 102 | 100% | 1e-23 | 100% | KM233059.1 |
| Zaire ebolavirus isolate Ebola virus *H. sapiens*-wt/SLE/2014/ManoRiver-G3750.1, partial genome | | | | | |
| 102 | 102 | 100% | 1e-23 | 100% | KM233058.1 |
| Zaire ebolavirus isolate Ebola virus *H. sapiens*-wt/SLE/2014/ManoRiver-G3735.2, partial genome | | | | | |
| 102 | 102 | 100% | 1e-23 | 100% | KM233057.1 |
| Zaire ebolavirus isolate Ebola virus *H. sapiens*-wt/SLE/2014/ManoRiver-G3735.1, partial genome | | | | | |
| 102 | 102 | 100% | 1e-23 | 100% | KM233056.1 |
| Zaire ebolavirus isolate Ebola virus *H. sapiens*-wt/SLE/2014/ManoRiver-G3734.1, partial genome | | | | | |
| 102 | 102 | 100% | 1e-23 | 100% | KM233055.1 |
| Zaire ebolavirus isolate Ebola virus *H. sapiens*-wt/SLE/2014/ManoRiver-G3729, partial genome | | | | | |
| 102 | 102 | 100% | 1e-23 | 100% | KM233054.1 |
| Zaire ebolavirus isolate Ebola virus *H. sapiens*-wt/SLE/2014/ManoRiver-G3724, partial genome | | | | | |
| 102 | 102 | 100% | 1e-23 | 100% | KM233053.1 |
| Zaire ebolavirus isolate Ebola virus *H. sapiens*-wt/SLE/2014/ManoRiver-G3713.4, partial genome | | | | | |
| 102 | 102 | 100% | 1e-23 | 100% | KM233052.1 |
| Zaire ebolavirus isolate Ebola virus *H. sapiens*-wt/SLE/2014/ManoRiver-G3713.3, partial genome | | | | | |
| 102 | 102 | 100% | 1e-23 | 100% | KM233051.1 |

-continued

| | | | | | |
|---|---|---|---|---|---|
| Zaire ebolavirus isolate Ebola virus *H. sapiens*-wt/SLE/2014/ManoRiver-G3713.2, partial genome | | | | | |
| 102 | 102 | 100% | 1e-23 | 100% | KM233050.1 |
| Zaire ebolavirus isolate Ebola virus *H. sapiens*-wt/SLE/2014/ManoRiver-G3707, partial genome | | | | | |
| 102 | 102 | 100% | 1e-23 | 100% | KM233049.1 |
| Zaire ebolavirus isolate Ebola virus *H. sapiens*-wt/SLE/2014/ManoRiver-EM124.4, partial genome | | | | | |
| 102 | 102 | 100% | 1e-23 | 100% | KM233048.1 |
| Zaire ebolavirus isolate Ebola virus *H. sapiens*-wt/SLE/2014/ManoRiver-EM124.3, partial genome | | | | | |
| 102 | 102 | 100% | 1e-23 | 100% | KM233047.1 |
| Zaire ebolavirus isolate Ebola virus *H. sapiens*-wt/SLE/2014/ManoRiver-EM124.2, partial genome | | | | | |
| 102 | 102 | 100% | 1e-23 | 100% | KM233046.1 |
| Zaire ebolavirus isolate Ebola virus *H. sapiens*-wt/SLE/2014/ManoRiver-EM124.1, partial genome | | | | | |
| 102 | 102 | 100% | 1e-23 | 100% | KM233045.1 |
| Zaire ebolavirus isolate Ebola virus *H. sapiens*-wt/SLE/2014/ManoRiver-EM121, partial genome | | | | | |
| 102 | 102 | 100% | 1e-23 | 100% | KM233044.1 |
| Zaire ebolavirus isolate Ebola virus *H. sapiens*-wt/SLE/2014/ManoRiver-EM120, partial genome | | | | | |
| 102 | 102 | 100% | 1e-23 | 100% | KM233043.1 |
| Zaire ebolavirus isolate Ebola virus *H. sapiens*-wt/SLE/2014/ManoRiver-EM119, partial genome | | | | | |
| 102 | 102 | 100% | 1e-23 | 100% | KM233042.1 |
| Zaire ebolavirus isolate Ebola virus *H. sapiens*-wt/SLE/2014/ManoRiver-EM115, partial genome | | | | | |
| 102 | 102 | 100% | 1e-23 | 100% | KM233041.1 |
| Zaire ebolavirus isolate Ebola virus *H. sapiens*-wt/SLE/2014/ManoRiver-EM113, partial genome | | | | | |
| 102 | 102 | 100% | 1e-23 | 100% | KM233040.1 |
| Zaire ebolavirus isolate Ebola virus *H. sapiens*-wt/SLE/2014/ManoRiver-EM112, partial genome | | | | | |
| 102 | 102 | 100% | 1e-23 | 100% | KM233039.1 |
| Zaire ebolavirus isolate Ebola virus *H. sapiens*-wt/SLE/2014/ManoRiver-EM111, partial genome | | | | | |
| 102 | 102 | 100% | 1e-23 | 100% | KM233038.1 |
| Zaire ebolavirus isolate Ebola virus *H. sapiens*-wt/SLE/2014/ManoRiver-EM110, partial genome | | | | | |
| 102 | 102 | 100% | 1e-23 | 100% | KM233037.1 |
| Zaire ebolavirus isolate Ebola virus *H. sapiens*-wt/SLE/2014/ManoRiver-EM106, partial genome | | | | | |
| 102 | 102 | 100% | 1e-23 | 100% | KM233036.1 |
| Zaire ebolavirus isolate Ebola virus *H. sapiens*-wt/SLE/2014/ManoRiver-EM104, partial genome | | | | | |
| 102 | 102 | 100% | 1e-23 | 100% | KM233035.1 |
| Zaire ebolavirus isolate Ebola virus *H. sapiens*-wt/SLE/2014/ManoRiver-G3687.1, partial genome | | | | | |
| 102 | 102 | 100% | 1e-23 | 100% | KM034563.1 |
| Zaire ebolavirus isolate Ebola virus *H. sapiens*-wt/SLE/2014/ManoRiver-G3686.1, partial genome | | | | | |
| 102 | 102 | 100% | 1e-23 | 100% | KM034562.1 |
| Zaire ebolavirus isolate Ebola virus *H. sapiens*-wt/SLE/2014/ManoRiver-G3683.1, partial genome | | | | | |
| 102 | 102 | 100% | 1e-23 | 100% | KM034561.1 |
| Zaire ebolavirus isolate Ebola virus *H. sapiens*-wt/SLE/2014/ManoRiver-G3682.1, partial genome | | | | | |
| 102 | 102 | 100% | 1e-23 | 100% | KM034560.1 |
| Zaire ebolavirus isolate Ebola virus *H. sapiens*-wt/SLE/2014/ManoRiver-G3680.1, partial genome | | | | | |
| 102 | 102 | 100% | 1e-23 | 100% | KM034559.1 |
| Zaire ebolavirus isolate Ebola virus *H. sapiens*-wt/SLE/2014/ManoRiver-G3679.1, partial genome | | | | | |
| 102 | 102 | 100% | 1e-23 | 100% | KM034558.1 |
| Zaire ebolavirus isolate Ebola virus *H. sapiens*-wt/SLE/2014/ManoRiver-G3677.2, partial genome | | | | | |
| 102 | 102 | 100% | 1e-23 | 100% | KM034557.1 |
| Zaire ebolavirus isolate Ebola virus *H. sapiens*-wt/SLE/2014/ManoRiver-G3677.1, partial genome | | | | | |
| 102 | 102 | 100% | 1e-23 | 100% | KM034556.1 |
| Zaire ebolavirus isolate Ebola virus *H. sapiens*-wt/SLE/2014/ManoRiver-G3676.2, partial genome | | | | | |
| 102 | 102 | 100% | 1e-23 | 100% | KM034555.1 |
| Zaire ebolavirus isolate Ebola virus *H. sapiens*-wt/SLE/2014/ManoRiver-G3676.1, partial genome | | | | | |
| 102 | 102 | 100% | 1e-23 | 100% | KM034554.1 |
| Zaire ebolavirus isolate Ebola virus *H. sapiens*-wt/SLE/2014/ManoRiver-G3670.1, partial genome | | | | | |
| 102 | 102 | 100% | 1e-23 | 100% | KM034553.1 |
| Zaire ebolavirus isolate Ebola virus *H. sapiens*-wt/SLE/2014/ManoRiver-EM098, partial genome | | | | | |
| 102 | 102 | 100% | 1e-23 | 100% | KM034552.1 |
| Zaire ebolavirus isolate Ebola virus *H. sapiens*-wt/SLE/2014/ManoRiver-EM096, partial genome | | | | | |
| 102 | 102 | 100% | 1e-23 | 100% | KM034551.1 |
| Zaire ebolavirus isolate Ebola virus *H. sapiens*-wt/SLE/2014/ManoRiver-EM095, partial genome | | | | | |
| 102 | 102 | 100% | 1e-23 | 100% | KM034550.1 |
| Zaire ebolavirus isolate *H. sapiens*-wt/SLE/2014/ManoRiver-EM095B, partial genome | | | | | |
| 102 | 102 | 100% | 1e-23 | 100% | KM034549.1 |
| Mutant Zaire ebolavirus, complete sequence | | | | | |
| 102 | 102 | 100% | 1e-23 | 100% | |

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

This application may be related to International Patent Application No. PCT/US2013/035750, filed Apr. 9, 2013, which claims the benefit of U.S. Provisional Application No. 61/621,975, filed Apr. 9, 2012, the entire contents of which are incorporated herein by reference.

This application may be related to International Patent Application No. PCT/US2011/047049, filed Aug. 9, 2011, which claims the benefit of U.S. Provisional Application No. 61/373,695, filed Aug. 13, 2010, the entire contents of which are incorporated herein by reference.

All patents and publications mentioned in this specification are herein incorporated by reference to the same extent as if each independent patent and publication was specifically and individually indicated to be incorporated by reference.

What is claimed is:

1. A method of amplifying a target RNA molecule in a reverse transcriptase and nicking amplification reaction, the method comprising:

(a) contacting a target RNA molecule in a crude sample with a reverse transcriptase primer in the presence of a reverse transcriptase and dNTPs under conditions permissive for cDNA synthesis, thereby generating a cDNA;

(b) contacting the cDNA with (i) forward and reverse primers, wherein each primer comprises at least one nicking enzyme recognition sequence and a 3'-terminal recognition region which specifically binds the cDNA in the presence of a nicking enzyme, and one or more 2' modified nucleotides in the recognition region, (ii) dNTPs, and (iii) a strand-displacement polymerase under conditions permissive for the isothermal amplification of the cDNA, thereby generating amplicons.

2. The method of claim 1, wherein the polynucleotide molecule is an Ebola virus (EBOV), human immunodeficiency virus (HIV), dengue virus, influenza B virus, or bovine diarrhea virus polynucleotide.

3. The method of claim 1, wherein the method comprises a one-step reaction where the reverse transcriptase and strand-displacement polvmerase are included in a single reaction and steps (a) and (b) are carried out at the same time.

4. The method of claim 1, wherein the reverse transcriptase enzyme and the strand-displacement DNA polymerase are the same or different enzymes.

5. The method of claim 1, wherein the method is carried out in about 5, 7, 10, 15, 20, 25, or 30 minutes.

6. The method of claim 1, wherein the primer used in step (a) has the same sequence as a primer used in step (b).

7. The method of claim 1, wherein the crude sample is a biological sample or an environmental sample.

8. The method of claim 7, wherein the biological sample is a swab of a mucosal membrane selected from the group consisting of buccal, nasal, eye, rectal, and vaginal or skin.

9. The method of claim 7, wherein the biological sample is a tissue sample obtained from a subject, necropsy, or culture media.

10. The method of claim 1, wherein the strand-displacement DNA polymerase is a 5'-exo-derivative selected from the group consisting of Bst DNA polymerase I, Gst DNA polymerase I, Gka DNA polymerase I, Gca DNA polymerase I, Gan DNA polymerase I, Gbo DNA polymerase I, Gsp70 DNA polymerase I, GspT3 DNA polymerase I, Gsp52 DNA polymerase I and/or fragments thereof.

11. The method of claim 1, wherein the nicking enzyme is one or more of Nt.BstNBI, Nt.BspD6I, Nt.BspQI, Nt.BsmAI, Nt.AlwI, N.Bst9I, or N.BstSEI.

12. The method of claim 1, wherein the reverse transcriptase is M-MLV RT, AMV RT, or RSV RT.

13. The method of claim 2, wherein the forward and reverse primers each comprise a nucleotide with a methoxy modification;

wherein the forward and reverse primers for detection of EBOV comprise primers selected from the group consisting of:

Forward primer:
(SEQ ID NO: 1)
GACTCGATATCGAGTCGCTTCCAmCAGTTATCmUmAmCmCmG,
and

Reverse Primer:
(SEQ ID NO: 2)
GACTCGATATCGAGTCGAAATGCmAACGAmCmAmCmCmU;

wherein the forward and reverse primers for detection of HIV comprise primers selected from the group consisting of:

Forward primers:
(SEQ ID NO: 6)
GACTCGATATCGAGTCTGACTAGmCGGAGGmCmTmAmGmAmAmG,
and (SEQ ID NO: 7)
GACTCGATATCGAGTCTGACTAGmCAGAGGmCmTmAmGmAmAmG,
and Reverse Primers:
(SEQ ID NO: 8)
GACTCGATATCGAGTCTATTGACmGCTCmTmCmGmCmAmC, -continued and (SEQ ID NO: 9)
GACTCGATATCGAGTCTACTGACmGCTCmTmCmGmCmAmC;

wherein the forward and reverse primers for detection of dengue virus comprise primers selected from the group consisting of:

Forward primer:
(SEQ ID NO: 11)
GACTCGATATCGAGTCCAAAAACmAGCATATTmGmAmCmGmC,
and

Reverse Primer:
(SEQ ID NO: 12)
GACTCGATATCGAGTCAGACAGCmAGGATCmTmCmTmGmG,
and (SEQ ID NO: 13)
GACTCGATATCGAGTCAGACAGCmAGGATCmTmGmTmGmG;

wherein the forward and reverse primers for detection of influenza B virus comprise primers selected from the group consisting of:

Forward primers:
(SEQ ID NO: 15)
GACTCGATATCGAGTCAAATGCAmGATGGTCTCmAmGmCmTmA, (SEQ ID NO: 16)
GACTCGATATCGAGTCAAATGCAmAATGGTCTCmAmGmCmTmA,
and (SEQ ID NO: 17)
GACTCGATATCGAGTCAAATGCAmGATGGTTTCmAmGmCmTmA,
and Reverse Primers:
(SEQ ID NO: 18)
GACTCGATATCGAGTCCTCCTTTmTCCCATTCCATmTmCmAmTmT, (SEQ ID NO: 19)
GACTCGATATCGAGTCCTCCCTTmTCCCATTCCATmTmCmAmTmT,
and (SEQ ID NO: 20)
GACTCGATATCGAGTCCTCCTTTmCCCCATTCCATmTmCmAmTmT;
or wherein the forward and reverse primers for detection of bovine diarrhea virus comprise primers selected from the group consisting of:

Forward primers:
(SEQ ID NO: 22)
GACTCGATATCGAGTCGGCCCACmTGTATTGCTmAmCmTmGmAmAmA,
and (SEQ ID NO: 23)
GACTCGATATCGAGTCGGCCCACmTGCACTGCTmAmCmTmAmAmAmA,
and Reverse Primer:
(SEQ ID NO: 24)
GACTCGATATCGAGTCTGTGATCmAACTCCmAmTmGmTmGmCmC, wherein mN indicates that the base N is a methoxy base.

14. The method of claim 13, wherein the modified nucleotide is one or more of 2'-O-methyl, 2'-methoxyethoxy, 2'-fluoro, 2'-hydroxyl, 2'-alkyl, 2'-allyl, 2'-O-[2-(methylamino)-2-oxoethyl], 4'-$CH_2$—O-2'-bridge, 4'-($CH_2$) 2-O-2'-bridge, 2'-LNA, and 2'-O—(N-methylcarbamate).

15. A kit for amplifying a polynucleotide molecule in a reverse transcriptase and nicking amplification reaction, the kit comprising:

a) forward and reverse primers each comprising a nucleotide with a methoxy modification;

wherein the forward and reverse primers are for the detection of EBOV and comprise primers selected from the group consisting of:

```
Forward primer:
                                          (SEQ ID NO: 1)
GACTCGATATCGAGTCGCTTCCAmCAGTTATCmUmAmCmCmG,
and

Reverse Primer:
                                          (SEQ ID NO: 2)
GACTCGATATCGAGTCGAAATGCmAACGAmCmAmCmCmU;
```

wherein the forward and reverse primers for detection of HIV comprise primers selected from the group consisting of:

```
Forward primers:
                                          (SEQ ID NO: 6)
GACTCGATATCGAGTCTGACTAGmCGGAGGmCmTmAmGmAmAmG,
and

                                          (SEQ ID NO: 7)
GACTCGATATCGAGTCTGACTAGmCAGAGGmCmTmAmGmAmAmG,
and

Reverse Primers:
                                          (SEQ ID NO: 8)
GACTCGATATCGAGTCTATTGACmGCTCmTmCmGmCmAmC,
and

                                          (SEQ ID NO: 9)
GACTCGATATCGAGTCTACTGACmGCTCmTmCmGmCmAmC;
```

wherein the forward and reverse primers for detection of dengue virus comprise primers selected from the group consisting of:

```
Forward primer:
                                         (SEQ ID NO: 11)
GACTCGATATCGAGTCCAAAAACmAGCATATTmGmAmCmGmC,
and

Reverse Primer:
                                         (SEQ ID NO: 12)
GACTCGATATCGAGTCAGACAGCmAGGATCmTmCmTmGmG,
and
```

-continued

```
                                         (SEQ ID NO: 13)
GACTCGATATCGAGTCAGACAGCmAGGATCmTmGmTmGmG;
```

wherein the forward and reverse primers for detection of influenza B virus comprise primers selected from the group consisting of:

```
Forward primers:
                                         (SEQ ID NO: 15)
GACTCGATATCGAGTCAAATGCAmGATGGTCTCmAmGmCmTmA,

                                         (SEQ ID NO: 16)
GACTCGATATCGAGTCAAATGCAmAATGGTCTCmAmGmCmTmA,
and

                                         (SEQ ID NO: 17)
GACTCGATATCGAGTCAAATGCAmGATGGTTTCmAmGmCmTmA,
and

Reverse Primers:
                                         (SEQ ID NO: 18)
GACTCGATATCGAGTCCTCCTTTmTCCCATTCCATmTmCmAmTmT,

                                         (SEQ ID NO: 19)
GACTCGATATCGAGTCCTCCCTTmTCCCATTCCATmTmCmAmTmT,
and

                                         (SEQ ID NO: 20)
GACTCGATATCGAGTCCTCCTTTmCCCCATTCCATmTmCmAmTmT;
or
```

wherein the forward and reverse primers for detection of bovine diarrhea virus comprise primers selected from the group consisting of:

```
Forward primers:
                                         (SEQ ID NO: 22)
GACTCGATATCGAGTCGGCCCACmTGTATTGCTmAmCmTmGmAmAmA,
and

                                         (SEQ ID NO: 23)
GACTCGATATCGAGTCGGCCCACmTGCACTGCTmAmCmTmAmAmAmA,
and

Reverse Primer:
                                         (SEQ ID NO: 24)
GACTCGATATCGAGTCTGTGATCmAACTCCmAmTmGmTmGmCmC,
```

wherein mN indicates that the base N is a methoxy base;

b) a reverse transcriptase enzyme;

c) a nicking enzyme;

d) a strand-displacement polymerase; and e) directions for use of the aforementioned primers and enzymes for amplifying a polynucleotide molecule.

* * * * *

SEQUENCE LISTING

```
<160> NUMBER OF SEQ ID NOS: 75

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (32)..(36)
<223> OTHER INFORMATION: Methoxy base

<400> SEQUENCE: 1

gactcgatat cgagtcgctt ccacagttat cuaccg                              36


<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (29)..(33)
<223> OTHER INFORMATION: Methoxy base

<400> SEQUENCE: 2

gactcgatat cgagtcgaaa tgcaacgaca ccu                                 33


<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3

gctacacgac tttygctgaa ggtagc                                         26


<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      probe
<220> FEATURE:
```

```
<223> OTHER INFORMATION: 5'-CALRed610nm-modified
<220> FEATURE:
<223> OTHER INFORMATION: 3'-BHQ2-modified

<400> SEQUENCE: 4

gctacacgac tttygctgaa ggtagc                                            26


<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-FAM or FITC-modified
<220> FEATURE:
<223> OTHER INFORMATION: 3'-BHQ1-modified

<400> SEQUENCE: 5

gctacacgac tttygctgaa ggtagc                                            26


<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (30)..(36)
<223> OTHER INFORMATION: Methoxy base

<400> SEQUENCE: 6

gactcgatat cgagtctgac tagcggaggc tagaag                                 36


<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (30)..(36)
<223> OTHER INFORMATION: Methoxy base

<400> SEQUENCE: 7

gactcgatat cgagtctgac tagcagaggc tagaag                                 36


<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: Methoxy base
```

-continued

<220> FEATURE:
<221> NAME/KEY: modified_base
<222> LOCATION: (28)..(33)
<223> OTHER INFORMATION: Methoxy base

<400> SEQUENCE: 8
gactcgatat cgagtctatt gacgctctcg cac 33

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (28)..(33)
<223> OTHER INFORMATION: Methoxy base

<400> SEQUENCE: 9
gactcgatat cgagtctact gacgctctcg cac 33

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
probe

<400> SEQUENCE: 10
cgcaagggag agagatgggt gcttgcg 27

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (32)..(36)
<223> OTHER INFORMATION: Methoxy base

<400> SEQUENCE: 11
gactcgatat cgagtccaaa aacagcatat tgacgc 36

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (30)..(34)

<223> OTHER INFORMATION: Methoxy base

<400> SEQUENCE: 12
gactcgatat cgagtcagac agcaggatct ctgg 34

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (30)..(34)
<223> OTHER INFORMATION: Methoxy base

<400> SEQUENCE: 13
gactcgatat cgagtcagac agcaggatct gtgg 34

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic probe

<400> SEQUENCE: 14
cgcatctggt ctttcccagc gatgcg 26

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (33)..(37)
<223> OTHER INFORMATION: Methoxy base

<400> SEQUENCE: 15
gactcgatat cgagtcaaat gcagatggtc tcagcta 37

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (33)..(37)
<223> OTHER INFORMATION: Methoxy base

<400> SEQUENCE: 16

```
gactcgatat cgagtcaaat gcaaatggtc tcagcta                          37


<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (33)..(37)
<223> OTHER INFORMATION: Methoxy base

<400> SEQUENCE: 17

gactcgatat cgagtcaaat gcagatggtt tcagcta                          37


<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (35)..(39)
<223> OTHER INFORMATION: Methoxy base

<400> SEQUENCE: 18

gactcgatat cgagtcctcc ttttcccatt ccattcatt                        39


<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (35)..(39)
<223> OTHER INFORMATION: Methoxy base

<400> SEQUENCE: 19

gactcgatat cgagtcctcc ctttcccatt ccattcatt                        39


<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: Methoxy base
<220> FEATURE:
```

<221> NAME/KEY: modified_base
<222> LOCATION: (35)..(39)
<223> OTHER INFORMATION: Methoxy base

<400> SEQUENCE: 20
gactcgatat cgagtcctcc tttccccatt ccattcatt 39

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic probe

<400> SEQUENCE: 21
gccaagctat gaacacagca aacttggc 28

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (33)..(39)
<223> OTHER INFORMATION: Methoxy base

<400> SEQUENCE: 22
gactcgatat cgagtcggcc cactgtattg ctactgaaa 39

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (33)..(39)
<223> OTHER INFORMATION: Methoxy base

<400> SEQUENCE: 23
gactcgatat cgagtcggcc cactgcactg ctactaaaa 39

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (30)..(36)
<223> OTHER INFORMATION: Methoxy base

<400> SEQUENCE: 24
gactcgatat cgagtctgtg atcaactcca tgtgcc 36

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic probe

<400> SEQUENCE: 25
cgctacatct ctgctgtaca tggtagcg 28

<210> SEQ ID NO 26
<211> LENGTH: 18958
<212> TYPE: DNA
<213> ORGANISM: Zaire ebolavirus

<400> SEQUENCE: 26
cggacacaca aaaagaaaga agaattttta ggatcttttg tgtgcgaata actatgagga 60
agattaataa ttttcctctc attgaaattt atatcggaat ttaaattgaa attgttactg 120
taatcacacc tggtttgttt cagagccaca tcacaaagat agagaacagc ctaggtctcc 180
gaagggaaca agggcaccag tgtgctcagt tgaaaatccc ttgtcaacat ctaggtctta 240
tcacatcaca agttccacct cagactctgc agggtgatcc aacaacccta atagaaaaat 300
tattgttaac ggacagcatt agttcacagt caaacaagca agattgagaa ttaaccttga 360
ttttgaactt caacacctag aggattggag attcaacaac cctaaaactt ggggtaaaac 420
attggaaata gttgaaagac aaattgctcg gaatcacaaa attccgagta tggattctcg 480
tcctcagaaa gtctggatga cgccgagtct tactgaatct gacatggatt accacaagat 540
cttgacagca ggtctgtccg ttcaacaggg gattgttcgg caaagagtca tcccagtgta 600
tcaagtaaac aatcttgagg aaatttgcca acttatcata caggcctttg aagcaggtgt 660
tgattttcaa gagagtgcgg acagtttcct tctcatgctt tgtcttcatc atgcgtacca 720
aggagatcac aaactttttct tggaaagtgg tgcagtcaag tatttggaag ggcacgggtt 780
ccgttttgaa gtcaagaaac gtgatggggt gaagcgcctt gaggaattgc tgccagcagt 840
atctagtgga aaaaacatta agagaacact tgctgccatg ccggaagagg agacgactga 900
agctaatgcc ggtcagtttc tctcttttgc aagtctattc cttccgaaat tggtagtagg 960
agaaaaggct tgccttgaga aagttcaaag gcaaattcaa gtacatgcag agcaaggact 1020
gatacaatat ccaacagctt ggcaatcagt aggacacatg atggtgattt tccgtttgat 1080
gcgaacaaat tttttgatca aatttctcct aatacaccaa gggatgcaca tggttgccgg 1140
gcatgatgcc aacgatgctg tgatttcaaa ttcagtggct caagctcgtt tttcaggttt 1200
attgattgtc aaaacagtcc ttgatcatat cctacaaaag acagaacgag gagttcgtct 1260
ccatcctctt gcaaggactg ccaaggtaaa aaatgaggtg aactccttta aggctgcact 1320
cagctccctg gccaagcatg gagagtatgc tcctttcgcc cgacttttga acctttctgg 1380
agtaaataat cttgagcatg gtcttttccc tcaactatcg gcaattgcac tcggagtcgc 1440
cacagcacac gggagcaccc tcgcaggagt aaatgttgga gaacagtatc aacagctcag 1500
agaggctgcc actgaagctg agaagcaact ccaacaatat gcagaatctc gcgaacttga 1560
ccatcttgga cttgatgatc aggaaaagaa aattcttatg aacttccatc agaaaaagaa 1620

-continued

```
cgaaatcagc ttccagcaaa caaacgctat ggtaactcta agaaaagagc gcctggccaa   1680
gctgacagaa gctatcactg ctgcatcact gcccaaaaca agtggacctt acgatgatga   1740
tgacgacatt ccctttccag gacccatcaa tgatgacgac aatcctggcc atcaagatga   1800
tgatccgact gactcacagg atacgaccat tcccgatgtg gtggttgatc ccgatgatgg   1860
aagctacggc gaataccaga gttactcgga aaacggcatg aatgcaccag atgacttggt   1920
cctattcgat ctagacgagg acgacgagga cactaagcca gtgcctaaca gattgaccaa   1980
gggtggacaa cagaaaaaca gtcaaaaggg ccagcataca gagggcagac agacacaatc   2040
caggccaact caaaatgtcc caggccctcg cagaacaatc caccacgcca gtgctccact   2100
cacggacaac gacagaggaa atgaaccctc cggctcaacc agccctcgca tgctgacacc   2160
aattaacgaa gaggcagacc cactggacga tgccgacgac gagacgtcta gtcttccgcc   2220
cttggagtca gacgatgaag aacaggacag ggacgaaact tccaaccgca cacccactgt   2280
cgccccaccg gctcccgtat acagagatca ctctgaaaag aaagaactcc cgcaagatga   2340
gcagcaagat caggaccaca ctcaagaggc caggaaccag gacagtgaca acacccagcc   2400
agaacactct tttgaggaga tgtatcgcca cattctaaga tcacagggac catttgatgc   2460
tgttttgtat tatcatatga tgaaggatga gcctgtagtt ttcagtacta gtgatggcaa   2520
agagtacacg tatccggact cccttgaaga ggaatatcca ccatggctca ctgaaaaaga   2580
ggccatgaat gaagagaata gatttgttac attggatggt caacaatttt attggccggt   2640
aatgaatcac aagaataaat tcatggcaat cctgcaacat catcagtgaa tgagaatgga   2700
ataatgggat gatttaaccg acaaatagct aacattaaat agtcaagaaa cgcaaacagg   2760
aagaattttt gatgtctaag gtgtgaatta ttatcacaat aaaagtgatt cttatttttg   2820
aatttaaagc tagcttatta ttactagccg tttttcaaag ttcaatttga gtcttaatgc   2880
aaataggcgt taagccacag ttatagccat aattgtaact caatatctta gctagcgatt   2940
tatctaaatt aaattacatt atgcttttat aacttaccta ctagcctgcc caacatttac   3000
acgatcgttt tataattaag aaaaaactaa tgatgaagat taaaaccttc atcatcctta   3060
cgtcaattga attctctagc actcgaagct tattgtcttc aatgtaaaag aaaagctggt   3120
ccaacaagat gacaactaga acaaagggca ggggccatac tgtggccacg actcaaaacg   3180
acagaatgcc aggccctgag ctttcgggct ggatctccga gcagctaatg accggaagaa   3240
ttcctgtaag cgacatcttc tgtgatattg agaacaatcc aggattatgt tacgcatccc   3300
aaatgcaaca aacaaagcca aacccgaaga tgcgcaacag tcaaacccaa acggacccaa   3360
tttgcaatca tagttttgag gaggtagtac aaacattggc ttcattggct actgttgtgc   3420
aacaacaaac tatcgcatca gaatcattag aacaacgtat tacgagtctt gagaatggtc   3480
taaagccagt ttatgatatg gcaaaaacaa tctcctcatt gaacagggtt tgtgctgaga   3540
tggttgcaaa atatgatctt ctggtgatga caaccggtcg ggcaacagca accactgcgg   3600
caactgaggc ttattgggct gaacatggtc aaccaccacc tggaccatca ctttatgaag   3660
aaagtgcaat tcggggtaag attgaatcta gagatgagac cgtccctcaa agtgttaggg   3720
aggcattcaa caatctagac agtaccactt cactaactga ggaaaatttt gggaaacctg   3780
acatttcagc aaaggatttg agaaacatta tgtatgatca cttgcctggt tttggaactg   3840
ctttccacca attagtacaa gtgatttgta aattgggaaa agatagcaac tcattggata   3900
tcattcatgc tgagttccag gccagcctgg ctgaaggaga ctctcctcaa tgtgccctaa   3960
```

```
ttcaaattac aaaaagagtt ccaatcttcc aagatgctgc tccacctgtc atccacatcc   4020
gctctcgagg tgacattccc cgagcttgcc agaaaagctt gcgtccagtc ccgccatcac   4080
ccaagattga tcgaggttgg gtatgtgttt tccagcttca agatggtaaa acacttggac   4140
tcaaaatttg agccaatctc ccttccctcc gaaagaggcg accaatagca gaggcttcaa   4200
ctgctgaact acagggtacg ttacattaat gatacacttg tgagtatcag ccctagataa   4260
tataagtcaa ttaaacgacc aagccaaaat tgttcatatc ccgctagcag cttaaaatat   4320
aaatgaaata ggagctatat ctctgacagt attataatca attgttatta agtaacccaa   4380
accaaaaatg atgaagatta agaaaaacct acctcgactg agagagtgtt tttccattaa   4440
ccttcatctt gtaaacgttg agcaaaattg ttacgaatat gaggcgggtt atattgccta   4500
ctgctcctcc tgaatatatg gaggccatat accctgtcag gtcaaattca acaattgcta   4560
ggggtggcaa caacaataca ggcttcctga caccggagtc agtcaatgga gacactccat   4620
cgaatccact caggccaatt gctgatgaca ccatcgacca tgctagccac acaccaggca   4680
gtgtgtcatc agcattcatc cttgaagcta tggtgaatgt catatcgggc cccaaagtgc   4740
taatgaagca aattccaatt tggcttcctc taggtgtcgc tgatcaaaag acctacagct   4800
ttgactcaac tacggccgcc atcatgcttg cttcatatac tatcacccat ttcggcaagg   4860
caaccaatcc acttgtcaga gtcaatcggc tgggtcctgg aatcccggat caccccctca   4920
ggctcctgcg aattggaaac caggccttcc tccaggagtt cgttcttccg ccagtccaac   4980
taccccagta tttcaccttt gatttgacag cactcaaact gatcacccaa ccactgcctg   5040
ctgcaacatg gaccgatgac actccaacag gatcaaatgg agcgctgcgt ccaggaattt   5100
cgtttcatcc aaaacttcgc cccattcttt tacctaacaa agtgggaag  aaggggaaca   5160
gtgccgatct aacatctcca gagaaaatcc aagcaataat gacttcactc caggacttta   5220
agatcgttcc aattgatcca accaaaaata tcatgggtat cgaagtgcca gaaactctgg   5280
tccacaagct gaccggtaag aaggtgactt ctaaaaatgg acaaccaatc atccctgttc   5340
ttttgccaaa gtacattggg ttggacccgg tggctccagg agacctcacc atggtaatca   5400
cacaggattg tgacacgtgt cattctcctg caagtcttcc agctgtgatt gagaagtaat   5460
tgcaataatt gactcagatc cagttttaca gaatcttctc agggatagtg ataacatcta   5520
tttagtaatc cgtctattag aggagatact tttaattgat caatatacta aaggtgcttt   5580
acaccattgt cttttttctc tcctaaatgt agaacttaac aaaagactca caatatactt   5640
gtcttaaaga gattgattga tgaaagatca tgactaataa cattacaaat aatcctacta   5700
taatcaatac ggtgattcaa atattaatct ttctaattgc acatactctc tgcccctatc   5760
ctcaaattgc ctacatgcct acatctgagg atagccagtg tgacttggat tggagatgta   5820
gggaagaaat cggaacccat ctccaggttg ttcacaatcc aagcacagac atcgcccttc   5880
taattaagaa aaaatcggcg atgaagatta agccgacagt gagcgcaatc ttcatctctc   5940
ttagattatt tgttttccag agtaggggtc atcaggtcct ttccaatcat ataaccaaaa   6000
taaacttcac tagaaggata ttgtgaggca acaacacaat gggtattaca ggaatattgc   6060
agttacctcg tgatcgattc aagaggacat cattctttct ttgggtaatt atccttttcc   6120
aaagaacatt ttccatccca cttggagtca tccacaatag cacattacaa gttagtgatg   6180
tcgacaaact agtttgtcgt gacaaactgt catccacaaa tcaattgaga tcagttggac   6240
tgaatctcga agggaatgga gtggcaactg acgtgccatc tgcaactaaa agatggggct   6300
tcaggtccgg tgtccctcca aaggtggtca attatgaagc tggtgaatgg gctgaaaact   6360
```

-continued

```
gctacaatct tgaaatcaaa aaacctgacg ggagtgagtg tctaccagca gcgccagacg   6420
ggattcgggg cttcccccgg tgccggtatg tgcacaaagt atcaggaacg ggaccgtgtg   6480
ccggagactt tgccttccac aaagagggtg ctttcttcct gtatgatcga cttgcttcca   6540
cagttatcta ccgaggaacg actttcgctg aaggtgtcgt tgcatttctg atactgcccc   6600
aagctaagaa ggacttcttc agctcacacc ccttgagaga gccggtcaat gcaacggagg   6660
acccgtccag tggctactat tctaccacaa ttagatatca ggctaccggt tttggaacca   6720
atgagacgga gtacttgttc gaggttgaca atttgaccta cgtccaactt gaatcaagat   6780
tcacgccaca gtttttgctc cagctgaatg agacaatata tgcaagtggg aaaaggagca   6840
acaccacggg aaaactaatt tggaaggtca accccgaaat tgatacaaca atcggggagt   6900
gggccttctg ggaaactaaa aaaacctcac tagaaaaatt cgcagtgaag agttgtcttt   6960
cacagctgta tcaaacggag ccaaagacat cagtggtcag agtccggcgc gaacttcttc   7020
cgacccagag acctacacaa caactgaaga ccacaaaatc atggcttcag aaaattcctc   7080
tgcaatggtt caagtgcaca atcaaggaag ggaagctgca gtgtcgcatc tgataaccct   7140
tgccacaatc tccacgagtc ctcaatcccc tacaaccaaa ccaggtcagg acaacagcac   7200
ccataataca cccgtgtata aacttgacat ctctgaggca actcaagttg aacaacatca   7260
tcgcagaaca gacaacgaca gcacagcctc cgacactccc cccgccacga ccgcagccgg   7320
acccccaaaa gcagagaaca tcaacacgag caagagcgct gactccctgg accccgccac   7380
cacgacaagt ccccaaaact acagcgagac cgctggcaac aacaacactc atcaccaaga   7440
taccggagaa gagagtgccg gcagcgggaa gctgggcttg attgccaata ctattgctgg   7500
agtcgcaggg ctgatcacag gcgggagaag aactcgaaga gaagcaattg tcaatgctca   7560
acccaaatgc aaccccaatc tacattactg gactactcag gatgaaggtg ctgcaatcgg   7620
attggcctgg ataccatatt tcgggccagc agccgaggga atttacacag aggggctaat   7680
gcacaatcaa gatggtttaa tctgtggatt gaggcagctg gccaatgaga cgactcaagc   7740
tcttcaactg ttcctgagag ccacaactga gctacgcacc ttttcaatcc tcaaccgtaa   7800
ggcaattgat ttcttgctgc agcgatgggg cggcacatgc cacattttgg gaccggactg   7860
ctgtatcgaa ccacatgatt ggaccaagaa cataacagac aaaattgatc agattattca   7920
tgattttgtt gataaaaccc ttccggacca gggggacaat gacaattggt ggactggatg   7980
gagacaatgg ataccggcag gtattggagt tacaggcgtt ataattgcag ttattgcttt   8040
attctgtata tgcaaatttg tcttttagtt tttcttcaga ttgcttcatg gcaaagctca   8100
gcctcaaatc aatgagatta ggatttaatt atatggatca cttgaatcta agattacttg   8160
acaaatgata atataataca ctggagcttt aaatatagcc aatgtgattc taactccttt   8220
aaactcacaa ttaatcataa acaaggtttg acatcaatct agttatatct ttgagaatga   8280
taaacttgat gaagattaag aaaaaggtaa tctttcgatt atctttagtc ttcatccttg   8340
attctacaat catgacagtt gtctttagtg acaagggaaa gaagcctttt tagtaagttg   8400
taataatcag atctgcgaac cggtagagtt taattgcaac ctaacacaca taaagcattg   8460
gtcaaaaagt caatagaaat ttaaacagtg agtggagaca actttcaaat ggaagctcca   8520
tacgagagag gacgcccccg agctgccaga cagcattcaa gggatggaca cgaccatcat   8580
gttcgagcac gatcatcatc cagagagaat tatcgaggtg agtaccgtca atcaaggagc   8640
gcctcacaag tgcgcgttcc tactgtattt cataagagga gagttgaacc attaacagtt   8700
```

-continued

```
cctccagcac ctaaagacat atgtccgacc ttgaaaaaag gatttttgtg tgacagtagt   8760
ttttgcaaaa aagatcacca gttggaaagt ttaactgata gggaattact cctactaatc   8820
gcccgtaaga cttgtggatc agtagaacaa caattaaata taactgcacc caaggactcg   8880
cgcttagcaa atccaacggc tgatgatttc cagcaagagg aaggtccaaa aattaccttg   8940
ttgacactga tcaagacggc agaacactgg gcgagacaag acatcaggac cacagaggat   9000
tcaaaattaa gagcattgtt gactctatgt gctgtgatga cgaggaaatt ctcaaaatcc   9060
cagctgagtc ttttatgtga gacacacctg aggcgcgagg ggcttgggca agatcaggca   9120
gaacccgttc tcgaagtata tcaacgatta cacagtgata aaggaggcag tttcgaagct   9180
gcactatggc aacaatggga tcgacaatcc ctaattatgt ttatcactgc attcttgaat   9240
atcgctctcc agttaccgtg tgaaagttct gctgtcgttg tttcagggtt aagaacattg   9300
gttcctcaat cagataatga ggaagcttca accaacccgg ggacatgctc atggtctgat   9360
gatggtaccc cttaataagg ctgactaaaa cactatataa ccttctactt gatcacaata   9420
ctccgtatac ctatcatcat atattcaatc aagacggtat cctttaaaac ttattcagta   9480
ctataatcac tctcgtttca aattaataag atatgcataa ttgctttaat atatgaagag   9540
gtatgataca accctaacag tgatcaaaga aaatcataat ctcttatcgc tcgtaatata   9600
acctgccaag catacctctt gcacaaagtg attcttgtac acaaataatg ttttactcta   9660
caggaggtag caacgatcca tcccatcaaa aaataagtat tttatgactt actaatgatc   9720
tcttaaaata ttaagaaaaa ctgacggaac acaaattctt tctgcttcaa gttgtggagg   9780
aggtctttgg tattggctat tgttatatta caatcaataa caagcttgta aaaatattgt   9840
tcttgtttca agaggtagat tgtgaccgga aacgctaaac taatgatgaa gattaatgcg   9900
gaggtctgat aagaataaac cttattattc agattaggcc ccaagaggca ttcttcatct   9960
ccttttagca aagtactatt tcagggtagt ccaattagtg acacgtcttt tagctgtata  10020
tcagtcgccc ctgagatacg ccacaaaagt gtctctaagc taaattggtc tgtacacatc  10080
tcatacattg tattaggggc aataatatct aattgaactt agccgtttaa aatttagtgc  10140
ataaacctgg gctaactcca ccaggtcaac tccattggct gaaaagaagc ccacctacaa  10200
cgaacatcac tttgagcgcc cttacaatta aaaaatagga acgtcgttcc aacaattgag  10260
cgcaaggttt caaggttgaa ctgagagtgc ctaaacacca aaatatcgat aattcagaca  10320
ccaagcaaga cctgagaagg aaccatggct aaagctacgg gacgatacaa tctaatatcg  10380
cccaaaaagg acctggagaa aggggttgtc ttaagcgacc tctgtaactt cctagttagt  10440
caaactattc aagggtggaa ggtctattgg gctggtattg agtttgatgt gactcacaaa  10500
ggaatggccc tattgcatag actgaaaact aatgactttg cccctgcatg gtcaatgaca  10560
aggaatctat ttcctcattt atttcaaaat ccgaattcca caattgagtc accactgtgg  10620
gcattgagag tcatccttgc agcaggggta caggaccagc tgattgacca gtctttgatt  10680
gaacccttag caggagccct tggtctgatc tctgattggc tgctaacaac caacactaac  10740
catttcaaca tgcgaacaca acgtgttaag gaacaattga gcctaaaaat gctgtcgttg  10800
attcgatcca atattctcaa gtttattaac caattggatg ctctacatgt cgtgaactac  10860
aacgggttgt tgagcagtat tgaaattgga actcaaaatc atacaatcat tataactcga  10920
actaacatgg gttttctggt ggagctccaa gaacccgaca aatcggcaat gaaccgcaag  10980
aagcctgggc cggcgaaatt ttccctcctt catgagtcca cactgaaagc atttacacaa  11040
gggtcctcga cacgaatgca aagtttgatt cttgaattta atagctctct tgctatctaa  11100
```

-continued ttaagatgga atacttcata ttgagctaac tcatatatgc tgactcaata gttatcttga 11160
catctctgct ttcataatca gatatataag cataataaat aaatactcat atttcttgat 11220
aatttgttta accacagata aatcctaact gtaagccagc ttccaagttg acacccttac 11280
aaaaaccagg actcagaatc cctcaaataa gagattccaa gacaacatca tagaattgct 11340
ttattatatg aataagcatg ttatcaccag aaatccaata tactaaatag ttaattgtaa 11400
ctgaacccgc aggtcacgtg tgttaggttt cacagattat atatattact aactccatac 11460
ccgtaattaa cattagataa gtagattaag aaaaacgctt gaggaagatt aagaaaaact 11520
gcttattggg tctttccgtg ttttagatga agcagttgac attcttcctc ttgatattaa 11580
atggctacac aacataccca atacccagac gccaggttat catcaccaat tgtattggac 11640
caatgtgacc tagtcactag agcttgcggg ttatattcat catactccct taatccgcaa 11700
ctacgcaact gtaaactccc gaaacatatc taccgtttaa aatatgatgt aactgttacc 11760
aagttcttaa gtgatgtacc agtggcgaca ttgccaatag atttcatagt cccaattctt 11820
ctcaaggcac tgtcaggcaa tgggttctgt cctgttgagc cgcggtgtca acagttctta 11880
gatgaaatca ttaagtacac aatgcaagat gctctcttcc tgaaatatta tctcaaaaat 11940
gtgggtgctc aagaggactg tgttgatgac cactttcaag agaaaatctt atcttcaatt 12000
cagggcaatg aatttttaca tcaaatgttc ttctggtatg acctggctat tttgactcga 12060
aggggtagat taaatcgagg aaactctaga tcaacatggt ttgttcatga tgatttaata 12120
gacatcttag gctatgggga ctatgttttt tggaagatcc caatttcaat gttacccctg 12180
aacacacaag gaatccccca tgctgctatg gattggtatc aggcatcagt attcaaagaa 12240
gcggttcaag ggcatacaca cattgtttct gtttctactg ccgacgtctt gataatgtgc 12300
aaagatttaa ttacatgtcg attcaacaca actctaatct caaagatagc agaggttgag 12360
gatccagttt gttctgatta tcccgatttt aagattgtgt ctatgcttta ccagagcgga 12420
gattacttac tctccatatt agggtctgat gggtataaaa ttattaagtt cctcgaacca 12480
ttgtgcttgg ccaaaattca attatgctca aagtacaccg agaggaaggg ccgattctta 12540
acacaaatgc atttagctgt aaatcacacc ctggaagaaa ttacagaaat gcgtgcacta 12600
aagccttcac aggatcaaaa gatccgtgaa ttccatagaa cattgataag gctggagatg 12660
acgccacaac aactttgtga gctattttcc attcaaaaac actgggggca tcctgtgcta 12720
catagtgaaa cagcaatcca aaaagttaaa aaacatgcca cggtgctaaa agcattacgc 12780
cctatagtga ttttcgagac atattgtgtt tttaaatata gtattgcaaa acattatttt 12840
gatagtcaag gatcttggta cagtgttact tcagatagga atttaacgcc aggtcttaat 12900
tcttatatca aaagaaatca attccccccg ttgccaatga ttaaagaact actatgggaa 12960
ttttaccacc ttgaccatcc tccacttttc tcaaccaaaa ttattagtga cttaagtatt 13020
tttataaaag acagagctac cgcagtggaa aggacatgct gggatgcagt attcgagcct 13080
aatgttctag gatataatcc acctcacaaa ttcagtacta aacgtgtacc agaacaattt 13140
ttagagcaag aaaacttttc tattgagaat gttctttcct acgcgcaaaa actcgagtat 13200
ctactaccac aataccggaa tttttctttc tcattgaaag agaaagagtt gaatgtaggt 13260
agaactttcg gaaaattgcc ttatccgact cgcaatgttc aaacactttg tgaagctctg 13320
ttagctgatg gtcttgctaa agcatttcct agcaatatga tggtagtcac agagcgtgag 13380
caaaaagaaa gcttattgca tcaagcatca tggcaccaca caagtgatga ttttggtgag 13440

-continued

```
catgccacag ttagagggag tagctttgta actgatttag agaaatacaa tcttgcattt  13500
agatatgagt ttacagcacc ttttatagaa tattgtaacc gttgctatgg tgttaagaat  13560
gtttttaatt ggatgcatta tacaatcccc cagtgttata tgcatgtcag tgattattat  13620
aatccaccgc ataacctcac tctggaaaat cgagacaacc cccccgaagg gcccagttca  13680
tacagaggtc atatgggagg gattgaagga ctgcaacaaa aactctggac aagtatttca  13740
tgtgctcaaa tttctttagt tgaaataaag actggtttta agttacgctc agctgtgatg  13800
ggtgacaatc agtgcattac cgttttatca gtcttcccct tagagactga cgcagacgag  13860
caggaacaga gcgccgaaga caatgcagcg agggtggccg ccagcctagc aaaagttaca  13920
agtgcctgtg gaatcttttt aaaacctgat gaaacatttg tacattcagg ttttatctat  13980
tttggaaaaa aacaatattt gaatggggtc caattgcctc agtcccttaa aacggctaca  14040
agaatggcac cattgtctga tgcaattttt gatgatcttc aagggaccct ggctagtata  14100
ggcactgctt ttgaacgatc catctctgag acacgacata tctttccttg caggataacc  14160
gcagctttcc atacgttttt ttcggtgaga atcttgcaac atcatcacct cgggttcaat  14220
aagggttttg accttggaca gttgacactt ggcaaacctc tggatttcgg aacaatatca  14280
ttggcactag cggtaccgca ggtgcttgga gggttatcct tcttgaatcc tgagaaatgt  14340
ttctaccgga atttaggaga tccagttacc tcaggcttat tccagttaaa aacttatctc  14400
cgaatgattg agatggatga tttattctta cctttaattg cgaagaaccc tgggaactgc  14460
actgccattg actttgtgct aaatcctagc ggattaaatg tccccgggtc gcaagactta  14520
acttcatttc tgcgccagat tgtgcgtagg actatcaccc taagtgcgaa aaacaaactt  14580
attaatactt tatttcatgc gtcagctgac ttcgaagacg aaatggtttg taaatggcta  14640
ttatcatcaa ctcctgttat gagtcgtttt gcggccgata tcttttcacg cacgcccagt  14700
gggaagcgat tgcaaattct aggataccta gaaggaacac gcacattatt agcctctaag  14760
atcatcaaca ataatacaga aacaccggtt ttggacagac tgaggaaaat aacattgcaa  14820
aggtggagtc tatggtttag ttatcttgat cattgtgata atatcctggc agaggcttta  14880
acccaaataa cttgcacagt tgatttagca cagatcctga gggaatattc atgggcacat  14940
attttagagg ggagacctct tattggagcc acacttccat gtatgattga gcaattcaaa  15000
gtggtttggc tgaaacccta cgaacaatgt ccgcagtgtt caaatgcaaa gcaacctggt  15060
gggaaaccat tcgtgtcagt ggcagtcaag aaacatattg ttagtgcatg gccgaacgca  15120
tcccgaataa gctggactat cggggatgga atcccataca ttggatcaag gacagaagat  15180
aagataggac aacctgctat taaaccaaaa tgtccttccg cagccttaag agaggccatt  15240
gaactggcgt cccgtttaac atgggtaact caaggcagtt cgaacagtga tttgctaata  15300
aaaccatttt tggaagcacg agtaaattta agtgttcaag aaatacttca aatgacccct  15360
tcacattact caggaaatat tgttcacagg tacaacgatc aatatagtcc tcattctttc  15420
atggccaatc gtatgagtaa ttcagcgacg cgattgattg tttctactaa cactttaggt  15480
gagttttcag gaggtggcca gtctgcacgc gacagcaata ttattttcca gaatgttata  15540
aattatgcag ttgcactgtt cgatattaaa tttagaaaca ctgaggctac agatatccaa  15600
tataatcgtg ctcaccttca tctaactaag tgttgcaccc gggaagtacc agctcagtat  15660
ttaacataca catctacatt ggatttagat ttaacaagat accgagaaaa cgaattgatt  15720
tatgacaata atcctctaaa aggaggactc aattgcaata tctcattcga taacccattt  15780
ttccaaggta aacggctaaa cattatagaa gatgatctta ttcgactgcc tcacttatct  15840
```

```
ggatgggagc tagccaagac catcatgcaa tcaattattt cagatagcaa caattcgtct  15900
acagacccaa ttagcagtgg agaaacaaga tcattcacta cccatttctt aacttatccc  15960
aagataggac ttctgtacag ttttggggcc tttataagtt attatcttgg caatacaatt  16020
cttcggacta agaaattaac acttgacaat tttttatatt acttaactac ccaaattcat  16080
aatctaccac atcgctcatt gcgaatactt aagccaacat tcaaacatgc aagcgttatg  16140
tcacggttaa tgagtattga tcctcatttt tctatttaca taggcggtgc ggcaggtgac  16200
agaggactct cagatgcggc caggttattt ttgagaacgt ccatttcatc ttttcttgca  16260
tttataaaag agtggataat taatcgcgga acaattgtcc ctttatggat agtatatccg  16320
ctagagggtc aaaacccaac acctgttaat aatttcctcc atcagatcgt agaactgctg  16380
gtgcatgatt catcaagaca acaggctttt aaaactacca taagtgatca tgtacatcct  16440
cacgacaatc ttgtttacac atgtaagagt acagccagca atttcttcca tgcgtcattg  16500
gcgtactgga gaagcaggca cagaaacagc aatcgaaaat acttggcaag agactcttca  16560
actggatcaa gcacaaacaa cagtgatggt catattgaga gaagtcaaga acaaaccacc  16620
agagatccac atgatggcac tgaacggaat ctagtcctac aaatgagcca tgaaataaaa  16680
agaacgacaa ttccacaaga aagcacgcac cagggtccgt cgttccagtc atttctaagt  16740
gactctgctt gtggtacagc aaatccaaaa ctaaatttcg atagatcgag acataatgtg  16800
aaatctcagg atcataactc ggcatccaag agggaaggtc atcaaataat ctcacaccgt  16860
ctagtcctac ctttctttac attgtctcaa gggacgcgcc aattaacgtc atccaatgag  16920
tcacaaaccc aagacgagat atcaaagtac ttacggcaat tgagatccgt cattgatacc  16980
acagtttatt gtaggtttac cggtatagtc tcgtccatgc attacaaact tgatgaggtc  17040
ctttgggaaa tagagagttt taagtcggct gtgacgctag cagagggaga aggtgctggt  17100
gccttactat tgattcagaa ataccaagtt aagaccttat ttttcaacac gctagctact  17160
gagtccagta tagagtcaga aatagtatca ggaacgacta ctcctaggat gcttctacct  17220
gttatgtcaa aattccataa tgaccaaatt gagattattc ttaacaattc ggcaagccaa  17280
ataacagaca taacaaatcc tacttggttc aaagaccaaa gagcaaggct acctaggcaa  17340
gtcgaggtta taaccatgga tgcagagacg acagaaaata taaacagatc gaaattgtac  17400
gaagctgtat ataaattgat cttacaccat attgatccca gcgtattgaa agcagtggtc  17460
cttaaagtct ttctaagtga tactgagggt atgttatggc taaatgataa tttagccccg  17520
ttttttgcca ctggttattt aattaagcca ataacgtcaa gtgctagatc tagtgagtgg  17580
tatctttgtc tgacgaactt cttatcaact acacgtaaga tgccacacca aaaccatctc  17640
agttgtaaac aggtaatact tacggcattg caactgcaaa ttcaacggag cccatactgg  17700
ctaagtcatt taactcagta tgctgactgc gatttacatt taagttatat ccgccttggt  17760
tttccatcat tagagaaagt actataccac aggtataacc tcgtcgattc aaaaagaggt  17820
ccactagtct ctatcactca gcacttggca catcttagag cagagattcg agaattgact  17880
aatgattata atcaacagcg acaaagtcgg actcaaacat atcactttat tcgtactgca  17940
aaaggacgaa tcacaaaact agtcaatgat tatttaaaat tctttcttat tgtgcaagca  18000
ttaaaacata atgggacatg gcaagctgag tttaagaaat taccagagtt gattagtgtg  18060
tgcaataggt tctatcatat tagagattgc aattgtgaag aacgtttctt agttcaaacc  18120
ttatatctac atagaatgca ggattctgaa gttaagctta tcgaaaggct gacagggctt  18180
```

-continued

```
ctgagtttat tcccggatgg tctctacagg tttgattgaa ttaccgtgca tagtatcctg  18240

atacttgtga aggttgatta tcaacgtaca gattataaaa aactcacaaa ttgctctcat  18300

acatcatatt gatcgaattt caataaataa ctatttaaat aacgaaagaa gtccttatat  18360

tatacactat atttagcctc tctccctgcg tgataatcaa aaaattcaca atgcagcatg  18420

tgtgacatat tacttccgcg atgaatctaa cgcaacataa taaactctgc actctttata  18480

attaagcttt aacaaaaggt ctgggctcat attgttattg atataataat gttgtatcaa  18540

tatcctgtca gatggaatag tgttttggtt gataacacga cttcttaaaa caaaattgat  18600

cttcaagatt aagtttttta taattatcat tactttaatt tgtcgattta aaaatggtga  18660

tagccttaat ctttgtgtaa aataagagat taggtgtaat aactttaaca ttttgtctag  18720

taagctacta tttcatacag aatgataaaa ttaaaagaaa aggcatgact gtaaaatcag  18780

aaataccttc tttacaatat agcagactag ataataatct tcgtgttaat gataattaag  18840

acattgacca cgctcatcag gaggctcgcc aggataaacg ttgcaaaaag gattcctgga  18900

aaaatggtcg cacacaaaaa tttaaaaata aatctatttc ttcttttttg tgtgtcca    18958
```

```
<210> SEQ ID NO 27
<211> LENGTH: 341
<212> TYPE: DNA
<213> ORGANISM: Homo sapiens

<400> SEQUENCE: 27

atagggcgga gggaagctca tcagtggggc cacgagctga gtgcgtcctg tcactccact     60

cccatgtccc ttgggaaggt ctgagactag ggccagaggc ggccctaaca gggctctccc    120

tgagcttcgg ggaggtgagt tcccagagaa cggggctccg cgcgaggtca gactgggcag    180

gagatgccgt ggaccccgcc cttcggggag gggcccggcg gatgcctcct ttgccggagc    240

ttggaacaga ctcacggcca gcgaagtgag ttcaatggct gaggtgaggt accccgcagg    300

ggacctcata acccaattca gactactctc ctccgcccat t                        341
```

```
<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(12)
<223> OTHER INFORMATION: a, c, t, g, unknown or other

<400> SEQUENCE: 28

gagtcnnnnn nn                                                         12
```

```
<210> SEQ ID NO 29
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, t, g, unknown or other

<400> SEQUENCE: 29

ggatcnnnnn                                                            10
```

<210> SEQ ID NO 30
<211> LENGTH: 10
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (6)..(10)
<223> OTHER INFORMATION: a, c, t, g, unknown or other

<400> SEQUENCE: 30 gagtcnnnnn 10

<210> SEQ ID NO 31
<211> LENGTH: 12
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (6)..(7)
<223> OTHER INFORMATION: a, c, t, g, unknown or other

<400> SEQUENCE: 31
gactcnngag tc 12

<210> SEQ ID NO 32
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (6)..(9)
<223> OTHER INFORMATION: a, c, t, g, unknown or other

<400> SEQUENCE: 32
gactcnnnng agtc 14

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (6)..(11)
<223> OTHER INFORMATION: a, c, t, g, unknown or other

<400> SEQUENCE: 33
gactcnnnnn ngagtc 16

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base

```
<222> LOCATION: (1)..(4)
<223> OTHER INFORMATION: a, c, t, g, unknown or other
<220> FEATURE:
<221> NAME/KEY: modified_base
<222> LOCATION: (10)..(15)
<223> OTHER INFORMATION: a, c, t, g, unknown or other
<220> FEATURE:
<221> NAME/KEY: modified_base
<222> LOCATION: (21)..(24)
<223> OTHER INFORMATION: a, c, t, g, unknown or other

<400> SEQUENCE: 34

nnnngactcn nnnnngagtc nnnn                                            24


<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: modified_base
<222> LOCATION: (10)..(13)
<223> OTHER INFORMATION: a, c, t, g, unknown or other
<220> FEATURE:
<221> NAME/KEY: modified_base
<222> LOCATION: (19)..(22)
<223> OTHER INFORMATION: a, c, t, g, unknown or other

<400> SEQUENCE: 35

nnnngactcn nnngagtcnn nn                                              22


<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36

cttcttagct tggggcagta tca                                             23


<210> SEQ ID NO 37
<211> LENGTH: 500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

aagatgactg caggagtcaa tgcgcagttg gtcccggcag accaggcgaa cattaccgaa     60

ttttacaaca agtccctttc atcctacaag gagaatgagg agaacatcca gtgtggggag    120

aacttcatgg acatggagtg cttcatgatt ctgaacccca gtcagcagct ggcaattgcc    180

gtcttgtctc tcacactggg caccttcaca gttctggaga acttgctggt gctgtgtgtc    240

accacagtta tctaccgagg aacgactttc gctgaaggtg tcgttgcatt tctgattcct    300

tcactcccgc agcctccgct gccggccctc ttaccacttc atcattagcc tggccgtggc    360

cgaccttctg ggagtgtca tttttgtcta cagctttgtt gactttcatg tgttccaccg    420

caaggacagc cccaacgtct ttctcttcaa attgggtggg gtcaccgcct ccttcacggc    480
```

ctctgtaggc agcctcttcc 500

<210> SEQ ID NO 38
<211> LENGTH: 89
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 38
gacugcagga gucugcugcu uccacaguua ucuaccgagg aacgacuuuc gcugaaggug 60
ucguugcauu ucugauuccu ucacucccg 89

<210> SEQ ID NO 39
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (31)..(36)
<223> OTHER INFORMATION: Methoxy base

<400> SEQUENCE: 39
gactcgatat cgagtccacg agcugagtgc guccug 36

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (31)..(35)
<223> OTHER INFORMATION: Methoxy base

<400> SEQUENCE: 40
gactcgatat cgagtcagac cttcccaagg gacau 35

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic probe

<400> SEQUENCE: 41
ccacgcctgt cactccactc cgcgtgg 27

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
cctctggccc tagtctcag 19

<210> SEQ ID NO 43
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
gcatctaatt tttcgcc 17

<210> SEQ ID NO 44
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
tctgtgcctg gattgat 17

<210> SEQ ID NO 45
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
ttttggacgt cttctcc 17

<210> SEQ ID NO 46
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
ttttgaacgt cttctcc 17

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
tatgttttgt ataaaagttc atttg 25

<210> SEQ ID NO 48
<211> LENGTH: 16
<212> TYPE: DNA
<213> ORGANISM: Zaire ebolavirus

<400> SEQUENCE: 48
acgactttyg ctgaag 16

<210> SEQ ID NO 49
<211> LENGTH: 16
<212> TYPE: DNA
<213> ORGANISM: Zaire ebolavirus

<400> SEQUENCE: 49
acgactttcg ctgaag 16

<210> SEQ ID NO 50
<211> LENGTH: 56
<212> TYPE: DNA
<213> ORGANISM: Zaire ebolavirus

<400> SEQUENCE: 50
tccacagtta tctaccgagg aacgactttc gctgaaggtg tcgttgcatt tctgat 56

<210> SEQ ID NO 51
<211> LENGTH: 59
<212> TYPE: DNA
<213> ORGANISM: Zaire ebolavirus

<400> SEQUENCE: 51
ttccacagtt atctaccgag gaacgacttt cgctgaaggt gtcgttgcat ttctgatac 59

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic
probe
<220> FEATURE:
<221> NAME/KEY: modified_base
<222> LOCATION: (14)..(14)
<223> OTHER INFORMATION: Methoxy base

<400> SEQUENCE: 52
gctacacgac tttggctgaa ggtagc 26

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
probe

<400> SEQUENCE: 53
gctaccttca gcraaagtcg gtagc 25

<210> SEQ ID NO 54
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (32)..(36)
<223> OTHER INFORMATION: Methoxy base

<400> SEQUENCE: 54
gactcgatat cgagtccttc cacagttatc taccga 36

<210> SEQ ID NO 55
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (32)..(36)
<223> OTHER INFORMATION: Methoxy base

<400> SEQUENCE: 55
gactcgatat cgagtcgctt ccacagttat ctaccg 36

<210> SEQ ID NO 56
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (32)..(36)
<223> OTHER INFORMATION: Methoxy base

<400> SEQUENCE: 56
gactcgatat cgagtcacag ttatctaccg aggaac 36

<210> SEQ ID NO 57
<211> LENGTH: 33
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (29)..(33)
<223> OTHER INFORMATION: Methoxy base

<400> SEQUENCE: 57
gactcgatat cgagtcaaat gcaacgacac ctt 33

<210> SEQ ID NO 58
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (29)..(33)
<223> OTHER INFORMATION: Methoxy base

<400> SEQUENCE: 58
gactcgatat cgagtcgaaa tgcaacgaca cct 33

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (29)..(33)
<223> OTHER INFORMATION: Methoxy base

<400> SEQUENCE: 59
gactcgatat cgagtcagaa atgcaacgac acc 33

<210> SEQ ID NO 60
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (32)..(36)
<223> OTHER INFORMATION: Methoxy base

<400> SEQUENCE: 60
gactcgcgcg cgagtcacag ttatctaccg aggaac 36

<210> SEQ ID NO 61
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (32)..(36)
<223> OTHER INFORMATION: Methoxy base

<400> SEQUENCE: 61
gactcgcgcg cgagtccaca gttatctacc gaggaa 36

<210> SEQ ID NO 62
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (32)..(36)
<223> OTHER INFORMATION: Methoxy base

<400> SEQUENCE: 62
gactcgcgcg cgagtcccac agttatctac cgagga 36

<210> SEQ ID NO 63
<211> LENGTH: 33
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (29)..(33)
<223> OTHER INFORMATION: Methoxy base

<400> SEQUENCE: 63
gactcgcgcg cgagtcaaat gcaacgacac ctt 33

<210> SEQ ID NO 64
<211> LENGTH: 33
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (29)..(33)
<223> OTHER INFORMATION: Methoxy base

<400> SEQUENCE: 64
gactcgcgcg cgagtcgaaa tgcaacgaca cct 33

<210> SEQ ID NO 65
<211> LENGTH: 33
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (24)..(24)
<223> OTHER INFORMATION: Methoxy base
<220> FEATURE:
<221> NAME/KEY: modified_base
<222> LOCATION: (29)..(33)
<223> OTHER INFORMATION: Methoxy base

<400> SEQUENCE: 65
gactcgcgcg cgagtcagaa atgcaacgac acc 33

<210> SEQ ID NO 66
<211> LENGTH: 55
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
ccacagttat ctaccgagga acgactttcg ctgaaggtgt cgttgcattt ctgat 55

<210> SEQ ID NO 67
<211> LENGTH: 71
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 67
tgactagcgg aggctagaag gagagagatg ggtgcgagag cgtcaatatt aagaggcgaa 60
aaattagatg c 71

<210> SEQ ID NO 68
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 68
tgactagcag aggctagaag gagagagatg ggtgcgagag cgtcagta 48

<210> SEQ ID NO 69
<211> LENGTH: 71
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 69
caaaaacagc atattgacgc tgggaaagac cagagatcct gctgtctctr caacatcaat 60
ccaggcacag a 71

<210> SEQ ID NO 70
<211> LENGTH: 47
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 70
caaaaacagc atattgacgc tgggaaagac cacagatcct gctgtct 47

<210> SEQ ID NO 71
<211> LENGTH: 73
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 71

aaatgcagat ggtctcagct atgaacacag caaaaacaat gaatggaatg ggaaaaggag     60

aagacgtcca aaa                                                        73


<210> SEQ ID NO 72
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72

aaatgcaaat ggtctcagct atgaacacag caaagacaat gaatggaatg ggaaagggag     60

aagacgttca aaa                                                        73


<210> SEQ ID NO 73
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73

aaatgcagat ggtttcagct atgaacacag caaaagcaat gaatggaatg gggaaaggag     60


<210> SEQ ID NO 74
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74

ggcccactgt attgctactg aaaatctctg ctgtacatgg cacatggagt tgatcacaaa     60

tgaactttta tacaaaacat a                                               81


<210> SEQ ID NO 75
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75

ggcccactgc actgctacta aaaatctctg ctgtacatgg cacatggagt tgatcaca       58
```